United States Patent
Alberati et al.

(10) Patent No.: US 8,178,538 B2
(45) Date of Patent: May 15, 2012

(54) PYRIDAZINONES

(75) Inventors: Daniela Alberati, Zofingen (CH); Luca Gobbi, Muttenz (CH); Matthias Koerner, Grenzach-Wyhlen (DE); Bernd Kuhn, Reinach (CH); Jens-Uwe Peters, Grenzach-Wyhlen (DE); Rosa Maria Rodriguez-Sarmiento, Basel (CH); Mark Rogers-Evans, Bottmingen (CH); Markus Rudolph, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 355 days.

(21) Appl. No.: 12/626,982

(22) Filed: Nov. 30, 2009

(65) Prior Publication Data

US 2010/0152193 A1     Jun. 17, 2010

(30) Foreign Application Priority Data

Dec. 4, 2008   (EP) .................................... 08170716

(51) Int. Cl.
*A61K 31/501* (2006.01)
*C07D 403/04* (2006.01)

(52) U.S. Cl. ................... 514/252.05; 544/224; 544/238; 514/247; 514/252.01

(58) Field of Classification Search ................ 544/224, 544/238; 514/247, 252.01, 252.05
See application file for complete search history.

(56) References Cited

FOREIGN PATENT DOCUMENTS

| EP | 1553096 | 7/2005 |
|----|---------|--------|
| WO | 2005/012485 | 2/2005 |
| WO | 2007/129183 | 11/2007 |
| WO | 2009/053799 | 4/2009 |

OTHER PUBLICATIONS

Lewis et al., Neuron, vol. 28 pp. 325-333 (2000).
Vandenberg et al., Exp. Opin. Ther. Targets vol. 5(4) pp. 507-518 (2001).
Nakazato et al., Exp. Opin Ther Patents vol. 10(1) pp. 75-98 (2000).
Sharma T., Br. J. Psychiatry, vol. 174 (Suppl. 28) pp. 44-51 (1999).
Javitt et al., Biol. Psychiatry vol. 45, pp. 668-679 (1999).
Beavo J., Physiol. Rev. vol. 75, pp. 725-748 (1995).
Conti et al., Prog. Nucleic Acid Res. Mol. Biol. vol. 63, pp. 1-38 (1999).
Soderling et al., Curr. Opin. Cell. Biol. vol. 12, pp. 174-179 (2000).
Manallack et al., J Med. Chem. vol. 48(10) pp. 3449-3462 (2005).
Fujishige et al., Eur. J. Biochem. vol. 266(3) pp. 1118-1127 (1999).
Soderling et al., Proc. Natl. Acad. Sci. USA, vol. 96/12 pp. 7071-7076 (1999).
Loughney et al., Gene vol. 234(1) pp. 109-117 (1999).
Fujishige et al., J. Biol. Chem. vol. 274 pp. 18438-18445 (1999).
Coskran et al., J. Histochem. Cytochem vol. 54(11) pp. 1205-1213 (2006).
Seeger et al., Brain Res vol. 985 pp. 113-126 (2003).
Graybiel A. M., Curr. Biol. vol. 10, pp. R509-R511 (2000).
Siuciak et al., Neuropharmacology vol. 51(2) pp. 386-396 (2006).
Siuciak et al., Neuropharmacology vol. 51(2) pp. 374-385 (2006).
Rodefer et al., Eur. J. Neuroscience vol. 2, pp. 1070-1076 (2005).
Sano, H. J., Neurochem, vol. 105 pp. 546-556 (2008).

*Primary Examiner* — Golam M Shameem
(74) *Attorney, Agent, or Firm* — George W. Johnston; Patricia S. Rocha-Tramaloni; Kimberly J. Prior

(57) ABSTRACT

The present invention is concerned with novel pyridazinones of formula (I)

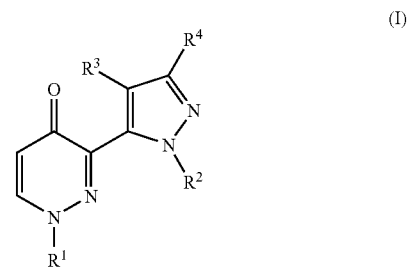

wherein $R^1$, $R^2$, $R^3$ and $R^4$ are as defined in the description and in the claims, as well as physiologically acceptable salts and esters thereof. These compounds inhibit PDE10A and can be used for the treatment of CNS disorders.

50 Claims, No Drawings

SEQUENCE LISTING

```
<160> NUMBER OF SEQ ID NOS: 2

<210> SEQ ID NO 1
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
```

PYRIDAZINONES

PRIORITY TO RELATED APPLICATION(S)

This application claims the benefit of European Patent Application No. 08170716.8, filed Dec. 4, 2008, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron,* 28:325-33, 2000). For decades research has focused on the "dopaminergic hyperactivity" hypothesis which has led to therapeutic interventions involving blockade of the dopaminergic system (Vandenberg R J and Aubrey K R., *Exp. Opin. Ther. Targets,* 5(4): 507-518, 2001; Nakazato A and Okuyama S, et al., *Exp. Opin. Ther. Patents,* 10(1): 75-98, 2000). This pharmacological approach, besides ameliorating positive symptoms in schizophrenic patients, poorly addresses negative and cognitive symptoms which are the best predictors of functional outcome (Sharma T., *Br. J. Psychiatry,* 174(*suppl.* 28): 44-51, 1999). In addition, current antipsychotic treatment is associated with adverse effects like weight gain, extrapyramidal symptoms or effects on glucose and lipid metabolism, related to their unspecific pharmacology.

In conclusion there is still a need for developing new antipsychotics with improved efficacy and safety profile. A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly, in healthy volunteers PCP-induced psychotomimetic action incorporates positive and negative symptoms as well as cognitive dysfunction, thus closely resembling schizophrenia in patients (Javitt D C et al., *Biol. Psychiatry,* 45: 668-679, 1999).

Cyclic nucleotides cyclic adenosine monophosphate (cAMP) and cyclic guanosine monophosphate (cGMP) are ubiquitous second messengers responsible for mediating the biological response of a variety of extracellular signals, including neurotransmitters, light and hormones. cAPM and cGMP regulate a variety of intracellular processes particularly in neurons of the central nervous system by activating cAMP- and cGMP-dependent kinases which then phosphorylate proteins involved in the regulation of synaptic transmission, neuronal differentiation and survival.

A crucial mechanism for controlling intracellular cyclic nucleotide levels and therefore cyclic nucleotide signaling is via hydrolysis of the 3',5'-phosphodiester bond by phosphodiesterases. Phosphodiesterases (PDEs) are a family of widely expressed enzymes encoded by 21 different genes in humans, with each gene encoding several splice variants (Beavo, J., *Physiol. Rev.* 1995, 75, 725-748; Conti, M., Jin, S. L., *Prog. Nucleic Acid Res. Mol. Biol.* 1999, 63, 1-38; Soderling, S. H., Beavo, J. A., *Curr. Opin. Cell Biol.* 2000, 12, 174-179, Manallack, D. T. et al. *J. Med. Chem.* 2005, 48 (10), 3449-3462).

The PDE families differ in their substrate specificy for the cyclic nucleotides, their mechanism of regulation and their sensitivity to inhibitors. Moreover, they are differentially localized in the organism, among the cells of an organ and even within the cells. These differences lead to a differentiated involvement of the PDE families in the various physiological functions.

PDE10A is a dual substrate PDE encoded by a single gene as reported in 1999 by three separate research groups (Fujishige K., et al., *Eur J Biochem* (1999) 266(3):1118-1127, Soderling S. H., et al., *Proc Natl Acad Sci USA* (1999) 96(12):7071-7076, Loughney K., et al., *Gene* (1999) 234(1):109-117). PDE10A is unique from other members of the multigene family with respect to amino acid sequence (779 aa), tissue-specific pattern of expression, affinity for cAMP and cGMP and the effect on PDE activity by specific and general inhibitors.

PDE10A has one of the most restricted distribution of any PDE family being primarily expressed in the brain particularly in the nucleus accumbens and the caudate putamen. Additionally thalamus, olfactory bulb, hippocampus and frontal cortex show moderate levels of PDE10A expression. All these brain areas have been suggested to be involved in the pathophysiology of schizophrenia and psychosis, suggesting a central role of PDE10A in this devastating mental illness. Outside the central nervous system PDE10A transcript expression is also observed in peripheral tissues like thyroid gland, pituitary gland, insulin secreting pancreatic cells and testes (Fujishige, K. et al., *J. Biol. Chem.* 1999, 274, 18438-18445, Sweet, L. (2005) WO 2005/012485). On the other hand expression of PDE10A protein has been observed only in enteric ganglia, in testis and epididdimal sperm (Coskran T. M, et al., *J. Histochem. Cytochem.* 2006, 54 (11), 1205-1213).

In the striatum both mRNA and protein are expressed only in the GABA (-aminobutyric acid)-containing medium spiny projection neurons making it an intriguing target for the treatment of diseases of the central nervous system (Fujishige, K. et al., *Eur. J. Biochem.* 1999, 266, 1118-1127; Seeger, T. F. et al., *Brain Res.* 2003, 985, 113-126). The striatal medium spiny neurons are the principal input site and first site for information integration in the basal ganglia circuit of the mammalian brain. The basal ganglia are a series of interconnected subcortical nuclei that integrate widespread cortical input with dopaminergic signaling to plan and execute relevant motor and cognitive patterns while suppressing unwanted or irrelevant patterns (Graybiel, A. M. *Curr. Biol.* 2000, 10, R509-R511 (2000).

Papaverine, a relatively specific PDE10A inhibitor, and PDE10A-knockout mice have been used to explore the physiology of this enzyme and the possible therapeutic utility of PDE10A inhibition Inhibition of this enzyme pharmacologically or through gene disruption causes a reduction in activity and a reduced response to psychomotor stimulants. Inhibition also reduces the conditioned avoidance response, a behavioural response that is predictive of clinical antipsychotic activity (Siuciak, J. A.; et al., *Neuropharmacology* 2006, 51 (2), 386-396; Siuciak, J. A.; et al., *Neuropharmacology* 2006, 51 (2), 374-385).

In addition PDE10A inhibition bears the potential to improve the negative and cognitive symptoms associated to schizophrenia. Indeed papaverine have been shown to attenuate the deficits in the extra-dimensional shift learning induced in rats by sub-chronic treatment with PCP, an animal paradigm of NMDA receptor hypofunction (Rodefer, J, S., et al., *Eur. J. Neuroscience* 2005, 2: 1070-1076). In addition increased social interaction in PDE10A2-deficient mice have been observed (Sano, H. *J. Neurochem.* 2008, 105, 546-556).

Diseases that can be treated with PDE10A inhibitors include, but are not limited to, diseases thought to be mediated in part by dysfunction of the basal ganglia, of other parts of the central nervous system and of other PDE10A expressing tissues. In particular, diseases can be treated, where inhibition of PDE10A can have therapeutic effects.

These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders.

PDE10A inhibitors might also be useful in preventing neurons from undergoing apoptosis by raising cAMP and cGMP levels and, thus, might possess anti-inflammatory properties. Neurodegenerative disorders treatable with PDE10A inhibitors include, but are not limited to, as Alzheimer's disease, Huntington's disease, Parkinson's disease, multiple sclerosis, stroke or spinal cord injury.

The growth of cancer cells is inhibited by cAMP and cGMP. Thus by raising cAMP and cGMP, PDE10A inhibitors can also be used for the treatment of different solid tumors and hematological malignancies such as renal cell carcinoma or breast cancer.

SUMMARY OF THE INVENTION

The invention provides novel pyridazinones of formula (I)

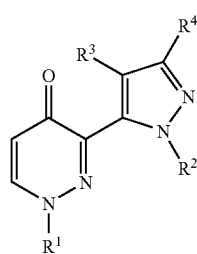

(I)

wherein
R$^1$ is aryl which is optionally substituted with 1 to 4 substituents independently selected from the group consisting of lower-alkyl, hydroxy-lower-alkyl, lower-alkoxy, fluoro-lower-alkyl, fluoro-lower-alkoxy, lower-alkyl-SO$_2$, fluoro-lower-alkyl-SO$_2$, halogen, lower-alkoxy-lower-alkyl, cyano, NO$_2$, lower-alkyl-SO, morpholinyl, NH$_2$—SO$_2$, N(H,lower-alkyl)-SO$_2$, N(lower-alkyl)$_2$-SO$_2$, piperidinyl-SO$_2$, pyrrolidinyl-SO$_2$, hydroxy, COOH, COO-lower-alkyl, COO-fluoro-lower-alkyl, lower-alkyl-C(O)O, CO-lower-alkyl, CONH$_2$, CON(H,lower-alkyl), CON(lower-alkyl)$_2$, lower-alkyl-CO—NH, lower-alkyl-CO—N(lower-alkyl), NH$_2$, N(H,lower-alkyl), N(lower-alkyl)$_2$, NH$_2$-lower-alkyl, N(H,lower-alkyl)-lower-alkyl, N(lower-alkyl)$_2$-lower-alkyl, cycloalkyl, phenyloxy and phenyl,
or wherein two substituents at adjacent positions on the aryl group are bound together to form a ring and said two bound substituents together are lower-alkylene, dioxo-lower-alkylene, dioxo-fluoro-lower-alyklene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)-C(O)-lower-alkylene, lower-alkylene-NH—C(O)-lower-alkylene, lower-alkylene-N(lower alkyl)-C(O)-lower-alkylene, C(O)—NH-lower-alkylene, or C(O)—N(lower-alkyl)-lower-alkylene;

R$^2$ is aryl or heteroaryl, which aryl or heteroaryl is optionally substituted with 1 to 4 substituents independently selected from the group consisting of halogen, cyano, lower-alkyl, lower-alkoxy, fluoro-lower-alkyl, fluoro-lower-alkoxy, lower-alkinyl, lower-alkyl-SO$_2$, fluoro-lower-alkyl-SO$_2$, tri(lower-alkyl)silyl-loweralkinyl, COOH, CONH$_2$, NH$_2$—SO$_2$, COO-lower-alkyl, 6-oxo-1,4,5,6-tetrahydropyridazinyl, lower-alkoxy-lower-alkyl, CON(H,lower-alkyl), CON(lower-alkyl)$_2$, N(H,lower-alkyl)-SO$_2$, N(lower-alkyl)$_2$-SO$_2$, lower-alkenyl, hydroxy, NO$_2$, morpholinyl, tetrahydropyridazinyl, piperidinyl, piperazinyl, (N-lower-alkyl)-piperazinyl, pyrrolidinyl, lower-alkyl-C(O)O, lower-alkyl-CO—NH, lower-alkyl-CO—N(lower-alkyl), imidazolyl, pyridinyl, CO-lower-alkyl, NH$_2$, N(H, lower-alkyl), N(lower-alkyl)$_2$, NH$_2$-lower-alkyl, N(H, lower-alkyl)-lower-alkyl, N(lower-alkyl)$_2$-lower-alkyl, cycloalkyl, phenyloxy and phenyl which is optionally substituted with 1 to 4 substituents independently selected from halogen, lower-alkoxy, lower-alkyl, fluoro-lower-alkyl, fluoro-lower-alkoxy, hydroxy and cyano,
or wherein two substituents at adjacent positions on the aryl or heteroaryl group are bound together to form a ring and said two bound substituents together are lower-alkylene, dioxo-lower-alkylene, dioxo-fluoro-lower-alyklene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)-C(O)-lower-alkylene, lower-alkylene-NH—C(O)-lower-alkylene, lower-alkylene-N(lower alkyl)-C(O)-lower-alkylene, C(O)—NH-lower-alkylene or C(O)—N(lower-alkyl)-lower-alkylene;

R$^3$ is hydrogen, lower-alkyl, fluoro-lower-alkyl, lower-alkoxy, fluoro-lower-alkoxy, halogen, hydroxy or phenyl; and R$^4$ is hydrogen, lower-alkyl, fluoro-lower-alkyl, lower-alkoxy, fluoro-lower-alkoxy, halogen, hydroxy or phenyl;
and pharmaceutically acceptable salts and esters thereof.

Further, the invention is concerned with a process for the manufacture of the above compounds, pharmaceutical compositions that contain such compounds as well as methods for the manufacture of compounds and compositions of the invention The present invention also provides methods for treating schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders.

The compounds of the present invention are also suitable for the treatment of diabetes and related disorders such as obesity by regulating the cAMP signaling system.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl," alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower-alkyl," alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

The term "alkenyl," alone or in combination with other groups, stands for a straight-chain or branched hydrocarbon residue comprising at least one olefinic bond and having up to 20, preferably up to 16, carbon atoms. The term "lower-alkenyl" refers to a straight-chain or branched hydrocarbon residue comprising an olefinic bond and having up to 7, preferably up to 4, carbon atoms, such as e.g. ethenyl or 2-propenyl.

The term "alkinyl", alone or in combination with other groups, stands for a straight-chain or branched hydrocarbon residue comprising a triple bond and having up to 20, preferably up to 16, carbon atoms. The term "lower-alkinyl" refers to a straight-chain or branched hydrocarbon residue comprising a triple bond and up to 7, preferably up to 4, carbon atoms, such as e.g. ethinyl or 2-propinyl.

The term "lower-alkylene," alone or in combination with other groups, refers to a branched or straight chain divalent lower-alkyl radical. This term is further exemplified by such radicals as methylene, ethylene, propylene and the like. The term "dioxo-lower-alkylene" refers to the group —O-lower-alkylene-O—.

The term "fluoro-lower-alkylene," alone or in combination with other groups, refers to a branched or straight chain divalent fluoro-lower-alkyl radical. This term is further exemplified by such radicals as —$CF_2$— and the like. The term "dioxo-fluoro-lower-alkylene" refers to the group —O-fluoro-lower-alkylene-O—.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "fluoro-lower-alkyl" refers to lower-alkyl groups as defined above which are mono- or multiply substituted with fluorine. Examples of fluoro-lower-alkyl groups are e.g. $CFH_2$, $CF_2H$, $CF_3$, $CF_3CH_2$, $CF_3(CH_2)_2$, $(CF_3)_2CH$ and $CF_2H$—$CF_2$.

The term "hydroxy-lower-alkyl" refers to a lower-alkyl group as defined above, which is substituted by 1 to 3 hydroxy groups. Examples of hydroxy-lower-alkyl groups are e.g. hydroxy-methyl, hydroxy-ethyl, hydroxy propyl, 3-hydroxy-propyl, 2-hydroxy-propyl, 3-hydroxy-prop-2-yl, 2,3-dihydroxy-propyl and 1,3-dihydroxy-prop-2-yl.

The term "alkoxy" refers to the group R'—O—, wherein R' is an alkyl group as defined above. The term "lower-alkoxy" refers to the group R'—O—, wherein R' is a lower-alkyl group as defined above.

The term "fluoro-lower-alkoxy" refers to the group R"—O—, wherein R" is fluoro-lower-alkyl as defined above. Examples of fluoro-lower-alkoxy groups are e.g. $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "aryl," alone or in combination, relates to a phenyl or naphthyl group, preferably a phenyl group, which is optionally substituted, unless specifically stated otherwise, by 1 to 5, preferably 1 to 3, substituents, independently selected from the group consisting of halogen, hydroxy, amino, $NO_2$, lower-alkyl, hydroxy-lower-alkyl, lower-alkoxy, carboxy, carboxy-lower-alkyl, $H_2NC(O)$, (H,lower-alkyl)NC(O), (lower-alkyl)$_2$NC(O), fluoro-lower-alkyl, lower-alkyl-$SO_2$, lower-alkyl-$SO_2$O, lower-alkyl-$SO_2$—NH, lower-alkyl-$SO_2$—N(lower-alkyl), $H_2NSO_2$, (H,lower-alkyl)$NSO_2$, (lower-alkyl)$_2NSO_2$, cyano, heteroaryl, cycloalkyl, phenyl and phenyloxy. Preferred substituents include halogen, lower-alkyl and lower-alkoxy. Furthermore, aryl groups can preferably be substituted as described in the description and claims below. For example, two substituents at adjacent positions on the aryl group can be bound together to form a ring wherein the two bound substituents together are lower-alkylene, dioxo-lower-alkylene, dioxo-fluoro-lower-alyklene, NH-lower-alkylene, N(lower alkyl)-lower-alkylene, lower-alkylene-NH-lower-alkylene, lower-alkylene-N (lower alkyl)-lower-alkylene, NH—C(O)-lower-alkylene, N(lower alkyl)-C(O)-lower-alkylene, lower-alkylene-NH—C(O)-lower-alkylene, lower-alkylene-N(lower alkyl)-C(O)-lower-alkylene, C(O)—NH-lower-alkylene or C(O)—N(lower-alkyl)-lower-alkylene. Examples of aryl, wherein two substituents at adjacent positions are bound together to form a ring include tetrahydronaphthaline, indane, benzocycloheptene, benzo[1,3]dioxole, 2,3-dihydro-benzo[1,4]dioxine, 3,4-dihydro-2H-benzo[b][1,4]dioxepine, 2,2-difluoro-benzo[1,3]dioxole, 2,3-dihydro-1H-indole, 2,3-dihydro-1H-isoindole, 1,3-dihydro-indol-2-one, 1,3-dihydro-isoindol-2-one, 1,2,3,4-tetrahydroquinoline or 1,2,3,4-tetrahydroisoquinoline, preferably benzo[1,3]dioxole, 2,2-difluoro-benzo[1,3]dioxole and 2,3-dihydro-benzo[1,4]dioxine.

The term "heteroaryl" refers to an aromatic 5 to 6 membered monocyclic ring or 9 to 10 membered bicyclic ring which contains 1, 2 or 3 atoms selected from nitrogen, oxygen and/or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, thiadiazolyl, benzoimidazolyl, indolyl, indazolyl, benzothiazolyl, benzoisothiazolyl, benzoxazolyl, benzoisoxazolyl, quinolinyl and isoquinolinyl. Preferred heteroaryl groups are thiazolyl and pyridinyl. Unless specifically stated otherwise, a heteroaryl group is optionally substituted as described earlier in connection with the term "aryl". Furthermore, heteroaryl groups are preferably substituted as described in the description and claims below. Preferred examples of heteroaryl, wherein two substituents at adjacent positions on the heteroaryl group are bound together to form a ring are those wherein said two bound substituents together are lower-alkylene, dioxo-lower-alkylene or dioxo-fluoro-lower-alyklene, e.g. 6,7-dihydro-5H-[2]pyrindine, 5,6,7,8-tetrahydroisoquinoline, 5,6,7,8-tetrahydroquinoline, [1,3]dioxolo[4,5-c]pyridine, 2,2-difluoro-[1,3]dioxolo[4,5-c]pyridine, 2,3-dihydro-[1,4]dioxino[2,3-c]pyridine, preferably 5,6,7,8-tetrahydroisoquinoline.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salts" refers to such salts. Compounds of formula (I) which comprise an acidic group, such as e.g. a COOH group, can further form salts with bases. Examples of such salts are alkaline, earth-alkaline and ammonium salts such as e.g. Na—, K—, Ca— and trimethylammoniumsalt. The term "pharmaceutically acceptable salts" also refers to such salts. Salts obtained by the addition of an acid are preferred.

The term "pharmaceutically acceptable esters" embraces compounds of formula (I) in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

"Therapeutically effective amount" means an amount that is effective to prevent, alleviate or ameliorate symptoms of disease or prolong the survival of the subject being treated.

In detail, the present invention relates to compounds of formula (I)

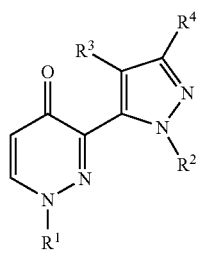

(I)

wherein
R¹ is aryl which is optionally substituted with 1 to 4 substituents independently selected from the group consisting of lower-alkyl, hydroxy-lower-alkyl, lower-alkoxy, fluoro-lower-alkyl, fluoro-lower-alkoxy, lower-alkyl-SO₂, fluoro-lower-alkyl-SO₂, halogen, lower-alkoxy-lower-alkyl, cyano, NO₂, lower-alkyl-SO, morpholinyl, NH₂—SO₂, N(H,lower-alkyl)-SO₂, N(lower-alkyl)₂-SO₂, piperidinyl-SO₂, pyrrolidinyl-SO₂, hydroxy, COOH, COO-lower-alkyl, COO-fluoro-lower-alkyl, lower-alkyl-C(O)O, CO-lower-alkyl, CONH₂, CON(H,lower-alkyl), CON(lower-alkyl)₂, lower-alkyl-CO—NH, lower-alkyl-CO—N(lower-alkyl), NH₂, N(H,lower-alkyl), N(lower-alkyl)₂, NH₂-lower-alkyl, N(H,lower-alkyl)-lower-alkyl, N(lower-alkyl)₂-lower-alkyl, cycloalkyl, phenyloxy and phenyl,
or wherein two substituents at adjacent positions on the aryl group are bound together to form a ring and said two bound substituents together are lower-alkylene, dioxo-lower-alkylene, dioxo-fluoro-lower-alyklene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)-C(O)-lower-alkylene, lower-alkylene-NH—C(O)-lower-alkylene, lower-alkylene-N(lower alkyl)-C(O)-lower-alkylene, C(O)—NH-lower-alkylene or C(O)—N(lower-alkyl)-lower-alkylene;

R² is aryl or heteroaryl, which aryl or heteroaryl is optionally substituted with 1 to 4 substituents independently selected from the group consisting of halogen, cyano, lower-alkyl, lower-alkoxy, fluoro-lower-alkyl, fluoro-lower-alkoxy, lower-alkinyl, lower-alkyl-SO₂, fluoro-lower-alkyl-SO₂, tri(lower-alkyl)silyl-loweralkinyl, COOH, CONH₂, NH₂—SO₂, COO-lower-alkyl, 6-oxo-1,4,5,6-tetrahydropyridazinyl, lower-alkoxy-lower-alkyl, CON(H,lower-alkyl), CON(lower-alkyl)₂, N(H,lower-alkyl)-SO₂, N(lower-alkyl)₂-SO₂, lower-alkenyl, hydroxy, NO₂, morpholinyl, tetrahydropyridazinyl, piperidinyl, piperazinyl, (N-lower-alkyl)-piperazinyl, pyrrolidinyl, lower-alkyl-C(O)O, lower-alkyl-CO—NH, lower-alkyl-CO—N(lower-alkyl), imidazolyl, pyridinyl, CO-lower-alkyl, NH₂, N(H, lower-alkyl), N(lower-alkyl)₂, NH₂-lower-alkyl, N(H, lower-alkyl)-lower-alkyl, N(lower-alkyl)₂-lower-alkyl, cycloalkyl, phenyloxy and phenyl which is optionally substituted with 1 to 4 substituents independently selected from halogen, lower-alkoxy, lower-alkyl, fluoro-lower-alkyl, fluoro-lower-alkoxy, hydroxy and cyano,
or wherein two substituents at adjacent positions on the aryl or heteroaryl group are bound together to form a ring and said two bound substituents together are lower-alkylene, dioxo-lower-alkylene, dioxo-fluoro-lower-alyklene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)-C(O)-lower-alkylene, lower-alkylene-NH—C(O)-lower-alkylene, lower-alkylene-N(lower alkyl)-C(O)-lower-alkylene, C(O)—NH-lower-alkylene or C(O)—N(lower-alkyl)-lower-alkylene;

R³ is hydrogen, lower-alkyl, fluoro-lower-alkyl, lower-alkoxy, fluoro-lower-alkoxy, halogen, hydroxy or phenyl; and R⁴ is hydrogen, lower-alkyl, fluoro-lower-alkyl, lower-alkoxy, fluoro-lower-alkoxy, halogen, hydroxy or phenyl;
and pharmaceutically acceptable salts and esters thereof.

Compounds of formula (I) are individually preferred; physiologically acceptable salts thereof are individually preferred; and pharmaceutically acceptable esters thereof are individually preferred, with the compounds of formula (I) being particularly preferred.

The compounds of formula (I) can have one or more asymmetric C atoms and can therefore exist as an enantiomeric mixture, mixture of stereoisomers or as optically pure compounds.

Preferred compounds of formula (I) as described above are those, wherein
R¹ is aryl which is optionally substituted with 1 to 4 substituents independently selected from the group consisting of lower-alkyl, lower-alkoxy, fluoro-lower-alkyl, fluoro-lower-alkoxy, lower-alkyl-SO₂, halogen, lower-alkoxy-lower-alkyl, cyano, NO₂, lower-alkyl-SO, morpholinyl, NH₂—SO₂, N(H,lower-alkyl)-SO₂, N(lower-alkyl)₂-SO₂, hydroxy, COOH, COO-lower-alkyl, lower-alkyl-C(O)O, CO-lower-alkyl, CONH₂, CON(H,lower-alkyl), CON(lower-alkyl)₂, lower-alkyl-CO—NH, lower-alkyl-CO—N(lower-alkyl), NH₂, N(H,lower-alkyl), N(lower-alkyl)₂, NH$_2$-lower-alkyl, N(H,lower-alkyl)-lower-alkyl, N(lower-alkyl)$_2$-lower-alkyl, cycloalkyl, phenyloxy and phenyl, or wherein two substituents at adjacent positions on the aryl group are bound together to form a ring and said two bound substituents together are lower-alkylene, dioxo-lower-alkylene, dioxo-fluoro-lower-alyklene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)-C(O)-lower-alkylene, lower-alkylene-NH—C(O)-lower-alkylene, lower-alkylene-N(lower alkyl)-C(O)-lower-alkylene, C(O)—NH-lower-alkylene or C(O)—N(lower-alkyl)-lower-alkylene;

and

R$^2$ is aryl or heteroaryl, which aryl or heteroaryl are optionally substituted with 1 to 4 substituents independently selected from the group consisting of halogen, cyano, lower-alkyl, lower-alkoxy, fluoro-lower-alkyl, lower-alkinyl, lower-alkyl-SO$_2$, tri(lower-alkyl)silyl-loweralkinyl, COOH, CONH$_2$, NH$_2$—SO$_2$, COO-lower-alkyl, 6-oxo-1,4,5,6-tetrahydropyridazinyl, lower-alkoxy-lower-alkyl, CON(H,lower-alkyl), CON(lower-alkyl)$_2$, N(H,lower-alkyl)-SO$_2$, N(lower-alkyl)$_2$-SO$_2$, lower-alkenyl, hydroxy, NO$_2$, morpholinyl, tetrahydropyridazinyl, piperidinyl, piperazinyl, (N-lower-alkyl)-piperazinyl, pyrrolidinyl, lower-alkyl-C(O)O, lower-alkyl-CO—NH, lower-alkyl-CO—N(lower-alkyl), imidazolyl, pyridinyl, CO-lower-alkyl, NH$_2$, N(H,lower-alkyl), N(lower-alkyl)$_2$, NH$_2$-lower-alkyl, N(H,lower-alkyl)-lower-alkyl, N(lower-alkyl)-$_2$-lower-alkyl, cycloalkyl, phenyloxy and phenyl which is optionally substituted with 1 to 4 substituents independently selected from halogen, lower-alkoxy, lower-alkyl, fluoro-lower-alkyl, fluoro-lower-alkoxy, hydroxy and cyano, or wherein two substituents at adjacent positions on the aryl or heteroaryl group are bound together to form a ring and said two bound substituents together are lower-alkylene, dioxo-lower-alkylene, dioxo-fluoro-lower-alyklene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)-C(O)-lower-alkylene, lower-alkylene-NH—C(O)-lower-alkylene, lower-alkylene-N(lower alkyl)-C(O)-lower-alkylene, C(O)—NH-lower-alkylene or C(O)—N(lower-alkyl)-lower-alkylene.

A preferred embodiment of the present invention relates to compounds of formula (I) as described above, wherein R$^1$ is phenyl which is optionally substituted with 1 to 3 substituents independently selected from the group consisting of lower-alkyl, lower-alkoxy, fluoro-lower-alkyl, fluoro-lower-alkoxy and lower-alkyl-SO$_2$, or wherein two substituents at adjacent positions on the phenyl group are bound together to form a ring and said two bound substituents together are dioxo-fluoro-lower-alyklene. Preferably, R$^1$ is phenyl which is optionally substituted with fluoro-lower-alkyl, fluoro-lower-alkoxy or lower-alkyl-SO$_2$. More preferably, R$^1$ is phenyl, 3-trifluoromethyl-phenyl, 3-trifluoromethoxy-phenyl, 3-methylsulfonyl-phenyl, 4-trifluoromethoxy-phenyl or 4-difluoromethyl-phenyl.

Further preferred compounds are those, wherein R$^1$ is phenyl which is optionally substituted with 1 to 3 substituents independently selected from the group consisting of hydroxy-lower-alkyl, lower-alkoxy, fluoro-lower-alkyl, fluoro-lower-alkoxy, lower-alkyl-SO$_2$, fluoro-lower-alkyl-SO$_2$, halogen, cyano, N(H,lower-alkyl)-SO$_2$, N(lower-alkyl)$_2$-SO$_2$, piperidinyl-SO$_2$, pyrrolidinyl-SO$_2$, hydroxy, COO-lower-alkyl, COO-fluoro-lower-alkyl, CO-lower-alkyl, CON(H,lower-alkyl), CON(lower-alkyl)$_2$, lower-alkyl-CO—NH, lower-alkyl-CO—N(lower-alkyl) and N(lower-alkyl)$_2$-lower-alkyl, or wherein two substituents at adjacent positions on the aryl group are bound together to form a ring and said two bound substituents together are dioxo-lower-alkylene or dioxo-fluoro-lower-alyklene. Preferably, R$^1$ is phenyl which is optionally substituted with hydroxy-lower-alkyl, fluoro-lower-alkoxy, lower-alkyl-SO$_2$, fluoro-lower-alkyl-SO$_2$, cyano, hydroxy, COO-fluoro-lower-alkyl, CON(H,lower-alkyl), lower-alkyl-CO—NH or lower-alkyl-CO—N(lower-alkyl). More preferably, R$^1$ is 3-trifluoromethoxy-phenyl, 3-methylsulfonyl-phenyl, 3-difluoromethoxy-phenyl, 4-trifluoromethoxy-phenyl, 3-hydroxy-phenyl, 3-cyano-phenyl, 4-trifluoromethylsulfonyl-phenyl, 4-(2,2,2-trifluoroethoxy)-phenyl, 3-trifluoromethylsulfonyl-phenyl, 3-acetamide-phenyl, 3-(methylamide)-phenyl, 3-(N-methyl-acetamide)-phenyl, 3-(2-fluoro-ethoxycarbonyl)-phenyl or 3-(1-hydroxyethyl)-phenyl.

Other preferred compounds of the present invention are those, wherein R$^2$ is aryl selected from the group consisting of phenyl and naphthyl or is heteroaryl selected from the group consisting of pyridinyl and thiazolyl, which aryl or heteroaryl group is optionally substituted with 1 to 3 substituents independently selected from the group consisting of halogen, cyano, lower-alkyl, lower-alkoxy, fluoro-lower-alkyl, lower-alkinyl, lower-alkyl-SO$_2$, tri(lower-alkyl)silyl-loweralkinyl, COOH, CONH$_2$, NH$_2$—SO$_2$, COO-lower-alkyl, 6-oxo-1,4,5,6-tetrahydropyridazinyl, and phenyl which is optionally substituted with 1 to 3 substituents independently selected from halogen and lower-alkoxy, or wherein two substituents at adjacent positions on the aryl or heteroaryl group are bound together to form a ring and said two bound substituents together are lower-alkylene or dioxo-lower-alkylene. Preferably, R$^2$ is aryl selected from the group consisting of phenyl and naphthyl or is pyridinyl, which aryl or pyridinyl group is optionally substituted with 1 to 2 substituents independently selected from the group consisting of halogen, cyano, lower-alkyl, and lower-alkinyl, or wherein two substituents at adjacent positions on the aryl group are bound together to form a ring and said two bound substituents together are dioxo-lower-alkylene. More preferably, R$^2$ is phenyl, 2,5-difluoro-phenyl, 3-cyano-phenyl, 3-ethinyl-phenyl, 3-chloro-phenyl, 4-fluoro-phenyl, naphthyl, 3-fluoro-phenyl, pyridin-4-yl, 3-methyl-pyridin-4-yl or 2,3-dihydro-benzo[1,4]dioxin-6-yl.

Other preferred compounds of formula (I) as described above are those, wherein R$^2$ is aryl selected from the group consisting of phenyl and naphthyl or is heteroaryl selected from the group consisting of quinolinyl, thiazolyl, pyridinyl, isoquinolinyl and isothiazolyl, which aryl or heteroaryl group is optionally substituted with 1 to 3 substituents independently selected from the group consisting of halogen, cyano, lower-alkyl, lower-alkoxy, fluoro-lower-alkyl, fluoro-lower-alkoxy, lower-alkyl-SO$_2$, fluoro-lower-alkyl-SO$_2$, NH$_2$—SO$_2$, N(lower-alkyl)$_2$-SO$_2$, hydroxy and lower-alkyl-CO—NH, or wherein two substituents at adjacent positions on the aryl or heteroaryl group are bound together to form a ring and said two bound substituents together are dioxo-lower-alkylene or dioxo-fluoro-lower-alyklene. Preferably, R$^2$ is aryl selected from the group consisting of phenyl and naphthyl or is heteroaryl selected from the group consisting of quinolinyl and pyridinyl, which aryl or heteroaryl group is optionally substituted with 1 to 2 substituents independently selected from the group consisting of halogen, cyano and lower-alkyl, or wherein two substituents at adjacent positions on the aryl or heteroaryl group are bound together to form a ring and said two bound substituents together are dioxo-lower-alkylene. More preferably, R$^2$ is 2,4-difluoro-phenyl, 3-cyano-phenyl, 2,5-difluoro-phenyl, phenyl, 2-fluoro-phenyl, 3-chloro-phenyl, naphthyl, 2,3-dihydro-benzo[1,4]dioxin-6-yl, 6-fluoro-quinolin-4-yl, 2-methyl-pyridin-4-yl or quinolin-4-yl.

Another preferred embodiment of the present invention refers to compounds as defined above, wherein $R^3$ is hydrogen or lower-alkyl, particularly wherein $R^3$ is hydrogen. Other preferred compounds of the present invention are those, wherein $R^4$ is hydrogen.

In particular, preferred compounds are the compounds of formula (I) described in the examples as individual compounds as well as pharmaceutically acceptable salts as well as pharmaceutically acceptable esters thereof. Furthermore, the substituents as found in the specific examples described below, individually constitute separate preferred embodiments of the present invention.

Preferred compounds of formula (I) are those selected from the group consisting of:

3-(2-Benzo[1,3]dioxol-5-yl-2H-pyrazol-3-yl)-1-phenyl-1H-pyridazin-4-one,
1-(4-Methoxy-phenyl)-3-(2-phenyl-2H-pyrazol-3-yl)-1H-pyridazin-4-one,
3-[2-(2-Methoxy-phenyl)-2H-pyrazol-3-yl]-1-phenyl-1H-pyridazin-4-one,
1-Phenyl-3-(2-o-tolyl-2H-pyrazol-3-yl)-1H-pyridazin-4-one,
1-Phenyl-3-[2-(3-trifluoromethyl-phenyl)-2H-pyrazol-3-yl]-1H-pyridazin-4-one,
3-[2-(2,5-Difluoro-phenyl)-2H-pyrazol-3-yl]-1-(3-trifluoromethyl-phenyl)-1H-pyridazin-4-one,
1-(3-Trifluoromethyl-phenyl)-3-[2-(2-trifluoromethyl-phenyl)-2H-pyrazol-3-yl]-1H-pyridazin-4-one,
3-[2-(2,5-Dimethyl-phenyl)-2H-pyrazol-3-yl]-1-(3-trifluoromethyl-phenyl)-1H-pyridazin-4-one,
3-[2-(2,5-Difluoro-phenyl)-2H-pyrazol-3-yl]-1-phenyl-1H-pyridazin-4-one,
1-Phenyl-3-[2-(2-trifluoromethyl-phenyl)-2H-pyrazol-3-yl]-1H-pyridazin-4-one,
3-[2-(2,5-Dimethyl-phenyl)-2H-pyrazol-3-yl]-1-phenyl-1H-pyridazin-4-one,
3-[2-(2,5-Dichloro-phenyl)-2H-pyrazol-3-yl]-1-phenyl-1H-pyridazin-4-one,
1-Phenyl-3-(2-pyridin-2-yl-2H-pyrazol-3-yl)-1H-pyridazin-4-one,
3-{5-[4-Oxo-1-(3-trifluoromethyl-phenyl)-1,4-dihydro-pyridazin-3-yl]-pyrazol-1-yl}-benzonitrile,
1-Phenyl-3-(2-pyridin-4-yl-2H-pyrazol-3-yl)-1H-pyridazin-4-one,
3-[5-(4-Oxo-1-phenyl-1,4-dihydro-pyridazin-3-yl)-pyrazol-1-yl]-benzonitrile,
1-(3-Ethyl-phenyl)-3-(2-phenyl-2H-pyrazol-3-yl)-1H-pyridazin-4-one,
1-(3-Methoxy-phenyl)-3-(2-phenyl-2H-pyrazol-3-yl)-1H-pyridazin-4-one,
1-Phenyl-3-(2-phenyl-2H-pyrazol-3-yl)-1H-pyridazin-4-one,
3-[2-(4-Methanesulfonyl-phenyl)-2H-pyrazol-3-yl]-1-phenyl-1H-pyridazin-4-one,
1-(3-Ethyl-phenyl)-3-[2-(4-methanesulfonyl-phenyl)-2H-pyrazol-3-yl]-1H-pyridazin-4-one,
1-(3-Ethyl-phenyl)-3-(2-pyridin-4-yl-2H-pyrazol-3-yl)-1H-pyridazin-4-one,
3-[2-(3-Bromo-phenyl)-2H-pyrazol-3-yl]-1-phenyl-1H-pyridazin-4-one,
3-[2-(2-Methyl-pyridin-4-yl)-2H-pyrazol-3-yl]-1-phenyl-1H-pyridazin-4-one,
3-[2-(2-Chloro-pyridin-4-yl)-2H-pyrazol-3-yl]-1-phenyl-1H-pyridazin-4-one,
3-(2-Phenyl-2H-pyrazol-3-yl)-1-(3-trifluoromethoxy-phenyl)-1H-pyridazin-4-one,
3-(2-Pyridin-4-yl-2H-pyrazol-3-yl)-1-(3-trifluoromethoxy-phenyl)-1H-pyridazin-4-one,
3-[2-(2-Fluoro-phenyl)-2H-pyrazol-3-yl]-1-(3-trifluoromethoxy-phenyl)-1H-pyridazin-4-one,
3-{5-[4-Oxo-1-(3-trifluoromethoxy-phenyl)-1,4-dihydro-pyridazin-3-yl]-pyrazol-1-yl}-benzonitrile,
1-(3-Methanesulfonyl-phenyl)-3-(2-phenyl-2H-pyrazol-3-yl)-1H-pyridazin-4-one,
1-Phenyl-3-[2-(3-trimethylsilanylethynyl-phenyl)-2H-pyrazol-3-yl]-1H-pyridazin-4-one,
3-[2-(3-Ethynyl-phenyl)-2H-pyrazol-3-yl]-1-phenyl-1H-pyridazin-4-one,
3-(2-Phenyl-2H-pyrazol-3-yl)-1-(4-trifluoromethoxy-phenyl)-1H-pyridazin-4-one,
3-[2-(2-Fluoro-phenyl)-2H-pyrazol-3-yl]-1-(4-trifluoromethoxy-phenyl)-1H-pyridazin-4-one,
3-(2-Pyridin-4-yl-2H-pyrazol-3-yl)-1-(4-trifluoromethoxy-phenyl)-1H-pyridazin-4-one,
3-{5-[4-Oxo-1-(4-trifluoromethoxy-phenyl)-1,4-dihydro-pyridazin-3-yl]-pyrazol-1-yl}-benzonitrile,
3-[2-(2-Fluoro-phenyl)-2H-pyrazol-3-yl]-1-(3-trifluoromethyl-phenyl)-1H-pyridazin-4-one,
3-[2-(4-Chloro-phenyl)-2H-pyrazol-3-yl]-1-phenyl-1H-pyridazin-4-one,
1-Phenyl-3-(2-p-tolyl-2H-pyrazol-3-yl)-1H-pyridazin-4-one,
3-(2-Phenyl-2H-pyrazol-3-yl)-1-(3-trifluoromethyl-phenyl)-1H-pyridazin-4-one,
3-[2-(4-Methoxy-phenyl)-2H-pyrazol-3-yl]-1-(3-trifluoromethyl-phenyl)-1H-pyridazin-4-one,
3-[2-(3-Chloro-phenyl)-2H-pyrazol-3-yl]-1-(3-trifluoromethyl-phenyl)-1H-pyridazin-4-one,
3-{5-[4-Oxo-1-(3-trifluoromethoxy-phenyl)-1,4-dihydro-pyridazin-3-yl]-pyrazol-1-yl}-benzamide,
3-(2-p-Tolyl-2H-pyrazol-3-yl)-1-(3-trifluoromethoxy-phenyl)-1H-pyridazin-4-one,
4-{5-[4-Oxo-1-(3-trifluoromethoxy-phenyl)-1,4-dihydro-pyridazin-3-yl]-pyrazol-1-yl}-benzoic acid,
4-{5-[4-Oxo-1-(3-trifluoromethoxy-phenyl)-1,4-dihydro-pyridazin-3-yl]-pyrazol-1-yl}-benzenesulfonamide,
3-[2-(4-Chloro-phenyl)-2H-pyrazol-3-yl]-1-(3-trifluoromethoxy-phenyl)-1H-pyridazin-4-one,
3-[2-(3-Chloro-phenyl)-2H-pyrazol-3-yl]-1-(3-trifluoromethoxy-phenyl)-1H-pyridazin-4-one,
3-[2-(4-Fluoro-phenyl)-2H-pyrazol-3-yl]-1-(3-trifluoromethoxy-phenyl)-1H-pyridazin-4-one,
3-[2-(2,3-Dimethyl-phenyl)-2H-pyrazol-3-yl]-1-(3-trifluoromethoxy-phenyl)-1H-pyridazin-4-one,
3-[2-(3-Chloro-2-methyl-phenyl)-2H-pyrazol-3-yl]-1-(3-trifluoromethoxy-phenyl)-1H-pyridazin-4-one,
3-[2-(2-Bromo-4-fluoro-phenyl)-2H-pyrazol-3-yl]-1-(3-trifluoromethoxy-phenyl)-1H-pyridazin-4-one,
3-[2-(3-Fluoro-2-methyl-phenyl)-2H-pyrazol-3-yl]-1-(3-trifluoromethoxy-phenyl)-1H-pyridazin-4-one,
3-[2-(3-Fluoro-4-methyl-phenyl)-2H-pyrazol-3-yl]-1-(3-trifluoromethoxy-phenyl)-1H-pyridazin-4-one,
3-{5-[4-Oxo-1-(3-trifluoromethoxy-phenyl)-1,4-dihydro-pyridazin-3-yl]-pyrazol-1-yl}-benzoic acid methyl ester,
3-[2-(5,6,7,8-Tetrahydro-isoquinolin-1-yl)-2H-pyrazol-3-yl]-1-(3-trifluoromethoxy-phenyl)-1H-pyridazin-4-one,
2-{5-[4-Oxo-1-(3-trifluoromethoxy-phenyl)-1,4-dihydro-pyridazin-3-yl]-pyrazol-1-yl}-isonicotinic acid ethyl ester,
3-(2-Pyridin-2-yl-2H-pyrazol-3-yl)-1-(3-trifluoromethoxy-phenyl)-1H-pyridazin-4-one, 3-{5-[1-(3-Methanesulfonyl-phenyl)-4-oxo-1,4-dihydro-pyridazin-3-yl]-pyrazol-1-yl}-benzamide,
1-(3-Methanesulfonyl-phenyl)-3-(2-p-tolyl-2H-pyrazol-3-yl)-1H-pyridazin-4-one,
4-{5-[1-(3-Methanesulfonyl-phenyl)-4-oxo-1,4-dihydro-pyridazin-3-yl]-pyrazol-1-yl}-benzoic acid,
4-{5-[1-(3-Methanesulfonyl-phenyl)-4-oxo-1,4-dihydro-pyridazin-3-yl]-pyrazol-1-yl}-benzenesulfonamide,
3-[2-(4-Chloro-phenyl)-2H-pyrazol-3-yl]-1-(3-methanesulfonyl-phenyl)-1H-pyridazin-4-one,
3-[2-(3-Chloro-phenyl)-2H-pyrazol-3-yl]-1-(3-methanesulfonyl-phenyl)-1H-pyridazin-4-one,
2-{5-[1-(3-Methanesulfonyl-phenyl)-4-oxo-1,4-dihydro-pyridazin-3-yl]-pyrazol-1-yl}-benzoic acid,
3-[2-(4-Fluoro-phenyl)-2H-pyrazol-3-yl]-1-(3-methanesulfonyl-phenyl)-1H-pyridazin-4-one,
3-[2-(2,3-Dimethyl-phenyl)-2H-pyrazol-3-yl]-1-(3-methanesulfonyl-phenyl)-1H-pyridazin-4-one,
3-[2-(3-Chloro-2-methyl-phenyl)-2H-pyrazol-3-yl]-1-(3-methanesulfonyl-phenyl)-1H-pyridazin-4-one,
3-[2-(3-Fluoro-2-methyl-phenyl)-2H-pyrazol-3-yl]-1-(3-methanesulfonyl-phenyl)-1H-pyridazin-4-one,
3-[2-(3-Fluoro-4-methyl-phenyl)-2H-pyrazol-3-yl]-1-(3-methanesulfonyl-phenyl)-1H-pyridazin-4-one,
3-{5-[1-(3-Methanesulfonyl-phenyl)-4-oxo-1,4-dihydro-pyridazin-3-yl]-pyrazol-1-yl}-benzoic acid methyl ester,
1-(3-Methanesulfonyl-phenyl)-3-[2-(5,6,7,8-tetrahydro-isoquinolin-1-yl)-2H-pyrazol-3-yl]-1H-pyridazin-4-one,
2-{5-[1-(3-Methanesulfonyl-phenyl)-4-oxo-1,4-dihydro-pyridazin-3-yl]-pyrazol-1-yl}-4,6-dimethyl-nicotinonitrile,
2-{5-[1-(3-Methanesulfonyl-phenyl)-4-oxo-1,4-dihydro-pyridazin-3-yl]-pyrazol-1-yl}-isonicotinic acid ethyl ester,
1-(3-Methanesulfonyl-phenyl)-3-(2-pyridin-2-yl-2H-pyrazol-3-yl)-1H-pyridazin-4-one,
4-{5-[4-Oxo-1-(3-trifluoromethoxy-phenyl)-1,4-dihydro-pyridazin-3-yl]-pyrazol-1-yl}-benzonitrile,
3-[2-(2,4-Difluoro-phenyl)-2H-pyrazol-3-yl]-1-(3-trifluoromethoxy-phenyl)-1H-pyridazin-4-one,
3-{2-[4-(6-Oxo-1,4,5,6-tetrahydro-pyridazin-3-yl)-phenyl]-2H-pyrazol-3-yl}-1-(3-trifluoromethoxy-phenyl)-1H-pyridazin-4-one,
3-[2-(2,3-Dihydro-benzo[1,4]dioxin-6-yl)-2H-pyrazol-3-yl]-1-(3-trifluoromethoxy-phenyl)-1H-pyridazin-4-one,
3-(2-Naphthalen-1-yl-2H-pyrazol-3-yl)-1-(3-trifluoromethoxy-phenyl)-1H-pyridazin-4-one,
3-[2-(3-Fluoro-phenyl)-2H-pyrazol-3-yl]-1-(3-trifluoromethoxy-phenyl)-1H-pyridazin-4-one,
3-[2-(2,5-Difluoro-phenyl)-2H-pyrazol-3-yl]-1-(3-trifluoromethoxy-phenyl)-1H-pyridazin-4-one,
3-[2-(4-Isopropyl-phenyl)-2H-pyrazol-3-yl]-1-(3-trifluoromethoxy-phenyl)-1H-pyridazin-4-one,
3-[2-(2,3-Dihydro-benzo[1,4]dioxin-6-yl)-2H-pyrazol-3-yl]-1-(3-methanesulfonyl-phenyl)-1H-pyridazin-4-one,
1-(3-Methanesulfonyl-phenyl)-3-(2-naphthalen-1-yl-2H-pyrazol-3-yl)-1H-pyridazin-4-one,
3-[2-(3-Fluoro-phenyl)-2H-pyrazol-3-yl]-1-(3-methanesulfonyl-phenyl)-1H-pyridazin-4-one,
3-[2-(2,5-Difluoro-phenyl)-2H-pyrazol-3-yl]-1-(3-methanesulfonyl-phenyl)-1H-pyridazin-4-one,
3-[2-(4-Isopropyl-phenyl)-2H-pyrazol-3-yl]-1-(3-methanesulfonyl-phenyl)-1H-pyridazin-4-one,
3-(4-Ethyl-2-phenyl-2H-pyrazol-3-yl)-1-(3-methanesulfonyl-phenyl)-1H-pyridazin-4-one,
1-(3-Methanesulfonyl-phenyl)-3-[2-(2-methyl-pyridin-4-yl)-2H-pyrazol-3-yl]-1H-pyridazin-4-one,
1-(3-Difluoromethoxy-phenyl)-3-(2-pyridin-2-yl-2H-pyrazol-3-yl)-1H-pyridazin-4-one,
3-(2-Benzo[1,3]dioxol-5-yl-2H-pyrazol-3-yl)-1-(3-methanesulfonyl-phenyl)-1H-pyridazin-4-one,
3-(2-Benzo[1,3]dioxol-5-yl-2H-pyrazol-3-yl)-1-(3-difluoromethoxy-phenyl)-1H-pyridazin-4-one,
3-{5-[1-(3-Methanesulfonyl-phenyl)-4-oxo-1,4-dihydro-pyridazin-3-yl]-pyrazol-1-yl}-benzonitrile,
3-{2-[4-(2-Fluoro-4-methoxy-phenyl)-thiazol-2-yl]-2H-pyrazol-3-yl}-1-(3-methanesulfonyl-phenyl)-1H-pyridazin-4-one,
1-(3-Methanesulfonyl-phenyl)-3-{2-[4-(2-methoxy-phenyl)-thiazol-2-yl]-2H-pyrazol-3-yl}-1H-pyridazin-4-one,
1-(3-Difluoromethoxy-phenyl)-3-[2-(2,3-dihydro-benzo[1,4]dioxin-6-yl)-2H-pyrazol-3-yl]-1H-pyridazin-4-one,
1-(3-Difluoromethoxy-phenyl)-3-[2-(3-fluoro-phenyl)-2H-pyrazol-3-yl]-1H-pyridazin-4-one,
1-(4-Difluoromethoxy-phenyl)-3-[2-(2,3-dihydro-benzo[1,4]dioxin-6-yl)-2H-pyrazol-3-yl]-1H-pyridazin-4-one,
1-(4-Difluoromethoxy-phenyl)-3-[2-(3-fluoro-phenyl)-2H-pyrazol-3-yl]-1H-pyridazin-4-one, and
1-(2,2-Difluoro-benzo[1,3]dioxol-5-yl)-3-[2-(2,3-dihydro-benzo[1,4]dioxin-6-yl)-2H-pyrazol-3-yl]-1H-pyridazin-4-one
and pharmaceutically acceptable salts and esters thereof.

Particularly preferred compounds of formula (I) are those selected from the group consisting of:
3-{5-[4-Oxo-1-(3-trifluoromethyl-phenyl)-1,4-dihydro-pyridazin-3-yl]-pyrazol-1-yl}-benzonitrile,
1-Phenyl-3-(2-pyridin-4-yl-2H-pyrazol-3-yl)-1H-pyridazin-4-one,
3-(2-Phenyl-2H-pyrazol-3-yl)-1-(3-trifluoromethoxy-phenyl)-1H-pyridazin-4-one,
3-(2-Pyridin-4-yl-2H-pyrazol-3-yl)-1-(3-trifluoromethoxy-phenyl)-1H-pyridazin-4-one,
1-(3-Methanesulfonyl-phenyl)-3-(2-phenyl-2H-pyrazol-3-yl)-1H-pyridazin-4-one,
3-[2-(3-Ethynyl-phenyl)-2H-pyrazol-3-yl]-1-phenyl-1H-pyridazin-4-one,
3-(2-Pyridin-4-yl-2H-pyrazol-3-yl)-1-(4-trifluoromethoxy-phenyl)-1H-pyridazin-4-one,
3-{5-[4-Oxo-1-(4-trifluoromethoxy-phenyl)-1,4-dihydro-pyridazin-3-yl]-pyrazol-1-yl}-benzonitrile,
3-[2-(4-Fluoro-phenyl)-2H-pyrazol-3-yl]-1-(3-trifluoromethoxy-phenyl)-1H-pyridazin-4-one,
3-[2-(3-Chloro-phenyl)-2H-pyrazol-3-yl]-1-(3-methanesulfonyl-phenyl)-1H-pyridazin-4-one,
3-[2-(2,3-Dihydro-benzo[1,4]dioxin-6-yl)-2H-pyrazol-3-yl]-1-(3-trifluoromethoxy-phenyl)-1H-pyridazin-4-one,
3-(2-Naphthalen-1-yl-2H-pyrazol-3-yl)-1-(3-trifluoromethoxy-phenyl)-1H-pyridazin-4-one,
1-(3-Methanesulfonyl-phenyl)-3-(2-naphthalen-1-yl-2H-pyrazol-3-yl)-1H-pyridazin-4-one,
3-[2-(3-Fluoro-phenyl)-2H-pyrazol-3-yl]-1-(3-methanesulfonyl-phenyl)-1H-pyridazin-4-one,
3-[2-(2,5-Difluoro-phenyl)-2H-pyrazol-3-yl]-1-(3-methanesulfonyl-phenyl)-1H-pyridazin-4-one,
1-(3-Methanesulfonyl-phenyl)-3-[2-(2-methyl-pyridin-4-yl)-2H-pyrazol-3-yl]-1H-pyridazin-4-one,
3-{5-[1-(3-Methanesulfonyl-phenyl)-4-oxo-1,4-dihydro-pyridazin-3-yl]-pyrazol-1-yl}-benzonitrile, and
1-(4-Difluoromethoxy-phenyl)-3-[2-(3-fluoro-phenyl)-2H-pyrazol-3-yl]-1H-pyridazin-4-one,
and pharmaceutically acceptable salts and esters thereof.

Other preferred compounds of formula (I) as described above are those selected from the group consisting of
3-{3-[2-(3-Fluoro-phenyl)-2H-pyrazol-3-yl]-4-oxo-4H-pyridazin-1-yl}-N,N-dimethyl-benzenesulfonamide, 1-(2,2-Difluoro-benzo[1,3]dioxol-5-yl)-3-[2-(3-fluoro-phenyl)-2H-pyrazol-3-yl]-1H-pyridazin-4-one,
3-[2-(3,4-Difluoro-phenyl)-2H-pyrazol-3-yl]-1-(3-methanesulfonyl-phenyl)-1H-pyridazin-4-one,
3-[2-(2,4-Difluoro-phenyl)-2H-pyrazol-3-yl]-1-(3-methanesulfonyl-phenyl)-1H-pyridazin-4-one,
3-(2-Benzo[1,3]dioxol-4-yl-2H-pyrazol-3-yl)-1-(3-methanesulfonyl-phenyl)-1H-pyridazin-4-one,
3-[3-(2-Benzo[1,3]dioxol-5-yl-2H-pyrazol-3-yl)-4-oxo-4H-pyridazin-1-yl]-N,N-dimethyl-benzenesulfonamide,
3-{3-[2-(3-Cyano-phenyl)-2H-pyrazol-3-yl]-4-oxo-4H-pyridazin-1-yl}-N,N-dimethyl-benzenesulfonamide,
3-(2-Benzo[1,3]dioxol-5-yl-2H-pyrazol-3-yl)-1-(3-fluoro-phenyl)-1H-pyridazin-4-one,
1-(3-Fluoro-phenyl)-3-[2-(3-fluoro-phenyl)-2H-pyrazol-3-yl]-1H-pyridazin-4-one,
3-{5-[1-(3-Fluoro-phenyl)-4-oxo-1,4-dihydro-pyridazin-3-yl]-pyrazol-1-yl}-benzonitrile,
1-Benzo[1,3]dioxol-4-yl-3-(2-benzo[1,3]dioxol-5-yl-2H-pyrazol-3-yl)-1H-pyridazin-4-one,
1-Benzo[1,3]dioxol-4-yl-3-[2-(3-fluoro-phenyl)-2H-pyrazol-3-yl]-1H-pyridazin-4-one,
3-[5-(1-Benzo[1,3]dioxol-4-yl-4-oxo-1,4-dihydro-pyridazin-3-yl)-pyrazol-1-yl]-benzonitrile,
3-[2-(6-Fluoro-quinolin-4-yl)-2H-pyrazol-3-yl]-1-(3-methanesulfonyl-phenyl)-1H-pyridazin-4-one,
1-(3-Difluoromethoxy-phenyl)-3-[2-(2,5-difluoro-phenyl)-2H-pyrazol-3-yl]-1H-pyridazin-4-one,
1-(2,2-Difluoro-benzo[1,3]dioxol-5-yl)-3-[2-(2,5-difluoro-phenyl)-2H-pyrazol-3-yl]-1H-pyridazin-4-one,
3-{3-[2-(2,5-Difluoro-phenyl)-2H-pyrazol-3-yl]-4-oxo-4H-pyridazin-1-yl}-N,N-dimethyl-benzenesulfonamide,
3-{5-[1-(2,2-Difluoro-benzo[1,3]dioxol-5-yl)-4-oxo-1,4-dihydro-pyridazin-3-yl]-pyrazol-1-yl}-benzonitrile,
3-[2-(2,2-Difluoro-benzo[1,3]dioxol-4-yl)-2H-pyrazol-3-yl]-1-(3-methanesulfonyl-phenyl)-1H-pyridazin-4-one,
1-(3-Methanesulfonyl-phenyl)-3-(2-thiazol-2-yl-2H-pyrazol-3-yl)-1H-pyridazin-4-one,
1-(3-Methanesulfonyl-phenyl)-3-[2-(3-trifluoromethoxy-phenyl)-2H-pyrazol-3-yl]-1H-pyridazin-4-one,
3-[2-(2,3-Dihydro-benzo[1,4]dioxin-5-yl)-2H-pyrazol-3-yl]-1-(3-methanesulfonyl-phenyl)-1H-pyridazin-4-one,
3-[2-(2-Methyl-pyridin-4-yl)-2H-pyrazol-3-yl]-1-(3-trifluoromethoxy-phenyl)-1H-pyridazin-4-one,
3-(4-Ethyl-2-phenyl-2H-pyrazol-3-yl)-1-(3-trifluoromethoxy-phenyl)-1H-pyridazin-4-one,
3-[2-(3-Methanesulfonyl-phenyl)-2H-pyrazol-3-yl]-1-(3-trifluoromethoxy-phenyl)-1H-pyridazin-4-one,
1-(2,2-Difluoro-benzo[1,3]dioxol-4-yl)-3-[2-(3-fluoro-phenyl)-2H-pyrazol-3-yl]-1H-pyridazin-4-one,
1-(2,2-Difluoro-benzo[1,3]dioxol-4-yl)-3-[2-(2,5-difluoro-phenyl)-2H-pyrazol-3-yl]-1H-pyridazin-4-one,
3-{5-[1-(2,2-Difluoro-benzo[1,3]dioxol-4-yl)-4-oxo-1,4-dihydro-pyridazin-3-yl]-pyrazol-1-yl}-benzonitrile,
1-(2,2-Difluoro-benzo[1,3]dioxol-4-yl)-3-[2-(2-methyl-pyridin-4-yl)-2H-pyrazol-3-yl]-1H-pyridazin-4-one,
3-[2-(2-Methyl-pyridin-4-yl)-2H-pyrazol-3-yl]-1-(4-trifluoromethoxy-phenyl)-1H-pyridazin-4-one,
1-(2,2-Difluoro-benzo[1,3]dioxol-5-yl)-3-[2-(2-methyl-pyridin-4-yl)-2H-pyrazol-3-yl]-1H-pyridazin-4-one,
N,N-Dimethyl-3-{3-[2-(2-methyl-pyridin-4-yl)-2H-pyrazol-3-yl]-4-oxo-4H-pyridazin-1-yl}-benzenesulfonamide,
1-(3-Fluoro-phenyl)-3-[2-(2-methyl-pyridin-4-yl)-2H-pyrazol-3-yl]-1H-pyridazin-4-one,
3-[2-(3-Fluoro-phenyl)-2H-pyrazol-3-yl]-1-(4-trifluoromethoxy-phenyl)-1H-pyridazin-4-one,
3-[2-(2,5-Difluoro-phenyl)-2H-pyrazol-3-yl]-1-(4-trifluoromethoxy-phenyl)-1H-pyridazin-4-one,
3-[2-(6-Fluoro-quinolin-4-yl)-2H-pyrazol-3-yl]-1-(4-trifluoromethoxy-phenyl)-1H-pyridazin-4-one,
3-[2-(4-Fluoro-phenyl)-2H-pyrazol-3-yl]-1-(4-trifluoromethoxy-phenyl)-1H-pyridazin-4-one,
4-{5-[4-Oxo-1-(4-trifluoromethoxy-phenyl)-1,4-dihydro-pyridazin-3-yl]-pyrazol-1-yl}-benzonitrile,
3-(2-Pyridin-3-yl-2H-pyrazol-3-yl)-1-(4-trifluoromethoxy-phenyl)-1H-pyridazin-4-one,
3-[2-(3-Methanesulfonyl-phenyl)-2H-pyrazol-3-yl]-1-(4-trifluoromethoxy-phenyl)-1H-pyridazin-4-one,
1-(4-Trifluoromethoxy-phenyl)-3-[2-(3-trifluoromethoxy-phenyl)-2H-pyrazol-3-yl]-1H-pyridazin-4-one,
N,N-Dimethyl-3-{5-[4-oxo-1-(4-trifluoromethoxy-phenyl)-1,4-dihydro-pyridazin-3-yl]-pyrazol-1-yl}-benzenesulfonamide,
3-[2-(3-Chloro-phenyl)-2H-pyrazol-3-yl]-1-(4-trifluoromethoxy-phenyl)-1H-pyridazin-4-one,
3-[2-(2,2-Difluoro-benzo[1,3]dioxol-4-yl)-2H-pyrazol-3-yl]-1-(4-trifluoromethoxy-phenyl)-1H-pyridazin-4-one,
3-[2-(2,2-Difluoro-benzo[1,3]dioxol-5-yl)-2H-pyrazol-3-yl]-1-(4-trifluoromethoxy-phenyl)-1H-pyridazin-4-one,
3-[2-(3-Trifluoromethanesulfonyl-phenyl)-2H-pyrazol-3-yl]-1-(4-trifluoromethoxy-phenyl)-1H-pyridazin-4-one,
3-[2-(6-Fluoro-quinolin-4-yl)-2H-pyrazol-3-yl]-1-(3-trifluoromethoxy-phenyl)-1H-pyridazin-4-one,
1-(4-Difluoromethoxy-phenyl)-3-[2-(6-fluoro-quinolin-4-yl)-2H-pyrazol-3-yl]-1H-pyridazin-4-one,
1-(3-Difluoromethoxy-phenyl)-3-[2-(6-fluoro-quinolin-4-yl)-2H-pyrazol-3-yl]-1H-pyridazin-4-one,
1-(2,2-Difluoro-benzo[1,3]dioxol-5-yl)-3-[2-(6-fluoro-quinolin-4-yl)-2H-pyrazol-3-yl]-1H-pyridazin-4-one,
1-(4-Methanesulfonyl-phenyl)-3-(2-phenyl-2H-pyrazol-3-yl)-1H-pyridazin-4-one,
3-[2-(4-Fluoro-phenyl)-2H-pyrazol-3-yl]-1-(4-methanesulfonyl-phenyl)-1H-pyridazin-4-one,
3-[2-(3-Fluoro-phenyl)-2H-pyrazol-3-yl]-1-(4-methanesulfonyl-phenyl)-1H-pyridazin-4-one,
4-{5-[1-(4-Methanesulfonyl-phenyl)-4-oxo-1,4-dihydro-pyridazin-3-yl]-pyrazol-1-yl}-benzonitrile,
3-[2-(4-Chloro-phenyl)-2H-pyrazol-3-yl]-1-(4-methanesulfonyl-phenyl)-1H-pyridazin-4-one,
3-[2-(3-Chloro-phenyl)-2H-pyrazol-3-yl]-1-(4-methanesulfonyl-phenyl)-1H-pyridazin-4-one,
1-(4-Methanesulfonyl-phenyl)-3-[2-(4-trifluoromethoxy-phenyl)-2H-pyrazol-3-yl]-1H-pyridazin-4-one,
1-(3-Trifluoromethoxy-phenyl)-3-[2-(3-trifluoromethoxy-phenyl)-2H-pyrazol-3-yl]-1H-pyridazin-4-one,
N,N-Dimethyl-3-{5-[4-oxo-1-(3-trifluoromethoxy-phenyl)-1,4-dihydro-pyridazin-3-yl]-pyrazol-1-yl}-benzenesulfonamide,
3-[2-(2,2-Difluoro-benzo[1,3]dioxol-4-yl)-2H-pyrazol-3-yl]-1-(3-trifluoromethoxy-phenyl)-1H-pyridazin-4-one,
3-[2-(2,2-Difluoro-benzo[1,3]dioxol-5-yl)-2H-pyrazol-3-yl]-1-(3-trifluoromethoxy-phenyl)-1H-pyridazin-4-one,
3-[2-(3-Trifluoromethanesulfonyl-phenyl)-2H-pyrazol-3-yl]-1-(3-trifluoromethoxy-phenyl)-1H-pyridazin-4-one,
1-(4-Difluoromethoxy-phenyl)-3-[2-(3-methanesulfonyl-phenyl)-2H-pyrazol-3-yl]-1H-pyridazin-4-one,
1-(4-Difluoromethoxy-phenyl)-3-[2-(3-trifluoromethoxy-phenyl)-2H-pyrazol-3-yl]-1H-pyridazin-4-one,
3-[2-(2,2-Difluoro-benzo[1,3]dioxol-4-yl)-2H-pyrazol-3-yl]-1-(4-difluoromethoxy-phenyl)-1H-pyridazin-4-one,
1-(4-Difluoromethoxy-phenyl)-3-[2-(2-fluoro-phenyl)-2H-pyrazol-3-yl]-1H-pyridazin-4-one, 1-(3-Difluoromethoxy-phenyl)-3-[2-(3-methanesulfonyl-phenyl)-2H-pyrazol-3-yl]-1H-pyridazin-4-one,
1-(3-Difluoromethoxy-phenyl)-3-[2-(3-trifluoromethoxy-phenyl)-2H-pyrazol-3-yl]-1H-pyridazin-4-one,
3-[2-(2,2-Difluoro-benzo[1,3]dioxol-4-yl)-2H-pyrazol-3-yl]-1-(3-difluoromethoxy-phenyl)-1H-pyridazin-4-one,
1-(3-Difluoromethoxy-phenyl)-3-[2-(2-fluoro-phenyl)-2H-pyrazol-3-yl]-1H-pyridazin-4-one,
1-(2,2-Difluoro-benzo[1,3]dioxol-5-yl)-3-[2-(3-methanesulfonyl-phenyl)-2H-pyrazol-3-yl]-1H-pyridazin-4-one,
1-(2,2-Difluoro-benzo[1,3]dioxol-5-yl)-3-[2-(2,2-difluoro-benzo[1,3]dioxol-4-yl)-2H-pyrazol-3-yl]-1H-pyridazin-4-one,
1-(2,2-Difluoro-benzo[1,3]dioxol-5-yl)-3-[2-(2-fluoro-phenyl)-2H-pyrazol-3-yl]-1H-pyridazin-4-one,
3-[2-(4-Fluoro-phenyl)-2H-pyrazol-3-yl]-1-(3-hydroxy-phenyl)-1H-pyridazin-4-one,
N-(3-{5-[4-Oxo-1-(4-trifluoromethoxy-phenyl)-1,4-dihydro-pyridazin-3-yl]-pyrazol-1-yl}-phenyl)-acetamide,
3-[2-(6-Fluoro-2-methyl-quinolin-4-yl)-2H-pyrazol-3-yl]-1-(3-trifluoromethoxy-phenyl)-1H-pyridazin-4-one,
3-(2-Quinolin-4-yl-2H-pyrazol-3-yl)-1-(3-trifluoromethoxy-phenyl)-1H-pyridazin-4-one,
N-(3-{5-[4-Oxo-1-(3-trifluoromethoxy-phenyl)-1,4-dihydro-pyridazin-3-yl]-pyrazol-1-yl}-phenyl)-acetamide,
N-(3-{5-[1-(3-Dimethylsulfamoyl-phenyl)-4-oxo-1,4-dihydro-pyridazin-3-yl]-pyrazol-1-yl}-phenyl)-acetamide,
3-[2-(4-Hydroxy-phenyl)-2H-pyrazol-3-yl]-1-(3-methanesulfonyl-phenyl)-1H-pyridazin-4-one,
3-[2-(3-Chloro-phenyl)-2H-pyrazol-3-yl]-1-phenyl-1H-pyridazin-4-one,
3-[2-(2-Fluoro-phenyl)-2H-pyrazol-3-yl]-1-phenyl-1H-pyridazin-4-one,
3-(2-Naphthalen-1-yl-2H-pyrazol-3-yl)-1-phenyl-1H-pyridazin-4-one,
4-{5-[4-Oxo-1-(4-trifluoromethoxy-phenyl)-1,4-dihydro-pyridazin-3-yl]-pyrazol-1-yl}-benzenesulfonamide,
3-(2-Quinolin-4-yl-2H-pyrazol-3-yl)-1-(4-trifluoromethoxy-phenyl)-1H-pyridazin-4-one,
3-[2-(6-Fluoro-quinolin-4-yl)-2H-pyrazol-3-yl]-1-phenyl-1H-pyridazin-4-one,
3-(2-Naphthalen-1-yl-2H-pyrazol-3-yl)-1-(3-trifluoromethyl-phenyl)-1H-pyridazin-4-one,
3-[2-(6-Fluoro-quinolin-4-yl)-2H-pyrazol-3-yl]-1-(3-trifluoromethyl-phenyl)-1H-pyridazin-4-one,
1-(3-Bromo-phenyl)-3-(2-naphthalen-1-yl-2H-pyrazol-3-yl)-1H-pyridazin-4-one,
1-(4-Methanesulfonyl-phenyl)-3-(2-quinolin-4-yl-2H-pyrazol-3-yl)-1H-pyridazin-4-one,
3-(2-Isoquinolin-5-yl-2H-pyrazol-3-yl)-1-(4-methanesulfonyl-phenyl)-1H-pyridazin-4-one,
3-[2-(2-Chloro-pyridin-4-yl)-2H-pyrazol-3-yl]-1-(4-trifluoromethoxy-phenyl)-1H-pyridazin-4-one,
3-[2-(6-Fluoro-2-methyl-quinolin-4-yl)-2H-pyrazol-3-yl]-1-(4-trifluoromethoxy-phenyl)-1H-pyridazin-4-one,
3-{3-[2-(6-Fluoro-2-methyl-quinolin-4-yl)-2H-pyrazol-3-yl]-4-oxo-4H-pyridazin-1-yl}-N,N-dimethyl-benzenesulfonamide,
N,N-Dimethyl-3-[4-oxo-3-(2-quinolin-4-yl-2H-pyrazol-3-yl)-4H-pyridazin-1-yl]-benzenesulfonamide,
1-(3-Methoxy-phenyl)-3-(2-quinolin-4-yl-2H-pyrazol-3-yl)-1H-pyridazin-4-one,
3-[2-(6-Fluoro-quinolin-4-yl)-2H-pyrazol-3-yl]-1-(3-methoxy-phenyl)-1H-pyridazin-4-one,
3-[2-(6-Fluoro-2-methyl-quinolin-4-yl)-2H-pyrazol-3-yl]-1-(3-methoxy-phenyl)-1H-pyridazin-4-one,
3-[2-(2-Ethoxy-pyridin-4-yl)-2H-pyrazol-3-yl]-1-(4-trifluoromethoxy-phenyl)-1H-pyridazin-4-one,
1-(3-Methoxy-phenyl)-3-(2-naphthalen-1-yl-2H-pyrazol-3-yl)-1H-pyridazin-4-one,
3-[2-(2,3-Dihydro-benzo[1,4]dioxin-6-yl)-2H-pyrazol-3-yl]-1-(3-methoxy-phenyl)-1H-pyridazin-4-one,
3-(2-Quinolin-5-yl-2H-pyrazol-3-yl)-1-(3-trifluoromethoxy-phenyl)-1H-pyridazin-4-one,
1-(3-Difluoromethoxy-phenyl)-3-(2-quinolin-5-yl-2H-pyrazol-3-yl)-1H-pyridazin-4-one,
3-[2-(2-Chloro-pyridin-4-yl)-2H-pyrazol-3-yl]-1-(3-difluoromethoxy-phenyl)-1H-pyridazin-4-one,
3-[2-(3-Chloro-phenyl)-2H-pyrazol-3-yl]-1-(3-difluoromethoxy-phenyl)-1H-pyridazin-4-one,
3-[4-Oxo-3-(2-quinolin-4-yl-2H-pyrazol-3-yl)-4H-pyridazin-1-yl]-benzonitrile,
3-{3-[2-(2-Fluoro-phenyl)-2H-pyrazol-3-yl]-4-oxo-4H-pyridazin-1-yl}-N,N-dimethyl-benzamide,
3-{3-[2-(3-Chloro-phenyl)-2H-pyrazol-3-yl]-4-oxo-4H-pyridazin-1-yl}-N,N-dimethyl-benzamide,
N,N-Diethyl-3-{3-[2-(3-fluoro-phenyl)-2H-pyrazol-3-yl]-4-oxo-4H-pyridazin-1-yl}-benzenesulfonamide,
3-(2-Phenyl-2H-pyrazol-3-yl)-1-(4-trifluoromethyl-phenyl)-1H-pyridazin-4-one,
3-[2-(2-Fluoro-phenyl)-2H-pyrazol-3-yl]-1-(4-trifluoromethyl-phenyl)-1H-pyridazin-4-one,
3-[2-(3-Chloro-phenyl)-2H-pyrazol-3-yl]-1-(4-trifluoromethyl-phenyl)-1H-pyridazin-4-one,
3-(2-Quinolin-4-yl-2H-pyrazol-3-yl)-1-(3-trifluoromethyl-phenyl)-1H-pyridazin-4-one,
3-(2-Quinolin-8-yl-2H-pyrazol-3-yl)-1-(4-trifluoromethoxy-phenyl)-1H-pyridazin-4-one,
3-(2-o-Tolyl-2H-pyrazol-3-yl)-1-(4-trifluoromethyl-phenyl)-1H-pyridazin-4-one,
3-{5-[4-Oxo-1-(4-trifluoromethyl-phenyl)-1,4-dihydro-pyridazin-3-yl]-pyrazol-1-yl}-benzonitrile,
1-(3-Chloro-phenyl)-3-[2-(2-fluoro-phenyl)-2H-pyrazol-3-yl]-1H-pyridazin-4-one,
1-(3-Chloro-phenyl)-3-[2-(3-chloro-phenyl)-2H-pyrazol-3-yl]-1H-pyridazin-4-one,
3-[2-(3-Methyl-isothiazol-5-yl)-2H-pyrazol-3-yl]-1-(4-trifluoromethoxy-phenyl)-1H-pyridazin-4-one,
1-(3-Chloro-phenyl)-3-(2-naphthalen-1-yl-2H-pyrazol-3-yl)-1H-pyridazin-4-one,
3-(2-Naphthalen-1-yl-2H-pyrazol-3-yl)-1-(4-trifluoromethyl-phenyl)-1H-pyridazin-4-one,
1-(4-Chloro-phenyl)-3-(2-naphthalen-1-yl-2H-pyrazol-3-yl)-1H-pyridazin-4-one,
3-[2-(6-Chloro-quinolin-4-yl)-2H-pyrazol-3-yl]-1-(4-trifluoromethoxy-phenyl)-1H-pyridazin-4-one,
3-(2-Isoquinolin-5-yl-2H-pyrazol-3-yl)-1-(4-trifluoromethoxy-phenyl)-1H-pyridazin-4-one,
3-(2-Isoquinolin-4-yl-2H-pyrazol-3-yl)-1-(4-trifluoromethoxy-phenyl)-1H-pyridazin-4-one,
3-(2-Quinolin-5-yl-2H-pyrazol-3-yl)-1-(4-trifluoromethoxy-phenyl)-1H-pyridazin-4-one,
1-(4-Chloro-phenyl)-3-[2-(2-fluoro-phenyl)-2H-pyrazol-3-yl]-1H-pyridazin-4-one,
1-(4-Chloro-phenyl)-3-[2-(3-chloro-phenyl)-2H-pyrazol-3-yl]-1H-pyridazin-4-one,
1-(3-Dimethylaminomethyl-phenyl)-3-[2-(2-fluoro-phenyl)-2H-pyrazol-3-yl]-1H-pyridazin-4-one,
3-[2-(2-Fluoro-phenyl)-2H-pyrazol-3-yl]-1-[3-(piperidine-1-sulfonyl)-phenyl]-1H-pyridazin-4-one,
3-[2-(2-Fluoro-phenyl)-2H-pyrazol-3-yl]-1-(4-trifluoromethanesulfonyl-phenyl)-1H-pyridazin-4-one, 1-(4-Dimethylaminomethyl-phenyl)-3-[2-(2-fluoro-phenyl)-2H-pyrazol-3-yl]-1H-pyridazin-4-one,
3-(2-Isoquinolin-5-yl-2H-pyrazol-3-yl)-1-(4-trifluoromethanesulfonyl-phenyl)-1H-pyridazin-4-one,
3-(2-Quinolin-5-yl-2H-pyrazol-3-yl)-1-(4-trifluoromethanesulfonyl-phenyl)-1H-pyridazin-4-one,
3-[2-(4-Chloro-naphthalen-1-yl)-2H-pyrazol-3-yl]-1-phenyl-1H-pyridazin-4-one,
3-[2-(4-Chloro-naphthalen-1-yl)-2H-pyrazol-3-yl]-1-(4-trifluoromethyl-phenyl)-1H-pyridazin-4-one,
3-[2-(2-Fluoro-phenyl)-2H-pyrazol-3-yl]-1-[3-(pyrrolidine-1-sulfonyl)-phenyl]-1H-pyridazin-4-one,
4-{3-[2-(2-Fluoro-phenyl)-2H-pyrazol-3-yl]-4-oxo-4H-pyridazin-1-yl}-N-methyl-benzenesulfonamide,
3-[2-(7-Chloro-quinolin-4-yl)-2H-pyrazol-3-yl]-1-(4-trifluoromethoxy-phenyl)-1H-pyridazin-4-one,
N,N-Diethyl-3-[4-oxo-3-(2-quinolin-5-yl-2H-pyrazol-3-yl)-4H-pyridazin-1-yl]-benzenesulfonamide,
3-(2-Quinolin-4-yl-2H-pyrazol-3-yl)-1-(4-trifluoromethanesulfonyl-phenyl)-1H-pyridazin-4-one,
3-[2-(4-Chloro-naphthalen-1-yl)-2H-pyrazol-3-yl]-1-(4-chloro-phenyl)-1H-pyridazin-4-one,
3-[2-(4-Chloro-naphthalen-1-yl)-2H-pyrazol-3-yl]-1-(3-chloro-phenyl)-1H-pyridazin-4-one,
N,N-Diethyl-3-[3-(2-isoquinolin-5-yl-2H-pyrazol-3-yl)-4-oxo-4H-pyridazin-1-yl]-benzenesulfonamide,
3-(2-Isoquinolin-8-yl-2H-pyrazol-3-yl)-1-(4-trifluoromethoxy-phenyl)-1H-pyridazin-4-one,
1-(4-Trifluoromethoxy-phenyl)-3-[2-(2-trifluoromethyl-pyridin-4-yl)-2H-pyrazol-3-yl]-1H-pyridazin-4-one,
3-[3-(2-Isoquinolin-5-yl-2H-pyrazol-3-yl)-4-oxo-4H-pyridazin-1-yl]-benzonitrile,
3-{3-[2-(7-Chloro-quinolin-4-yl)-2H-pyrazol-3-yl]-4-oxo-4H-pyridazin-1-yl}-benzonitrile,
1-[3-(Pyrrolidine-1-sulfonyl)-phenyl]-3-(2-quinolin-5-yl-2H-pyrazol-3-yl)-1H-pyridazin-4-one,
3-[2-(7-Chloro-quinolin-4-yl)-2H-pyrazol-3-yl]-1-[3-(pyrrolidine-1-sulfonyl)-phenyl]-1H-pyridazin-4-one,
3-{3-[2-(7-Chloro-quinolin-4-yl)-2H-pyrazol-3-yl]-4-oxo-4H-pyridazin-1-yl}-N,N-diethyl-benzenesulfonamide,
3-{3-[2-(7-Chloro-quinolin-4-yl)-2H-pyrazol-3-yl]-4-oxo-4H-pyridazin-1-yl}-N-methyl-benzenesulfonamide,
3-[3-(2-Isoquinolin-8-yl-2H-pyrazol-3-yl)-4-oxo-4H-pyridazin-1-yl]-N,N-dimethyl-benzenesulfonamide,
3-[2-(2-Fluoro-phenyl)-2H-pyrazol-3-yl]-1-[4-(2,2,2-trifluoro-ethoxy)-phenyl]-1H-pyridazin-4-one,
3-(2-Phenyl-2H-pyrazol-3-yl)-1-[4-(2,2,2-trifluoro-ethoxy)-phenyl]-1H-pyridazin-4-one,
3-[2-(3-Chloro-phenyl)-2H-pyrazol-3-yl]-1-[4-(2,2,2-trifluoro-ethoxy)-phenyl]-1H-pyridazin-4-one,
3-[2-(3-Fluoro-phenyl)-2H-pyrazol-3-yl]-1-[4-(2,2,2-trifluoro-ethoxy)-phenyl]-1H-pyridazin-4-one,
3-(2-Quinolin-4-yl-2H-pyrazol-3-yl)-1-[4-(2,2,2-trifluoro-ethoxy)-phenyl]-1H-pyridazin-4-one,
3-{3-[2-(2-Methyl-pyridin-4-yl)-2H-pyrazol-3-yl]-4-oxo-4H-pyridazin-1-yl}-benzonitrile,
3-(2-Isoquinolin-5-yl-2H-pyrazol-3-yl)-1-[3-(pyrrolidine-1-sulfonyl)-phenyl]-1H-pyridazin-4-one,
N-Methyl-3-{3-[2-(2-methyl-pyridin-4-yl)-2H-pyrazol-3-yl]-4-oxo-4H-pyridazin-1-yl}-benzenesulfonamide,
3-[3-(2-Isoquinolin-5-yl-2H-pyrazol-3-yl)-4-oxo-4H-pyridazin-1-yl]-N-methyl-benzenesulfonamide,
3-[2-(6-Chloro-quinolin-4-yl)-2H-pyrazol-3-yl]-1-[3-(pyrrolidine-1-sulfonyl)-phenyl]-1H-pyridazin-4-one,
1-[3-(Piperidine-1-sulfonyl)-phenyl]-3-(2-quinolin-5-yl-2H-pyrazol-3-yl)-1H-pyridazin-4-one,
3-(2-Isoquinolin-5-yl-2H-pyrazol-3-yl)-1-[3-(piperidine-1-sulfonyl)-phenyl]-1H-pyridazin-4-one,
3-[2-(6-Chloro-quinolin-4-yl)-2H-pyrazol-3-yl]-1-[3-(piperidine-1-sulfonyl)-phenyl]-1H-pyridazin-4-one,
3-[2-(7-Chloro-quinolin-4-yl)-2H-pyrazol-3-yl]-1-[3-(piperidine-1-sulfonyl)-phenyl]-1H-pyridazin-4-one,
N,N-Diethyl-3-{3-[2-(2-fluoro-phenyl)-2H-pyrazol-3-yl]-4-oxo-4H-pyridazin-1-yl}-benzenesulfonamide,
3-{3-[2-(3-Fluoro-phenyl)-2H-pyrazol-3-yl]-4-oxo-4H-pyridazin-1-yl}-benzonitrile,
3-[2-(3-Fluoro-phenyl)-2H-pyrazol-3-yl]-1-[3-(pyrrolidine-1-sulfonyl)-phenyl]-1H-pyridazin-4-one,
4-{3-[2-(3-Fluoro-phenyl)-2H-pyrazol-3-yl]-4-oxo-4H-pyridazin-1-yl}-N-methyl-benzenesulfonamide,
3-[2-(3-Fluoro-phenyl)-2H-pyrazol-3-yl]-1-[3-(piperidine-1-sulfonyl)-phenyl]-1H-pyridazin-4-one,
3-{3-[2-(2,5-Difluoro-phenyl)-2H-pyrazol-3-yl]-4-oxo-4H-pyridazin-1-yl}-benzonitrile,
3-[2-(2,5-Difluoro-phenyl)-2H-pyrazol-3-yl]-1-[3-(pyrrolidine-1-sulfonyl)-phenyl]-1H-pyridazin-4-one,
1-(3-Hydroxy-phenyl)-3-(2-naphthalen-1-yl-2H-pyrazol-3-yl)-1H-pyridazin-4-one,
3-[2-(2,3-Dihydro-benzo[1,4]dioxin-6-yl)-2H-pyrazol-3-yl]-1-(3-hydroxy-phenyl)-1H-pyridazin-4-one,
3-(2-Phenyl-2H-pyrazol-3-yl)-1-(4-trifluoromethanesulfonyl-phenyl)-1H-pyridazin-4-one,
3-[2-(3-Chloro-phenyl)-2H-pyrazol-3-yl]-1-(4-trifluoromethanesulfonyl-phenyl)-1H-pyridazin-4-one,
3-[2-(2,3-Dichloro-phenyl)-2H-pyrazol-3-yl]-1-(4-trifluoromethanesulfonyl-phenyl)-1H-pyridazin-4-one,
3-(2-Phenyl-2H-pyrazol-3-yl)-1-(3-trifluoromethanesulfonyl-phenyl)-1H-pyridazin-4-one,
3-[2-(2-Fluoro-phenyl)-2H-pyrazol-3-yl]-1-(3-trifluoromethanesulfonyl-phenyl)-1H-pyridazin-4-one,
3-[2-(3-Chloro-phenyl)-2H-pyrazol-3-yl]-1-(3-trifluoromethanesulfonyl-phenyl)-1H-pyridazin-4-one,
3-{5-[4-Oxo-1-(3-trifluoromethanesulfonyl-phenyl)-1,4-dihydro-pyridazin-3-yl]-pyrazol-1-yl}-benzonitrile,
3-[2-(2,3-Dichloro-phenyl)-2H-pyrazol-3-yl]-1-(3-trifluoromethanesulfonyl-phenyl)-1H-pyridazin-4-one,
3-{3-[2-(2-Fluoro-phenyl)-2H-pyrazol-3-yl]-4-oxo-4H-pyridazin-1-yl}-benzonitrile,
3-{3-[2-(3-Chloro-phenyl)-2H-pyrazol-3-yl]-4-oxo-4H-pyridazin-1-yl}-benzonitrile,
3-[2-(3-Chloro-2-fluoro-phenyl)-2H-pyrazol-3-yl]-1-(4-trifluoromethanesulfonyl-phenyl)-1H-pyridazin-4-one,
3-[2-(3-Chloro-2-fluoro-phenyl)-2H-pyrazol-3-yl]-1-(3-trifluoromethanesulfonyl-phenyl)-1H-pyridazin-4-one,
3-[2-(2,3-Dihydro-benzo[1,4]dioxin-6-yl)-2H-pyrazol-3-yl]-1-(3-fluoromethoxy-phenyl)-1H-pyridazin-4-one,
1-(3-Fluoromethoxy-phenyl)-3-(2-naphthalen-1-yl-2H-pyrazol-3-yl)-1H-pyridazin-4-one,
N-(3-{3-[2-(2-Fluoro-phenyl)-2H-pyrazol-3-yl]-4-oxo-4H-pyridazin-1-yl}-phenyl)-acetamide,
3-{3-[2-(2-Fluoro-phenyl)-2H-pyrazol-3-yl]-4-oxo-4H-pyridazin-1-yl}-N-methyl-benzamide,
N-(3-{3-[2-(2-Fluoro-phenyl)-2H-pyrazol-3-yl]-4-oxo-4H-pyridazin-1-yl}-phenyl)-N-methyl-acetamide,
3-[3-(2-Naphthalen-1-yl-2H-pyrazol-3-yl)-4-oxo-4H-pyridazin-1-yl]-benzoic acid 2-fluoro-ethyl ester,
3-[3-(2-Naphthalen-1-yl-2H-pyrazol-3-yl)-4-oxo-4H-pyridazin-1-yl]-benzoic acid 3-fluoro-propyl ester,
3-[3-(2-Naphthalen-1-yl-2H-pyrazol-3-yl)-4-oxo-4H-pyridazin-1-yl]-benzoic acid methyl ester,
3-[2-(2-Fluoro-phenyl)-2H-pyrazol-3-yl]-1-[3-(1-hydroxy-ethyl)-phenyl]-1H-pyridazin-4-one, and 1-(3-Acetyl-phenyl)-3-[2-(2-fluoro-phenyl)-2H-pyrazol-3-yl]-1H-pyridazin-4-one, and pharmaceutically acceptable salts and esters thereof.

Other particularly preferred compounds of formula (I) as described above are those selected from the group consisting of 3-[2-(2,4-Difluoro-phenyl)-2H-pyrazol-3-yl]-1-(3-methanesulfonyl-phenyl)-1H-pyridazin-4-one,
1-(3-Difluoromethoxy-phenyl)-3-[2-(2,5-difluoro-phenyl)-2H-pyrazol-3-yl]-1H-pyridazin-4-one,
3-[2-(2-Methyl-pyridin-4-yl)-2H-pyrazol-3-yl]-1-(3-trifluoromethoxy-phenyl)-1H-pyridazin-4-one,
1-(3-Difluoromethoxy-phenyl)-3-[2-(6-fluoro-quinolin-4-yl)-2H-pyrazol-3-yl]-1H-pyridazin-4-one,
3-(2-Quinolin-4-yl-2H-pyrazol-3-yl)-1-(4-trifluoromethoxy-phenyl)-1H-pyridazin-4-one,
3-[2-(3-Chloro-phenyl)-2H-pyrazol-3-yl]-1-(3-difluoromethoxy-phenyl)-1H-pyridazin-4-one,
3-[4-Oxo-3-(2-quinolin-4-yl-2H-pyrazol-3-yl)-4H-pyridazin-1-yl]-benzonitrile,
3-[2-(2-Fluoro-phenyl)-2H-pyrazol-3-yl]-1-(4-trifluoromethanesulfonyl-phenyl)-1H-pyridazin-4-one,
3-[2-(2-Fluoro-phenyl)-2H-pyrazol-3-yl]-1-[4-(2,2,2-trifluoro-ethoxy)-phenyl]-1H-pyridazin-4-one,
3-[2-(3-Chloro-phenyl)-2H-pyrazol-3-yl]-1-[4-(2,2,2-trifluoro-ethoxy)-phenyl]-1H-pyridazin-4-one,
3-(2-Quinolin-4-yl-2H-pyrazol-3-yl)-1-[4-(2,2,2-trifluoro-ethoxy)-phenyl]-1H-pyridazin-4-one,
3-[2-(2,3-Dihydro-benzo[1,4]dioxin-6-yl)-2H-pyrazol-3-yl]-1-(3-hydroxy-phenyl)-1H-pyridazin-4-one,
3-(2-Phenyl-2H-pyrazol-3-yl)-1-(3-trifluoromethanesulfonyl-phenyl)-1H-pyridazin-4-one,
3-{5-[4-Oxo-1-(3-trifluoromethanesulfonyl-phenyl)-1,4-dihydro-pyridazin-3-yl]-pyrazol-1-yl}-benzonitrile,
3-{3-[2-(3-Chloro-phenyl)-2H-pyrazol-3-yl]-4-oxo-4H-pyridazin-1-yl}-benzonitrile,
N-(3-{3-[2-(2-Fluoro-phenyl)-2H-pyrazol-3-yl]-4-oxo-4H-pyridazin-1-yl}-phenyl)-acetamide,
3-{3-[2-(2-Fluoro-phenyl)-2H-pyrazol-3-yl]-4-oxo-4H-pyridazin-1-yl}-N-methyl-benzamide,
N-(3-{3-[2-(2-Fluoro-phenyl)-2H-pyrazol-3-yl]-4-oxo-4H-pyridazin-1-yl}-phenyl)-N-methyl-acetamide,
3-[3-(2-Naphthalen-1-yl-2H-pyrazol-3-yl)-4-oxo-4H-pyridazin-1-yl]-benzoic acid 2-fluoro-ethyl ester, and
3-[2-(2-Fluoro-phenyl)-2H-pyrazol-3-yl]-1-[3-(1-hydroxy-ethyl)-phenyl]-1H-pyridazin-4-one, and pharmaceutically acceptable salts and esters thereof.

In one embodiment, the compounds of formula (I) as described above do not comprise compounds selected from the group consisting of 3-[2-(2-Fluoro-phenyl)-2H-pyrazol-3-yl]-1-(3-trifluoromethyl-phenyl)-1H-pyridazin-4-one,
3-[2-(4-Chloro-phenyl)-2H-pyrazol-3-yl]-1-phenyl-1H-pyridazin-4-one,
1-Phenyl-3-(2-p-tolyl-2H-pyrazol-3-yl)-1H-pyridazin-4-one,
3-(2-Phenyl-2H-pyrazol-3-yl)-1-(3-trifluoromethyl-phenyl)-1H-pyridazin-4-one,
3-[2-(4-Methoxy-phenyl)-2H-pyrazol-3-yl]-1-(3-trifluoromethyl-phenyl)-1H-pyridazin-4-one, and
3-[2-(3-Chloro-phenyl)-2H-pyrazol-3-yl]-1-(3-trifluoromethyl-phenyl)-1H-pyridazin-4-one.

It will be appreciated that the compounds of general formula (I) in this invention can be derivatized at functional groups to provide derivatives which are capable of conversion back to the parent compound in vivo.

The invention further relates to a process for the manufacture of compounds of formula (I) as defined above, which process comprises reacting a compound of formula (II)

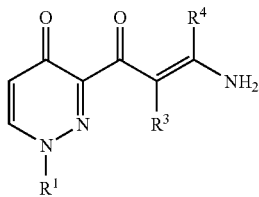

with a compound of the formula $R^2$—NH—$NH_2$, wherein $R^1$, $R^2$, $R^3$ and $R^4$ are as defined above.

The reaction of a compound of formula (II) with a compound of the formula $R^2$—NH—$NH_2$ can be carried out under conditions as described in the examples or under conditions well known to the person skilled in the art. For example, the reaction can be performed in solvents like DMF, acetic acid, ethanol, water, a mixture of ethanol with hydrochloric acid and the like at elevated temperatures e.g. at 100-200° C., at atmospheric pressure or elevated pressure. The reaction can be performed at the reflux temperature of the respective solvent, or it can be performed at temperatures above boiling point by applying sealed tubes and using microwave irradiation conditions.

The present invention also relates to compounds of formula (I) as defined above, when prepared by a process as described above.

The compounds of formula (II) and $R^2$—NH—$NH_2$, can be prepared by methods known in the art or as described below or in analogy thereto. Unless otherwise indicated, $R^1$, $R^2$, $R^3$, and $R^4$ are as described above.

The pyridazinones of the general formula I of the present invention can be prepared starting from anilines of formula 2 (see scheme 1 below). Anilines 2 are either commercially available or can be prepared from commercial precursors as e.g. from their corresponding nitro compounds by reductive methods. Another option is to convert commercial anilines into the desired anilines 2 by standard methods known in the art. Conversion of anilines 2 into their corresponding diazonium salts of general formula 3 can be done using standard methods known to those skilled in the art as e.g. treatment of the aniline in a mineral acid as e.g. hydrochloric acid, sulfuric acid or phosphoric acid with sodium nitrite. The formed diazonium salts 3 can be used without any further purification for the condensation with suitable 1,3-diketones 4 resulting in diazo compounds of general formula 5. This reaction is preferentially performed in an alcohol/water mixture at low temperatures (0-5° C.) at almost neutral pH value (pH 5-6) which can be achieved by adding suitable basic salts like e.g. ammonium acetate. The diazo compounds of formula 5 can tautomerize to the corresponding hydrazones.

The pyridazin-4-one ring can be formed by reacting the intermediate diazo compounds of formula 5 with $C_1$-equivalents like e.g. formaldehyde, N,N-dimethylformamide or N,N-dimethylformamide dimethyl acetal. The reaction with N,N-dimethylformamide dimethyl acetal affords the pyridazinone intermediates of general formula 6 bearing a 1,3-diketone equivalent as side chain.

The side chain 1,3-diketone equivalent of pyridazinones 6 is used to form the final products of general formula I by condensing pyridazinones 6 with suitable hydrazines of general formula 7. This reaction is usually performed in solvents like DMF, acetic acid, ethanol, water, a mixture of ethanol with hydrochloric acid and the like at elevated temperatures. The reaction can be performed at the reflux temperature of the respective solvent, or it can be performed at temperatures above boiling point by applying sealed tubes and using microwave irradiation conditions.

Hydrazines of general formula 7 are commercially available or can be prepared by methods known to those skilled in the art. Straightforward synthetic methods starting from commercial precursors include the conversion of the corresponding anilines with sodium nitrite and tin-(II)-chloride and the treatment of hydrazine hydrate with aromatic/heteroaromatic halides.

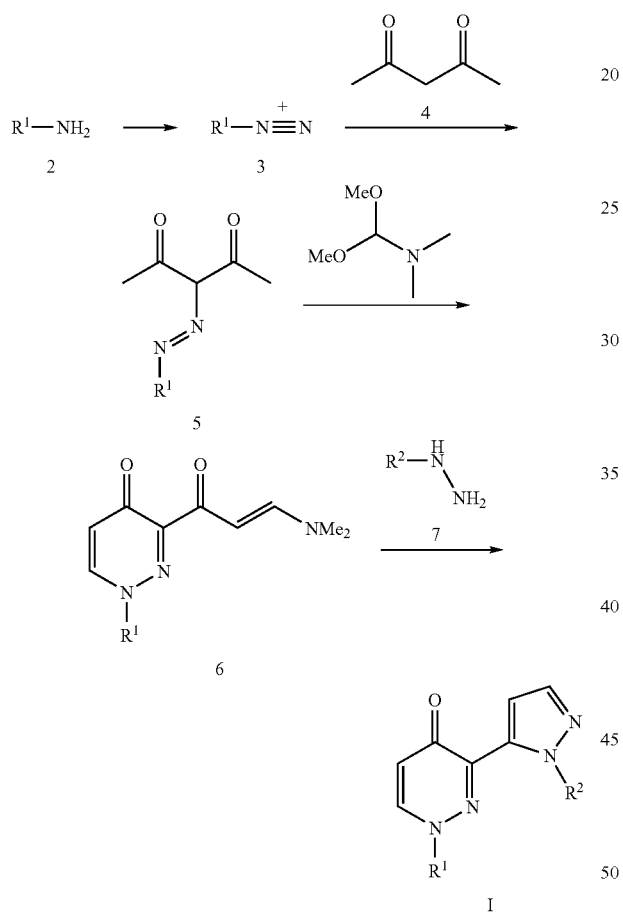

The pyridazinones of the general formula I can also be prepared starting from anilines of formula 2 according to scheme 2 (see below).

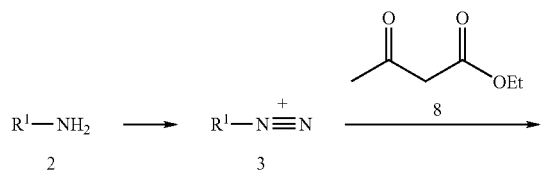

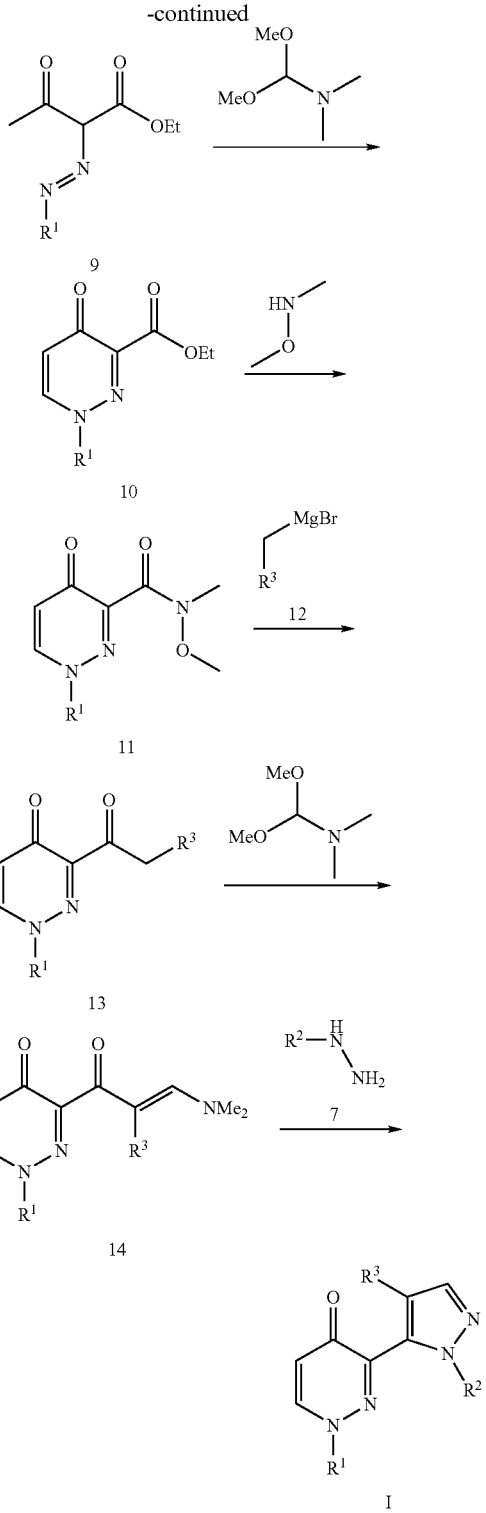

Conversion of anilines 2 into their corresponding diazonium salts of general formula 3 can be done as described above. The formed diazonium salts 3 can be used without any further purification for the condensation with suitable ketoesters 8 resulting in diazo compounds of general formula 9. This reaction is preferentially performed in an alcohol/water mixture at low temperatures (0-5° C.) at almost neutral pH value (pH 5-6) which can be achieved by adding suitable basic salts like e.g. ammonium acetate. The diazo compounds of formula 9 can tautomerize to the corresponding hydrazones.

The pyridazin-4-one ring can be formed by reacting the intermediate diazo compounds of formula 9 with $C_1$-equivalents like e.g. formaldehyde, N,N-dimethylformamide or N,N-dimethylformamide dimethyl acetal. The reaction with N,N-dimethylformamide dimethyl acetal affords the pyridazinone intermediates of general formula 10 bearing an ester equivalent as side chain.

The ester side chain equivalent of pyridazinones 10 can be converted into a ketone most conveniently by functionalisation into a suitable activated species such as a Weinreb amide 11 therefore disposed towards displacement with an organometalic species, most commonly a Grignard reagent of general formula 12 in e.g. a non protic solvent such as THF or hexane to give the corresponding ketone 13. This can be again reacted with $C_1$-equivalents like e.g. formaldehyde, N,N-dimethylformamide or N,N-dimethylformamide dimethyl acetal. The reaction with N,N-dimethylformamide dimethyl acetal affords the diketone equivalent of general formula 14 which is used to form the final products of general formula I by condensing with suitable hydrazines of general formula 7. This reaction is usually performed in solvents like DMF, acetic acid, ethanol, water, a mixture of ethanol with hydrochloric acid and the like at elevated temperatures. The reaction can be performed at the reflux temperature of the respective solvent, or it can be performed at temperatures above boiling point by applying sealed tubes and using microwave irradiation conditions.

Hydrazines of general formula 7 are commercially available or can be prepared by methods known to those skilled in the art. Straightforward synthetic methods starting from commercial precursors include the conversion of the corresponding anilines with sodium nitrite and tin-(II)-chloride and the treatment of hydrazine hydrate with aromatic/heteroaromatic halides.

Certain substituents on the groups $R^1$, $R^2$, $R^3$, and $R^4$ may not be inert to the conditions of the synthesis sequences described above and may require protection by standard protecting groups known in the art. For instance, an amino or hydroxyl group can be protected as an acetyl or tert.-butoxycarbonyl derivative. Alternatively, some substituents can be derived from others at the end of the reaction sequence. For instance, a compound of formula I can be synthesized bearing a nitro-, an ethoxycarbonyl, an ether, a sulfonic acid substituent on the groups $R^1$, $R^2$, $R^3$, and $R^4$, which substituents are finally converted to an amino- (e.g. by reduction of a nitro group or cleavage of a suitable amino protective group (e.g. removal of a Boc group with TFA)), alkylamino- (e.g. by reductive amination of an amino group), dialkylamino- (e.g. by alkylation of an amino group, reduction of an appropriate acylamino group with lithium aluminum hydride or Eschweiler-Clarke reaction with an appropriate amino or alkylamino group), acylamino- (by amide formation from an amino group e.g. with appropriate acyl halides or with appropriate carboxylic acids after their activation with CDI, EDC etc.), alkylsulfonylamino (e.g. by reaction of an amino group with sulfonyl chlorides), arylsulfonylamino substituent (e.g. by reaction of an amino group with sulfonyl chlorides), hydroxyl- (by cleavage of a suitable hydroxy protective group (e.g. hydrogenolytic removal of a benzyl ether or oxidative cleavage of a p-methoxy benzyl ether), ether- (e.g. by Williamson's ether synthesis from a hydroxyl group) or to a carboxamide substituent (e.g. by amide formation from a carboxylic acid group with appropriate amines after activation of the carboxylic acid group with CDI, EDC etc. or conversion to an acyl chloride), or to a sulfonamide substituent by standard procedures.

The corresponding salts with acids can be obtained by standard methods known to the person skilled in the art, e.g. by dissolving the compound of formula (I) in a suitable solvent such as e.g. dioxan or THF and adding an appropriate amount of the corresponding acid. The products can usually be isolated by filtration or by chromatography. The conversion of a compound of formula (I) into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxytris(dimethylamino) phosphonium hexafluorophosphate (BOP), N,N-dicylohexylcarbodiimide (DCC), N-(3-dimethylaminopropyl)-N'-ethylcarbodiimide hydrochloride (EDC) or O-(1,2-dihydro-2-oxo-1-pyridyl)-N,N,N',N'-tetramethyluroniumtetrafluoroborate (TPTU), or by direct reaction with a suitable alcohol under acidic conditions, as for example in the presence of a strong mineral acid like hydrochloric acid, sulfuric acid and the like. Compounds having a hydroxyl group can be converted to esters with suitable acids by analogous methods.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

As described above, the novel compounds of the present invention inhibit PDE10A activity. The compounds of the present invention can therefore be used, either alone or in combination with other drugs, for the treatment and/or prophylaxis of diseases which are modulated by PDE10A inhibitors. These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive/compulsive disorders, acute stress disorder or generalized anxiety disorder, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders. Other disorders are diabetes and related disorders, such as type 2 diabetes mellitus, neurodegenerative disorders such as Alzheimer's disease, Huntington's disease, Parkinson's disease, multiple sclerosis, stroke or spinal cord injury, solid tumors and hematological malignancies such as renal cell carcinoma or breast cancer.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by PDE10A inhibitors, particularly as therapeutically active substances for the treatment and/or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer.

In another preferred embodiment, the invention relates to a method for the therapeutic and/or prophylactic treatment of diseases which are modulated by PDE10A inhibitors, particularly for the therapeutic and/or prophylactic treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer, which method comprises administering a compound as defined above to a human being or animal.

The invention also embraces the use of compounds as defined above for the therapeutic and/or prophylactic treatment of diseases which are modulated by PDE10A inhibitors, particularly for the therapeutic and/or prophylactic treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer.

The invention also relates to the use of compounds as described above for the preparation of pharmaceutical compositions for the therapeutic and/or prophylactic treatment of diseases which are modulated by PDE10A inhibitors, particularly for the therapeutic and/or prophylactic treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer. Such medicaments comprise a compound as described above.

Prevention and/or treatment of schizophrenia is a preferred indication. Furthermore, prevention and/or treatment of positive, negative and/or cognitive symptoms associated with schizophrenia is preferred.

The following tests were carried out in order to determine the activity of the compounds of the present invention. PDE10 activity of the compounds of the present invention is determined using a Scintillation Proximity Assay (SPA)-based method similar to the one previously described (Fawcett, L. et al., Proc Natl Acad Sci USA (2000) 97(7):3702-3707).

PDE10A1 and PDE10A2 are two splice variants of PDE10A. There are these 2 splice variants known, which differ in the N-terminal part of the protein. The catalytic domains of PDE10A1 and PDE10A2 are identical. The assay for PDE10A2 described below is therefore also representative for PDE10A1 and also for PDE10A in general.

The PDE10A2 assay was performed in a two step procedure in 96-well micro titer plates. The reaction mixture of 80 µl contained 20 mM HEPES/10 mM $MgCl_2$/0.05 mg/ml buffer (pH 7.5), 50 nM cGMP (Sigma) and 50 nM [$^3$H]-cGMP (GE Healthcare), 0.25 nM PDE10A2 with or without a specific test compound. A range of concentrations of the potential inhibitor was used to generate data for calculating the concentration of inhibitor resulting in 50% of the effect (e.g. $IC_{50}$, the concentration of the competitor inhibiting PDE10A2 activity 50%). Non-specific activity was tested without the enzyme. The reaction was initiated by addition of the substrate solution (cGMP and [$^3$H]-cGMP) and allowed to progress for 30 minutes at room temperature. The reaction was terminated by transferring 50 µl of the reaction mixture into an OptiPlate (Perkin Elmer) containing 25 µl of YSi-SPA scintillation beads (GE Healthcare) in 18 mM zinc sulphate solution (stop reagent). After 1 h under shaking, the plate was centrifuged one minute at 1000 rpm to allow beads to settle. Afterwards, radioactive counts were measured on a Perkin Elmer TopCount Scintillation plate reader.

The catalytic domain of human PDE10A2, residues serine 449 to aspartate 789, was amplified by PCR using cDNA (Origene) and the oligonucleotides 5'-GGGGACAAGTTT GTACAAAAAAGCAGGCTTAGTACCTA-GAGGATCAAGCATTTGTACTTCAGAAG-3' (SEQ ID NO. 1) (with AttB1 recombination site in bold and thrombin protease cleavage site in italics) and 5'-GGGGAC-CACTTTGTACAAGAAAGCTGGGT-CAATCTTCAGATGCA GCTG-3' (SEQ ID NO. 2) (with AttB2 recombination site in bold) which conferred Gateway recombination sites. The PCR product was used in a BP recombination reaction with pDONR221 to generate pENTR Thm-PDE10A2(S449-D789) which was DNA sequence verified and then used in an LR recombination reaction with a Gateway modified version of pET11a. The resulting expression vector, placT7.2H6-(gw1)-Thm-PDE10A2(S449-D789) was DNA sequence confirmed and transformed into *E. coli* strain BL21(DE3) pLysS and recombinant protein was produced in TB medium at 20° C. by induction to a final IPTG concentration of 0.5 mM at an optical density of 1.0 at 600 nm for 20 hours. About 30% of the protein was in the soluble fraction of the cell homogenate. The protein was purified using sequential chromatography on Ni-NTA and HiTrapQ/HiTrapS. After thrombin digest at room temperature a HiTrapChelating/HiTrap Benzamindin chromatography removed impurities, uncleaved protein and thrombin. Final purification of PDE10A2(S449-D789) was performed on a Superdex 75 size exclusion chromatography equilibrated with 25 mM HEPES pH 8.4, 0.15 M NaCl. The yield of pure protein was 2 mg/liter of culture volume is relatively low. The purity of the protein was >95%, monomeric and monodisperse as shown by SDS-PAGE, HPLC and analytical ultracentrifugation.

The compounds according to formula (I) preferably have an $IC_{50}$ value below 10 µM, preferably below 5 µM, more preferably below 1 µM. Preferably, the $IC_{50}$ values are above 0.01 nM. The following table shows data for some examples.

| Example | PDE10A2 inhibition $IC_{50}$ [µmol/l] |
| --- | --- |
| 1 | 0.063 |
| 4 | 0.050 |
| 13 | 1.426 |
| 14 | 0.038 |
| 15 | 0.167 |
| 17 | 0.025 |
| 18 | 0.080 |
| 25 | 0.378 |
| 26 | 0.014 |
| 27 | 0.117 |
| 28 | 0.017 |
| 30 | 0.045 |
| 32 | 0.005 |
| 34 | 0.040 |
| 35 | 0.143 |
| 36 | 0.029 |
| 43 | 0.888 |
| 48 | 0.009 |
| 49 | 0.027 |
| 58 | 0.067 |
| 64 | 0.039 |
| 78 | 1.148 |
| 79 | 0.007 |
| 80 | 0.003 |
| 85 | 0.002 |
| 86 | 0.068 |
| 87 | 0.049 |
| 88 | 0.629 |
| 89 | 2.272 |
| 90 | 0.037 |
| 94 | 0.055 |
| 95 | 1.205 |
| 98 | 0.222 |
| 100 | 0.105 |
| 101 | 0.037 |
| 105 | 0.054 |
| 106 | 0.040 |
| 109 | 0.072 |
| 114 | 0.082 |
| 116 | 0.033 |
| 122 | 0.028 |
| 124 | 0.057 |
| 129 | 0.080 |
| 133 | 0.071 |
| 138 | 0.037 |
| 145 | 0.072 |
| 149 | 0.014 |
| 150 | 0.005 |
| 153 | 0.067 |
| 157 | 0.092 |
| 162 | 0.155 |
| 165 | 0.051 |
| 171 | 0.046 |
| 174 | 0.184 |
| 177 | 0.027 |
| 183 | 0.047 |
| 186 | 0.002 |
| 192 | 0.013 |
| 200 | 0.046 |
| 203 | 0.013 |
| 206 | 0.017 |
| 207 | 0.005 |
| 216 | 0.020 |
| 224 | 0.022 |
| 232 | 0.012 |
| 237 | 0.101 |
| 244 | 0.046 |
| 255 | 0.005 |
| 257 | 0.003 |
| 259 | 0.001 |
| 267 | 0.040 |
| 277 | 0.004 |
| 281 | 0.017 |
| 284 | 0.011 |
| 287 | 0.015 |
| 292 | 0.021 |
| 293 | 0.038 |
| 294 | 0.006 |
| 295 | 0.002 |
| 298 | 0.026 |

The present invention also encompasses pharmaceutical compositions of compounds of formula I and/or their pharmaceutically acceptable salts thereof, including pharmaceutical compositions for enteral, parenteral or topical administration. Such compositions can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

Pharmaceutical compositions can be prepared in a manner familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage at which compounds of formula I can be administered can vary within wide limits depending on the disease to be controlled, the age and the individual condition of the patient and the mode of administration, and will, of course, be fitted to the individual requirements in each particular case. For adult patients a daily dosage of about 0.1 to 2000 mg, especially about 1 to 500 mg, comes into consideration. Depending on severity of the disease and the precise pharmacokinetic profile the compound could be administered with one or several daily dosage units, e.g. in 1 to 3 dosage units.

The pharmaceutical compositions conveniently contain about 0.1-500 mg, preferably 1-200 mg, of a compound of formula I.

The following examples serve to illustrate the present invention in more detail. They are, however, not intended to limit its scope in any manner.

EXAMPLES

A. Starting Materials

A-1: 3-((E)-3-Dimethylamino-acryloyl)-1-phenyl-1H-pyridazin-4-one

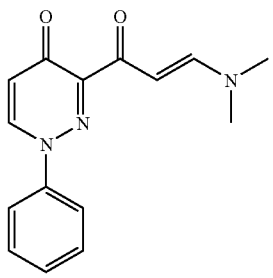

a) 3-Phenylazo-pentane-2,4-dione

A solution of aniline (5.0 g, 54 mmol) in 1N HCl (100 ml) is cooled to 0-5° C. and reacted with a solution of sodium nitrite (3.89 g, 56 mmol) in H$_2$O (sulfination flask with mechanic stirrer). Stirring is continued for 30 min at 0-5° C. (suspension of diazonium salt). In parallel, a solution of 2,4-pentadione (6.7 g; 67 mmol) in EtOH (15 ml) and water (250 ml) is prepared and cooled to 0-5° C. The pentadione solution is added to the suspension of the diazonium salt while vigorously stirring. After completion, NH$_4$OAc is added until the pH reaches 5-6. The creamy yellow suspension is stirred for another 3 h at the same temperature. The solid material is filtered, washed with water, transferred into a flask and dried. Residual water can be removed with either ethyl acetate or acetone (in this case better) yielding 10.4 g (95%) of the desired product. DC: R$_f$=0.4 (EE/heptane=1:3)

b) 3-((E)-3-Dimethylamino-acryloyl)-1-phenyl-1H-pyridazin-4-one

3-Phenylazo-pentane-2,4-dione (10.4 g; 51 mmol) is dissolved in N,N-dimethylformamide dimethyl acetal (50 ml) and heated at 110° C. for 30 min. The reaction progress is monitored by e.g. TLC. Residual solvent of dark solution formed is removed after checking the reaction progress. The product is purified by flash chromatography on silica gel (eluent: dichloromethane with 5% 1M NH$_3$ in MeOH) yielding 11.9 g (86%) of an amorphous material. MS: M=270.4 (M+H)$^+$

A-2: 3-((E)-3-Dimethylamino-acryloyl)-1-(4-methoxyl-phenyl)-1H-pyridazin-4-one

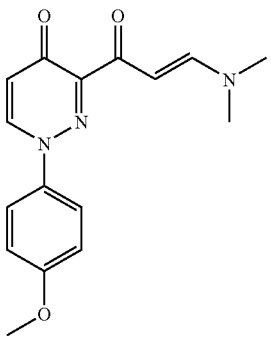

According to the method described for the synthesis of starting material A-1, starting material A-2 was prepared starting from p-anisidine and 2,4-pentadione in 83% yield for the two-step synthesis as amorphous material. MS: M=300.0 (M+H)$^+$

A-3: 3-((E)-3-Dimethylamino-acryloyl)-1-(3-trifluoromethyl-phenyl)-1H-pyridazin-4-one

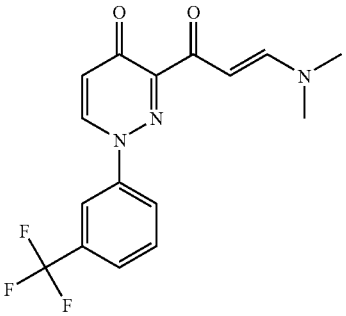

According to the method described for the synthesis of starting material A-1, starting material A-3 was prepared starting from 3-trifluoromethylaniline and 2,4-pentadione in 77% yield for the two-step synthesis as amorphous material. MS: M=338.0 (M+H)$^+$

A-4: 3-((E)-3-Dimethylamino-acryloyl)-1-(3-ethyl-phenyl)-1H-pyridazin-4-one

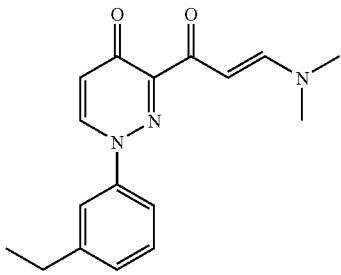

According to the method described for the synthesis of starting material A-1, starting material A-4 was prepared starting from 3-ethylaniline and 2,4-pentadione in 95% yield for the two-step synthesis as amorphous material. MS: M=298.3 (M+H)+

A-5: 3-((E)-3-Dimethylamino-acryloyl)-1-(3-methoxy-phenyl)-1H-pyridazin-4-one

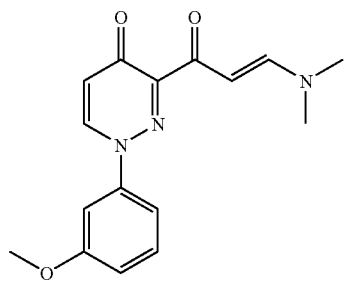

According to the method described for the synthesis of starting material A-1, starting material A-5 was prepared starting from m-anisidine and 2,4-pentadione in 85% yield for the two-step synthesis as amorphous material. MS: M=300.1 (M+H)+

A-6: 3-((E)-3-Dimethylamino-acryloyl)-1-(3-trifluoromethoxy-phenyl)-1H-pyridazin-4-one

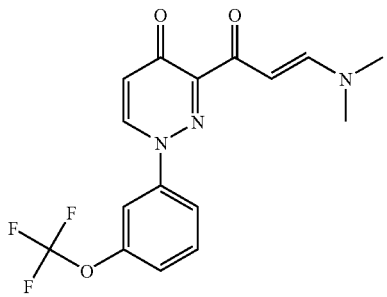

According to the method described for the synthesis of starting material A-1, starting material A-6 was prepared starting from 3-trifluoromethoxyaniline and 2,4-pentadione in 72% yield for the two-step synthesis as amorphous material.
MS: M=354.1 (M+H)+

A-7: 3-((E)-3-Dimethylamino-acryloyl)-1-(3-methansulfonyl-phenyl)-1H-pyridazin-4-one

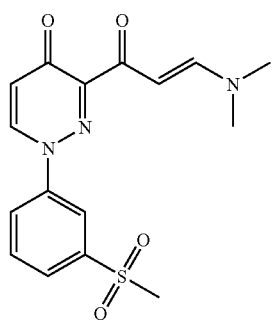

According to the method described for the synthesis of starting material A-1, starting material A-7 was prepared starting from 3-methansulfonylaniline and 2,4-pentadione in 44% yield for the two-step synthesis as amorphous material. MS: M=348.2 (M+H)+

A-8: 3-((E)-3-Dimethylamino-acryloyl)-1-(4-trifluoromethoxy-phenyl)-1H-pyridazin-4-one

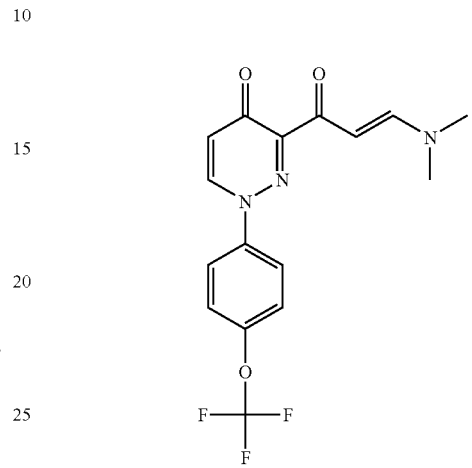

According to the method described for the synthesis of starting material A-1, starting material A-8 was prepared starting from 4-trifluoromethoxyaniline and 2,4-pentadione in 90% yield for the two-step synthesis as amorphous material. MS: M=354.2 (M+H)+

A-9: 1-(4-Difluoromethoxy-phenyl)-3-((E)-3-dimethylamino-acryloyl)-1H-pyridazin-4-one

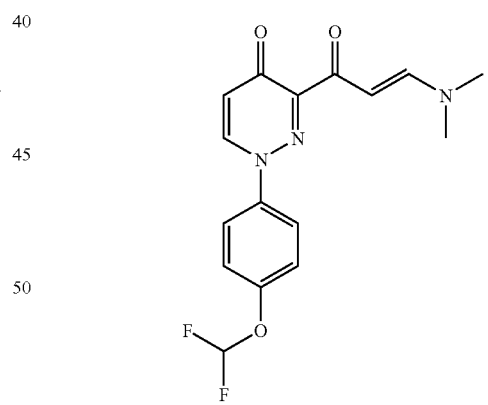

a)
3-(4-Difluoromethoxy-phenylazo)-pentane-2,4-dione

A solution of 4-difluoromethoxy-phenylamine (2 g, 13 mmol) was cooled at −6° C. and phosphoric acid (85%, 13 mL) followed by nitric acid (65%, 9 mL) very slowly. When the mixture reached the room temperature it was stirred 15 minutes for complete dissolution. The solution was cooled again to −6° C. and solid sodium nitrite (0.954 g, 13.8 mmol) was added during 5 minutes followed by crushed ice. The reaction mixture was added into a suspension of pentane-2,4-dione (1.32 g, 13.2 mmol) and potassium acetate (24.1 g, 251 mmol) in ethanol (130 mL) at 0° C. Stirring is continued for 15 min at 0-5° C. and an aqueous solution 2M of sodium carbonate is added until the pH is 9-10. The solution is extracted with dichloromethane (4×200 mL). The combined organic layers were washed with water, dried with magnesium sulphate, filtrated and the solvent was removed in the vacuum to obtain 3.6 g (100%) of the final product that was used as a crude on the next step. MS: M=269.1 (M−H)$^+$ b) 1-(4-Difluoromethoxy-phenyl)-3-((E)-3-dimethylamino-acryloyl)-1H-pyridazin-4-one 3-(4-Difluoromethoxy-phenylazo)-pentane-2,4-dione (3.2 g; 12 mmol) is dissolved in N,N-dimethylformamide dimethyl acetal (20 ml) and heated at 110° C. for 60 min. The N,N-dimethylformamide dimethyl acetal is evaporated and the product is purified by flash chromatography on silica gel (eluent: dichloromethane-methanol 1/0 to 9/1) to yield 3.34 g (84%) of an amorphous yellow material. MS: M=336.3 (M+H)$^+$ A-10: 1-(3-Difluoromethoxy-phenyl)-3-((E)-3-dimethylamino-acryloyl)-1H-pyridazin-4-one

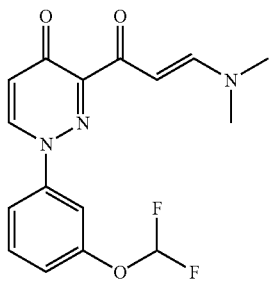

According to the method described for the synthesis of starting material A-9, starting material A-10 was prepared from 3-difluoromethoxy-phenylamine and 2,4-pentadione in 90% yield for the two-step synthesis as brown solid. MS: M=336.3 (M+H)$^+$ A-11: 1-(2,2-Difluoro-benzo[1,3]dioxol-5-yl)-3-((E)-3-dimethylamino-acryloyl)-1H-pyridazin-4-one

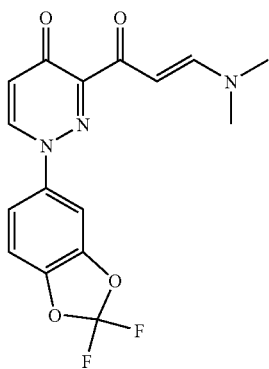

According to the method described for the synthesis of starting material A-9, starting material A-11 was prepared from 2,2-difluoro-benzo[1,3]dioxol-5-ylamine and 2,4-pentadione in 50% yield for the two-step synthesis as brown solid. MS: M=350.2 (M+H)$^+$ A-12: 3-[3-((E)-3-Dimethylamino-acryloyl)-4-oxo-4H-pyridazin-1-yl]-N,N-dimethyl-benzenesulfonamide

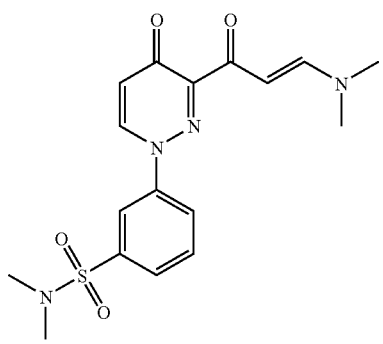

According to the method described for the synthesis of starting material A-9, starting material A-12 was prepared from 3-amino-N,N-dimethyl-benzenesulfonamide and 2,4-pentadione as amorphous material. MS: M=377.2 (M+H)$^+$ A-13: 3-((E)-3-Dimethylamino-acryloyl)-1-(3-fluoro-phenyl)-1H-pyridazin-4-one

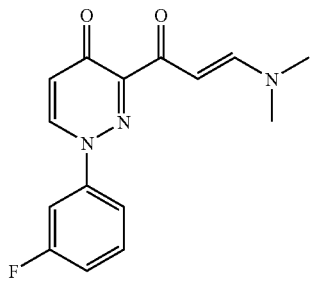

According to the method described for the synthesis of starting material A-1, starting material A-13 was prepared from 3-fluoroaniline and 2,4-pentadione as amorphous material. MS: M=288.1 (M+H)$^+$ A-14: 1-Benzo[1,3]dioxol-4-yl-3-((E)-3-dimethylamino-acryloyl)-1H-pyridazin-4-one

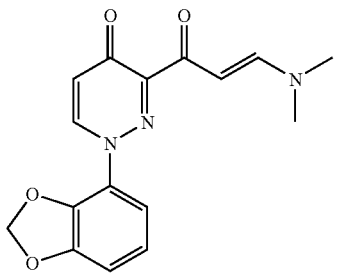

According to the method described for the synthesis of starting material A-9, starting material A-14 was prepared from benzo[1,3]dioxol-4-ylamine and 2,4-pentadione as amorphous material. MS: M=314.2 (M+H)$^+$ A-15: 1-(2,2-Difluoro-benzo[1,3]dioxol-4-yl)-3-((E)-3-dimethylamino-acryloyl)-1H-pyridazin-4-one

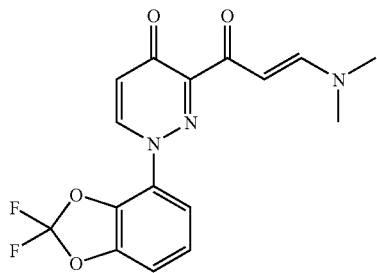

According to the method described for the synthesis of starting material A-9, starting material A-15 was prepared from 2,2-difluoro-benzo[1,3]dioxol-4-ylamine and 2,4-pentadione as amorphous material. MS: M=350.2 (M+H)$^+$ A-16: 3-((E)-3-Dimethylamino-acryloyl)-1-(4-methansulfonyl-phenyl)-1H-pyridazin-4-one

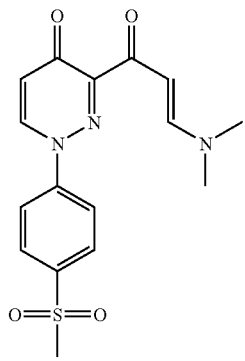

According to the method described for the synthesis of starting material A-9, starting material A-16 was prepared starting from 4-methansulfonylaniline and 2,4-pentadione as amorphous material. MS: M=348.2 (M+H)$^+$ A-17: 3-((E)-3-Dimethylamino-acryloyl)-1-(3-hydroxyphenyl)-1H-pyridazin-4-one

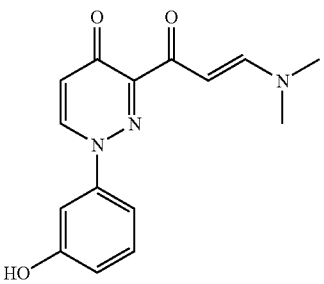

According to the method described for the synthesis of starting material A-9, starting material A-17 was prepared from 3-aminophenol and 2,4-pentadione as amorphous material. MS: M=286.1 (M+H)$^+$ A-18: 1-(3-Bromo-phenyl)-3-((E)-3-dimethylamino-acryloyl)-1H-pyridazin-4-one

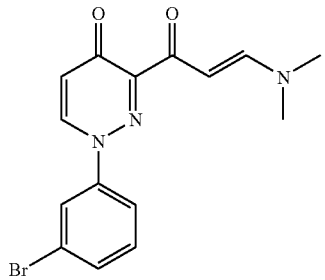

According to the method described for the synthesis of starting material A-1, starting material A-18 was prepared from 3-bromoaniline and 2,4-pentadione as amorphous material. MS: M=348.0 (M+H)$^+$ A-19: 3-[3-((E)-3-Dimethylamino-acryloyl)-4-oxo-4H-pyridazin-1-yl]-benzonitrile

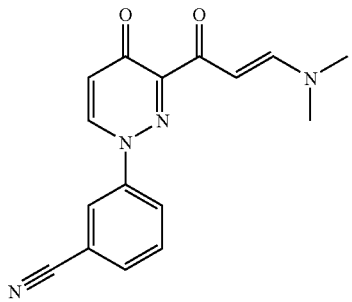

According to the method described for the synthesis of starting material A-9, starting material A-19 was prepared from 3-aminobenzonitrile and 2,4-pentadione as amorphous material. MS: M=295.3 (M+H)$^+$ A-20: 3-[3-((E)-3-Dimethylamino-acryloyl)-4-oxo-4H-pyridazin-1-yl]-N,N-dimethyl-benzamide

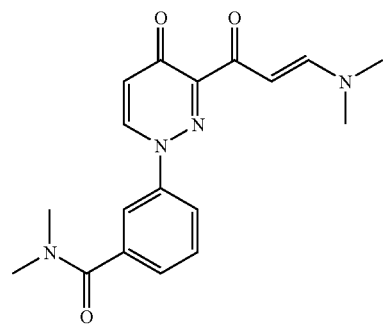

According to the method described for the synthesis of starting material A-9, starting material A-20 was prepared from 3-amino-N,N-dimethyl-benzamide and 2,4-pentadione as amorphous material. MS: M=341.2 (M+H)$^+$ A-21: 3-[3-((E)-3-Dimethylamino-acryloyl)-4-oxo-4H-pyridazin-1-yl]-N,N-diethyl-benzenesulfonamide

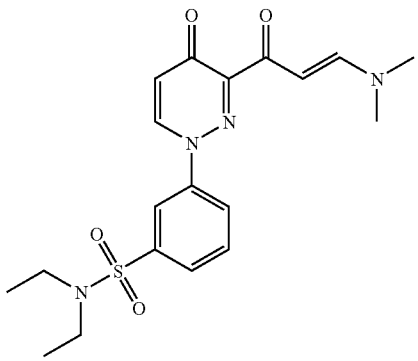

According to the method described for the synthesis of starting material A-9, starting material A-21 was prepared from 3-amino-N,N-diethyl-benzenesulfonamide and 2,4-pentadione as amorphous material. MS: M=405.4 (M+H)$^+$ A-22: 3-((E)-3-Dimethylamino-acryloyl)-1-(4-trifluoromethyl-phenyl)-1H-pyridazin-4-one

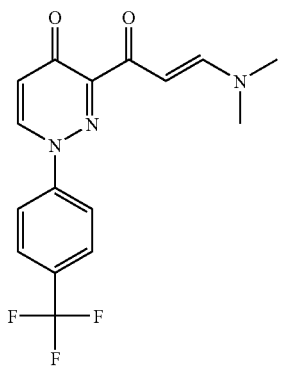

According to the method described for the synthesis of starting material A-1, starting material A-22 was prepared starting from 4-trifluoromethylaniline and 2,4-pentadione as amorphous material. MS: M=338.1 (M+H)$^+$ A-23: 1-(3-Chloro-phenyl)-3-((E)-3-dimethylamino-acryloyl)-1H-pyridazin-4-one

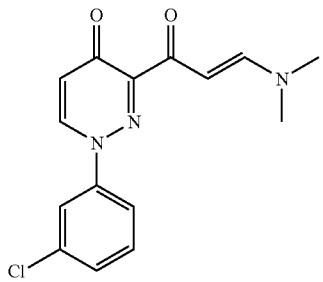

According to the method described for the synthesis of starting material A-1, starting material A-23 was prepared from 3-chloroaniline and 2,4-pentadione as amorphous material. MS: M=304.1 (M+H)$^+$ A-24: 1-(4-Chloro-phenyl)-3-((E)-3-dimethylamino-acryloyl)-1H-pyridazin-4-one

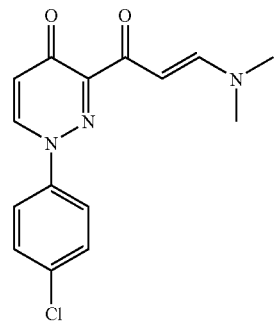

According to the method described for the synthesis of starting material A-1, starting material A-24 was prepared from 4-chloroaniline and 2,4-pentadione as amorphous material. MS: M=304.1 (M+H)$^+$ A-25: 3-((E)-3-Dimethylamino-acryloyl)-1-(3-dimethylaminomethyl-phenyl)-1H-pyridazin-4-one

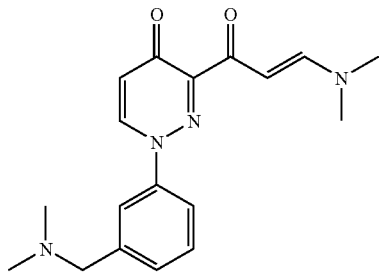

According to the method described for the synthesis of starting material A-9, starting material A-25 was prepared from 3-dimethylaminomethyl-phenylamine and 2,4-pentadione as amorphous material. MS: M=327.3 (M+H)$^+$ A-26: 3-((E)-3-Dimethylamino-acryloyl)-1-[3-(piperidine-1-sulfonyl)-phenyl]-1H-pyridazin-4-one

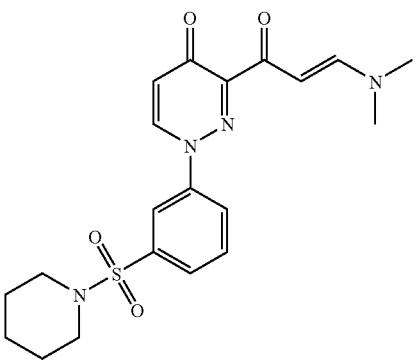

According to the method described for the synthesis of starting material A-9, starting material A-26 was prepared from 3-(piperidine-1-sulfonyl)-phenylamine and 2,4-pentadione as amorphous material. MS: M=417.2 (M+H)⁺

A-27: 3-((E)-3-Dimethylamino-acryloyl)-1-(4-trifluoromethansulfonyl-phenyl)-1H-pyridazin-4-one

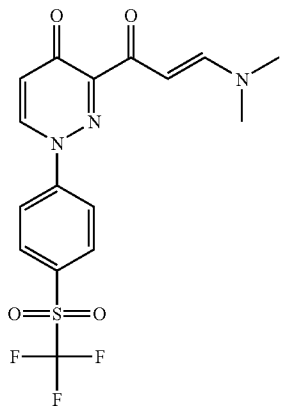

According to the method described for the synthesis of starting material A-9, starting material A-27 was prepared starting from 4-trifluoromethansulfonyl-phenylamine and 2,4-pentadione as amorphous material. MS: M=402.2 (M+H)⁺

A-28: 3-((E)-3-Dimethylamino-acryloyl)-1-(4-dimethylaminomethyl-phenyl)-1H-pyridazin-4-one

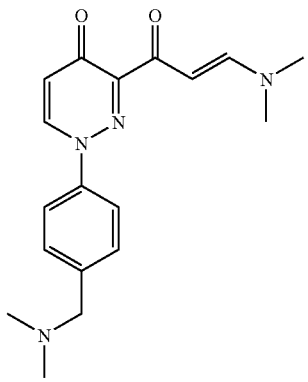

According to the method described for the synthesis of starting material A-9, starting material A-28 was prepared from 4-dimethylaminomethyl-phenylamine and 2,4-pentadione as amorphous material. MS: M=327.3 (M+H)⁺

A-29: 3-((E)-3-Dimethylamino-acryloyl)-1-[3-(pyrrolidine-1-sulfonyl)-phenyl]-1H-pyridazin-4-one

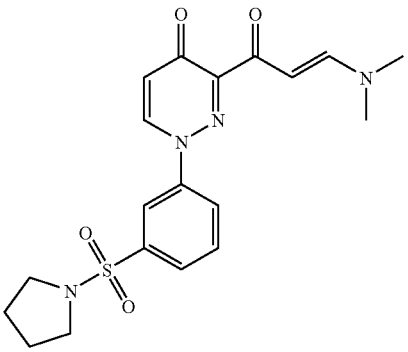

According to the method described for the synthesis of starting material A-9, starting material A-29 was prepared from 3-(pyrrolidine-1-sulfonyl)-phenylamine and 2,4-pentadione as amorphous material. MS: M=403.2 (M+H)⁺

A-30: 4-[3-((E)-3-Dimethylamino-acryloyl)-4-oxo-4H-pyridazin-1-yl]-N-methyl-benzenesulfonamide

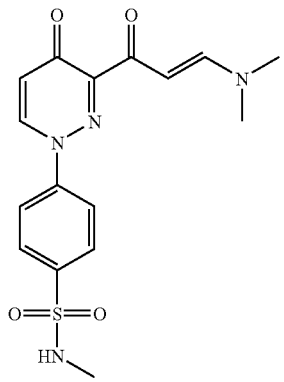

According to the method described for the synthesis of starting material A-9, starting material A-30 was prepared from 4-amino-N-methyl-benzenesulfonamide and 2,4-pentadione as amorphous material. MS: M=363.1 (M+H)⁺

A-31: 3-[3-((E)-3-Dimethylamino-acryloyl)-4-oxo-4H-pyridazin-1-yl]-N-methyl-benzenesulfonamide

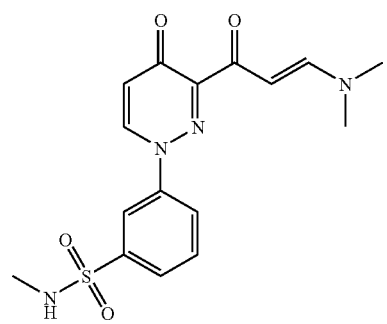

According to the method described for the synthesis of starting material A-9, starting material A-31 was prepared from 3-amino-N-methyl-benzenesulfonamide and 2,4-pentadione as amorphous material. MS: M=363.2 (M+H)+

A-32: 3-((E)-3-Dimethylamino-acryloyl)-1-[4-(2,2,2-trifluoro-ethoxy)-phenyl]-1H-pyridazin-4-one

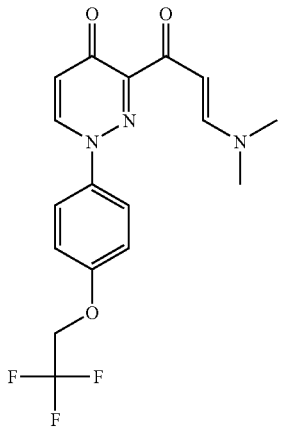

According to the method described for the synthesis of starting material A-9, starting material A-32 was prepared from 4-(2,2,2-trifluoro-ethoxy)-phenylamine and 2,4-pentadione as amorphous material. MS: M=368.1 (M+H)+

A-33: 3-((E)-3-Dimethylamino-acryloyl)-1-(3-trifluoromethansulfonyl-phenyl)-1H-pyridazin-4-one

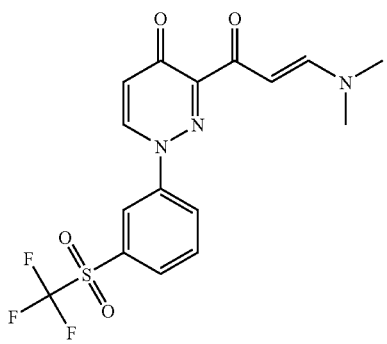

According to the method described for the synthesis of starting material A-9, starting material A-33 was prepared starting from 3-trifluoromethansulfonyl-phenylamine and 2,4-pentadione as amorphous material. MS: M=402.2 (M+H)+

A-34: N-{3-[3-((E)-3-Dimethylamino-acryloyl)-4-oxo-4H-pyridazin-1-yl]-phenyl}-acetamide

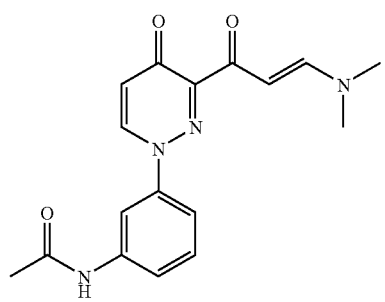

According to the method described for the synthesis of starting material A-1, starting material A-34 was prepared from N-(3-amino-phenyl)-acetamide and 2,4-pentadione as amorphous material. MS: M=327.2 (M+H)+

A-35: 3-[3-((E)-3-Dimethylamino-acryloyl)-4-oxo-4H-pyridazin-1-yl]-N-methyl-benzamide

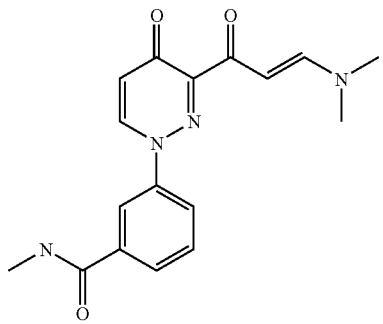

According to the method described for the synthesis of starting material A-1, starting material A-35 was prepared from 3-amino-N-methyl-benzamide and 2,4-pentadione as amorphous material. MS: M=327.2 (M+H)+

A-36: 3-((E)-3-Dimethylamino-acryloyl)-1-[3-(1-hydroxy-ethyl)-phenyl]-1H-pyridazin-4-one

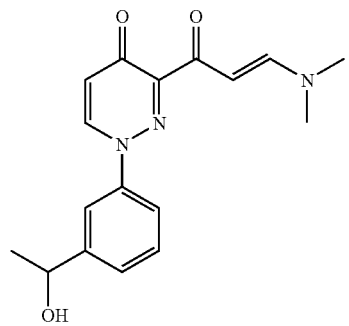

According to the method described for the synthesis of starting material A-9, starting material A-36 was prepared from 1-(3-amino-phenyl)-ethanol and 2,4-pentadione as amorphous material. MS: M=314.2 (M+H)+

B. Final Products

Example 1

3-(2-Benzo[1,3]dioxol-5-yl-2H-pyrazol-3-yl)-1-phenyl-1H-pyridazin-4-one

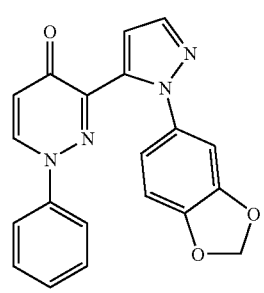

3-((E)-3-Dimethylamino-acryloyl)-1-phenyl-1H-pyridazin-4-one (A-1) (0.2 g; 0.74 mmol) and 3,4-methylenedioxyphenylhydrazine (0.136 g; 0.89 mmol) are dissolved in a sealed tube in acetic acid (4 ml) and irradiated at 180° C. for 10 min. The solvent of the reaction mixture is removed and the crude product is purified by preparative HPLC yielding 0.80 g (30%) of the final product. MS: M=359.0 (M+H)⁺

Example 2

1-(4-Methoxy-phenyl)-3-(2-phenyl-2H-pyrazol-3-yl)-1H-pyridazin-4-one

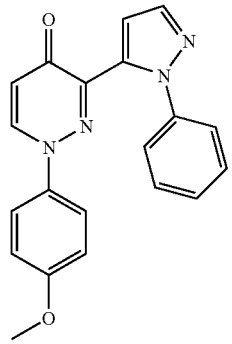

The product was obtained starting from 3-((E)-3-Dimethylamino-acryloyl)-1-(4-methoxyl-phenyl)-1H-pyridazin-4-one (A-2) and phenylhydrazine according to the method described for Example 1 in 81% yield. MS: M=345.0 (M+H)⁺

Example 3

3-[2-(2-Methoxy-phenyl)-2H-pyrazol-3-yl]-1-phenyl-1H-pyridazin-4-one

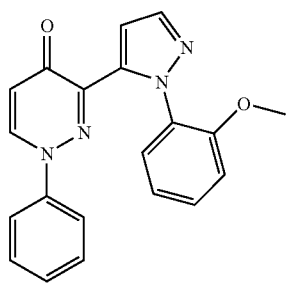

The product was obtained starting from 3-((E)-3-Dimethylamino-acryloyl)-1-phenyl-1H-pyridazin-4-one (A-1) and 2-methoxy-phenylhydrazine×HCl according to the method described for Example 1 in 61% yield. MS: M=345.1 (M+H)⁺

Example 4

1-Phenyl-3-(2-o-tolyl-2H-pyrazol-3-yl)-1H-pyridazin-4-one

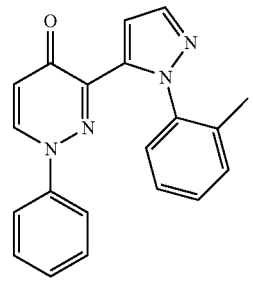

The product was obtained starting from 3-((E)-3-Dimethylamino-acryloyl)-1-phenyl-1H-pyridazin-4-one (A-1) and o-tolylhydrazine×HCl according to the method described for Example 1 in 55% yield. MS: M=329.1 (M+H)⁺

Example 5

1-Phenyl-3-[2-(3-trifluoromethyl-phenyl)-2H-pyrazol-3-yl]-1H-pyridazin-4-one

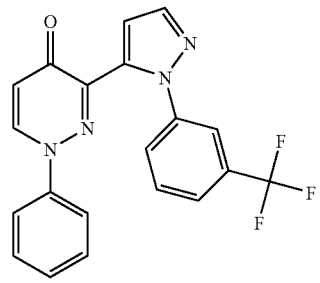

The product was obtained starting from 3-((E)-3-Dimethylamino-acryloyl)-1-phenyl-1H-pyridazin-4-one (A-1) and 3-(trifluoromethyl)-phenylhydrazine according to the method described for Example 1 in 58% yield. MS: M=383.0 (M+H)⁺

Example 6

3-[2-(2,5-Difluoro-phenyl)-2H-pyrazol-3-yl]-1-(3-trifluoromethyl-phenyl)-1H-pyridazin-4-one

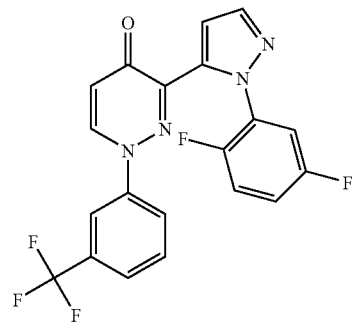

The product was obtained starting from 3-((E)-3-Dimethylamino-acryloyl)-1-(3-trifluoromethyl-phenyl)-1H-pyridazin-4-one (A-3) and 2,5-difluorophenylhydrazine according to the method described for Example 1 in 32% yield. MS: M=419.1 (M+H)⁺

Example 7

1-(3-Trifluoromethyl-phenyl)-3-[2-(2-trifluoromethyl-phenyl)-2H-pyrazol-3-yl]-1H-pyridazin-4-one

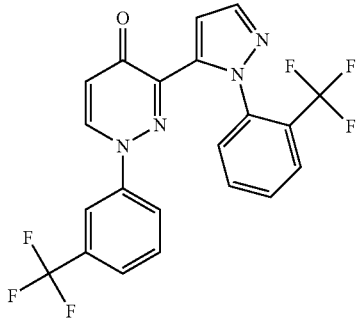

The product was obtained starting from 3-((E)-3-Dimethylamino-acryloyl)-1-(3-trifluoromethyl-phenyl)-1H-pyridazin-4-one (A-3) and o-trifluoromethyl-phenylhydrazine according to the method described for Example 1 in 46% yield. MS: M=451.1 (M+H)⁺

Example 8

3-[2-(2,5-Dimethyl-phenyl)-2H-pyrazol-3-yl]-1-(3-trifluoromethyl-phenyl)-1H-pyridazin-4-one

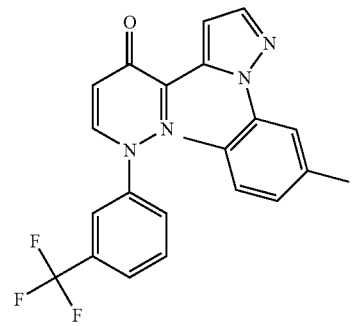

The product was obtained starting from 3-((E)-3-Dimethylamino-acryloyl)-1-(3-trifluoromethyl-phenyl)-1H-pyridazin-4-one (A-3) and 2,5-dimethyl-phenylhydrazine×HCl according to the method described for Example 1 in 88% yield. MS: M=411.1 (M+H)⁺

Example 9

3-[2-(2,5-Difluoro-phenyl)-2H-pyrazol-3-yl]-1-phenyl-1H-pyridazin-4-one

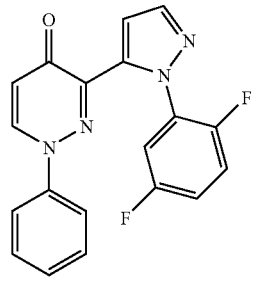

The product was obtained starting from 3-((E)-3-Dimethylamino-acryloyl)-1-phenyl-1H-pyridazin-4-one (A-1) and 2,5-difluorophenylhydrazine according to the method described for Example 1 in 24% yield. MS: M=351.1 (M+H)⁺

Example 10

1-Phenyl-3-[2-(2-trifluoromethyl-phenyl)-2H-pyrazol-3-yl]-1H-pyridazin-4-one

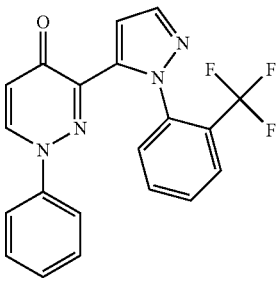

The product was obtained starting from 3-((E)-3-Dimethylamino-acryloyl)-1-phenyl-1H-pyridazin-4-one (A-1) and o-trifluoromethyl-phenylhydrazine according to the method described for Example 1 in 34% yield. MS: M=383.0 (M+H)⁺

Example 11

3-[2-(2,5-Dimethyl-phenyl)-2H-pyrazol-3-yl]-1-phenyl-1H-pyridazin-4-one

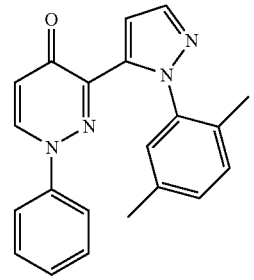

The product was obtained starting from 3-((E)-3-Dimethylamino-acryloyl)-1-phenyl-1H-pyridazin-4-one (A-1) and 2,5-dimethyl-phenylhydrazine×HCl according to the method described for Example 1 in 74% yield. MS: M=343.2 (M+H)⁺

Example 12

3-[2-(2,5-Dichloro-phenyl)-2H-pyrazol-3-yl]-1-phenyl-1H-pyridazin-4-one

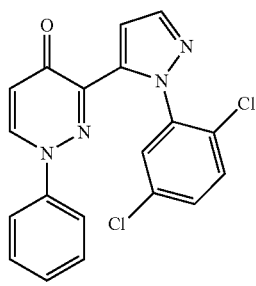

The product was obtained starting from 3-((E)-3-Dimethylamino-acryloyl)-1-phenyl-1H-pyridazin-4-one (A-1) and 2,5-dichlorophenylhydrazine according to the method described for Example 1 in 23% yield. MS: M=383.0 (M+H)⁺

Example 13

1-Phenyl-3-(2-pyridin-2-yl-2H-pyrazol-3-yl)-1H-pyridazin-4-one

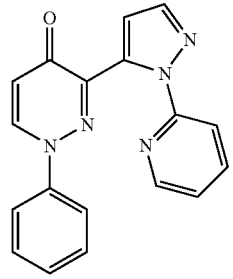

The product was obtained starting from 3-((E)-3-Dimethylamino-acryloyl)-1-phenyl-1H-pyridazin-4-one (A-1) and 2-hydrazinopyridine according to the method described for Example 1 in 64% yield. MS: M=316.1 (M+H)⁺

Example 14

3-{5-[4-Oxo-1-(3-trifluoromethyl-phenyl)-1,4-dihydro-pyridazin-3-yl]-pyrazol-1-yl}-benzonitrile

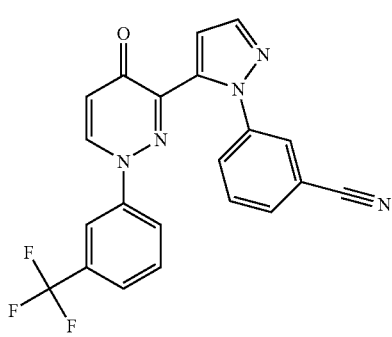

The product was obtained starting from 3-((E)-3-Dimethylamino-acryloyl)-1-(3-trifluoromethyl-phenyl)-1H-pyridazin-4-one (A-3) and 3-hydrazino-benzonitrile in ethanol as solvent according to the method described for Example 1 in 59% yield. MS: M=408.1 (M+H)⁺

Example 15

1-Phenyl-3-(2-pyridin-4-yl-2H-pyrazol-3-yl)-1H-pyridazin-4-one

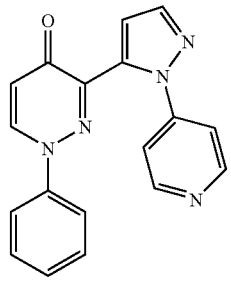

The product was obtained starting from 3-((E)-3-Dimethylamino-acryloyl)-1-phenyl-1H-pyridazin-4-one (A-1) and 4-hydrazinopyridine according to the method described for Example 1 in 11% yield. MS: M=316.1 (M+H)⁺

Example 16

3-[5-(4-Oxo-1-phenyl-1,4-dihydro-pyridazin-3-yl)-pyrazol-1-yl]-benzonitrile

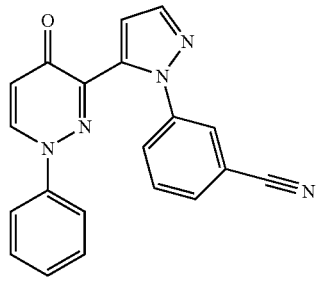

The product was obtained starting from 3-((E)-3-Dimethylamino-acryloyl)-1-phenyl-1H-pyridazin-4-one (A-1) and 3-hydrazino-benzonitrile in ethanol as solvent according to the method described for Example 1 in 55% yield. MS: M=340.1 (M+H)⁺

Example 17

1-(3-Ethyl-phenyl)-3-(2-phenyl-2H-pyrazol-3-yl)-1H-pyridazin-4-one

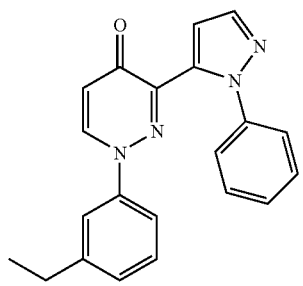

The product was obtained starting from 3-((E)-3-Dimethylamino-acryloyl)-1-(3-ethyl-phenyl)-1H-pyridazin-4-one (A-4) and phenylhydrazine according to the method described for Example 1 in 87% yield. MS: M=343.1 (M+H)⁺

Example 18

1-(3-Methoxy-phenyl)-3-(2-phenyl-2H-pyrazol-3-yl)-1H-pyridazin-4-one

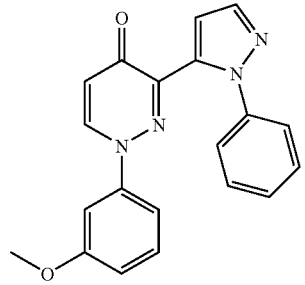

The product was obtained starting from 3-((E)-3-Dimethylamino-acryloyl)-1-(3-methoxy-phenyl)-1H-pyridazin-4-one (A-5) and phenylhydrazine according to the method described for Example 1 in 71% yield. MS: M=345.1 (M+H)⁺

Example 19

1-Phenyl-3-(2-phenyl-2H-pyrazol-3-yl)-1H-pyridazin-4-one

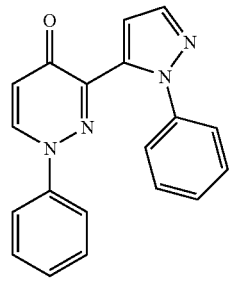

The product was obtained starting from 3-((E)-3-Dimethylamino-acryloyl)-1-phenyl-1H-pyridazin-4-one (A-1) and phenylhydrazine according to the method described for Example 1 in 81% yield. MS: M=315.1 (M+H)⁺

Example 20

3-[2-(4-Methanesulfonyl-phenyl)-2H-pyrazol-3-yl]-1-phenyl-1H-pyridazin-4-one

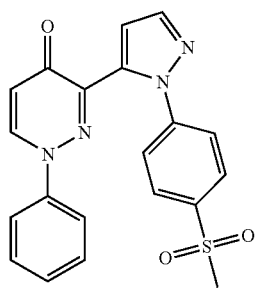

The product was obtained starting from 3-((E)-3-Dimethylamino-acryloyl)-1-phenyl-1H-pyridazin-4-one (A-1) and 4-(methylsulfonyl)phenylhydrazine according to the method described for Example 1 in 12% yield. MS: M=392.9 (M+H)⁺

Example 21

1-(3-Ethyl-phenyl)-3-[2-(4-methanesulfonyl-phenyl)-2H-pyrazol-3-yl]-1H-pyridazin-4-one

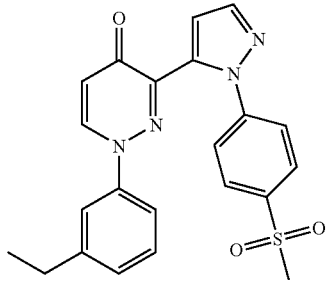

The product was obtained starting from 3-((E)-3-Dimethylamino-acryloyl)-1-(3-ethyl-phenyl)-1H-pyridazin-4-one (A-4) and 4-(methylsulfonyl)phenylhydrazine according to the method described for Example 1 in 50% yield. MS: M=421.1 (M+H)⁺

Example 22

1-(3-Ethyl-phenyl)-3-(2-pyridin-4-yl-2H-pyrazol-3-yl)-1H-pyridazin-4-one

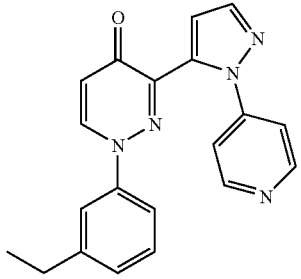

The product was obtained starting from 3-((E)-3-Dimethylamino-acryloyl)-1-(3-ethyl-phenyl)-1H-pyridazin-4-one (A-4) and 4-hydrazinopyridine according to the method described for Example 1 in 47% yield. MS: M=344.1 (M+H)⁺

Example 23

3-[2-(3-Bromo-phenyl)-2H-pyrazol-3-yl]-1-phenyl-1H-pyridazin-4-one

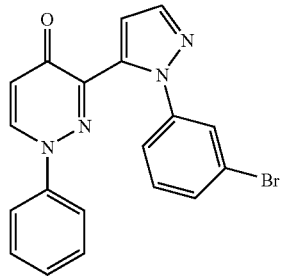

The product was obtained starting from 3-((E)-3-Dimethylamino-acryloyl)-1-phenyl-1H-pyridazin-4-one (A-1) and 3-bromophenylhydrazine according to the method described for Example 1 in 80% yield. MS: M=392.8 (M+H)+

Example 24

3-[2-(2-Methyl-pyridin-4-yl)-2H-pyrazol-3-yl]-1-phenyl-1H-pyridazin-4-one

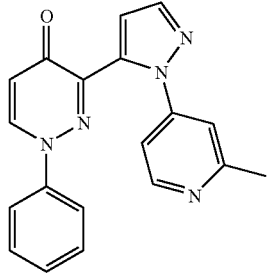

The product was obtained starting from 3-((E)-3-Dimethylamino-acryloyl)-1-phenyl-1H-pyridazin-4-one (A-1) and 4-hydrazino-2-methylpyridine according to the method described for Example 1 in 37% yield. MS: M=330.1 (M+H)+

Example 25

3-[2-(2-Chloro-pyridin-4-yl)-2H-pyrazol-3-yl]-1-phenyl-1H-pyridazin-4-one

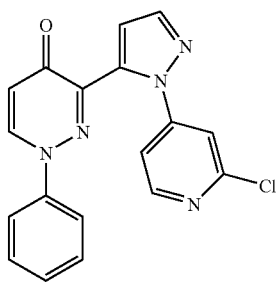

The product was obtained starting from 3-((E)-3-Dimethylamino-acryloyl)-1-phenyl-1H-pyridazin-4-one (A-1) and 2-chloro-4-hydrazinopyridine according to the method described for Example 1 in 9% yield. MS: M=350.1 (M+H)+

Example 26

3-(2-Phenyl-2H-pyrazol-3-yl)-1-(3-trifluoromethoxy-phenyl)-1H-pyridazin-4-one

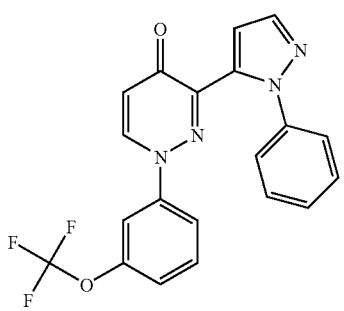

The product was obtained starting from 3-((E)-3-Dimethylamino-acryloyl)-1-(3-trifluoromethoxy-phenyl)-1H-pyridazin-4-one (A-6) and phenylhydrazine according to the method described for Example 1 in 64% yield. MS: M=399.1 (M+H)+

Example 27

3-(2-Pyridin-4-yl-2H-pyrazol-3-yl)-1-(3-trifluoromethoxy-phenyl)-1H-pyridazin-4-one

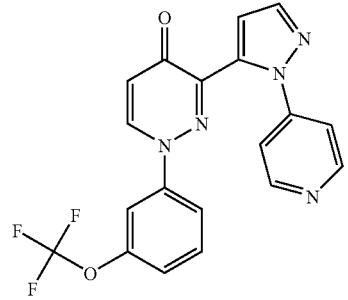

The product was obtained starting from 3-((E)-3-Dimethylamino-acryloyl)-1-(3-trifluoromethoxy-phenyl)-1H-pyridazin-4-one (A-6) and 4-hydrazinopyridine according to the method described for Example 1 in 16% yield. MS: M=400.2 (M+H)+

Example 28

3-[2-(2-Fluoro-phenyl)-2H-pyrazol-3-yl]-1-(3-trifluoromethoxy-phenyl)-1H-pyridazin-4-one

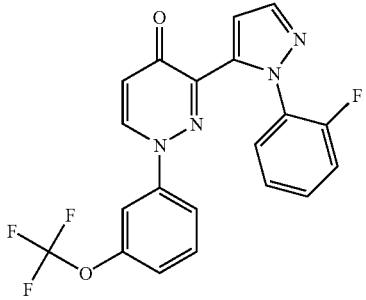

The product was obtained starting from 3-((E)-3-Dimethylamino-acryloyl)-1-(3-trifluoromethoxy-phenyl)-1H-pyridazin-4-one (A-6) and 2-fluoro-phenylhydrazine according to the method described for Example 1 in 69% yield. MS: M=417.0 (M+H)+

Example 29

3-{5-[4-Oxo-1-(3-trifluoromethoxy-phenyl)-1,4-dihydro-pyridazin-3-yl]-pyrazol-1-yl}-benzonitrile

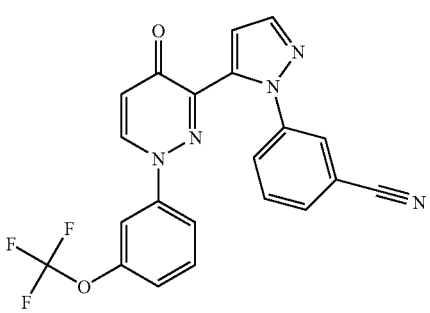

The product was obtained starting from 3-((E)-3-Dimethylamino-acryloyl)-1-(3-trifluoromethoxy-phenyl)-1H-pyridazin-4-one (A-6) and 3-hydrazino-benzonitrile in ethanol as solvent according to the method described for Example 1 in 18% yield. MS: M=424.1 (M+H)+

Example 30

1-(3-Methanesulfonyl-phenyl)-3-(2-phenyl-2H-pyrazol-3-yl)-1H-pyridazin-4-one

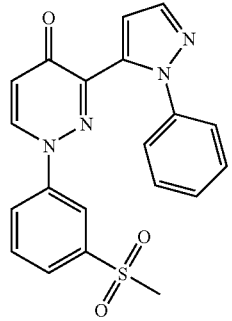

The product was obtained starting from 3-((E)-3-Dimethylamino-acryloyl)-1-(3-methansulfonyl-phenyl)-1H-pyridazin-4-one (A-7) and phenylhydrazine according to the method described for Example 1 in 47% yield. MS: M=393.0 (M+H)+

Example 31

1-Phenyl-3-[2-(3-trimethylsilanylethynyl-phenyl)-2H-pyrazol-3-yl]-1H-pyridazin-4-one

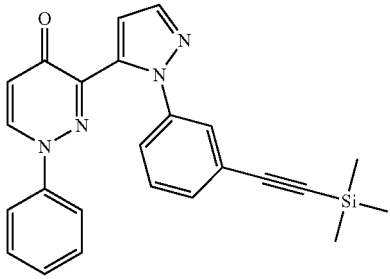

A mixture of 3-[2-(3-bromo-phenyl)-2H-pyrazol-3-yl]-1-phenyl-1H-pyridazin-4-one (example 23, 87 mg, 0.22 mmol), ethynyltrimethylsilane (47 ul, 0.33 mmol), CuI (3 mg, 0.01 mmol), (PPh$_3$)$_2$PdCl$_2$ (10 mg, 0.01 mmol), PPh$_3$ (122 mg, 0.44 mmol) and dimethylamine (596 ul, 3.3 mmol of a solution in ethanol) in DMF (0.9 ml) is heated at 120° C. for 20 minutes under microwave irradiation. After purification of the crude product by preparative HPLC 50 mg (55% yield) of the product is obtained as solid material.

MS: M=411.2 (M+H)+

Example 32

3-[2-(3-Ethynyl-phenyl)-2H-pyrazol-3-yl]-1-phenyl-1H-pyridazin-4-one

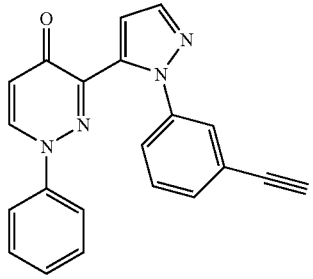

A mixture of 1-phenyl-3-[2-(3-trimethylsilanylethynyl-phenyl)-2H-pyrazol-3-yl]-1H-pyridazin-4-one (example 31, 50 mg, 0.12 mmol) is dissolved in THF (2 ml). Tetrabutylammoniumfluoride trihydrate (77 mg, 0.24 mmol) is added at 0° C. and the reaction mixture is allowed to warm up to ambient temperature within 15 minutes. Stirring is continued for another 2 hours. The reaction mixture is quenched with water and extracted with ethyl acetate. The solvent is removed and the obtained crude product is triturated with diethyl ether. The solid material is filtrated and dried to obtain 39 mg (94% yield) of the product.

MS: M=339.3 (M+H)+

Example 33

3-(2-Phenyl-2H-pyrazol-3-yl)-1-(4-trifluoromethoxy-phenyl)-1H-pyridazin-4-one

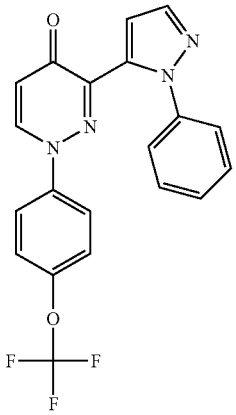

The product was obtained starting from 3-((E)-3-Dimethylamino-acryloyl)-1-(4-trifluoromethoxy-phenyl)-1H-pyridazin-4-one (A-8) and phenylhydrazine according to the method described for Example 1 in 64% yield. MS: M=399.1 (M+H)+

Example 34

3-[2-(2-Fluoro-phenyl)-2H-pyrazol-3-yl]-1-(4-trifluoromethoxy-phenyl)-1H-pyridazin-4-one

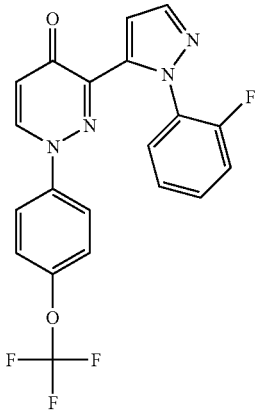

The product was obtained starting from 3-((E)-3-Dimethylamino-acryloyl)-1-(4-trifluoromethoxy-phenyl)-1H-pyridazin-4-one (A-8) and 2-fluoro-phenylhydrazine according to the method described for Example 1 in 65% yield. MS: M=417.0 (M+H)+

Example 35

3-(2-Pyridin-4-2H-pyrazol-3-yl)-1-(4-trifluoromethoxy-phenyl)-1H-pyridazin-4-one

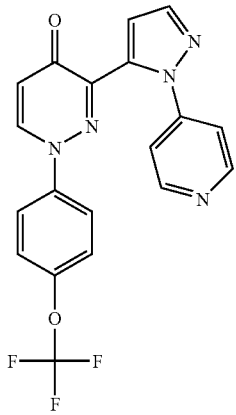

The product was obtained starting from 3-((E)-3-Dimethylamino-acryloyl)-1-(4-trifluoromethoxy-phenyl)-1H-pyridazin-4-one (A-8) and 4-hydrazinopyridine according to the method described for Example 1 in 32% yield. MS: M=400.2 (M+H)+

Example 36

3-{5-[4-Oxo-1-(4-trifluoromethoxy-phenyl)-1,4-dihydro-pyridazin-3-yl]-pyrazol-1-yl}-benzonitrile

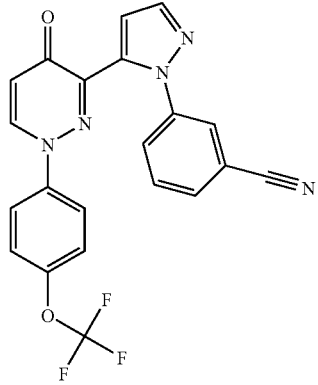

The product was obtained starting from 3-((E)-3-Dimethylamino-acryloyl)-1-(4-trifluoromethoxy-phenyl)-1H-pyridazin-4-one (A-8) and 3-hydrazino-benzonitrile in ethanol as solvent according to the method described for Example 1 in 21% yield. MS: M=424.1 (M+H)+

Example 37

3-[2-(2-Fluoro-phenyl)-2H-pyrazol-3-yl]-1-(3-trifluoromethyl-phenyl)-1H-pyridazin-4-one

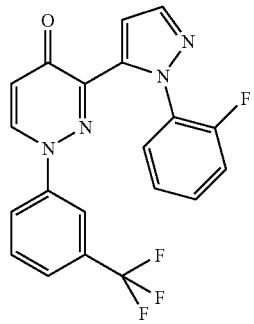

The product was obtained starting from 3-((E)-3-Dimethylamino-acryloyl)-1-(3-trifluoromethyl-phenyl)-1H-pyridazin-4-one (A-3) and 2-fluoro-phenylhydrazine according to the method described for Example 1 in 57% yield.
MS: M=401.0 (M+H)+

Example 38

3-[2-(4-Chloro-phenyl)-2H-pyrazol-3-yl]-1-phenyl-1H-pyridazin-4-one

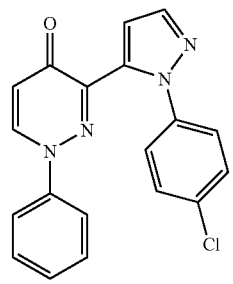

The product was obtained starting from 3-((E)-3-Dimethylamino-acryloyl)-1-phenyl-1H-pyridazin-4-one (A-1) and 4-chloro-phenylhydrazine×HCl according to the method described for Example 1 in 51% yield.

MS: M=349.2 (M+H)+

Example 39

1-Phenyl-3-(2-p-tolyl-2H-pyrazol-3-yl)-1H-pyridazin-4-one

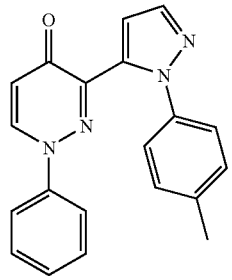

The product was obtained starting from 3-((E)-3-Dimethylamino-acryloyl)-1-phenyl-1H-pyridazin-4-one (A-1) and p-tolylhydrazine×HCl according to the method described for Example 1 in 67% yield.

MS: M=329.1 (M+H)+

Example 40

3-(2-Phenyl-2H-pyrazol-3-yl)-1-(3-trifluoromethyl-phenyl)-1H-pyridazin-4-one

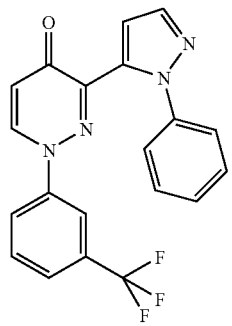

The product was obtained starting from 3-((E)-3-Dimethylamino-acryloyl)-1-(3-trifluoromethyl-phenyl)-1H-pyridazin-4-one (A-3) and phenylhydrazine according to the method described for Example 1 in 10% yield. MS: M=383.4 (M+H)+

Example 41

3-[2-(4-Methoxy-phenyl)-2H-pyrazol-3-yl]-1-(3-trifluoromethyl-phenyl)-1H-pyridazin-4-one

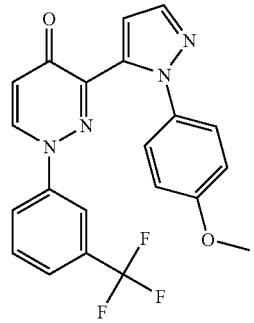

The product was obtained starting from 3-((E)-3-Dimethylamino-acryloyl)-1-(3-trifluoromethyl-phenyl)-1H-pyridazin-4-one (A-3) and 4-methoxy-phenylhydrazine×HCl according to the method described for Example 1 in 10% yield. MS: M=413.5 (M+H)+

Example 42

3-[2-(3-Chloro-phenyl)-2H-pyrazol-3-yl]-1-(3-trifluoromethyl-phenyl)-1H-pyridazin-4-one

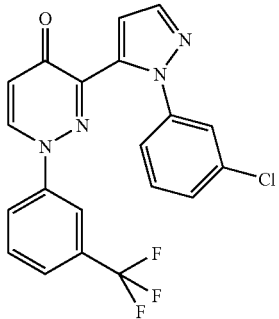

The product was obtained starting from 3-((E)-3-Dimethylamino-acryloyl)-1-(3-trifluoromethyl-phenyl)-1H-pyridazin-4-one (A-3) and 3-chloro-phenylhydrazine×HCl according to the method described for Example 1 in 51% yield. MS: M=417.4 (M+H)+

Example 43

3-{5-[4-Oxo-1-(3-trifluoromethoxy-phenyl)-1,4-dihydro-pyridazin-3-yl]-pyrazol-1-yl}-benzamide

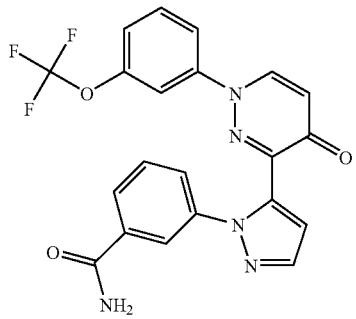

3-((E)-3-Dimethylamino-acryloyl)-1-(3-trifluoromethoxy-phenyl)-1H-pyridazin-4-one (A-6) and 3-hydrazino-benzamide (2 eq) were dissolved in a sealed tube in acetic acid and irradiated in MW at 120° C. for 15 min. The solvent of the reaction mixture was removed and the crude product was purified by preparative HPLC yielding the desired product.

MS: M=442.9 (M+H)+

Example 44

3-(2-p-Tolyl-2H-pyrazol-3-yl)-1-(3-trifluoromethoxy-phenyl)-1H-pyridazin-4-one

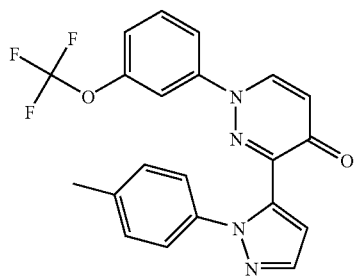

Reaction of 3-((E)-3-Dimethylamino-acryloyl)-1-(3-trifluoromethoxy-phenyl)-1H-pyridazin-4-one (A-6) and p-tolyl-hydrazine according to example 43 gave the desired product. MS: M=413.3 (M+H)+

Example 45

4-{5-[4-Oxo-1-(3-trifluoromethoxy-phenyl)-1,4-dihydro-pyridazin-3-yl]-pyrazol-1-yl}-benzoic acid

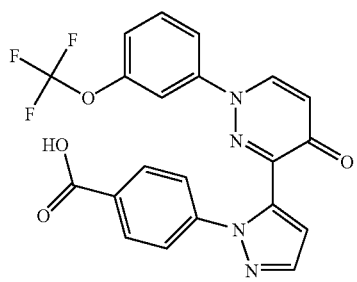

Reaction of 3-((E)-3-Dimethylamino-acryloyl)-1-(3-trifluoromethoxy-phenyl)-1H-pyridazin-4-one (A-6) and 4-hydrazino-benzoic acid according to example 43 gave the desired product. MS: M=442.9 (M)+

Example 46

4-{5-[4-Oxo-1-(3-trifluoromethoxy-phenyl)-1,4-dihydro-pyridazin-3-yl]-pyrazol-1-yl}-benzenesulfonamide

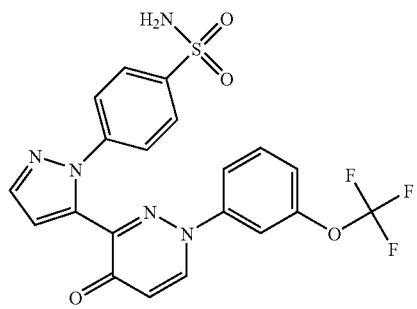

Reaction of 3-((E)-3-Dimethylamino-acryloyl)-1-(3-trifluoromethoxy-phenyl)-1H-pyridazin-4-one (A-6) and 4-hydrazino-benzenesulfonamide according to example 43 gave the desired product. MS: M=478.0 (M+H)+

Example 47

3-[2-(4-Chloro-phenyl)-2H-pyrazol-3-yl]-1-(3-trifluoromethoxy-phenyl)-1H-pyridazin-4-one

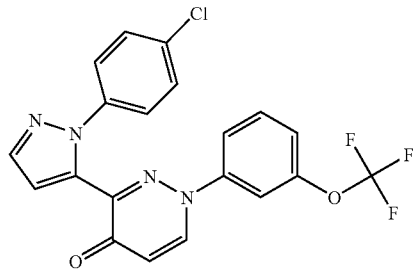

Reaction of 3-((E)-3-Dimethylamino-acryloyl)-1-(3-trifluoromethoxy-phenyl)-1H-pyridazin-4-one (A-6) and (4-chloro-phenyl)-hydrazine according to example 43 gave the desired product. MS: M=432.9 (M+H)+

Example 48

3-[2-(3-Chloro-phenyl)-2H-pyrazol-3-yl]-1-(3-trifluoromethoxy-phenyl)-1H-pyridazin-4-one

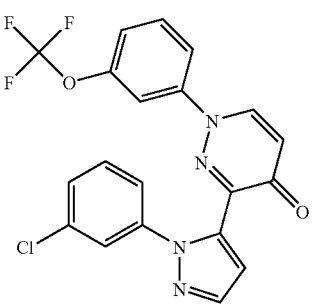

Reaction of 3-((E)-3-Dimethylamino-acryloyl)-1-(3-trifluoromethoxy-phenyl)-1H-pyridazin-4-one (A-6) and (3-chloro-phenyl)-hydrazine according to example 43 gave the desired product. MS: M=433.2 (M+H)+

Example 49

3-[2-(4-Fluoro-phenyl)-2H-pyrazol-3-yl]-1-(3-trifluoromethoxy-phenyl)-1H-pyridazin-4-one

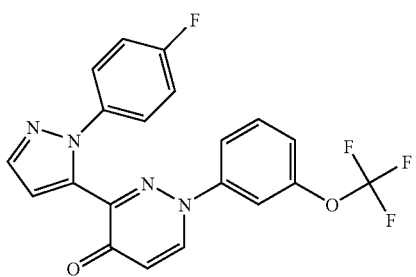

Reaction of 3-((E)-3-dimethylamino-acryloyl)-1-(3-trifluoromethoxy-phenyl)-1H-pyridazin-4-one (A-6) and (4-fluoro-phenyl)-hydrazine according to example 43 gave the desired product. MS: M=416.9 (M+H)+

Example 50

3-[2-(2,3-Dimethyl-phenyl)-2H-pyrazol-3-yl]-1-(3-trifluoromethoxy-phenyl)-1H-pyridazin-4-one

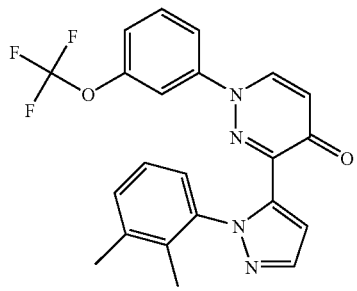

Reaction of 3-((E)-3-dimethylamino-acryloyl)-1-(3-trifluoromethoxy-phenyl)-1H-pyridazin-4-one (A-6) and (2,3-dimethyl-phenyl)-hydrazine according to example 43 gave the desired product. MS: M=425.8 (M)+

Example 51

3-[2-(3-Chloro-2-methyl-phenyl)-2H-pyrazol-3-yl]-1-(3-trifluoromethoxy-phenyl)-1H-pyridazin-4-one

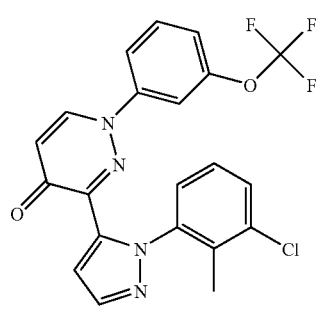

Reaction of 3-((E)-3-dimethylamino-acryloyl)-1-(3-trifluoromethoxy-phenyl)-1H-pyridazin-4-one (A-6) and (3-chloro-2-methyl-phenyl)-hydrazine according to example 43 gave the desired product. MS: M=447.3 (M+H)+

Example 52

3-[2-(2-Bromo-4-fluoro-phenyl)-2H-pyrazol-3-yl]-1-(3-trifluoromethoxy-phenyl)-1H-pyridazin-4-one

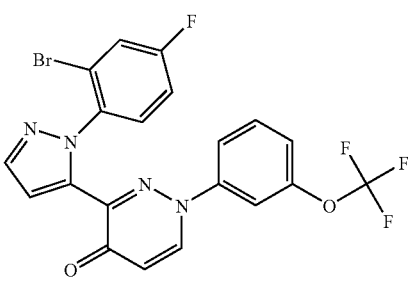

Reaction of 3-((E)-3-dimethylamino-acryloyl)-1-(3-trifluoromethoxy-phenyl)-1H-pyridazin-4-one (A-6) and (2-bromo-4-fluoro-phenyl)-hydrazine according to example 43 gave the desired product. MS: M=496.9 (M+H)+

Example 53

3-[2-(3-Fluoro-2-methyl-phenyl)-2H-pyrazol-3-yl]-1-(3-trifluoromethoxy-phenyl)-1H-pyridazin-4-one

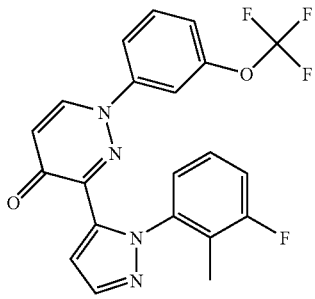

Reaction of 3-((E)-3-dimethylamino-acryloyl)-1-(3-trifluoromethoxy-phenyl)-1H-pyridazin-4-one (A-6) and (3-fluoro-2-methyl-phenyl)-hydrazine according to example 43 gave the desired product. MS: M=431.3 (M+H)+

Example 54

3-[2-(3-Fluoro-4-methyl-phenyl)-2H-pyrazol-3-yl]-1-(3-trifluoromethoxy-phenyl)-1H-pyridazin-4-one

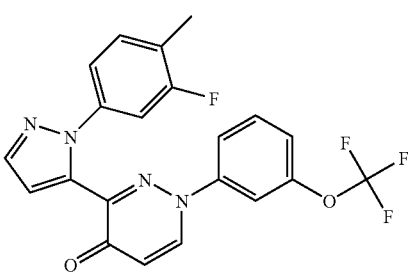

Reaction of 3-((E)-3-dimethylamino-acryloyl)-1-(3-trifluoromethoxy-phenyl)-1H-pyridazin-4-one (A-6) and (3-fluoro-4-methyl-phenyl)-hydrazine according to example 43 gave the desired product. MS: M=431.0 (M+H)+

Example 55

3-{5-[4-Oxo-1-(3-trifluoromethoxy-phenyl)-1,4-dihydro-pyridazin-3-yl]-pyrazol-1-yl}-benzoic acid methyl ester

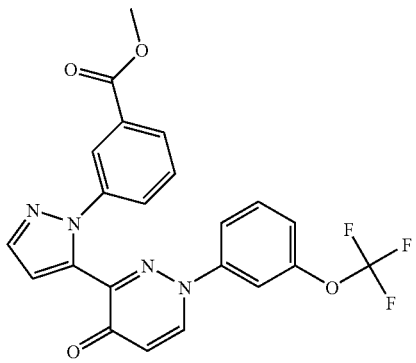

Reaction of 3-((E)-3-dimethylamino-acryloyl)-1-(3-trifluoromethoxy-phenyl)-1H-pyridazin-4-one (A-6) and 3-hydrazino-benzoic acid methyl ester according to example 43 gave the desired product. MS: M=456.9 (M+H)+

Example 56

2-{5-[4-Oxo-1-(3-trifluoromethoxy-phenyl)-1,4-dihydro-pyridazin-3-yl]-pyrazol-1-yl}-isonicotinic acid ethyl ester

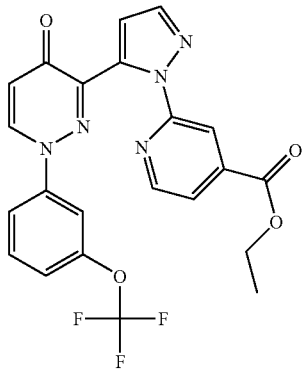

Reaction of 3-((E)-3-dimethylamino-acryloyl)-1-(3-trifluoromethoxy-phenyl)-1H-pyridazin-4-one (A-6) and 2-hydrazino-isonicotinic acid ethyl ester (described in Anales Real Soc. Espan. Fis. Quire. (Madrid) Ser. B (1963), 59(3), 179-84) according to example 43 gave the desired product. MS: M=454.0 (M+H)+

Example 57

3-(2-Pyridin-2-yl-2H-pyrazol-3-yl)-1-(3-trifluoromethoxy-phenyl)-1H-pyridazin-4-one

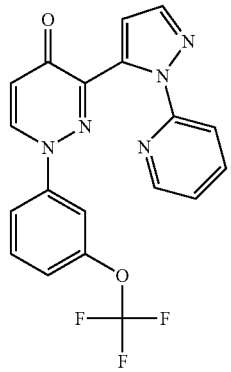

Reaction of 3-((E)-3-dimethylamino-acryloyl)-1-(3-trifluoromethoxy-phenyl)-1H-pyridazin-4-one (A-6) and pyridin-2-yl-hydrazine according to example 43 gave the desired product. MS: M=472.0 (M+H)+

Example 58

3-[2-(5,6,7,8-Tetrahydro-isoquinolin-1-yl)-2H-pyrazol-3-yl]-1-(3-trifluoromethoxy-phenyl)-1H-pyridazin-4-one

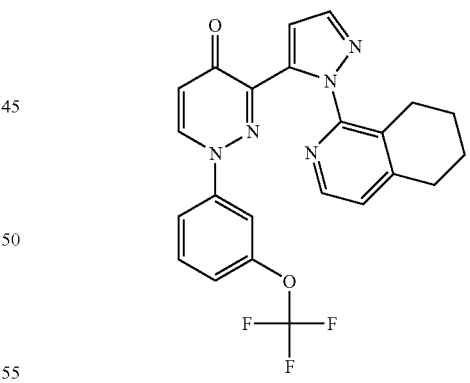

Reaction of 3-((E)-3-dimethylamino-acryloyl)-1-(3-trifluoromethoxy-phenyl)-1H-pyridazin-4-one (A-6) and (5,6,7,8-tetrahydro-isoquinolin-1-yl)-hydrazine (prepared from the commercial 5,6,7,8-tetrahydro-isoquinolin-1-ylamine using sodium nitrite and tin(II) chloride in analogy to that described in J. Med. Chem. 2003, 46, 4676-4686) according to example 43 gave the desired product. MS: M=400.0 (M+H)+.

Example 59

3-{5-[1-(3-Methanesulfonyl-phenyl)-4-oxo-1,4-dihydro-pyridazin-3-yl]-pyrazol-1-yl}-benzamide

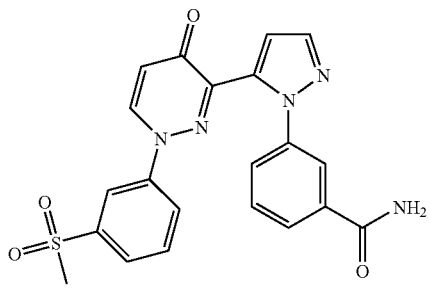

Reaction of 3-((E)-3-dimethylamino-acryloyl)-1-(3-methansulfonyl-phenyl)-1H-pyridazin-4-one (A-7) and 3-hydrazino-benzamide according to example 43 gave the desired product. MS: M=436.7 (M+H)$^+$

Example 60

1-(3-Methanesulfonyl-phenyl)-3-(2-p-tolyl-2H-pyrazol-3-yl)-1H-pyridazin-4-one

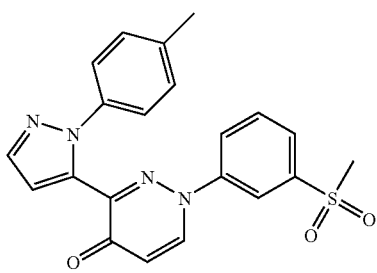

Reaction of 3-((E)-3-dimethylamino-acryloyl)-1-(3-methansulfonyl-phenyl)-1H-pyridazin-4-one (A-7) and p-tolyl-hydrazine according to example 43 gave the desired product. MS: M=407.3 (M+H)$^+$

Example 61

4-{5-[1-(3-Methanesulfonyl-phenyl)-4-oxo-1,4-dihydro-pyridazin-3-yl]-pyrazol-1-yl}-benzoic acid

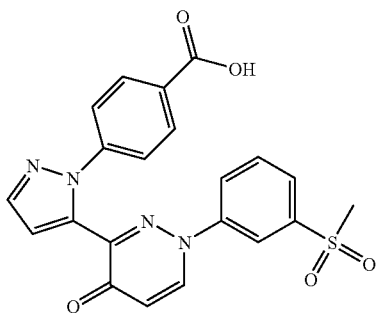

Reaction of 3-((E)-3-dimethylamino-acryloyl)-1-(3-methansulfonyl-phenyl)-1H-pyridazin-4-one (A-7) and 4-hydrazino-benzoic acid according to example 43 gave the desired product. MS: M=437.0 (M+H)$^+$

Example 62

4-{5-[1-(3-Methanesulfonyl-phenyl)-4-oxo-1,4-dihydro-pyridazin-3-yl]-pyrazol-1-yl}-benzenesulfonamide

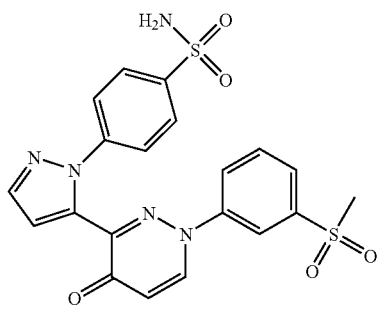

Reaction of 3-((E)-3-dimethylamino-acryloyl)-1-(3-methansulfonyl-phenyl)-1H-pyridazin-4-one (A-7) and 4-hydrazino-benzenesulfonamide according to example 43 gave the desired product. MS: M=471.9 (M+H)$^+$

Example 63

3-[2-(4-Chloro-phenyl)-2H-pyrazol-3-yl]-1-(3-methanesulfonyl-phenyl)-1H-pyridazin-4-one

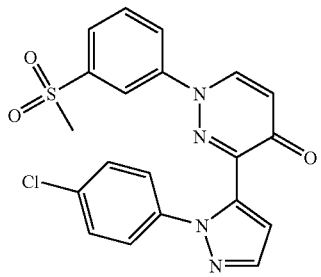

Reaction of 3-((E)-3-dimethylamino-acryloyl)-1-(3-methansulfonyl-phenyl)-1H-pyridazin-4-one (A-7) and (4-chloro-phenyl)-hydrazine according to example 43 gave the desired product. MS: M=426.6 (M+H)$^+$

Example 64

3-[2-(3-Chloro-phenyl)-2H-pyrazol-3-yl]-1-(3-methanesulfonyl-phenyl)-1H-pyridazin-4-one

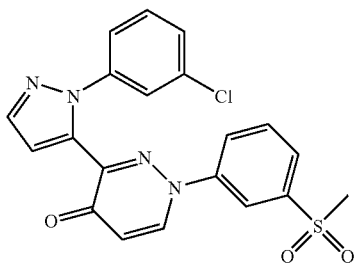

Reaction of 3-((E)-3-dimethylamino-acryloyl)-1-(3-methansulfonyl-phenyl)-1H-pyridazin-4-one (A-7) and (3-chloro-phenyl)-hydrazine according to example 43 gave the desired product. MS: M=427.1 (M+H)+

Example 65

2-{5-[1-(3-Methanesulfonyl-phenyl)-4-oxo-1,4-dihydro-pyridazin-3-yl]-pyrazol-1-yl}-benzoic acid

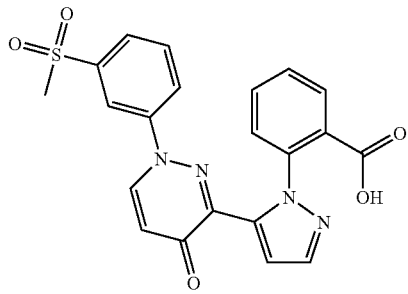

Reaction of 3-((E)-3-dimethylamino-acryloyl)-1-(3-methansulfonyl-phenyl)-1H-pyridazin-4-one (A-7) and 2-hydrazino-benzoic acid according to example 43 gave the desired product. MS: M=437.0 (M+H)+

Example 66

3-[2-(4-Fluoro-phenyl)-2H-pyrazol-3-yl]-1-(3-methanesulfonyl-phenyl)-1H-pyridazin-4-one

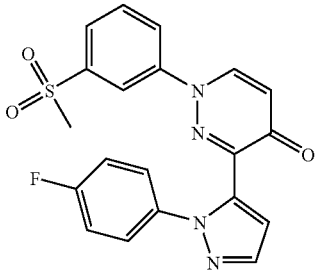

Reaction of 3-((E)-3-dimethylamino-acryloyl)-1-(3-methansulfonyl-phenyl)-1H-pyridazin-4-one (A-7) and (4-fluorophenyl)-hydrazine according to example 43 gave the desired product. MS: M=411.2 (M+H)+

Example 67

3-[2-(2,3-Dimethyl-phenyl)-2H-pyrazol-3-yl]-1-(3-methanesulfonyl-phenyl)-1H-pyridazin-4-one

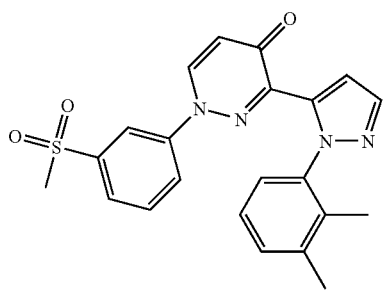

Reaction of 3-((E)-3-dimethylamino-acryloyl)-1-(3-methansulfonyl-phenyl)-1H-pyridazin-4-one (A-7) and (2,3-dimethyl-phenyl)-hydrazine according to example 43 gave the desired product. MS: M=421.3 (M+H)+

Example 68

3-[2-(3-Chloro-2-methyl-phenyl)-2H-pyrazol-3-yl]-1-(3-methanesulfonyl-phenyl)-1H-pyridazin-4-one

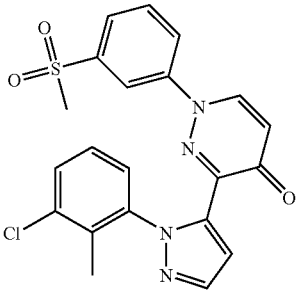

Reaction of 3-((E)-3-dimethylamino-acryloyl)-1-(3-methansulfonyl-phenyl)-1H-pyridazin-4-one (A-7) and (3-chloro-2-methyl-phenyl)-hydrazine according to example 43 gave the desired product. MS: M=441.0 (M)+

Example 69

3-[2-(3-Fluoro-2-methyl-phenyl)-2H-pyrazol-3-yl]-1-(3-methanesulfonyl-phenyl)-1H-pyridazin-4-one

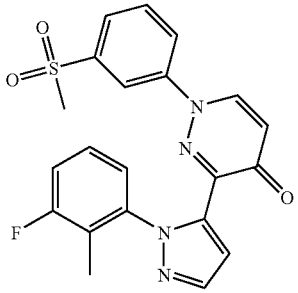

Reaction of 3-((E)-3-dimethylamino-acryloyl)-1-(3-methansulfonyl-phenyl)-1H-pyridazin-4-one (A-7) and (3-fluoro-2-methyl-phenyl)-hydrazine according to example 43 gave the desired product. MS: M=425.2 (M+H)+

Example 70

3-[2-(3-Fluoro-4-methyl-phenyl)-2H-pyrazol-3-yl]-1-(3-methanesulfonyl-phenyl)-1H-pyridazin-4-one

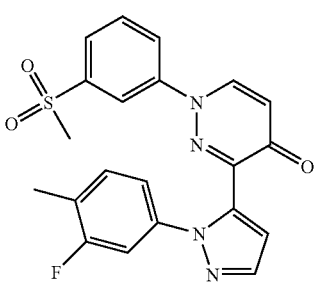

Reaction of 3-((E)-3-dimethylamino-acryloyl)-1-(3-methansulfonyl-phenyl)-1H-pyridazin-4-one (A-7) and (3-fluoro-4-methyl-phenyl)-hydrazine according to example 43 gave the desired product. MS: M=425.3 (M+H)+

Example 71

3-{5-[1-(3-Methanesulfonyl-phenyl)-4-oxo-1,4-dihydro-pyridazin-3-yl]-pyrazol-1-yl}-benzoic acid methyl ester

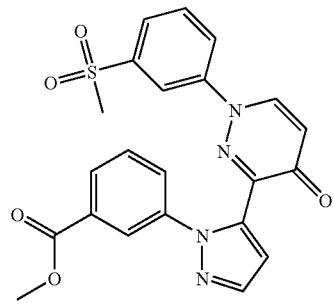

Reaction of 3-((E)-3-dimethylamino-acryloyl)-1-(3-methansulfonyl-phenyl)-1H-pyridazin-4-one (A-7) and 3-hydrazino-benzoic acid methyl ester according to example 43 gave the desired product. MS: M=451.0 (M+H)+

Example 72

1-(3-Methanesulfonyl-phenyl)-3-[2-(5,6,7,8-tetrahydro-isoquinolin-1-yl)-2H-pyrazol-3-yl]-1H-pyridazin-4-one

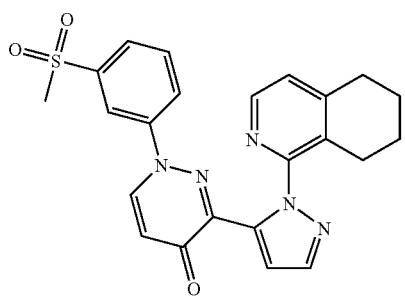

Reaction of 3-((E)-3-dimethylamino-acryloyl)-1-(3-methansulfonyl-phenyl)-1H-pyridazin-4-one (A-7) and (5,6,7,8-tetrahydro-isoquinolin-1-yl)-hydrazine (prepared from the commercial 5,6,7,8-tetrahydro-isoquinolin-1-ylamine using sodium nitrite and tin(II) chloride in analogy to that described in J. Med. Chem. 2003, 46, 4676-4686) according to example 43 gave the desired product. MS: M=448.0 (M+H)+

Example 73

2-{5-[1-(3-Methanesulfonyl-phenyl)-4-oxo-1,4-dihydro-pyridazin-3-yl]-pyrazol-1-yl}-4,6-dimethyl-nicotinonitrile

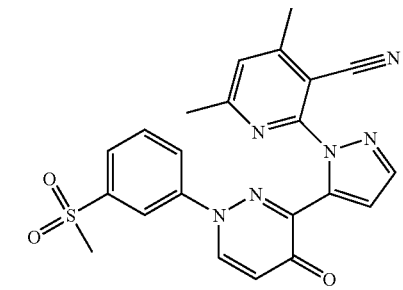

Reaction of 3-((E)-3-dimethylamino-acryloyl)-1-(3-methansulfonyl-phenyl)-1H-pyridazin-4-one (A-7) and 2-hydrazino-4,6-dimethyl-nicotinonitrile according to example 43 gave the desired product. MS: M=447.0 (M+H)+

Example 74

2-{5-[1-(3-Methanesulfonyl-phenyl)-4-oxo-1,4-dihydro-pyridazin-3-yl]-pyrazol-1-yl}-isonicotinic acid ethyl ester

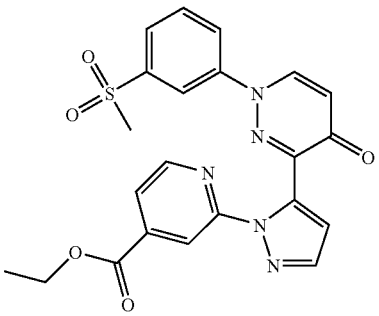

Reaction of 3-((E)-3-dimethylamino-acryloyl)-1-(3-methansulfonyl-phenyl)-1H-pyridazin-4-one (A-7) and 2-hydrazino-isonicotinic acid ethyl ester according to example 43 gave the desired product. MS: M=466.0 (M+H)+

Example 75

1-(3-Methanesulfonyl-phenyl)-3-(2-pyridin-2-yl-2H-pyrazol-3-yl)-1H-pyridazin-4-one

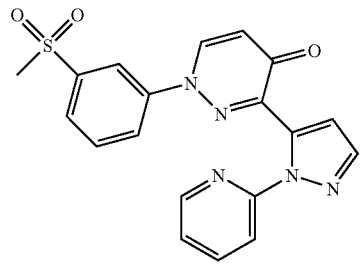

Reaction of 3-((E)-3-dimethylamino-acryloyl)-1-(3-methansulfonyl-phenyl)-1H-pyridazin-4-one (A-7) and pyridin-2-yl-hydrazine according to example 43 gave the desired product. MS: M=393.9 (M+H)+

Example 76

4-{5-[4-Oxo-1-(3-trifluoromethoxy-phenyl)-1,4-dihydro-pyridazin-3-yl]-pyrazol-1-yl}-benzonitrile

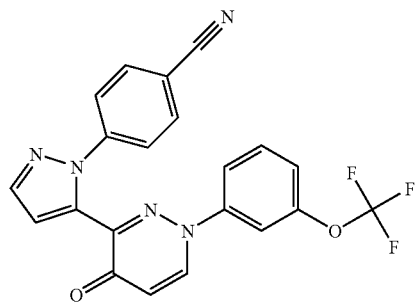

Reaction of 3-((E)-3-dimethylamino-acryloyl)-1-(3-trifluoromethoxy-phenyl)-1H-pyridazin-4-one (A-6) and 4-hydrazino-benzonitrile according to example 43 gave the desired product. MS: M=424.2 (M+H)+

Example 77

3-[2-(2,4-Difluoro-phenyl)-2H-pyrazol-3-yl]-1-(3-trifluoromethoxy-phenyl)-1H-pyridazin-4-one

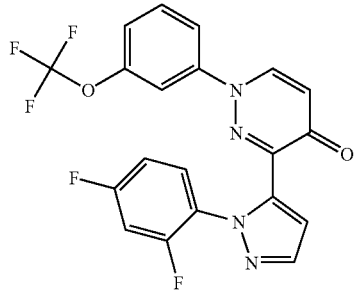

Reaction of 3-((E)-3-dimethylamino-acryloyl)-1-(3-trifluoromethoxy-phenyl)-1H-pyridazin-4-one (A-6) and (2,4-difluoro-phenyl)-hydrazine according to example 43 gave the desired product. MS: M=435.1 (M+H)+

Example 78

3-{2-[4-(6-Oxo-1,4,5,6-tetrahydro-pyridazin-3-yl)-phenyl]-2H-pyrazol-3-yl}-1-(3-trifluoromethoxy-phenyl)-1H-pyridazin-4-one

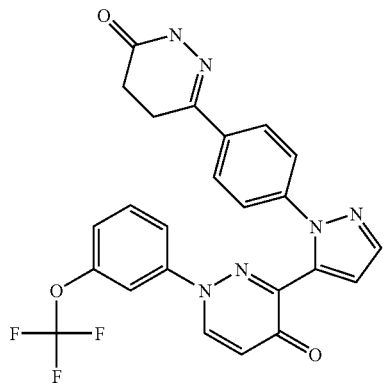

Reaction of 3-((E)-3-dimethylamino-acryloyl)-1-(3-trifluoromethoxy-phenyl)-1H-pyridazin-4-one (A-6) and 6-(4-hydrazino-phenyl)-4,5-dihydro-2H-pyridazin-3-one (described in Journal of Medicinal Chemistry (1990), 33(10), 2870-5) according to example 43 gave the desired product. MS: M=495.0 (M+H)+

Example 79

3-[2-(2,3-Dihydro-benzo[1,4]dioxin-6-yl)-2H-pyrazol-3-yl]-1-(3-trifluoromethoxy-phenyl)-1H-pyridazin-4-one

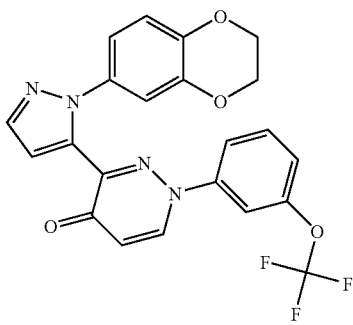

Reaction of 3-((E)-3-dimethylamino-acryloyl)-1-(3-trifluoromethoxy-phenyl)-1H-pyridazin-4-one (A-6) and (2,3-dihydro-benzo[1,4]dioxin-6-yl)-hydrazine according to example 43 gave the desired product. MS: M=456.9 (M+H)+

Example 80

3-(2-Naphthalen-1-yl-2H-pyrazol-3-yl)-1-(3-trifluoromethoxy-phenyl)-1H-pyridazin-4-one

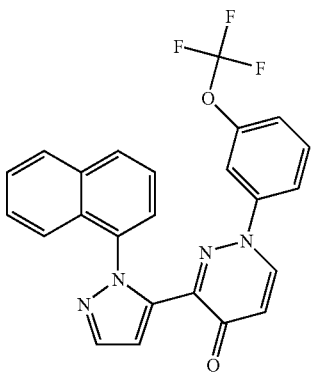

Reaction of 3-((E)-3-dimethylamino-acryloyl)-1-(3-trifluoromethoxy-phenyl)-1H-pyridazin-4-one (A-6) and naphthalen-1-yl-hydrazine according to example 43 gave the desired product. MS: M=449.0 (M+H)$^+$

Example 81

3-[2-(3-Fluoro-phenyl)-2H-pyrazol-3-yl]-1-(3-trifluoromethoxy-phenyl)-1H-pyridazin-4-one

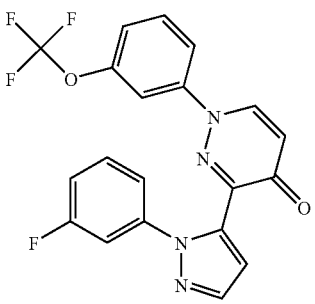

Reaction of 3-((E)-3-dimethylamino-acryloyl)-1-(3-trifluoromethoxy-phenyl)-1H-pyridazin-4-one (A-6) and (3-fluoro-phenyl)-hydrazine according to example 43 gave the desired product. MS: M=416.9 (M+H)$^+$

Example 82

3-[2-(2,5-Difluoro-phenyl)-2H-pyrazol-3-yl]-1-(3-trifluoromethoxy-phenyl)-1H-pyridazin-4-one

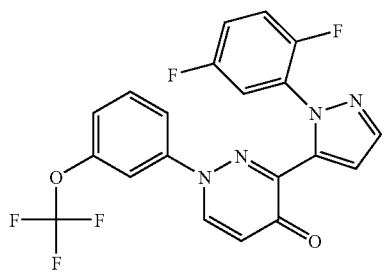

Reaction of 3-((E)-3-dimethylamino-acryloyl)-1-(3-trifluoromethoxy-phenyl)-1H-pyridazin-4-one (A-6) and (2,5-difluoro-phenyl)-hydrazine according to example 43 gave the desired product. MS: M=435.0 (M+H)$^+$

Example 83

3-[2-(4-Isopropyl-phenyl)-2H-pyrazol-3-yl]-1-(3-trifluoromethoxy-phenyl)-1H-pyridazin-4-one

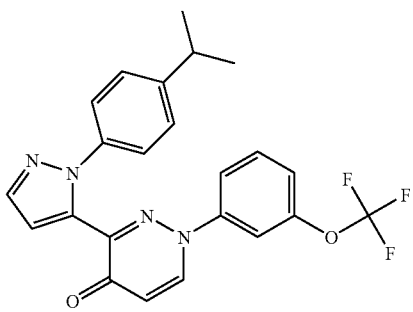

Reaction of 3-((E)-3-dimethylamino-acryloyl)-1-(3-trifluoromethoxy-phenyl)-1H-pyridazin-4-one (A-6) and (4-isopropyl-phenyl)-hydrazine according to example 43 gave the desired product. MS: M=441.0 (M+H)$^+$

Example 84

3-[2-(2,3-Dihydro-benzo[1,4]dioxin-6-yl)-2H-pyrazol-3-yl]-1-(3-methanesulfonyl-phenyl)-1H-pyridazin-4-one

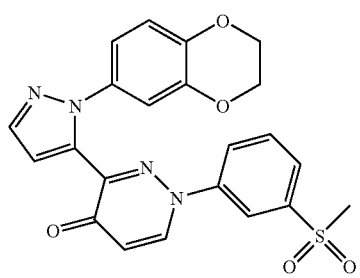

Reaction of 3-((E)-3-dimethylamino-acryloyl)-1-(3-methansulfonyl-phenyl)-1H-pyridazin-4-one (A-7) and (2,3-dihydro-benzo[1,4]dioxin-6-yl)-hydrazine according to example 43 gave the desired product. MS: M=451 (M+H)$^+$

Example 85

1-(3-Methanesulfonyl-phenyl)-3-(2-naphthalen-1-yl-2H-pyrazol-3-yl)-1H-pyridazin-4-one

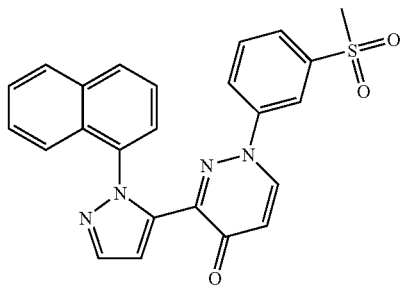

3-((E)-3-dimethylamino-acryloyl)-1-(3-methansulfonyl-phenyl)-1H-pyridazin-4-one (A-7) and naphthalen-1-yl-hydrazine (2 eq) were dissolved in a sealed tube in DMF with 2 drops acetic acid and irradiated in MW at 120° C. for 15 min. The solvent of the reaction mixture was removed and the crude product was purified by preparative HPLC yielding the desired product.
MS: M=442.9 (M+H)$^+$

Example 86

3-[2-(3-Fluoro-phenyl)-2H-pyrazol-3-yl]-1-(3-methanesulfonyl-phenyl)-1H-pyridazin-4-one

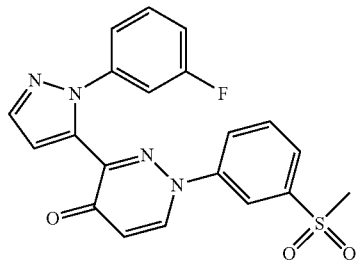

Reaction of 3-((E)-3-dimethylamino-acryloyl)-1-(3-methansulfonyl-phenyl)-1H-pyridazin-4-one (A-7) and (3-fluoro-phenyl)-hydrazine according to example 43 gave the desired product. MS: M=410.6 (M+H)$^+$

Example 87

3-[2-(2,5-Difluoro-phenyl)-2H-pyrazol-3-yl]-1-(3-methanesulfonyl-phenyl)-1H-pyridazin-4-one

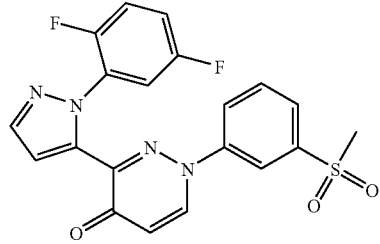

Reaction of 3-((E)-3-dimethylamino-acryloyl)-1-(3-methansulfonyl-phenyl)-1H-pyridazin-4-one (A-7) and (2,5-difluoro-phenyl)-hydrazine according to example 43 gave the desired product. MS: M=428.6 (M+H)$^+$

Example 88

3-[2-(4-Isopropyl-phenyl)-2H-pyrazol-3-yl]-1-(3-methanesulfonyl-phenyl)-1H-pyridazin-4-one

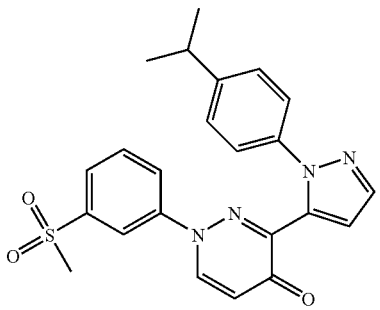

Reaction of 3-((E)-3-dimethylamino-acryloyl)-1-(3-methansulfonyl-phenyl)-1H-pyridazin-4-one (A-7) and (4-isopropyl-phenyl)-hydrazine according to example 85 gave the desired product. MS: M=435.3 (M+H)$^+$

Example 89

3-(4-Ethyl-2-phenyl-2H-pyrazol-3-yl)-1-(3-methanesulfonyl-phenyl)-1H-pyridazin-4-one

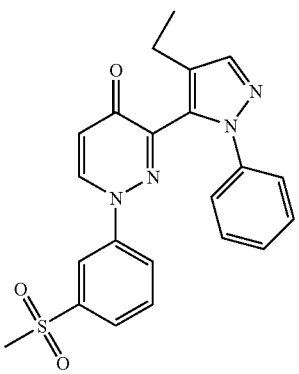

a) Preparation of 2-(3-methanesulfonyl-phenylazo)-3-oxo-butyric acid ethyl ester.

A solution of sodium nitrite (1.22 g, 1.05 eq.) in water (6 ml) was added dropwise to a solution of 3-methylsulphonylaniline hydrochloride in 1N HCl (60 ml) at 0° and stirred at this temperature for 30 mins. A solution of ethylacetoacetate (2.74 g, 2.66 ml) in ethanolic (6 ml) water (100 ml) was then added at this temperature, followed by ammonium acetate to pH 6 and stirring at this temperature for 3 h. Dilution with EtOAc, separation of phases and concentration of the organic phase gave the crude product (5.33 g) which was directly used for the next stage. MS: M=313.1 (M+H)$^+$ b) 1-(3-Methanesulfonyl-phenyl)-4-oxo-1,4-dihydro-pyridazine-3-carboxylic acid ethyl ester.

A solution of 2-(3-methanesulfonyl-phenylazo)-3-oxo-butyric acid ethyl ester (5 g) in dry DMF was treated with N,N-dimethylformamide-dimethyl acetal (2.098 g, 1.1 eq) and the mixture stirred at 90° for 2 h. Further addition of N,N-dimethylformamide-dimethyl acetal (0.3 eq) and stirring at 90° for 1 h followed by concentration and purification by silica gel chromatography (gradient elution: heptane/ethyl acetate, then dichloromethane/methanol) gave 2.4 g (47%) of the title compound. MS: M=323.0 (M+H)+ c) 1-(3-Methanesulfonyl-phenyl)-4-oxo-1,4-dihydro-pyridazine-3-carboxylic acid methoxy-methyl-amide.

To a solution of N,O-dimethylhydroxylamine hydrochloride (3 eq, 1.725 g) in dry dichloromethane (60 ml) at −5°, was slowly added Me₃Al (2M solution in toluene, 3 eq) and the mixture stirred at room temperature for 30 min, then cooled to −5° followed by the slow addition of a solution of 1-(3-methanesulfonyl-phenyl)-4-oxo-1,4-dihydro-pyridazine-3-carboxylic acid ethyl ester (1.9 g) in dry dichloromethane (30 ml). The mixture was warmed and stirred at room temperature for 1 h then portioned between dichloromethane and 1N NOH and after layer separation and concentration, purified by silica gel chromatography using dichloromethane/methanol to give the product (0.92 g, 46%). MS: M=338.1 (M+H)+ d) 3-Butyryl-1-(3-methanesulfonyl-phenyl)-1H-pyridazin-4-one.

To a solution of 1-(3-methanesulfonyl-phenyl)-4-oxo-1,4-dihydro-pyridazine-3-carboxylic acid methoxy-methyl-amide (0.35 g) in dry THF at −10°, was added n-propyl magnesium bromide (2.0M in THF, 1.1 eq.) and after 1 h at this temperature the mixture was partitioned between EtOAc and water, the organic phase evaporated and partially purified by silica gel chromatography (dichloromethane/methanol) and used directly for the next step (0.115 g). MS: M=321.1 (M+H)+ e) 3-{2-[1-Dimethylamino-meth-(E)-ylidene]-butyryl}-1-(3-methanesulfonyl-phenyl)-1H-pyridazin-4-one.

A solution of 3-butyryl-1-(3-methanesulfonyl-phenyl)-1H-pyridazin-4-one (0.96 g) in dry DMF (3 ml) was treated with N,N-dimethylformamide-dimethyl acetal (1.1 eq) and the mixture stirred at 120° for 16 h. Concentration to 1.5 ml and further addition of N,N-dimethylformamide-dimethyl acetal (1.35 eq) and stirring at 120° for 15 h followed by concentration and purification by silica gel chromatography (dichloromethane/methanol) gave the crude product (0.37 mg) which was used directly for the next stage.

MS: M=376.2 (M+H)+ f) 3-(4-Ethyl-2-phenyl-2H-pyrazol-3-yl)-1-(3-methanesulfonyl-phenyl)-1H-pyridazin-4-one.

3-{2-[1-Dimethylamino-meth-(E)-ylidene]-butyryl}-1-(3-methanesulfonyl-phenyl)-1H-pyridazin-4-one and phenyl hydrazine (1.5 eq) were dissolved in a sealed tube in DMF with 2 drops acetic acid and irradiated in MW at 120° C. for 15 min. The solvent of the reaction mixture was removed and the crude product was purified by preparative HPLC yielding the desired product. MS: M=421.2 (M+H)+

Example 90

1-(3-Methanesulfonyl-phenyl)-3-[2-(2-methyl-pyridin-4-yl)-2H-pyrazol-3-yl]-1H-pyridazin-4-one

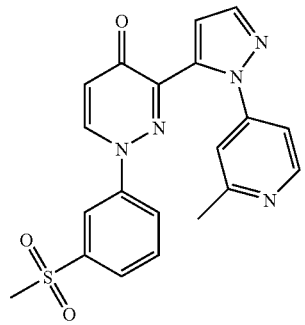

3-((E)-3-Dimethylamino-acryloyl)-1-(3-methansulfonyl-phenyl)-1H-pyridazin-4-one (A-7) (0.05 g; 0.144 mmol) and 4-hydrazino-2-methylpyridine (0.03 g; 0.187 mmol) are dissolved in a sealed tube in dimethylformamide (0.6 ml) and irradiated at 180° C. for 10 min. The solvent of the reaction mixture is removed and the crude product is purified by preparative HPLC yielding 0.02 g (34.1%) of the final product. MS: M=408.4 (M+H)+

Example 91

1-(3-Difluoromethoxy-phenyl)-3-(2-pyridin-2-yl-2H-pyrazol-3-yl)-1H-pyridazin-4-one

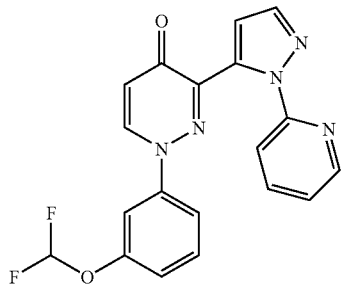

1-(3-Difluoromethoxy-phenyl)-3-((E)-3-dimethylamino-acryloyl)-1H-pyridazin-4-one (A-10) (0.05 g; 0.149 mmol) and 2-hydrazinopyridine (0.021 g; 0.194 mmol) are dissolved in a sealed tube in ethanol (0.6 ml) with catalytic amounts of HCl and irradiated at 160° C. for 5 min. The solvent of the reaction mixture is removed and the crude product is purified by preparative HPLC yielding 0.023 g (40.5%) of the final product. MS: M=382.2 (M+H)+

Example 92

3-(2-Benzo[1,3]dioxol-5-yl-2H-pyrazol-3-yl)-1-(3-methanesulfonyl-phenyl)-1H-pyridazin-4-one

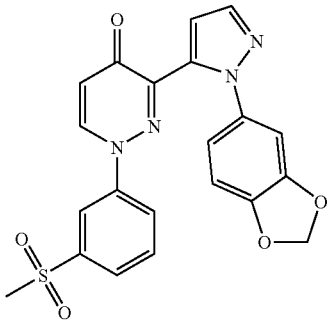

The product was obtained starting from 3-((E)-3-Dimethylamino-acryloyl)-1-(3-methansulfonyl-phenyl)-1H-pyridazin-4-one (A-7) and benzo[1,3]dioxol-5-yl-hydrazine (prepared from the corresponding amino derivative using sodium nitrite and tin(II) chloride as described in J. Med. Chem. 2003, 46, 4676-4686) according to the method described for Example 91 in 10% yield. MS: M=437.3 (M+H)+

Example 93

3-(2-Benzo[1,3]dioxol-5-yl-2H-pyrazol-3-yl)-1-(3-difluoromethoxy-phenyl)-1H-pyridazin-4-one

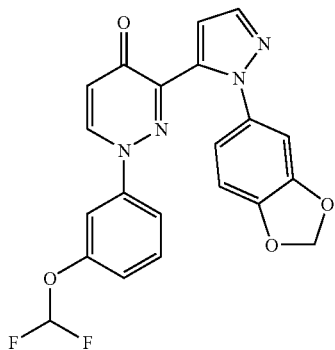

The product was obtained starting from 1-(3-Difluoromethoxy-phenyl)-3-((E)-3-dimethylamino-acryloyl)-1H-pyridazin-4-one (A-10) and benzo[1,3]dioxol-5-yl-hydrazine (prepared from the corresponding amino derivative using sodium nitrite and tin(II) chloride as described in J. Med. Chem. 2003, 46, 4676-4686) according to the method described for Example 91 in 16% yield. MS: M=425.2 (M+H)$^+$

Example 94

3-{5-[1-(3-Methanesulfonyl-phenyl)-4-oxo-1,4-dihydro-pyridazin-3-yl]-pyrazol-1-yl}-benzonitrile

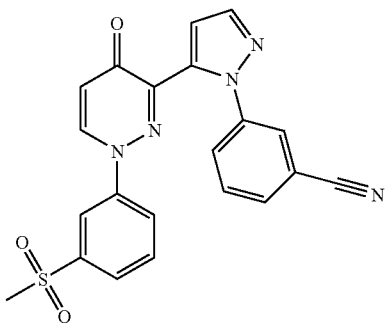

The product was obtained starting from 3-((E)-3-Dimethylamino-acryloyl)-1-(3-methansulfonyl-phenyl)-1H-pyridazin-4-one (A-7) and 3-hydrazino-benzonitrile according to the method described for Example 91 in 61% yield. MS: M=418.3 (M+H)$^+$

Example 95

3-{2-[4-(2-Fluoro-4-methoxy-phenyl)-thiazol-2-yl]-2H-pyrazol-3-yl}-1-(3-methanesulfonyl-phenyl)-1H-pyridazin-4-one

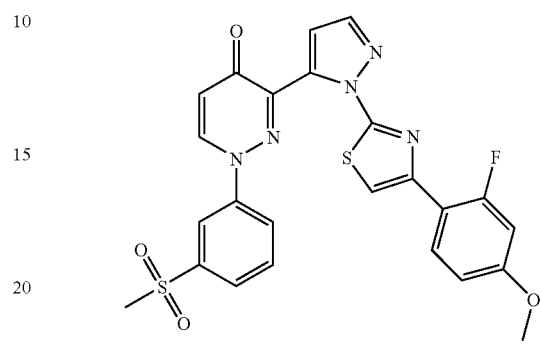

The product was obtained starting from 3-((E)-3-Dimethylamino-acryloyl)-1-(3-methansulfonyl-phenyl)-1H-pyridazin-4-one (A-7) and [4-(2-fluoro-4-methoxy-phenyl)-thiazol-2-yl]-hydrazine according to the method described for Example 91 in 41% yield.

MS: M=524.13 (M+H)$^+$

Example 96

1-(3-Methanesulfonyl-phenyl)-3-{2-[4-(2-methoxy-phenyl)-thiazol-2-yl]-2H-pyrazol-3-yl}-1H-pyridazin-4-one

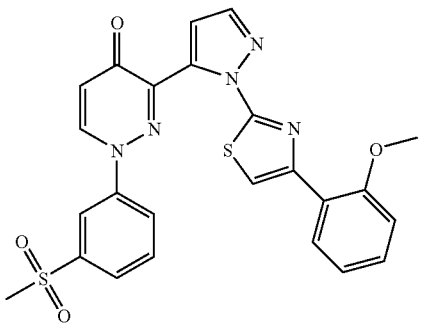

The product was obtained starting from 3-((E)-3-Dimethylamino-acryloyl)-1-(3-methansulfonyl-phenyl)-1H-pyridazin-4-one (A-7) and [4-(2-methoxy-phenyl)-thiazol-2-yl]-hydrazine according to the method described for Example 91 in 21% yield. MS: M=506.2.13 (M+H)$^+$

Example 97

1-(3-Difluoromethoxy-phenyl)-3-[2-(2,3-dihydro-benzo[1,4]dioxin-6-yl)-2H-pyrazol-3-yl]-1H-pyridazin-4-one

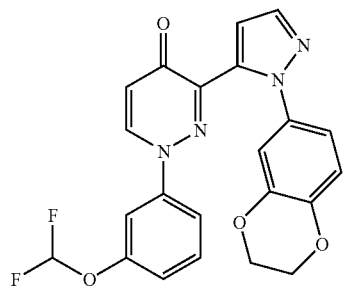

The product was obtained starting from 1-(3-Difluoromethoxy-phenyl)-3-((E)-3-dimethylamino-acryloyl)-1H-pyridazin-4-one (A-10) and (2,3-dihydro-benzo[1,4]dioxin-6-yl)-hydrazine according to the method described for Example 91 in 52% yield. MS: M=439.1 (M+H)$^+$

Example 98

1-(3-Difluoromethoxy-phenyl)-3-[2-(3-fluoro-phenyl)-2H-pyrazol-3-yl]-1H-pyridazin-4-one

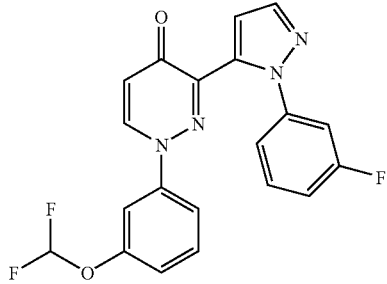

The product was obtained starting from 1-(3-Difluoromethoxy-phenyl)-3-((E)-3-dimethylamino-acryloyl)-1H-pyridazin-4-one (A-10) and (3-fluoro-phenyl)-hydrazine (prepared from the corresponding amino derivative using sodium nitrite and tin(II) chloride as described in J. Med. Chem. 2003, 46, 4676-4686) according to the method described for Example 91 in 37% yield. MS: M=399.1 (M+H)$^+$

Example 99

1-(4-Difluoromethoxy-phenyl)-3-[2-(2,3-dihydro-benzo[1,4]dioxin-6-yl)-2H-pyrazol-3-yl]-1H-pyridazin-4-one

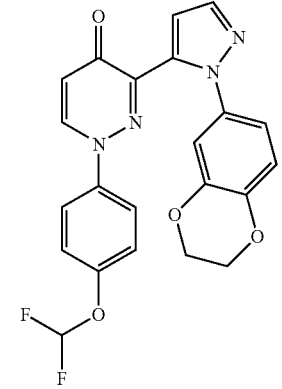

The product was obtained starting from 1-(4-Difluoromethoxy-phenyl)-3-((E)-3-dimethylamino-acryloyl)-1H-pyridazin-4-one (A-9) and (2,3-dihydro-benzo[1,4]dioxin-6-yl)-hydrazine according to the method described for Example 91 in 33% yield. MS: M=439.1 (M+H)$^+$

Example 100

1-(4-Difluoromethoxy-phenyl)-3-[2-(3-fluoro-phenyl)-2H-pyrazol-3-yl]-1H-pyridazin-4-one

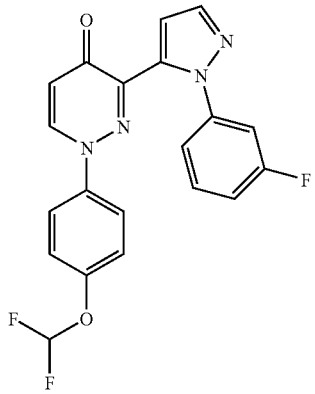

The product was obtained starting from 1-(4-Difluoromethoxy-phenyl)-3-((E)-3-dimethylamino-acryloyl)-1H-pyridazin-4-one (A-9) and (3-fluoro-phenyl)-hydrazine (prepared from the corresponding amino derivative using sodium nitrite and tin(II) chloride as described in J. Med. Chem.

2003, 46, 4676-4686) according to the method described for Example 91 in 62% yield. MS: M=399.1 (M+H)⁺

Example 101

1-(2,2-Difluoro-benzo[1,3]dioxol-5-yl)-3-[2-(2,3-dihydro-benzo[1,4]dioxin-6-yl)-2H-pyrazol-3-yl]-1H-pyridazin-4-one

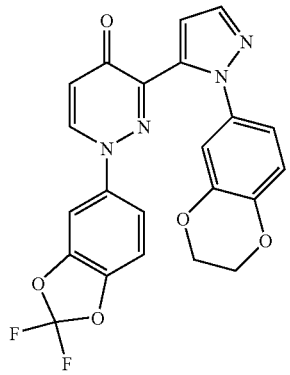

The product was obtained starting from 1-(2,2-Difluoro-benzo[1,3]dioxol-5-yl)-3-((E)-3-dimethylamino-acryloyl)-1H-pyridazin-4-one (A-11) and (2,3-dihydro-benzo[1,4]dioxin-6-yl)-hydrazine according to the method described for Example 91 in 22% yield.

MS: M=453.2 (M+H)⁺

Example 102

3-{3-[2-(3-Fluoro-phenyl)-2H-pyrazol-3-yl]-4-oxo-4H-pyridazin-1-yl}-N,N-dimethyl-benzenesulfonamide

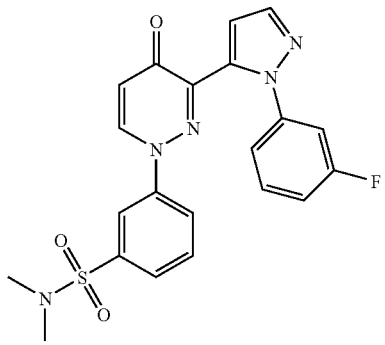

The product was obtained starting from 3-[3-((E)-3-Dimethylamino-acryloyl)-4-oxo-4H-pyridazin-1-yl]-N,N-dimethyl-benzenesulfonamide (A-12) and 3-fluoro-phenylhydrazine according to the method described for example 91. MS: M=440.2 (M+H)⁺

Example 103

1-(2,2-Difluoro-benzo[1,3]dioxol-5-yl)-3-[2-(3-fluoro-phenyl)-2H-pyrazol-3-yl]-1H-pyridazin-4-one

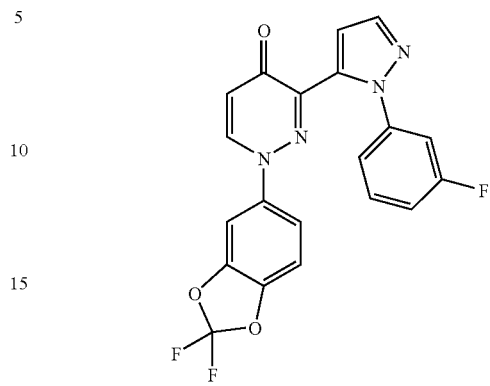

The product was obtained starting from 1-(2,2-Difluoro-benzo[1,3]dioxol-5-yl)-3-((E)-3-dimethylamino-acryloyl)-1H-pyridazin-4-one (A-11) and 3-fluoro-phenylhydrazine according to the method described for example 91. MS: M=413.2 (M+H)⁺

Example 104

3-[2-(3,4-Difluoro-phenyl)-2H-pyrazol-3-yl]-1-(3-methanesulfonyl-phenyl)-1H-pyridazin-4-one

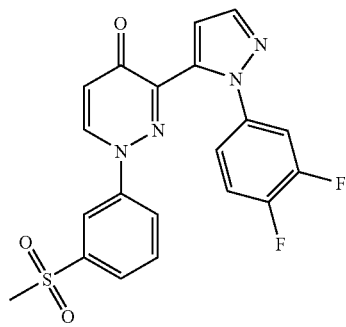

The product was obtained starting from 3-((E)-3-Dimethylamino-acryloyl)-1-(3-methansulfonyl-phenyl)-1H-pyridazin-4-one (A-7) and 3,4-difluoro-phenylhydrazine according to the method described for example 91. MS: M=429.2 (M+H)⁺

Example 105

3-[2-(2,4-Difluoro-phenyl)-2H-pyrazol-3-yl]-1-(3-methanesulfonyl-phenyl)-1H-pyridazin-4-one

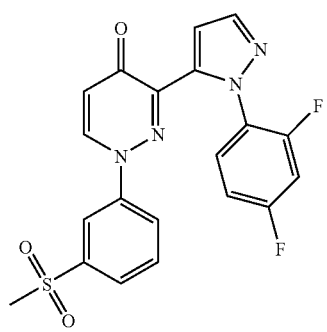

The product was obtained starting from 3-((E)-3-Dimethylamino-acryloyl)-1-(3-methansulfonyl-phenyl)-1H-pyridazin-4-one (A-7) and 2,4-difluoro-phenylhydrazine according to the method described for example 43. MS: M=429.1 (M+H)+

Example 106

3-(2-Benzo[1,3]dioxol-4-yl-2H-pyrazol-3-yl)-1-(3-methanesulfonyl-phenyl)-1H-pyridazin-4-one

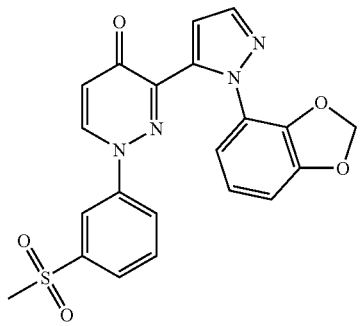

The product was obtained starting from 3-((E)-3-Dimethylamino-acryloyl)-1-(3-methansulfonyl-phenyl)-1H-pyridazin-4-one (A-7) and benzo[1,3]dioxol-4-yl-hydrazine (prepared from the corresponding amino derivative using sodium nitrite and tin(II) chloride as described in J. Med. Chem. 2003, 46, 4676-4686) according to the method described for example 91. MS: M=437.3 (M+H)+

Example 107

3-[3-(2-Benzo[1,3]dioxol-5-yl-2H-pyrazol-3-yl)-4-oxo-4H-pyridazin-1-yl]-N,N-dimethyl-benzenesulfonamide

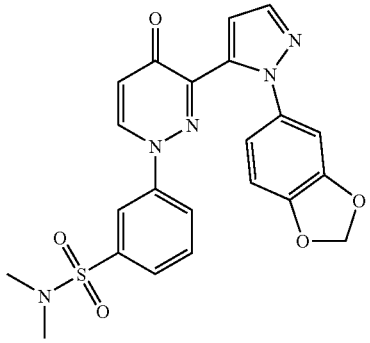

The product was obtained starting from 3-[3-((E)-3-Dimethylamino-acryloyl)-4-oxo-4H-pyridazin-1-yl]-N,N-dimethyl-benzenesulfonamide (A-12) and benzo[1,3]dioxol-5-yl-hydrazine (prepared from the corresponding amino derivative using sodium nitrite and tin(II) chloride as described in J. Med. Chem. 2003, 46, 4676-4686) according to the method described for example 91. MS: M=466.2 (M+H)+

Example 108

3-{3-[2-(3-Cyano-phenyl)-2H-pyrazol-3-yl]-4-oxo-4H-pyridazin-1-yl}-N,N-dimethyl-benzenesulfonamide

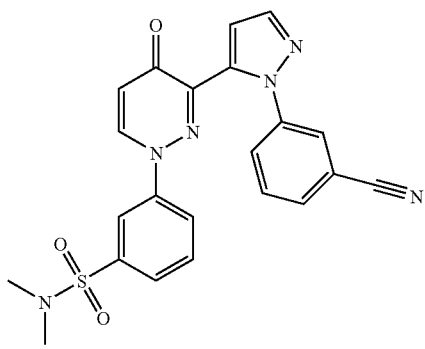

The product was obtained starting from 3-[3-((E)-3-Dimethylamino-acryloyl)-4-oxo-4H-pyridazin-1-yl]-N,N-dimethyl-benzenesulfonamide (A-12) and 3-hydrazino-benzonitrile in ethanol as solvent according to the method described for example 91. MS: M=447.3 (M+H)+

Example 109

3-(2-Benzo[1,3]dioxol-5-yl-2H-pyrazol-3-yl)-1-(3-fluoro-phenyl)-1H-pyridazin-4-one

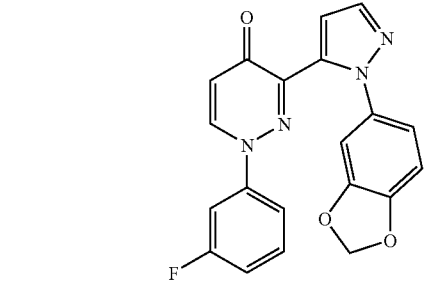

The product was obtained starting from 3-((E)-3-Dimethylamino-acryloyl)-1-(3-fluoro-phenyl)-1H-pyridazin-4-one (A-13) and benzo[1,3]dioxol-5-yl-hydrazine (prepared from the corresponding amino derivative using sodium nitrite and tin(II) chloride as described in J. Med. Chem. 2003, 46, 4676-4686) according to the method described for example 91.

MS: M=377.2 (M+H)+

Example 110

1-(3-Fluoro-phenyl)-3-[2-(3-fluoro-phenyl)-2H-pyrazol-3-yl]-1H-pyridazin-4-one

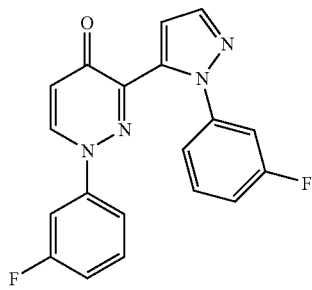

The product was obtained starting from 3-((E)-3-Dimethylamino-acryloyl)-1-(3-fluoro-phenyl)-1H-pyridazin-4-one (A-13) and 3-fluoro-phenylhydrazine according to the method described for example 91. MS: M=351.3 (M+H)$^+$

Example 111

3-{5-[1-(3-Fluoro-phenyl)-4-oxo-1,4-dihydro-pyridazin-3-yl]-pyrazol-1-yl}-benzonitrile

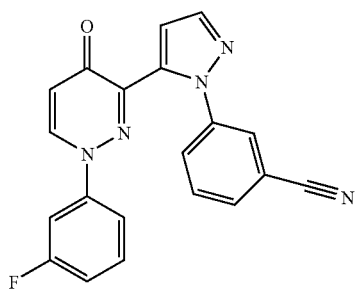

The product was obtained starting from 3-((E)-3-Dimethylamino-acryloyl)-1-(3-fluoro-phenyl)-1H-pyridazin-4-one (A-13) and 3-hydrazino-benzonitrile in ethanol as solvent according to the method described for example 91. MS: M=358.1 (M+H)$^+$

Example 112

1-Benzo[1,3]dioxol-4-yl-3-(2-benzo[1,3]dioxol-5-yl-2H-pyrazol-3-yl)-1H-pyridazin-4-one

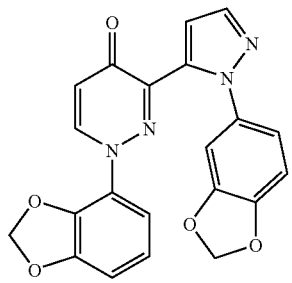

The product was obtained starting from 1-Benzo[1,3]dioxol-4-yl-3-((E)-3-dimethylamino-acryloyl)-1H-pyridazin-4-one (A-14) and benzo[1,3]dioxol-5-yl-hydrazine (prepared from the corresponding amino derivative using sodium nitrite and tin(II) chloride as described in J. Med. Chem. 2003, 46, 4676-4686) according to the method described for example 91. MS: M=403.2 (M+H)$^+$

Example 113

1-Benzo[1,3]dioxol-4-yl-3-[2-(3-fluoro-phenyl)-2H-pyrazol-3-yl]-1H-pyridazin-4-one

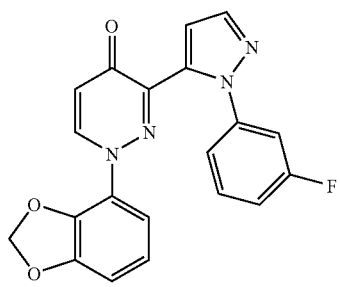

The product was obtained starting from 1-Benzo[1,3]dioxol-4-yl-3-((E)-3-dimethylamino-acryloyl)-1H-pyridazin-4-one (A-14) and 3-fluoro-phenylhydrazine according to the method described for example 91. MS: M=377.2 (M+H)$^+$

Example 114

3-[5-(1-Benzo[1,3]dioxol-4-yl-4-oxo-1,4-dihydro-pyridazin-3-yl)-pyrazol-1-yl]-benzonitrile

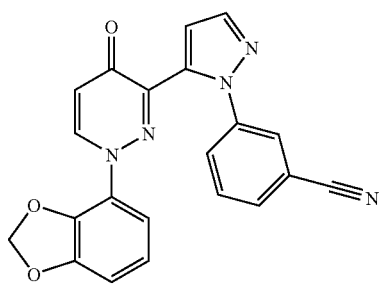

The product was obtained starting from 1-Benzo[1,3]dioxol-4-yl-3-((E)-3-dimethylamino-acryloyl)-1H-pyridazin-4-one (A-14) and 3-hydrazino-benzonitrile in ethanol as solvent according to the method described for example 91. MS: M=384.2 (M+H)$^+$

Example 115

3-[2-(6-Fluoro-quinolin-4-yl)-2H-pyrazol-3-yl]-1-(3-methanesulfonyl-phenyl)-1H-pyridazin-4-one

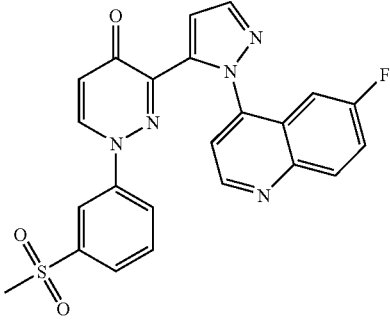

The product was obtained starting from 3-((E)-3-Dimethylamino-acryloyl)-1-(3-methansulfonyl-phenyl)-1H-pyridazin-4-one (A-7) and (6-fluoro-quinolin-4-yl)-hydrazine according to the method described for example 91. MS: M=462.3 (M+H)+

Example 116

1-(3-Difluoromethoxy-phenyl)-3-[2-(2,5-difluoro-phenyl)-2H-pyrazol-3-yl]-1H-pyridazin-4-one

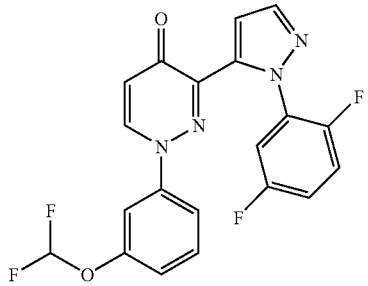

The product was obtained starting from 1-(3-Difluoromethoxy-phenyl)-3-((E)-3-dimethylamino-acryloyl)-1H-pyridazin-4-one (A-10) and 2,5-difluoro-phenylhydrazine according to the method described for example 91. MS: M=417.2 (M+H)+

Example 117

1-(2,2-Difluoro-benzo[1,3]dioxol-5-yl)-3-[2-(2,5-difluoro-phenyl)-2H-pyrazol-3-yl]-1H-pyridazin-4-one

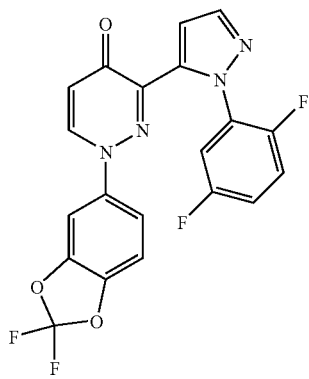

The product was obtained starting from 1-(2,2-Difluoro-benzo[1,3]dioxol-5-yl)-3-((E)-3-dimethylamino-acryloyl)-1H-pyridazin-4-one (A-11) and 2,5-difluoro-phenylhydrazine according to the method described for example 91. MS: M=431.2 (M+H)+

Example 118

3-{3-[2-(2,5-Difluoro-phenyl)-2H-pyrazol-3-yl]-4-oxo-4H-pyridazin-1-yl}-N,N-dimethyl-benzenesulfonamide

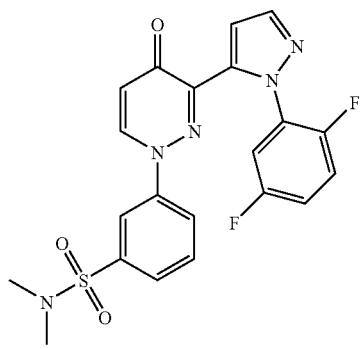

The product was obtained starting from 3-[3-((E)-3-Dimethylamino-acryloyl)-4-oxo-4H-pyridazin-1-yl]-N,N-dimethyl-benzenesulfonamide (A-12) and 2,5-difluoro-phenylhydrazine according to the method described for example 91. MS: M=458.2 (M+H)+

Example 119

3-{5-[1-(2,2-Difluoro-benzo[1,3]dioxol-5-yl)-4-oxo-1,4-dihydro-pyridazin-3-yl]-pyrazol-1-yl}-benzonitrile

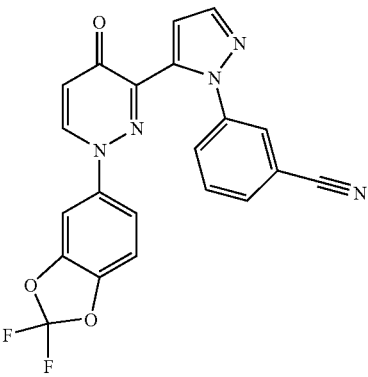

The product was obtained starting from 1-(2,2-Difluoro-benzo[1,3]dioxol-5-yl)-3-((E)-3-dimethylamino-acryloyl)-1H-pyridazin-4-one (A-11) and 3-hydrazino-benzonitrile in ethanol as solvent according to the method described for example 91. MS: M=420.2 (M+H)+

Example 120

3-[2-(2,2-Difluoro-benzo[1,3]dioxol-4-yl)-2H-pyrazol-3-yl]-1-(3-methanesulfonyl-phenyl)-1H-pyridazin-4-one

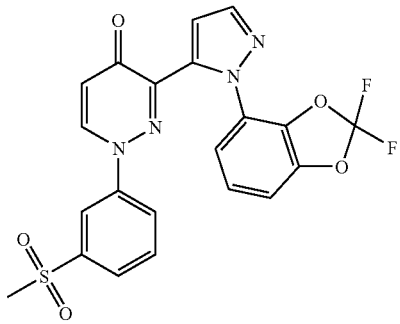

The product was obtained starting from 3-((E)-3-Dimethylamino-acryloyl)-1-(3-methansulfonyl-phenyl)-1H-pyridazin-4-one (A-7) and 2,2-difluoro-benzo[1,3]dioxol-4-yl-hydrazine (prepared from the corresponding amino derivative using sodium nitrite and tin(II) chloride as described in J. Med. Chem. 2003, 46, 4676-4686) according to the method described for example 91. MS: M=473.2 (M+H)$^+$

Example 121

1-(3-Methanesulfonyl-phenyl)-3-(2-thiazol-2-yl-2H-pyrazol-3-yl)-1H-pyridazin-4-one

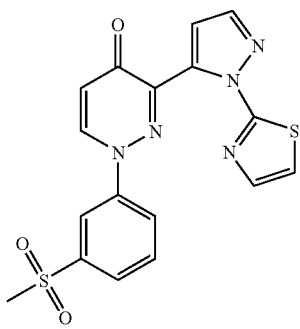

The product was obtained starting from 3-((E)-3-Dimethylamino-acryloyl)-1-(3-methansulfonyl-phenyl)-1H-pyridazin-4-one (A-7) and thiazol-2-yl-hydrazine according to the method described for example 91. MS: M=400.1 (M+H)$^+$

Example 122

1-(3-Methanesulfonyl-phenyl)-3-[2-(3-trifluoromethoxy-phenyl)-2H-pyrazol-3-yl]-1H-pyridazin-4-one

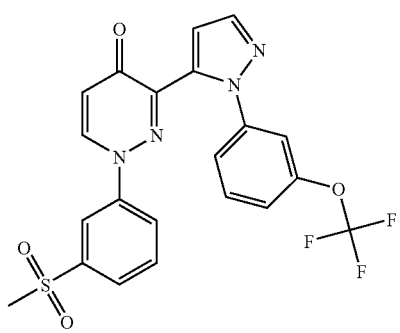

The product was obtained starting from 3-((E)-3-Dimethylamino-acryloyl)-1-(3-methansulfonyl-phenyl)-1H-pyridazin-4-one (A-7) and 3-trifluoromethoxy-phenylhydrazine according to the method described for example 43. MS: M=477.2 (M+H)$^+$

Example 123

3-[2-(2,3-Dihydro-benzo[1,4]dioxin-5-yl)-2H-pyrazol-3-yl]-1-(3-methanesulfonyl-phenyl)-1H-pyridazin-4-one

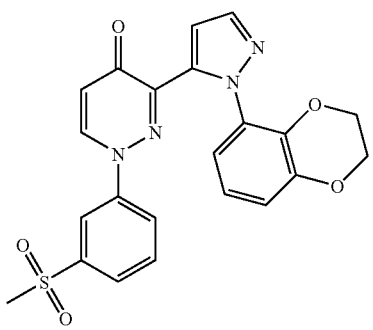

The product was obtained starting from 3-((E)-3-Dimethylamino-acryloyl)-1-(3-methansulfonyl-phenyl)-1H-pyridazin-4-one (A-7) and (2,3-dihydro-benzo[1,4]dioxin-5-yl)-hydrazine according to the method described for example 43. MS: M=451.2 (M+H)$^+$

Example 124

3-[2-(2-Methyl-pyridin-4-yl)-2H-pyrazol-3-yl]-1-(3-trifluoromethoxy-phenyl)-1H-pyridazin-4-one

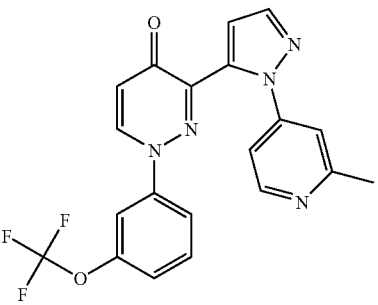

The product was obtained starting from 3-((E)-3-Dimethylamino-acryloyl)-1-(3-trifluoromethoxy-phenyl)-1H-pyridazin-4-one (A-6) and 4-hydrazino-2-methylpyridine according to the method described for example 43. MS: M=414.2 (M+H)$^+$

Example 125

3-(4-Ethyl-2-phenyl-2H-pyrazol-3-yl)-1-(3-trifluoromethoxy-phenyl)-1H-pyridazin-4-one

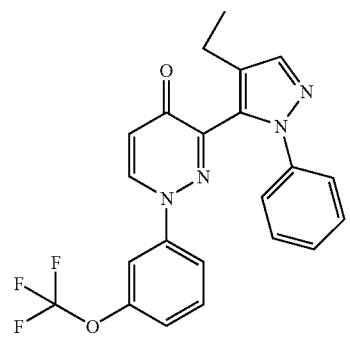

The product was obtained starting from 3-trifluoromethoxyaniline instead of 3-methylsulphonylaniline applying the synthesis sequence described for example 89. MS: M=427.2 (M+H)$^+$

Example 126

3-[2-(3-Methanesulfonyl-phenyl)-2H-pyrazol-3-yl]-1-(3-trifluoromethoxy-phenyl)-1H-pyridazin-4-one

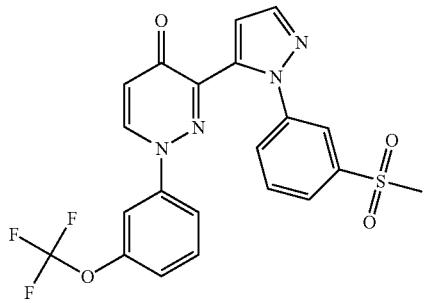

The product was obtained starting from 3-((E)-3-Dimethylamino-acryloyl)-1-(3-trifluoromethoxy-phenyl)-1H-pyridazin-4-one (A-6) and (3-methanesulfonyl-phenyl)-hydrazine according to the method described for example 43. MS: M=477.2 (M+H)$^+$

Example 127

1-(2,2-Difluoro-benzo[1,3]dioxol-4-yl)-3-[2-(3-fluoro-phenyl)-2H-pyrazol-3-yl]-1H-pyridazin-4-one

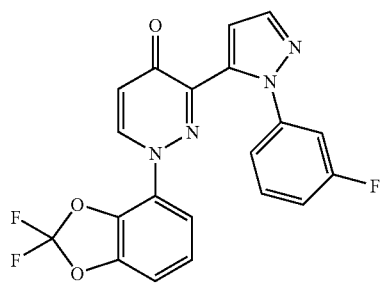

The product was obtained starting from 1-(2,2-Difluoro-benzo[1,3]dioxol-4-yl)-3-((E)-3-dimethylamino-acryloyl)-1H-pyridazin-4-one (A-15) and 3-fluoro-phenylhydrazine according to the method described for example 91. MS: M=413.2 (M+H)$^+$

Example 128

1-(2,2-Difluoro-benzo[1,3]dioxol-4-yl)-3-[2-(2,5-difluoro-phenyl)-2H-pyrazol-3-yl]-1H-pyridazin-4-one

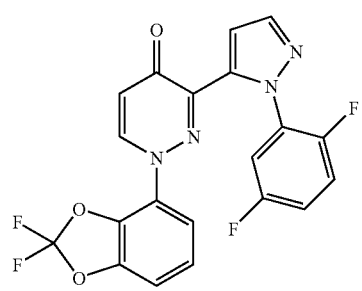

The product was obtained starting from 1-(2,2-Difluoro-benzo[1,3]dioxol-4-yl)-3-((E)-3-dimethylamino-acryloyl)-1H-pyridazin-4-one (A-15) and 2,5-difluoro-phenylhydrazine according to the method described for example 91. MS: M=431.2 (M+H)$^+$

Example 129

3-{5-[1-(2,2-Difluoro-benzo[1,3]dioxol-4-yl)-4-oxo-1,4-dihydro-pyridazin-3-yl]-pyrazol-1-yl}-benzonitrile

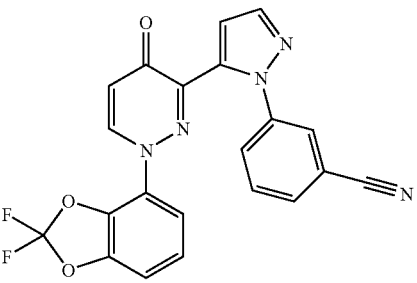

The product was obtained starting from 1-(2,2-Difluoro-benzo[1,3]dioxol-4-yl)-3-((E)-3-dimethylamino-acryloyl)-1H-pyridazin-4-one (A-15) and 3-hydrazino-benzonitrile in ethanol as solvent according to the method described for example 91. MS: M=420.2 (M+H)$^+$

Example 130

1-(2,2-Difluoro-benzo[1,3]dioxol-4-yl)-3-[2-(2-methyl-pyridin-4-yl)-2H-pyrazol-3-yl]-1H-pyridazin-4-one

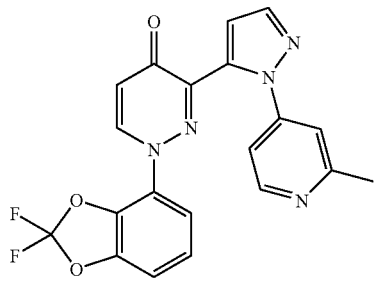

The product was obtained starting from 1-(2,2-Difluoro-benzo[1,3]dioxol-4-yl)-3-((E)-3-dimethylamino-acryloyl)-1H-pyridazin-4-one (A-15) and 4-hydrazino-2-methylpyridine according to the method described for example 91. MS: M=410.3 (M+H)$^+$

Example 131

3-[2-(2-Methyl-pyridin-4-yl)-2H-pyrazol-3-yl]-1-(4-trifluoromethoxy-phenyl)-1H-pyridazin-4-one

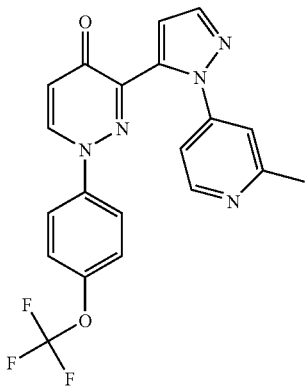

The product was obtained starting from 3-((E)-3-Dimethylamino-acryloyl)-1-(4-trifluoromethoxy-phenyl)-1H-pyridazin-4-one (A-8) and 4-hydrazino-2-methylpyridine according to the method described for example 91. MS: M=414.2 (M+H)$^+$

Example 132

1-(2,2-Difluoro-benzo[1,3]dioxol-5-yl)-3-[2-(2-methyl-pyridin-4-yl)-2H-pyrazol-3-yl]-1H-pyridazin-4-one

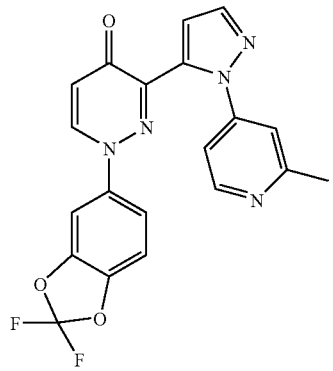

The product was obtained starting from 1-(2,2-Difluoro-benzo[1,3]dioxol-5-yl)-3-((E)-3-dimethylamino-acryloyl)-1H-pyridazin-4-one (A-11) and 4-hydrazino-2-methylpyridine according to the method described for example 91. MS: M=410.2 (M+H)$^+$

Example 133

N,N-Dimethyl-3-{3-[2-(2-methyl-pyridin-4-yl)-2H-pyrazol-3-yl]-4-oxo-4H-pyridazin-1-yl}-benzenesulfonamide

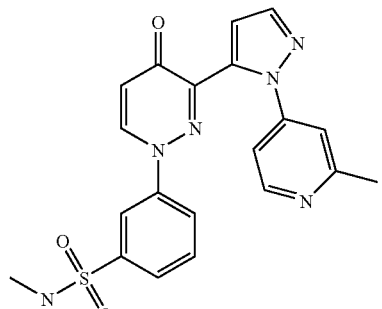

The product was obtained starting from 3-[3-((E)-3-Dimethylamino-acryloyl)-4-oxo-4H-pyridazin-1-yl]-N,N-dimethyl-benzenesulfonamide (A-12) and 4-hydrazino-2-methylpyridine according to the method described for example 91. MS: M=437.2 (M+H)$^+$

Example 134

1-(3-Fluoro-phenyl)-3-[2-(2-methyl-pyridin-4-yl)-2H-pyrazol-3-yl]-1H-pyridazin-4-one

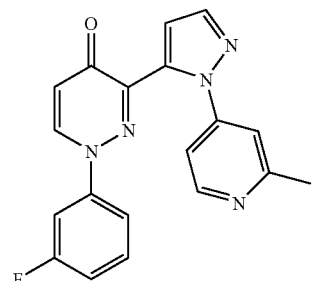

The product was obtained starting from 3-((E)-3-Dimethylamino-acryloyl)-1-(3-fluoro-phenyl)-1H-pyridazin-4-one (A-13) and 4-hydrazino-2-methylpyridine according to the method described for example 91. MS: M=348.2 (M+H)$^+$

Example 135

3-[2-(3-Fluoro-phenyl)-2H-pyrazol-3-yl]-1-(4-trifluoromethoxy-phenyl)-1H-pyridazin-4-one

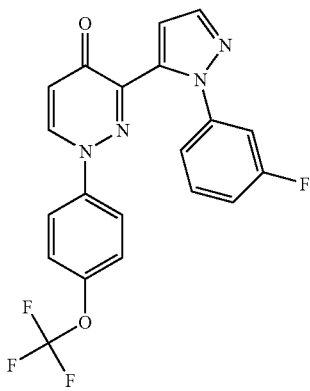

The product was obtained starting from 3-((E)-3-Dimethylamino-acryloyl)-1-(4-trifluoromethoxy-phenyl)-1H-pyridazin-4-one (A-8) and 3-fluoro-phenylhydrazine according to the method described for example 91. MS: M=417.2 (M+H)$^+$

Example 136

3-[2-(2,5-Difluoro-phenyl)-2H-pyrazol-3-yl]-1-(4-trifluoromethoxy-phenyl)-1H-pyridazin-4-one

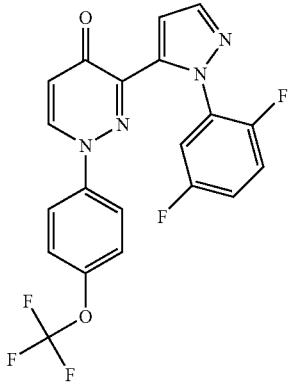

The product was obtained starting from 3-((E)-3-Dimethylamino-acryloyl)-1-(4-trifluoromethoxy-phenyl)-1H-pyridazin-4-one (A-8) and 2,5-difluoro-phenylhydrazine according to the method described for example 91. MS: M=435.3 (M+H)$^+$

Example 137

3-[2-(6-Fluoro-quinolin-4-yl)-2H-pyrazol-3-yl]-1-(4-trifluoromethoxy-phenyl)-1H-pyridazin-4-one

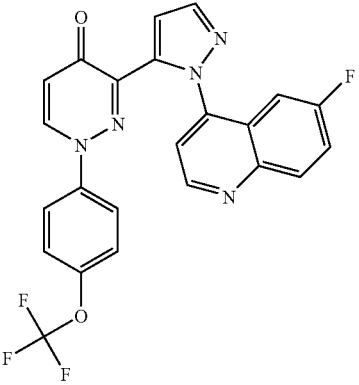

The product was obtained starting from 3-((E)-3-Dimethylamino-acryloyl)-1-(4-trifluoromethoxy-phenyl)-1H-pyridazin-4-one (A-8) and (6-fluoro-quinolin-4-yl)-hydrazine according to the method described for example 91. MS: M=468.2 (M+H)$^+$

Example 138

3-[2-(4-Fluoro-phenyl)-2H-pyrazol-3-yl]-1-(4-trifluoromethoxy-phenyl)-1H-pyridazin-4-one

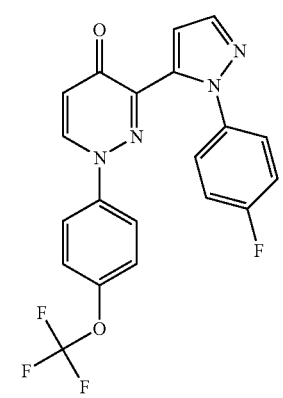

The product was obtained starting from 3-((E)-3-Dimethylamino-acryloyl)-1-(4-trifluoromethoxy-phenyl)-1H-pyridazin-4-one (A-8) and 4-fluoro-phenylhydrazine according to the method described for example 43. MS: M=417.1 (M+H)$^+$

Example 139

4-{5-[4-Oxo-1-(4-trifluoromethoxy-phenyl)-1,4-dihydro-pyridazin-3-yl]-pyrazol-1-yl}-benzonitrile

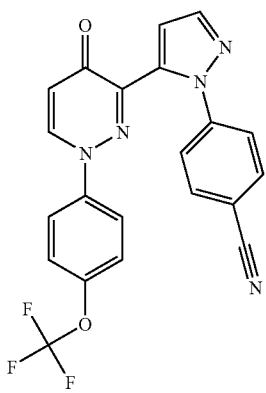

The product was obtained starting from 3-((E)-3-Dimethylamino-acryloyl)-1-(4-trifluoromethoxy-phenyl)-1H-pyridazin-4-one (A-8) and 4-hydrazino-benzonitrile in ethanol as solvent according to the method described for example 43. MS: M=424.1 (M+H)⁺

Example 140

3-(2-Pyridin-3-yl-2H-pyrazol-3-yl)-1-(4-trifluoromethoxy-phenyl)-1H-pyridazin-4-one

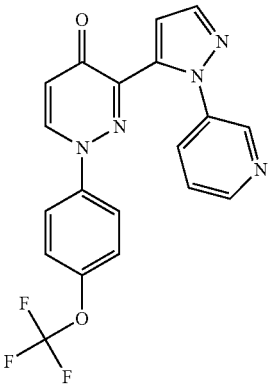

The product was obtained starting from 3-((E)-3-Dimethylamino-acryloyl)-1-(4-trifluoromethoxy-phenyl)-1H-pyridazin-4-one (A-8) and pyridine-3-yl-hydrazine according to the method described for example 43. MS: M=400.1 (M+H)⁺

Example 141

3-[2-(3-Methanesulfonyl-phenyl)-2H-pyrazol-3-yl]-1-(4-trifluoromethoxy-phenyl)-1H-pyridazin-4-one

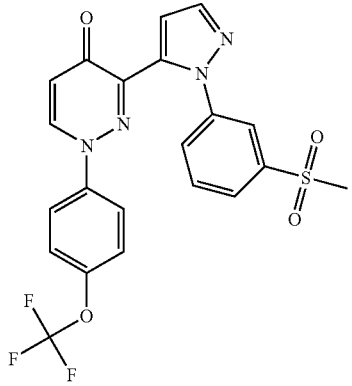

The product was obtained starting from 3-((E)-3-Dimethylamino-acryloyl)-1-(4-trifluoromethoxy-phenyl)-1H-pyridazin-4-one (A-8) and (3-methanesulfonyl-phenyl)-hydrazine according to the method described for example 91. MS: M=477.0 (M+H)⁺

Example 142

1-(4-Trifluoromethoxy-phenyl)-3-[2-(3-trifluoromethoxy-phenyl)-2H-pyrazol-3-yl]-1H-pyridazin-4-one

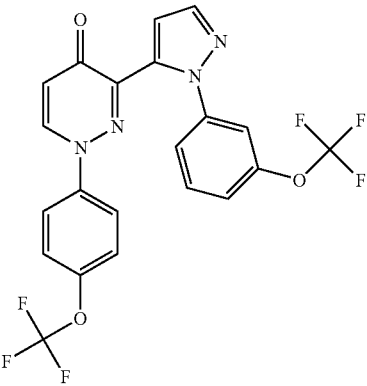

The product was obtained starting from 3-((E)-3-Dimethylamino-acryloyl)-1-(4-trifluoromethoxy-phenyl)-1H-pyridazin-4-one (A-8) and 3-trifluoromethoxy-phenylhydrazine according to the method described for example 91. MS: M=483.2 (M+H)⁺

Example 143

N,N-Dimethyl-3-{5-[4-oxo-1-(4-trifluoromethoxy-phenyl)-1,4-dihydro-pyridazin-3-yl]-pyrazol-1-yl}-benzenesulfonamide

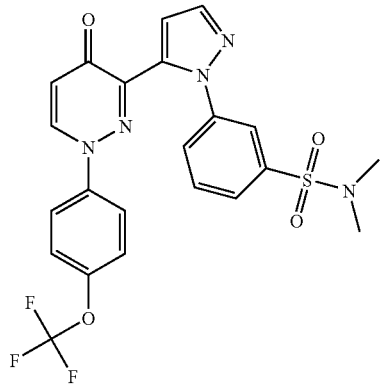

The product was obtained starting from 3-((E)-3-Dimethylamino-acryloyl)-1-(4-trifluoromethoxy-phenyl)-1H-pyridazin-4-one (A-8) and 3-hydrazino-N,N-dimethyl-benzenesulfonamide according to the method described for example 91.

MS: M=506.1 (M+H)$^+$

Example 144

3-[2-(3-Chloro-phenyl)-2H-pyrazol-3-yl]-1-(4-trifluoromethoxy-phenyl)-1H-pyridazin-4-one

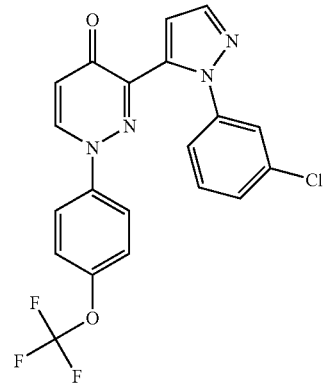

The product was obtained starting from 3-((E)-3-Dimethylamino-acryloyl)-1-(4-trifluoromethoxy-phenyl)-1H-pyridazin-4-one (A-8) and 3-chloro-phenylhydrazine according to the method described for example 91. MS: M=433.3 (M+H)$^+$

Example 145

3-[2-(2,2-Difluoro-benzo[1,3]dioxol-4-yl)-2H-pyrazol-3-yl]-1-(4-trifluoromethoxy-phenyl)-1H-pyridazin-4-one

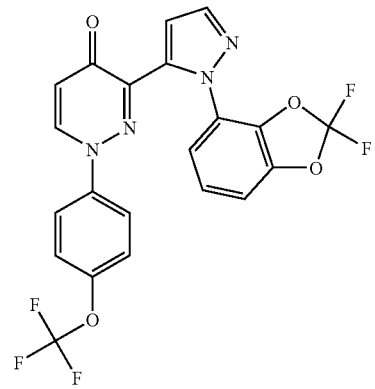

The product was obtained starting from 3-((E)-3-Dimethylamino-acryloyl)-1-(4-trifluoromethoxy-phenyl)-1H-pyridazin-4-one (A-8) and 2,2-difluoro-benzo[1,3]dioxol-4-yl-hydrazine (prepared from the corresponding amino derivative using sodium nitrite and tin(II) chloride as described in J. Med. Chem. 2003, 46, 4676-4686) according to the method described for example 91. MS: M=479.0 (M+H)$^+$

Example 146

3-[2-(2,2-Difluoro-benzo[1,3]dioxol-5-yl)-2H-pyrazol-3-yl]-1-(4-trifluoromethoxy-phenyl)-1H-pyridazin-4-one

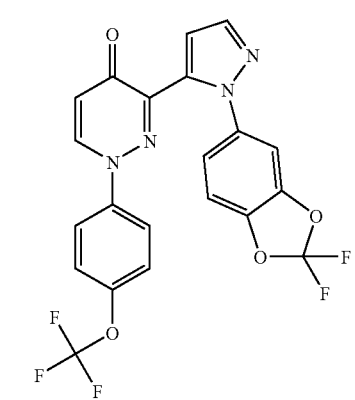

The product was obtained starting from 3-((E)-3-Dimethylamino-acryloyl)-1-(4-trifluoromethoxy-phenyl)-1H-pyridazin-4-one (A-8) and 2,2-difluoro-benzo[1,3]dioxol-5-yl-hydrazine (prepared from the corresponding amino derivative using sodium nitrite and tin(II) chloride as described in J. Med. Chem. 2003, 46, 4676-4686) according to the method described for example 91. MS: M=479.0 (M+H)$^+$

Example 147

3-[2-(3-Trifluoromethanesulfonyl-phenyl)-2H-pyrazol-3-yl]-1-(4-trifluoromethoxy-phenyl)-1H-pyridazin-4-one

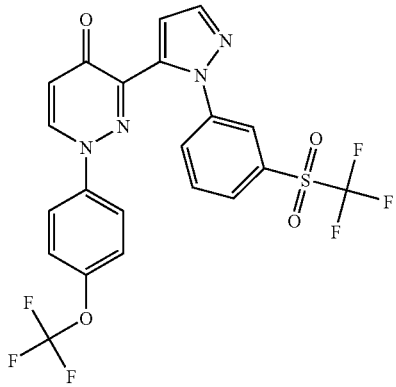

The product was obtained starting from 3-((E)-3-Dimethylamino-acryloyl)-1-(4-trifluoromethoxy-phenyl)-1H-pyridazin-4-one (A-8) and (3-trifluoromethanesulfonyl-phenyl)-hydrazine according to the method described for example 91. MS: M=531.1 (M+H)$^+$

Example 148

3-[2-(6-Fluoro-quinolin-4-yl)-2H-pyrazol-3-yl]-1-(3-trifluoromethoxy-phenyl)-1H-pyridazin-4-one

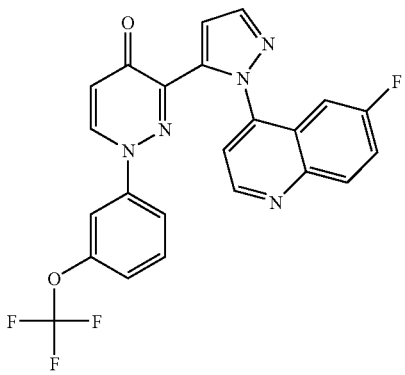

The product was obtained starting from 3-((E)-3-Dimethylamino-acryloyl)-1-(3-trifluoromethoxy-phenyl)-1H-pyridazin-4-one (A-6) and (6-fluoro-quinolin-4-yl)-hydrazine according to the method described for example 91. MS: M=468.2 (M+H)$^+$

Example 149

1-(4-Difluoromethoxy-phenyl)-3-[2-(6-fluoro-quinolin-4-yl)-2H-pyrazol-3-yl]-1H-pyridazin-4-one

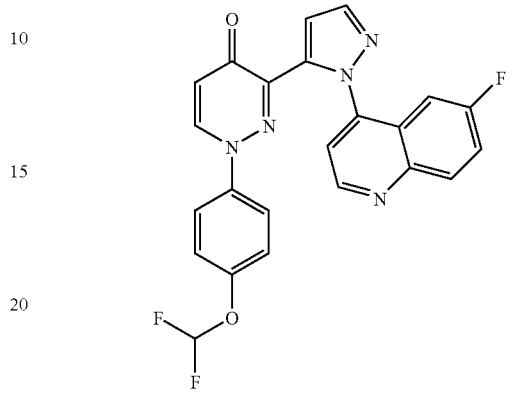

The product was obtained starting from 1-(4-Difluoromethoxy-phenyl)-3-((E)-3-dimethylamino-acryloyl)-1H-pyridazin-4-one (A-9) and (6-fluoro-quinolin-4-yl)-hydrazine according to the method described for example 91. MS: M=450.1 (M+H)$^+$

Example 150

1-(3-Difluoromethoxy-phenyl)-3-[2-(6-fluoro-quinolin-4-yl)-2H-pyrazol-3-yl]-1H-pyridazin-4-one

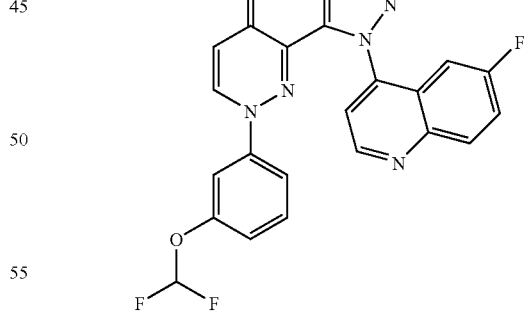

The product was obtained starting from 1-(3-Difluoromethoxy-phenyl)-3-((E)-3-dimethylamino-acryloyl)-1H-pyridazin-4-one (A-10) and (6-fluoro-quinolin-4-yl)-hydrazine according to the method described for example 91. MS: M=450.1 (M+H)$^+$

Example 151

1-(2,2-Difluoro-benzo[1,3]dioxol-5-yl)-3-[2-(6-fluoro-quinolin-4-yl)-2H-pyrazol-3-yl]-1H-pyridazin-4-one

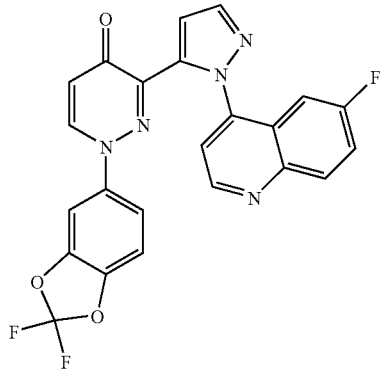

The product was obtained starting from 1-(2,2-Difluoro-benzo[1,3]dioxol-5-yl)-3-((E)-3-dimethylamino-acryloyl)-1H-pyridazin-4-one (A-11) and (6-fluoro-quinolin-4-yl)-hydrazine according to the method described for example 91. MS: M=464.1 (M+H)$^+$

Example 152

1-(4-Methanesulfonyl-phenyl)-3-(2-phenyl-2H-pyrazol-3-yl)-1H-pyridazin-4-one

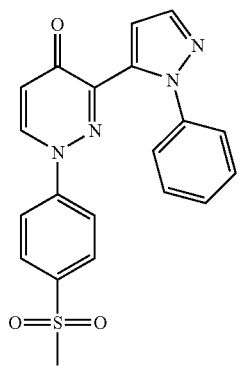

The product was obtained starting from 3-((E)-3-Dimethylamino-acryloyl)-1-(4-methansulfonyl-phenyl)-1H-pyridazin-4-one (A-16) and phenylhydrazine according to the method described for example 43. MS: M=393.1 (M+H)$^+$

Example 153

3-[2-(4-Fluoro-phenyl)-2H-pyrazol-3-yl]-1-(4-methanesulfonyl-phenyl)-1H-pyridazin-4-one

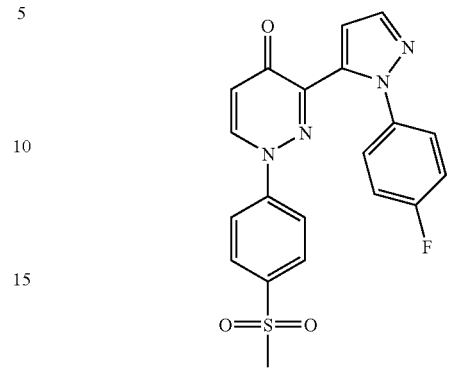

The product was obtained starting from 3-((E)-3-Dimethylamino-acryloyl)-1-(4-methansulfonyl-phenyl)-1H-pyridazin-4-one (A-16) and 4-fluoro-phenylhydrazine according to the method described for example 43. MS: M=411.1 (M+H)$^+$

Example 154

3-[2-(3-Fluoro-phenyl)-2H-pyrazol-3-yl]-1-(4-methanesulfonyl-phenyl)-1H-pyridazin-4-one

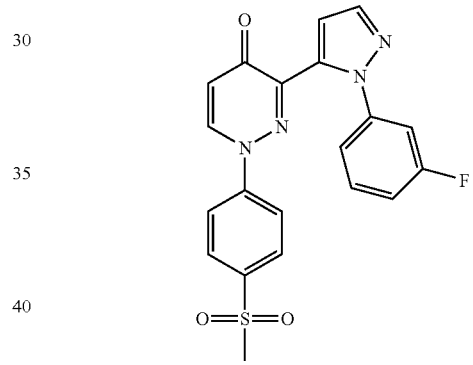

The product was obtained starting from 3-((E)-3-Dimethylamino-acryloyl)-1-(4-methansulfonyl-phenyl)-1H-pyridazin-4-one (A-16) and 3-fluoro-phenylhydrazine according to the method described for example 43. MS: M=411.1 (M+H)$^+$

Example 155

4-{5-[1-(4-Methanesulfonyl-phenyl)-4-oxo-1,4-dihydro-pyridazin-3-yl]-pyrazol-1-yl}-benzonitrile

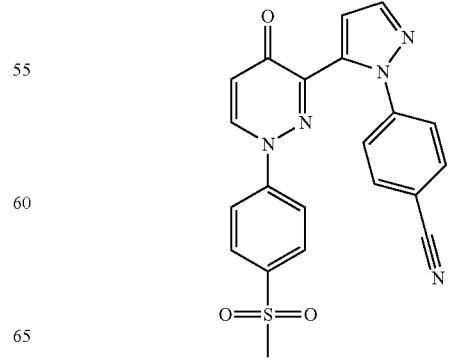

The product was obtained starting from 3-((E)-3-Dimethylamino-acryloyl)-1-(4-methansulfonyl-phenyl)-1H-pyridazin-4-one (A-16) and 4-hydrazino-benzonitrile in ethanol as solvent according to the method described for example 43. MS: M=418.1 (M+H)$^+$ Example 156

3-[2-(4-Chloro-phenyl)-2H-pyrazol-3-yl]-1-(4-methanesulfonyl-phenyl)-1H-pyridazin-4-one

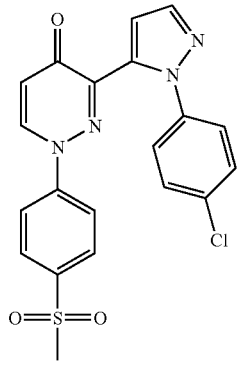

The product was obtained starting from 3-((E)-3-Dimethylamino-acryloyl)-1-(4-methansulfonyl-phenyl)-1H-pyridazin-4-one (A-16) and 4-chloro-phenylhydrazine according to the method described for example 43. MS: M=427.1 (M+H)$^+$ Example 157

3-[2-(3-Chloro-phenyl)-2H-pyrazol-3-yl]-1-(4-methanesulfonyl-phenyl)-1H-pyridazin-4-one

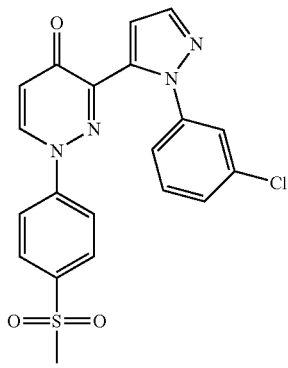

The product was obtained starting from 3-((E)-3-Dimethylamino-acryloyl)-1-(4-methansulfonyl-phenyl)-1H-pyridazin-4-one (A-16) and 3-chloro-phenylhydrazine according to the method described for example 43. MS: M=427.1 (M+H)$^+$ Example 158

1-(4-Methanesulfonyl-phenyl)-3-[2-(4-trifluoromethoxy-phenyl)-2H-pyrazol-3-yl]-1H-pyridazin-4-one

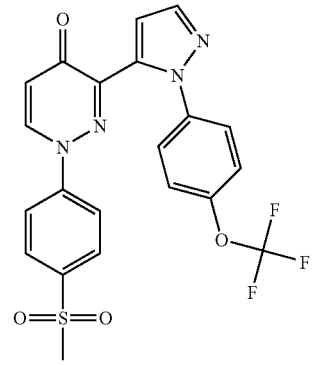

The product was obtained starting from 3-((E)-3-Dimethylamino-acryloyl)-1-(4-methansulfonyl-phenyl)-1H-pyridazin-4-one (A-16) and 4-trifluoromethoxy-phenylhydrazine according to the method described for example 43. MS: M=477.1 (M+H)$^+$ Example 159

1-(3-Trifluoromethoxy-phenyl)-3-[2-(3-trifluoromethoxy-phenyl)-2H-pyrazol-3-yl]-1H-pyridazin-4-one

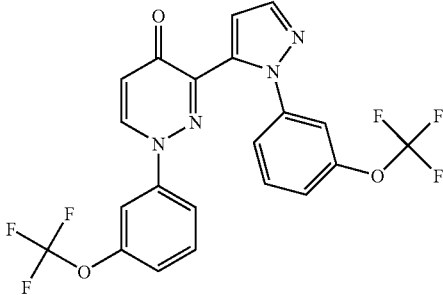

The product was obtained starting from 3-((E)-3-Dimethylamino-acryloyl)-1-(3-trifluoromethoxy-phenyl)-1H-pyridazin-4-one (A-6) and 3-trifluoromethoxy-phenylhydrazine according to the method described for example 91. MS: M=483.2 (M+H)$^+$ Example 160

N,N-Dimethyl-3-{5-[4-oxo-1-(3-trifluoromethoxy-phenyl)-1,4-dihydro-pyridazin-3-yl]-pyrazol-1-yl}-benzenesulfonamide

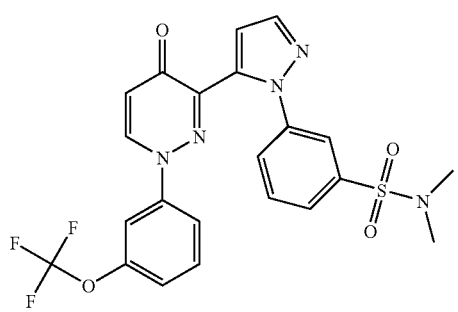

The product was obtained starting from 3-((E)-3-Dimethylamino-acryloyl)-1-(3-trifluoromethoxy-phenyl)-1H-pyridazin-4-one (A-6) and 3-hydrazino-N,N-dimethyl-benzenesulfonamide according to the method described for example 91.
MS: M=506.1 (M+H)+

Example 161

3-[2-(2,2-Difluoro-benzo[1,3]dioxol-4-yl)-2H-pyrazol-3-yl]-1-(3-trifluoromethoxy-phenyl)-1H-pyridazin-4-one

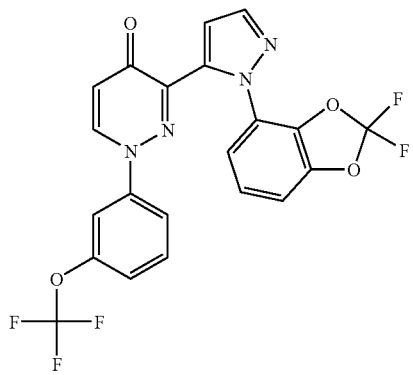

The product was obtained starting from 3-((E)-3-Dimethylamino-acryloyl)-1-(3-trifluoromethoxy-phenyl)-1H-pyridazin-4-one (A-6) and 2,2-difluoro-benzo[1,3]dioxol-4-yl-hydrazine (prepared from the corresponding amino derivative using sodium nitrite and tin(II) chloride as described in J. Med. Chem. 2003, 46, 4676-4686) according to the method described for example 91. MS: M=479.1 (M+H)+

Example 162

3-[2-(2,2-Difluoro-benzo[1,3]dioxol-5-yl)-2H-pyrazol-3-yl]-1-(3-trifluoromethoxy-phenyl)-1H-pyridazin-4-one

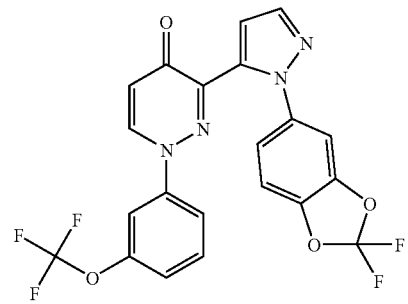

The product was obtained starting from 3-((E)-3-Dimethylamino-acryloyl)-1-(3-trifluoromethoxy-phenyl)-1H-pyridazin-4-one (A-6) and 2,2-difluoro-benzo[1,3]dioxol-5-yl-hydrazine (prepared from the corresponding amino derivative using sodium nitrite and tin(II) chloride as described in J. Med. Chem. 2003, 46, 4676-4686) according to the method described for example 91. MS: M=479.1 (M+H)+

Example 163

3-[2-(3-Trifluoromethanesulfonyl-phenyl)-2H-pyrazol-3-yl]-1-(3-trifluoromethoxy-phenyl)-1H-pyridazin-4-one

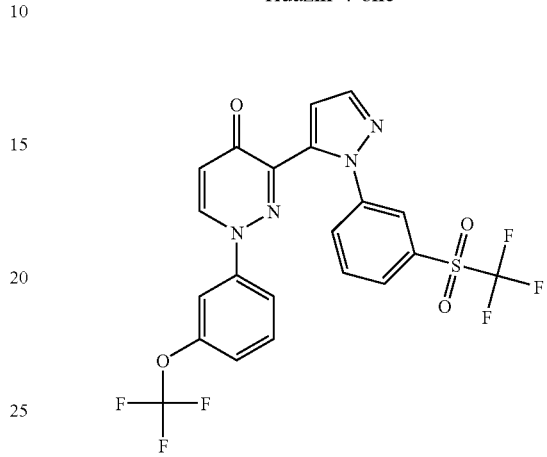

The product was obtained starting from 3-((E)-3-Dimethylamino-acryloyl)-1-(3-trifluoromethoxy-phenyl)-1H-pyridazin-4-one (A-6) and (3-trifluoromethanesulfonyl-phenyl)-hydrazine according to the method described for example 91. MS: M=531.1 (M+H)+

Example 164

1-(4-Difluoromethoxy-phenyl)-3-[2-(3-methanesulfonyl-phenyl)-2H-pyrazol-3-yl]-1H-pyridazin-4-one

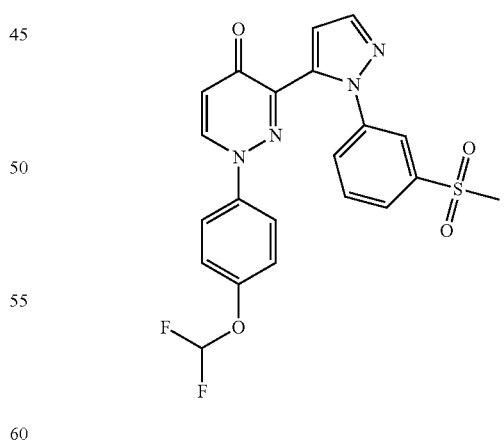

The product was obtained starting from 1-(4-Difluoromethoxy-phenyl)-3-((E)-3-dimethylamino-acryloyl)-1H-pyridazin-4-one (A-9) and (3-methanesulfonyl-phenyl)-hydrazine according to the method described for example 91. MS: M=459.3 (M+H)+

Example 165

1-(4-Difluoromethoxy-phenyl)-3-[2-(3-trifluoromethoxy-phenyl)-2H-pyrazol-3-yl]-1H-pyridazin-4-one

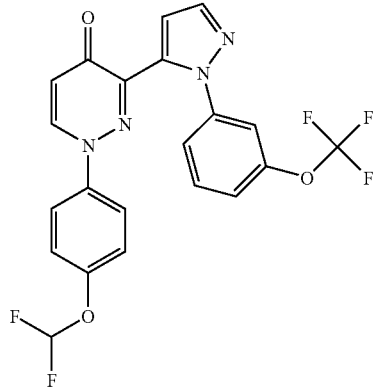

The product was obtained starting from 1-(4-Difluoromethoxy-phenyl)-3-((E)-3-dimethylamino-acryloyl)-1H-pyridazin-4-one (A-9) and 3-trifluoromethoxy-phenylhydrazine according to the method described for example 91. MS: M=465.2 (M+H)+

Example 166

3-[2-(2,2-Difluoro-benzo[1,3]dioxol-4-yl)-2H-pyrazol-3-yl]-1-(4-difluoromethoxy-phenyl)-1H-pyridazin-4-one

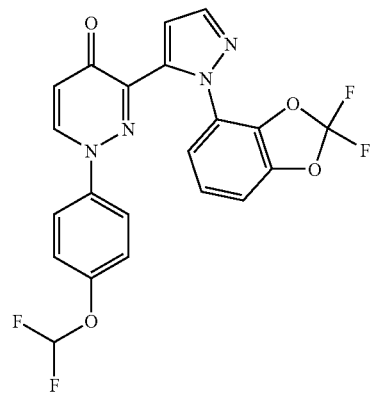

The product was obtained starting from 1-(4-Difluoromethoxy-phenyl)-3-((E)-3-dimethylamino-acryloyl)-1H-pyridazin-4-one (A-9) and 2,2-difluoro-benzo[1,3]dioxol-4-yl-hydrazine (prepared from the corresponding amino derivative using sodium nitrite and tin(II) chloride as described in J. Med. Chem. 2003, 46, 4676-4686) according to the method described for example 91. MS: M=461.3 (M+H)+

Example 167

1-(4-Difluoromethoxy-phenyl)-3-[2-(2-fluoro-phenyl)-2H-pyrazol-3-yl]-1H-pyridazin-4-one

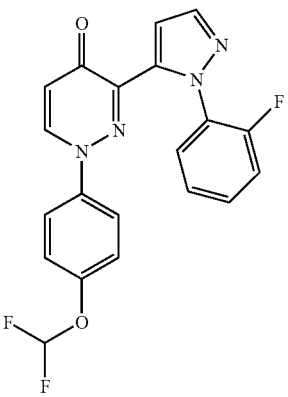

The product was obtained starting from 1-(4-Difluoromethoxy-phenyl)-3-((E)-3-dimethylamino-acryloyl)-1H-pyridazin-4-one (A-9) and 2-fluoro-phenylhydrazine according to the method described for example 91. MS: M=399.1 (M+H)+

Example 168

1-(3-Difluoromethoxy-phenyl)-3-[2-(3-methanesulfonyl-phenyl)-2H-pyrazol-3-yl]-1H-pyridazin-4-one

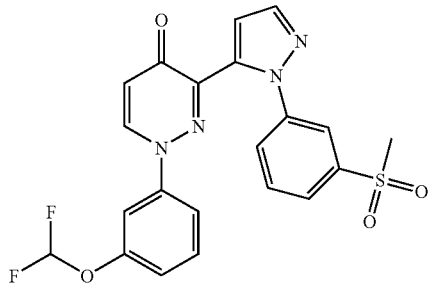

The product was obtained starting from 1-(3-Difluoromethoxy-phenyl)-3-((E)-3-dimethylamino-acryloyl)-1H-pyridazin-4-one (A-10) and (3-methane sulfonyl-phenyl)-hydrazine according to the method described for example 91. MS: M=459.3 (M+H)+

Example 169

1-(3-Difluoromethoxy-phenyl)-3-[2-(3-trifluoromethoxy-phenyl)-2H-pyrazol-3-yl]-1H-pyridazin-4-one

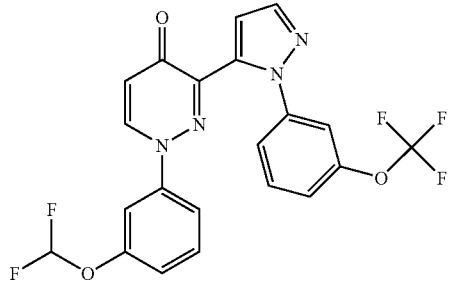

The product was obtained starting from 1-(3-Difluoromethoxy-phenyl)-3-((E)-3-dimethylamino-acryloyl)-1H-pyridazin-4-one (A-10) and 3-trifluoromethoxy-phenylhydrazine according to the method described for example 91. MS: M=465.1 (M+H)+

Example 170

3-[2-(2,2-Difluoro-benzo[1,3]dioxol-4-yl)-2H-pyrazol-3-yl]-1-(3-difluoromethoxy-phenyl)-1H-pyridazin-4-one

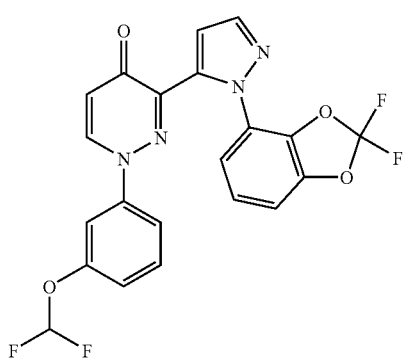

The product was obtained starting from 1-(3-Difluoromethoxy-phenyl)-3-((E)-3-dimethylamino-acryloyl)-1H-pyridazin-4-one (A-10) and 2,2-difluoro-benzo[1,3]dioxol-4-yl-hydrazine (prepared from the corresponding amino derivative using sodium nitrite and tin(II) chloride as described in J. Med. Chem. 2003, 46, 4676-4686) according to the method described for example 91. MS: M=461.3 (M+H)+

Example 171

1-(3-Difluoromethoxy-phenyl)-3-[2-(2-fluoro-phenyl)-2H-pyrazol-3-yl]-1H-pyridazin-4-one

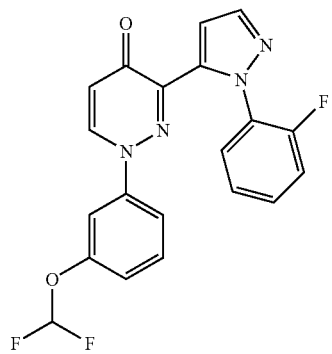

The product was obtained starting from 1-(3-Difluoromethoxy-phenyl)-3-((E)-3-dimethylamino-acryloyl)-1H-pyridazin-4-one (A-10) and 2-fluoro-phenylhydrazine according to the method described for example 91. MS: M=399.1 (M+H)+

Example 172

1-(2,2-Difluoro-benzo[1,3]dioxol-5-yl)-3-[2-(3-methanesulfonyl-phenyl)-2H-pyrazol-3-yl]-1H-pyridazin-4-one

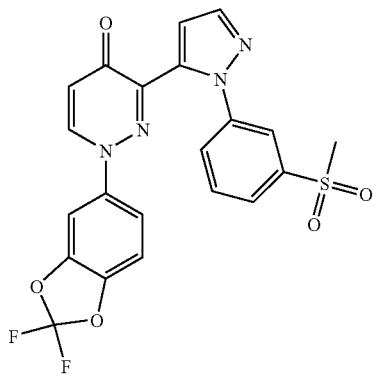

The product was obtained starting from 1-(2,2-Difluoro-benzo[1,3]dioxol-5-yl)-3-((E)-3-dimethylamino-acryloyl)-1H-pyridazin-4-one (A-11) and (3-methane sulfonyl-phenyl)-hydrazine according to the method described for example 91. MS: M=473.2 (M+H)+

Example 173

1-(2,2-Difluoro-benzo[1,3]dioxol-5-yl)-3-[2-(2,2-difluoro-benzo[1,3]dioxol-4-yl)-2H-pyrazol-3-yl]-1H-pyridazin-4-one

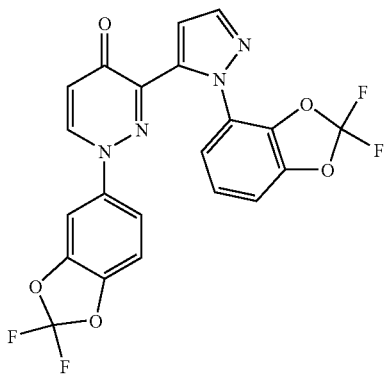

The product was obtained starting from 1-(2,2-Difluoro-benzo[1,3]dioxol-5-yl)-3-((E)-3-dimethylamino-acryloyl)-1H-pyridazin-4-one (A-11) and 2,2-difluoro-benzo[1,3]dioxol-4-yl-hydrazine (prepared from the corresponding amino derivative using sodium nitrite and tin(II) chloride as described in J. Med. Chem. 2003, 46, 4676-4686) according to the method described for example 91. MS: M=475.0 (M+H)$^+$

Example 174

1-(2,2-Difluoro-benzo[1,3]dioxol-5-yl)-3-[2-(2-fluoro-phenyl)-2H-pyrazol-3-yl]-1H-pyridazin-4-one

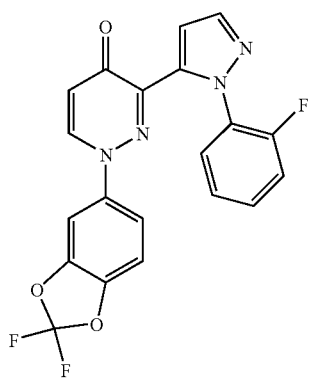

The product was obtained starting from 1-(2,2-Difluoro-benzo[1,3]dioxol-5-yl)-3-((E)-3-dimethylamino-acryloyl)-1H-pyridazin-4-one (A-11) and 2-fluoro-phenylhydrazine according to the method described for example 91.

MS: M=413.2 (M+H)$^+$

Example 175

3-[2-(4-Fluoro-phenyl)-2H-pyrazol-3-yl]-1-(3-hydroxy-phenyl)-1H-pyridazin-4-one

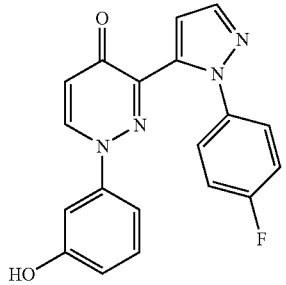

The product was obtained starting from 3-((E)-3-Dimethylamino-acryloyl)-1-(3-hydroxyphenyl)-1H-pyridazin-4-one (A-17) and 4-fluoro-phenylhydrazine according to the method described for example 43. MS: M=349.1 (M+H)$^+$

Example 176

N-(3-{5-[4-Oxo-1-(4-trifluoromethoxy-phenyl)-1,4-dihydro-pyridazin-3-yl]-pyrazol-1-yl}-phenyl)-acetamide

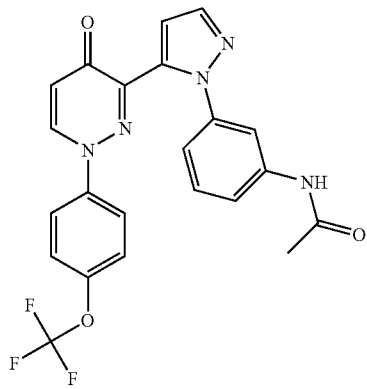

The product was obtained starting from 3-((E)-3-Dimethylamino-acryloyl)-1-(4-trifluoromethoxy-phenyl)-1H-pyridazin-4-one (A-8) and N-(3-hydrazino-phenyl)-acetamide according to the method described for example 91. MS: M=456.2 (M+H)$^+$

Example 177

3-[2-(6-Fluoro-2-methyl-quinolin-4-yl)-2H-pyrazol-3-yl]-1-(3-trifluoromethoxy-phenyl)-1H-pyridazin-4-one

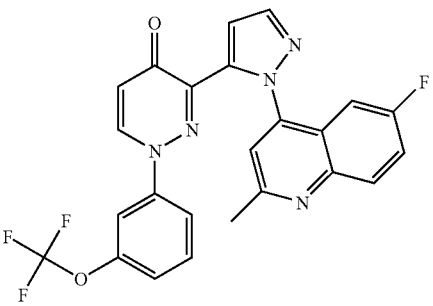

The product was obtained starting from 3-((E)-3-Dimethylamino-acryloyl)-1-(3-trifluoromethoxy-phenyl)-1H-pyridazin-4-one (A-6) and (6-fluoro-2-methyl-quinolin-4-yl)-hydrazine according to the method described for example 91. MS: M=482.2 (M+H)+

Example 178

3-(2-Quinolin-4-yl-2H-pyrazol-3-yl)-1-(3-trifluoromethoxy-phenyl)-1H-pyridazin-4-one

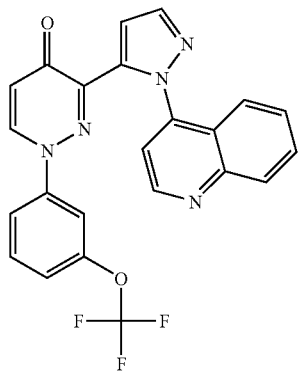

The product was obtained starting from 3-((E)-3-Dimethylamino-acryloyl)-1-(3-trifluoromethoxy-phenyl)-1H-pyridazin-4-one (A-6) and quinolin-4-yl-hydrazine according to the method described for example 91. MS: M=450.2 (M+H)+

Example 179

N-(3-{5-[4-Oxo-1-(3-trifluoromethoxy-phenyl)-1,4-dihydro-pyridazin-3-yl]-pyrazol-1-yl}-phenyl)-acetamide

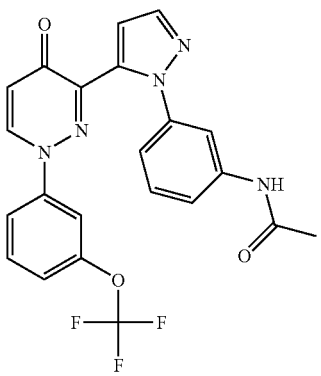

The product was obtained starting from 3-((E)-3-Dimethylamino-acryloyl)-1-(3-trifluoromethoxy-phenyl)-1H-pyridazin-4-one (A-6) and N-(3-hydrazino-phenyl)-acetamide according to the method described for example 91. MS: M=456.2 (M+H)+

Example 180

N-(3-{5-[1-(3-Dimethylsulfamoyl-phenyl)-4-oxo-1,4-dihydro-pyridazin-3-yl]-pyrazol-1-yl}-phenyl)-acetamide

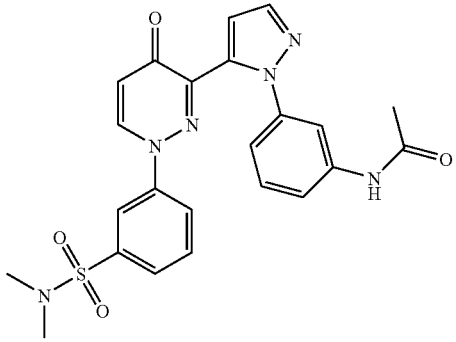

The product was obtained starting from 3-[3-((E)-3-Dimethylamino-acryloyl)-4-oxo-4H-pyridazin-1-yl]-N,N-dimethyl-benzenesulfonamide (A-12) and N-(3-hydrazino-phenyl)-acetamide according to the method described for example 91. MS: M=479.1 (M+H)+

Example 181

3-[2-(4-Hydroxy-phenyl)-2H-pyrazol-3-yl]-1-(3-methanesulfonyl-phenyl)-1H-pyridazin-4-one

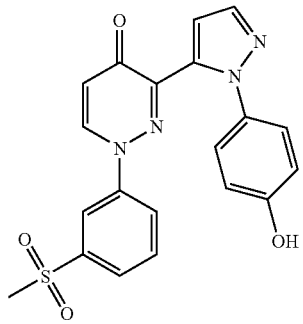

The product was obtained starting from 3-((E)-3-Dimethylamino-acryloyl)-1-(3-methansulfonyl-phenyl)-1H-pyridazin-4-one (A-7) and 4-hydroxy-phenylhydrazine according to the method described for example 43. MS: M=409.1 (M+H)+

Example 182

3-[2-(3-Chloro-phenyl)-2H-pyrazol-3-yl]-1-phenyl-1H-pyridazin-4-one

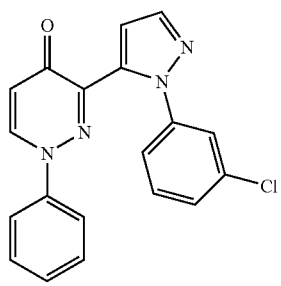

The product was obtained starting from 3-((E)-3-Dimethylamino-acryloyl)-1-phenyl-1H-pyridazin-4-one (A-1) and 3-chloro-phenylhydrazine according to the method described for example 1. MS: M=349.2 (M+H)⁺

Example 183

3-[2-(2-Fluoro-phenyl)-2H-pyrazol-3-yl]-1-phenyl-1H-pyridazin-4-one

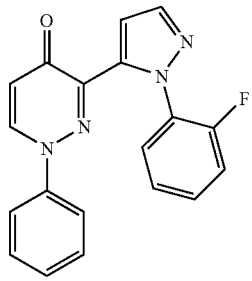

The product was obtained starting from 3-((E)-3-Dimethylamino-acryloyl)-1-phenyl-1H-pyridazin-4-one (A-1) and 2-fluoro-phenylhydrazine according to the method described for example 1. MS: M=333.2 (M+H)⁺

Example 184

3-(2-Naphthalen-1-yl-2H-pyrazol-3-yl)-1-phenyl-1H-pyridazin-4-one

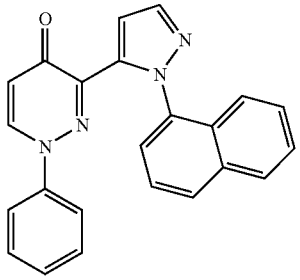

The product was obtained starting from 3-((E)-3-Dimethylamino-acryloyl)-1-phenyl-1H-pyridazin-4-one (A-1) and naphthalen-1-yl-hydrazine according to the method described for example 1. MS: M=365.1 (M+H)⁺

Example 185

4-{5-[4-Oxo-1-(4-trifluoromethoxy-phenyl)-1,4-dihydro-pyridazin-3-yl]-pyrazol-1-yl}-benzenesulfonamide

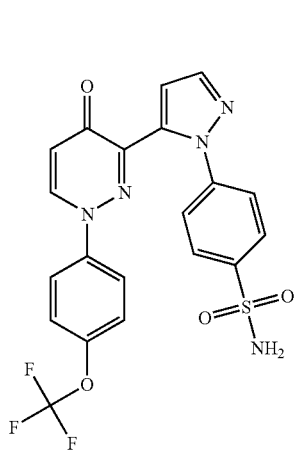

The product was obtained starting from 3-((E)-3-Dimethylamino-acryloyl)-1-(4-trifluoromethoxy-phenyl)-1H-pyridazin-4-one (A-8) and 4-hydrazino-benzenesulfonamide according to the method described for example 43. MS: M=478.1 (M+H)⁺

Example 186

3-(2-Quinolin-4-yl-2H-pyrazol-3-yl)-1-(4-trifluoromethoxy-phenyl)-1H-pyridazin-4-one

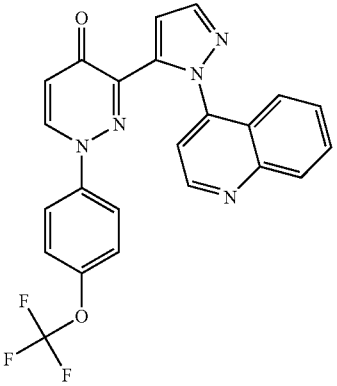

The product was obtained starting from 3-((E)-3-Dimethylamino-acryloyl)-1-(4-trifluoromethoxy-phenyl)-1H-pyridazin-4-one (A-8) and quinolin-4-yl-hydrazine according to the method described for example 43. MS: M=450.1 (M+H)⁺

Example 187

3-[2-(6-Fluoro-quinolin-4-yl)-2H-pyrazol-3-yl]-1-phenyl-1H-pyridazin-4-one

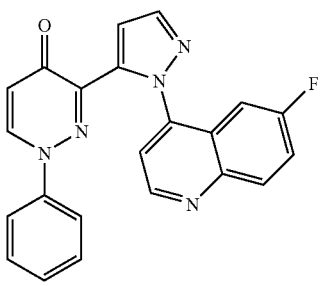

The product was obtained starting from 3-((E)-3-Dimethylamino-acryloyl)-1-phenyl-1H-pyridazin-4-one (A-1) and (6-fluoro-quinolin-4-yl)-hydrazine according to the method described for example 1. MS: M=384.1 (M+H)⁺

Example 188

3-(2-Naphthalen-1-yl-2H-pyrazol-3-yl)-1-(3-trifluoromethyl-phenyl)-1H-pyridazin-4-one

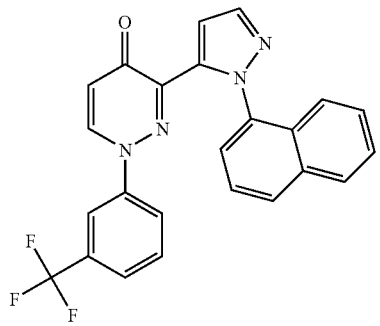

The product was obtained starting from 3-((E)-3-Dimethylamino-acryloyl)-1-(3-trifluoromethyl-phenyl)-1H-pyridazin-4-one (A-3) and naphthalen-1-yl-hydrazine according to the method described for example 1. MS: M=433.2 (M+H)$^+$

Example 189

3-[2-(6-Fluoro-quinolin-4-yl)-2H-pyrazol-3-yl]-1-(4-trifluoromethyl-phenyl)-1H-pyridazin-4-one

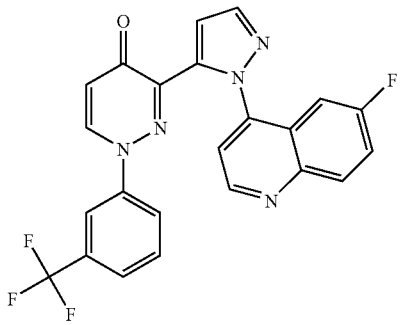

The product was obtained starting from 3-((E)-3-Dimethylamino-acryloyl)-1-(3-trifluoromethyl-phenyl)-1H-pyridazin-4-one (A-3) and (6-fluoro-quinolin-4-yl)-hydrazine according to the method described for example 1. MS: M=452.1 (M+H)$^+$

Example 190

1-(3-Bromo-phenyl)-3-(2-naphthalen-1-yl-2H-pyrazol-3-yl)-1H-pyridazin-4-one

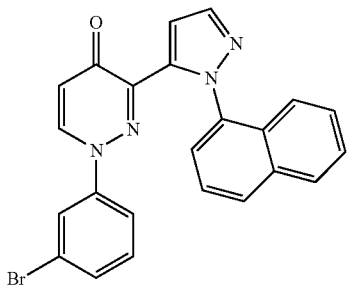

The product was obtained starting from 1-(3-Bromo-phenyl)-3-((E)-3-dimethylamino-acryloyl)-1H-pyridazin-4-one (A-18) and naphthalen-1-yl-hydrazine according to the method described for example 1. MS: M=443.2 (M+H)$^+$

Example 191

1-(4-Methanesulfonyl-phenyl)-3-(2-quinolin-4-yl-2H-pyrazol-3-yl)-1H-pyridazin-4-one

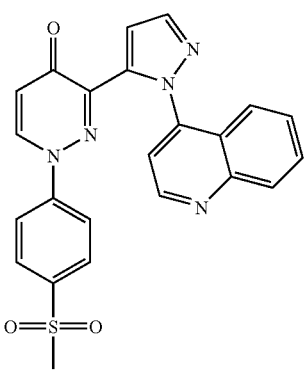

The product was obtained starting from 3-((E)-3-Dimethylamino-acryloyl)-1-(4-methansulfonyl-phenyl)-1H-pyridazin-4-one (A-16) and quinolin-4-yl-hydrazine according to the method described for example 43. MS: M=444.3 (M+H)$^+$

Example 192

3-(2-Isoquinolin-5-yl-2H-pyrazol-3-yl)-1-(4-methanesulfonyl-phenyl)-1H-pyridazin-4-one

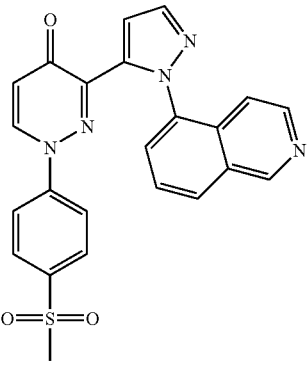

The product was obtained starting from 3-((E)-3-Dimethylamino-acryloyl)-1-(4-methansulfonyl-phenyl)-1H-pyridazin-4-one (A-16) and isoquinolin-5-yl-hydrazine according to the method described for example 43. MS: M=444.5 (M+H)$^+$

Example 193

3-[2-(2-Chloro-pyridin-4-yl)-2H-pyrazol-3-yl]-1-(4-trifluoromethoxy-phenyl)-1H-pyridazin-4-one

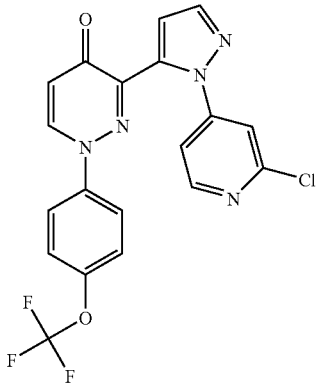

The product was obtained starting from 3-((E)-3-Dimethylamino-acryloyl)-1-(4-trifluoromethoxy-phenyl)-1H-pyridazin-4-one (A-8) and 4-hydrazino-2-chloropyridine according to the method described for example 43. MS: M=434.0 (M+H)+

Example 194

3-[2-(6-Fluoro-2-methyl-quinolin-4-yl)-2H-pyrazol-3-yl]-1-(4-trifluoromethoxy-phenyl)-1H-pyridazin-4-one

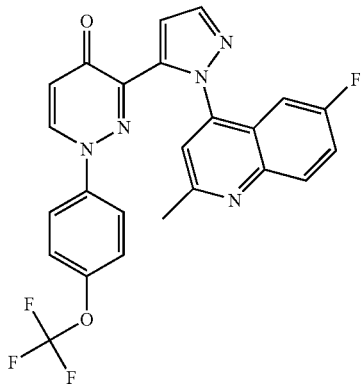

The product was obtained starting from 3-((E)-3-Dimethylamino-acryloyl)-1-(4-trifluoromethoxy-phenyl)-1H-pyridazin-4-one (A-8) and (6-fluoro-2-methyl-quinolin-4-yl)-hydrazine according to the method described for example 91. MS: M=482.2 (M+H)+

Example 195

3-{3-[2-(6-Fluoro-2-methyl-quinolin-4-yl)-2H-pyrazol-3-yl]-4-oxo-4H-pyridazin-1-yl}-N,N-dimethyl-benzenesulfonamide

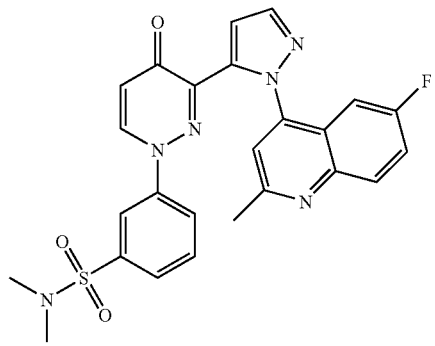

The product was obtained starting from 3-[3-((E)-3-Dimethylamino-acryloyl)-4-oxo-4H-pyridazin-1-yl]-N,N-dimethyl-benzenesulfonamide (A-12) and (6-fluoro-2-methyl-quinolin-4-yl)-hydrazine according to the method described for example 91.
MS: M=505.1 (M+H)+

Example 196

N,N-Dimethyl-3-[4-oxo-3-(2-quinolin-4-yl-2H-pyrazol-3-yl)-4H-pyridazin-1-yl]-benzenesulfonamide

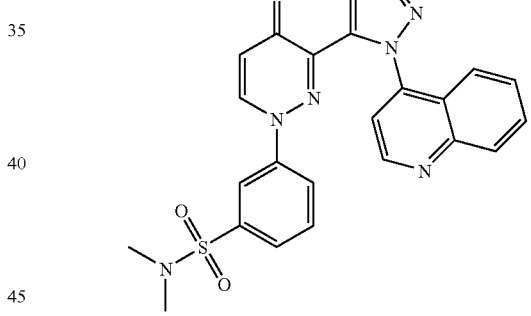

The product was obtained starting from 3-[3-((E)-3-Dimethylamino-acryloyl)-4-oxo-4H-pyridazin-1-yl]-N,N-dimethyl-benzenesulfonamide (A-12) and quinolin-4-yl-hydrazine according to the method described for example 91. MS: M=473.3 (M+H)+

Example 197

1-(3-Methoxy-phenyl)-3-(2-quinolin-4-yl-2H-pyrazol-3-yl)-1H-pyridazin-4-one

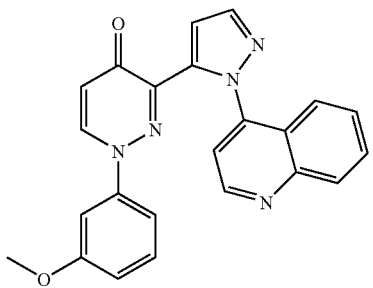

The product was obtained starting from 3-((E)-3-Dimethylamino-acryloyl)-1-(3-methoxy-phenyl)-1H-pyridazin-4-one (A-5) and quinolin-4-yl-hydrazine according to the method described for example 91. MS: M=396.0 (M+H)+

Example 198

3-[2-(6-Fluoro-quinolin-4-yl)-2H-pyrazol-3-yl]-1-(3-methoxy-phenyl)-1H-pyridazin-4-one

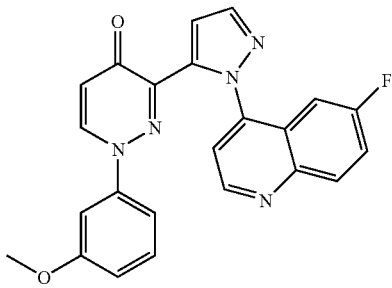

The product was obtained starting from 3-((E)-3-Dimethylamino-acryloyl)-1-(3-methoxy-phenyl)-1H-pyridazin-4-one (A-5) and (6-fluoro-quinolin-4-yl)-hydrazine according to the method described for example 91. MS: M=414.3 (M+H)+

Example 199

3-[2-(6-Fluoro-2-methyl-quinolin-4-yl)-2H-pyrazol-3-yl]-1-(3-methoxy-phenyl)-1H-pyridazin-4-one

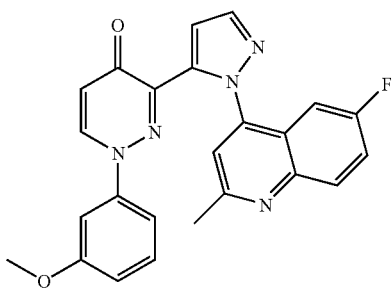

The product was obtained starting from 3-((E)-3-Dimethylamino-acryloyl)-1-(3-methoxy-phenyl)-1H-pyridazin-4-one (A-5) and (6-fluoro-2-methyl-quinolin-4-yl)-hydrazine according to the method described for example 91. MS: M=428.2 (M+H)+

Example 200

3-[2-(2-Ethoxy-pyridin-4-yl)-2H-pyrazol-3-yl]-1-(4-trifluoromethoxy-phenyl)-1H-pyridazin-4-one

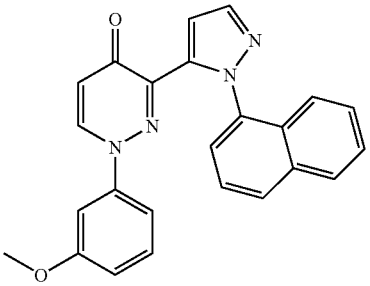

The product was obtained starting from 3-((E)-3-Dimethylamino-acryloyl)-1-(4-trifluoromethoxy-phenyl)-1H-pyridazin-4-one (A-8) and 4-hydrazino-2-ethoxypyridine according to the method described for example 43. MS: M=444.2 (M+H)+

Example 201

1-(3-Methoxy-phenyl)-3-(2-naphthalen-1-yl-2H-pyrazol-3-yl)-1H-pyridazin-4-one

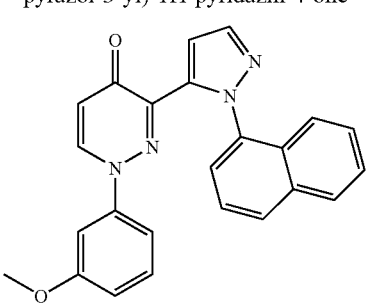

The product was obtained starting from 3-((E)-3-Dimethylamino-acryloyl)-1-(3-methoxy-phenyl)-1H-pyridazin-4-one (A-5) and naphthalen-1-yl-hydrazine according to the method described for example 91. MS: M=395.1 (M+H)+

Example 202

3-[2-(2,3-Dihydro-benzo[1,4]dioxin-6-yl)-2H-pyrazol-3-yl]-1-(3-methoxy-phenyl)-1H-pyridazin-4-one

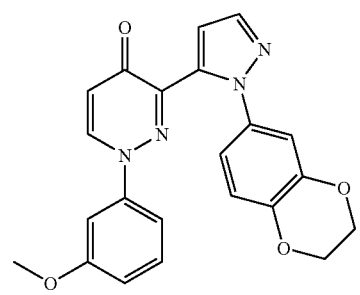

The product was obtained starting from 3-((E)-3-Dimethylamino-acryloyl)-1-(3-methoxy-phenyl)-1H-pyridazin-4-one (A-5) and (2,3-dihydro-benzo[1,4]dioxin-6-yl)-hydrazine according to the method described for example 91. MS: M=403.4 (M+H)+

Example 203

3-(2-Quinolin-5-yl-2H-pyrazol-3-yl)-1-(3-trifluoromethoxy-phenyl)-1H-pyridazin-4-one

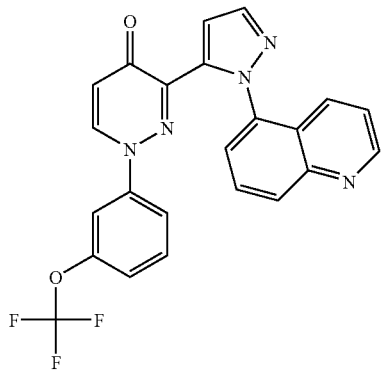

The product was obtained starting from 3-((E)-3-Dimethylamino-acryloyl)-1-(3-trifluoromethoxy-phenyl)-1H-pyridazin-4-one (A-6) and quinolin-5-yl-hydrazine according to the method described for example 91. MS: M=450.1 (M+H)+

Example 204

1-(3-Difluoromethoxy-phenyl)-3-(2-quinolin-5-yl-2H-pyrazol-3-yl)-1H-pyridazin-4-one

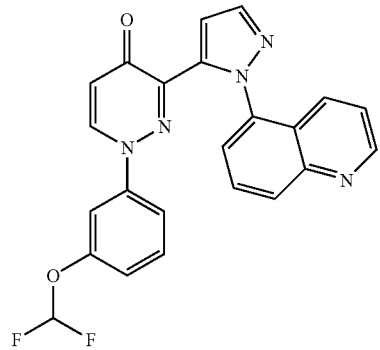

The product was obtained starting from 1-(3-Difluoromethoxy-phenyl)-3-((E)-3-dimethylamino-acryloyl)-1H-pyridazin-4-one (A-10) and quinolin-5-yl-hydrazine according to the method described for example 91. MS: M=432.2 (M+H)+

Example 205

3-[2-(2-Chloro-pyridin-4-yl)-2H-pyrazol-3-yl]-1-(3-difluoromethoxy-phenyl)-1H-pyridazin-4-one

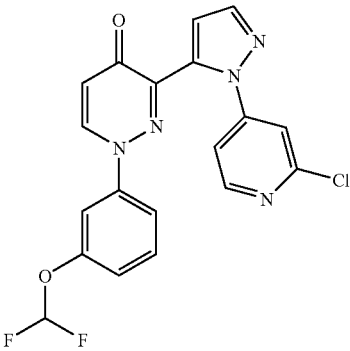

The product was obtained starting from 1-(3-Difluoromethoxy-phenyl)-3-((E)-3-dimethylamino-acryloyl)-1H-pyridazin-4-one (A-10) and 4-hydrazino-2-chloropyridine according to the method described for example 91. MS: M=416.1 (M+H)+

Example 206

3-[2-(3-Chloro-phenyl)-2H-pyrazol-3-yl]-1-(3-difluoromethoxy-phenyl)-1H-pyridazin-4-one

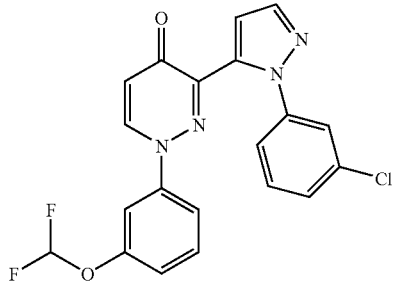

The product was obtained starting from 1-(3-Difluoromethoxy-phenyl)-3-((E)-3-dimethylamino-acryloyl)-1H-pyridazin-4-one (A-10) and 3-chloro-phenylhydrazine according to the method described for example 91. MS: M=415.2 (M+H)+

Example 207

3-[4-Oxo-3-(2-quinolin-4-yl-2H-pyrazol-3-yl)-4H-pyridazin-1-yl]-benzonitrile

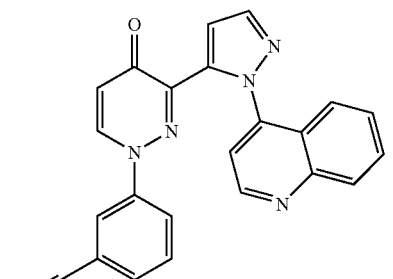

The product was obtained starting from 3-[3-((E)-3-Dimethylamino-acryloyl)-4-oxo-4H-pyridazin-1-yl]-benzonitrile (A-19) and quinolin-4-yl-hydrazine according to the method described for example 91. MS: M=391.1 (M+H)⁺

Example 208

3-{3-[2-(2-Fluoro-phenyl)-2H-pyrazol-3-yl]-4-oxo-4H-pyridazin-1-yl}-N,N-dimethyl-benzamide

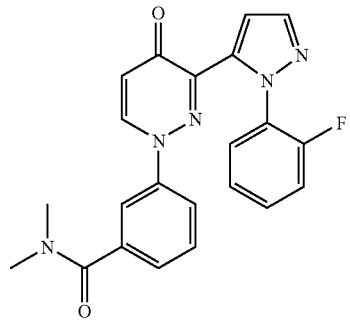

The product was obtained starting from 3-[3-((E)-3-Dimethylamino-acryloyl)-4-oxo-4H-pyridazin-1-yl]-N,N-dimethyl-benzamide (A-20) and 2-fluoro-phenylhydrazine according to the method described for example 91. MS: M=404.3 (M+H)⁺

Example 209

3-{3-[2-(3-Chloro-phenyl)-2H-pyrazol-3-yl]-4-oxo-4H-pyridazin-1-yl}-N,N-dimethyl-benzamide

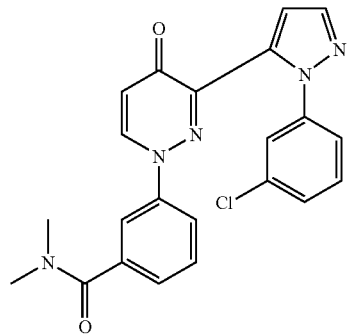

The product was obtained starting from 3-[3-((E)-3-Dimethylamino-acryloyl)-4-oxo-4H-pyridazin-1-yl]-N,N-dimethyl-benzamide (A-20) and 3-chloro-phenylhydrazine according to the method described for example 91. MS: M=420.2 (M+H)⁺

Example 210

N,N-Diethyl-3-{3-[2-(3-fluoro-phenyl)-2H-pyrazol-3-yl]-4-oxo-4H-pyridazin-1-yl}-benzenesulfonamide

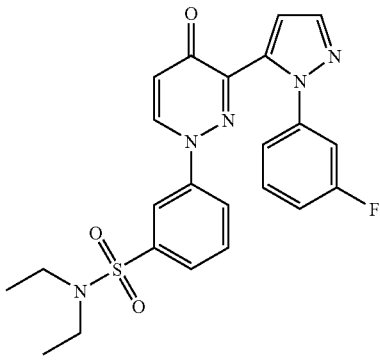

The product was obtained starting from 3-[3-((E)-3-Dimethylamino-acryloyl)-4-oxo-4H-pyridazin-1-yl]-N,N-diethyl-benzenesulfonamide (A-21) and 3-fluoro-phenylhydrazine according to the method described for example 91. MS: M=468.2 (M+H)⁺

Example 211

3-(2-Phenyl-2H-pyrazol-3-yl)-1-(4-trifluoromethyl-phenyl)-1H-pyridazin-4-one

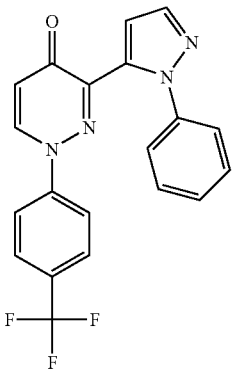

The product was obtained starting from 3-((E)-3-Dimethylamino-acryloyl)-1-(4-trifluoromethyl-phenyl)-1H-pyridazin-4-one (A-22) and phenylhydrazine according to the method described for example 1. MS: M=383.2 (M+H)⁺

Example 212

3-[2-(2-Fluoro-phenyl)-2H-pyrazol-3-yl]-1-(4-trifluoromethyl-phenyl)-1H-pyridazin-4-one

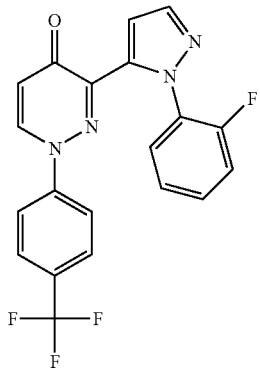

The product was obtained starting from 3-((E)-3-Dimethylamino-acryloyl)-1-(4-trifluoromethyl-phenyl)-1H-pyridazin-4-one (A-22) and 2-fluoro-phenylhydrazine according to the method described for example 1. MS: M=401.1 (M+H)$^+$

Example 213

3-[2-(3-Chloro-phenyl)-2H-pyrazol-3-yl]-1-(4-trifluoromethyl-phenyl)-1H-pyridazin-4-one

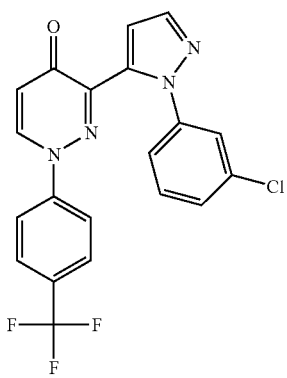

The product was obtained starting from 3-((E)-3-Dimethylamino-acryloyl)-1-(4-trifluoromethyl-phenyl)-1H-pyridazin-4-one (A-22) and 3-chloro-phenylhydrazine according to the method described for example 1. MS: M=417.2 (M+H)$^+$

Example 214

3-(2-Quinolin-4-yl-2H-pyrazol-3-yl)-1-(3-trifluoromethyl-phenyl)-1H-pyridazin-4-one

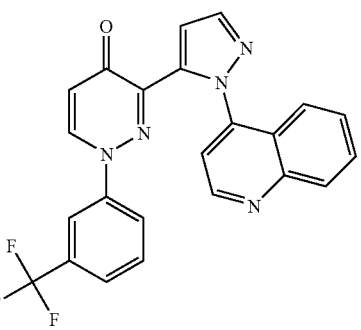

The product was obtained starting from 3-((E)-3-Dimethylamino-acryloyl)-1-(3-trifluoromethyl-phenyl)-1H-pyridazin-4-one (A-3) and quinolin-4-yl-hydrazine according to the method described for example 91. MS: M=434.3 (M+H)$^+$

Example 215

3-(2-Quinolin-8-yl-2H-pyrazol-3-yl)-1-(4-trifluoromethoxy-phenyl)-1H-pyridazin-4-one

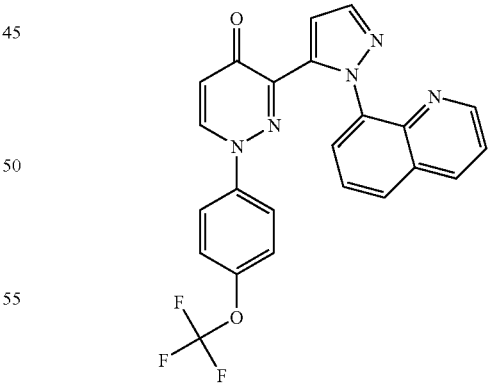

The product was obtained starting from 3-((E)-3-Dimethylamino-acryloyl)-1-(4-trifluoromethoxy-phenyl)-1H-pyridazin-4-one (A-8) and quinolin-8-yl-hydrazine according to the method described for example 43. MS: M=450.2 (M+H)$^+$

Example 216

3-(2-o-Tolyl-2H-pyrazol-3-yl)-1-(4-trifluoromethyl-phenyl)-1H-pyridazin-4-one

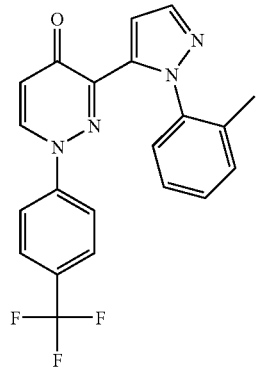

The product was obtained starting from 3-((E)-3-Dimethylamino-acryloyl)-1-(4-trifluoromethyl-phenyl)-1H-pyridazin-4-one (A-22) and o-tolylhydrazine according to the method described for example 1. MS: M=397.1 (M+H)$^+$

Example 217

3-{5-[4-Oxo-1-(4-trifluoromethyl-phenyl)-1,4-dihydro-pyridazin-3-yl]-pyrazol-1-yl}-benzonitrile

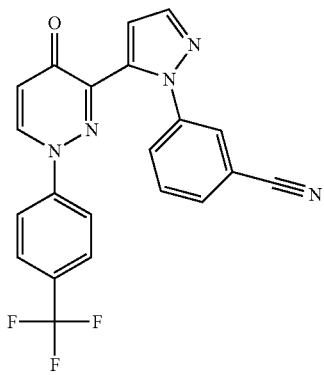

The product was obtained starting from 3-((E)-3-Dimethylamino-acryloyl)-1-(4-trifluoromethyl-phenyl)-1H-pyridazin-4-one (A-22) and 3-hydrazino-benzonitrile in ethanol as solvent according to the method described for example 1. MS: M=408.2 (M+H)$^+$

Example 218

1-(3-Chloro-phenyl)-3-[2-(2-fluoro-phenyl)-2H-pyrazol-3-yl]-1H-pyridazin-4-one

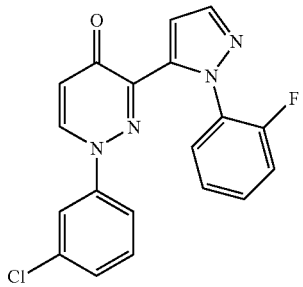

The product was obtained starting from 1-(3-Chloro-phenyl)-3-((E)-3-dimethylamino-acryloyl)-1H-pyridazin-4-one (A-23) and 2-fluoro-phenylhydrazine according to the method described for example 1. MS: M=367.0 (M+H)$^+$

Example 219

1-(3-Chloro-phenyl)-3-[2-(3-chloro-phenyl)-2H-pyrazol-3-yl]-1H-pyridazin-4-one

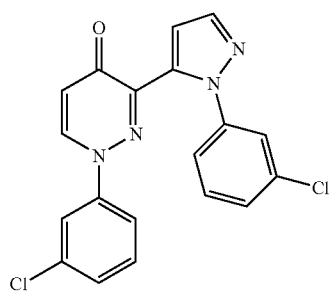

The product was obtained starting from 1-(3-Chloro-phenyl)-3-((E)-3-dimethylamino-acryloyl)-1H-pyridazin-4-one (A-23) and 3-chloro-phenylhydrazine according to the method described for example 1. MS: M=383.0 (M+H)$^+$

Example 220

3-[2-(3-Methyl-isothiazol-5-yl)-2H-pyrazol-3-yl]-1-(4-trifluoromethoxy-phenyl)-1H-pyridazin-4-one

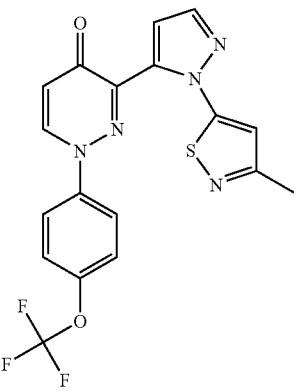

The product was obtained starting from 3-((E)-3-Dimethylamino-acryloyl)-1-(4-trifluoromethoxy-phenyl)-1H-pyridazin-4-one (A-8) and (3-methyl-isothiazol-5-yl)-hydrazine according to the method described for example 43. MS: M=420.0 (M+H)$^+$

Example 221

1-(3-Chloro-phenyl)-3-(2-naphthalen-1-yl-2H-pyrazol-3-yl)-1H-pyridazin-4-one

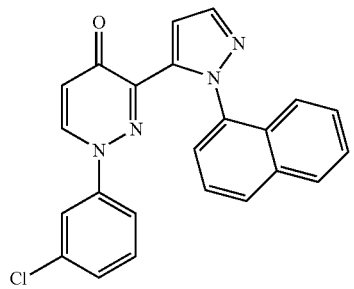

The product was obtained starting from 1-(3-Chloro-phenyl)-3-((E)-3-dimethylamino-acryloyl)-1H-pyridazin-4-one (A-23) and naphthalen-1-yl-hydrazine according to the method described for example 1. MS: M=399.1 (M+H)$^+$

Example 222

3-(2-Naphthalen-1-yl-2H-pyrazol-3-yl)-1-(4-trifluoromethyl-phenyl)-1H-pyridazin-4-one

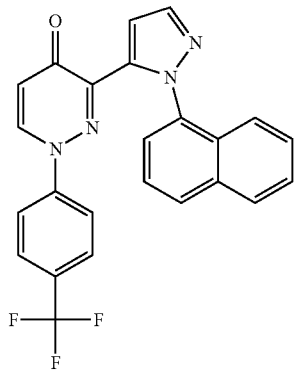

The product was obtained starting from 3-((E)-3-Dimethylamino-acryloyl)-1-(4-trifluoromethyl-phenyl)-1H-pyridazin-4-one (A-22) and naphthalen-1-yl-hydrazine according to the method described for example 1. MS: M=433.2 (M+H)$^+$

Example 223

1-(4-Chloro-phenyl)-3-(2-naphthalen-1-yl-2H-pyrazol-3-yl)-1H-pyridazin-4-one

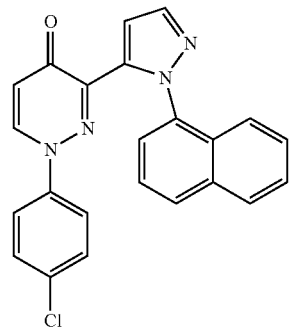

The product was obtained starting from 1-(4-Chloro-phenyl)-3-((E)-3-dimethylamino-acryloyl)-1H-pyridazin-4-one (A-24) and naphthalen-1-yl-hydrazine according to the method described for example 1. MS: M=399.1 (M+H)$^+$

Example 224

3-[2-(6-Chloro-quinolin-4-yl)-2H-pyrazol-3-yl]-1-(4-trifluoromethoxy-phenyl)-1H-pyridazin-4-one

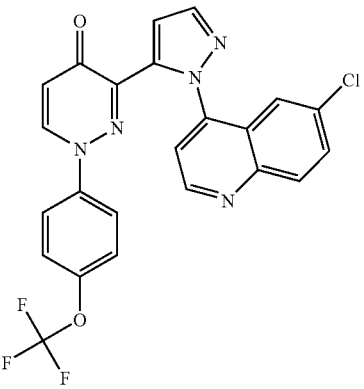

The product was obtained starting from 3-((E)-3-Dimethylamino-acryloyl)-1-(4-trifluoromethoxy-phenyl)-1H-pyridazin-4-one (A-8) and (6-chloro-quinolin-4-yl)-hydrazine according to the method described for example 91. MS: M=484.1 (M+H)$^+$

Example 225

3-(2-Isoquinolin-5-yl-2H-pyrazol-3-yl)-1-(4-trifluoromethoxy-phenyl)-1H-pyridazin-4-one

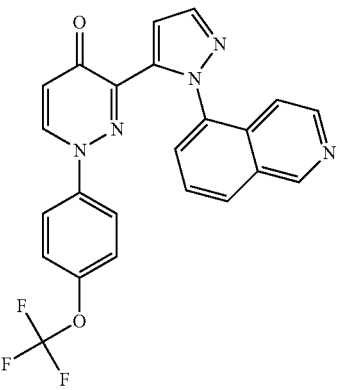

The product was obtained starting from 3-((E)-3-Dimethylamino-acryloyl)-1-(4-trifluoromethoxy-phenyl)-1H-pyridazin-4-one (A-8) and isoquinolin-5-yl-hydrazine according to the method described for example 91. MS: M=450.1 (M+H)$^+$

Example 226

3-(2-Isoquinolin-4-yl-2H-pyrazol-3-yl)-1-(4-trifluoromethoxy-phenyl)-1H-pyridazin-4-one

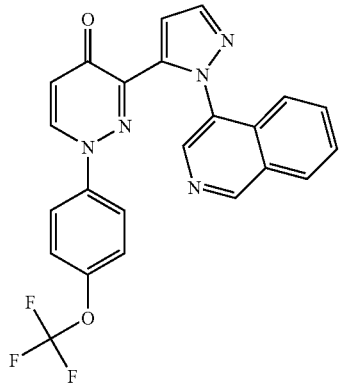

The product was obtained starting from 3-((E)-3-Dimethylamino-acryloyl)-1-(4-trifluoromethoxy-phenyl)-1H-pyridazin-4-one (A-8) and isoquinolin-4-yl-hydrazine according to the method described for example 91. MS: M=450.1 (M+H)$^+$

Example 227

3-(2-Quinolin-5-yl-2H-pyrazol-3-yl)-1-(4-trifluoromethoxy-phenyl)-1H-pyridazin-4-one

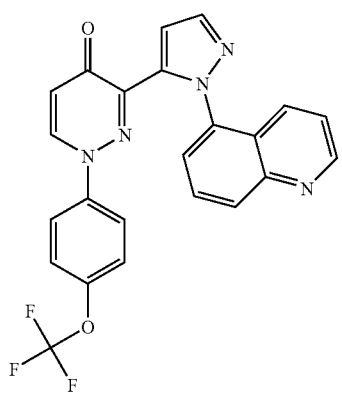

The product was obtained starting from 3-((E)-3-Dimethylamino-acryloyl)-1-(4-trifluoromethoxy-phenyl)-1H-pyridazin-4-one (A-8) and quinolin-5-yl-hydrazine according to the method described for example 91. MS: M=450.1 (M+H)$^+$

Example 228

1-(4-Chloro-phenyl)-3-[2-(2-fluoro-phenyl)-2H-pyrazol-3-yl]-1H-pyridazin-4-one

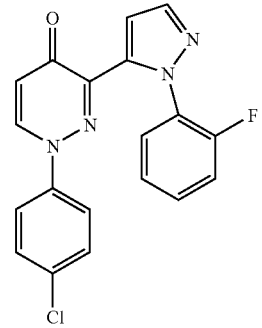

The product was obtained starting from 1-(4-Chloro-phenyl)-3-((E)-3-dimethylamino-acryloyl)-1H-pyridazin-4-one (A-24) and 2-fluoro-phenylhydrazine according to the method described for example 1. MS: M=367.1 (M+H)$^+$

Example 229

1-(4-Chloro-phenyl)-3-[2-(3-chloro-phenyl)-2H-pyrazol-3-yl]-1H-pyridazin-4-one

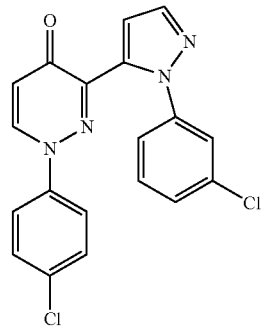

The product was obtained starting from 1-(4-Chloro-phenyl)-3-((E)-3-dimethylamino-acryloyl)-1H-pyridazin-4-one (A-24) and 3-chloro-phenylhydrazine according to the method described for example 1. MS: M=383.0 (M+H)$^+$

Example 230

1-(3-Dimethylaminomethyl-phenyl)-3-[2-(2-fluoro-phenyl)-2H-pyrazol-3-yl]-1H-pyridazin-4-one

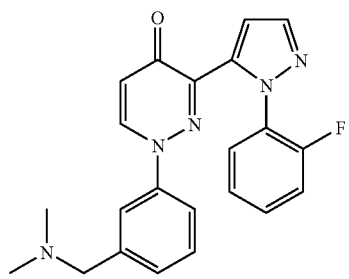

The product was obtained starting from 3-((E)-3-Dimethylamino-acryloyl)-1-(3-dimethylaminomethyl-phenyl)-1H-pyridazin-4-one (A-25) and 2-fluoro-phenylhydrazine according to the method described for example 91. MS: M=390.1 (M+H)⁺

Example 231

3-[2-(2-Fluoro-phenyl)-2H-pyrazol-3-yl]-1-[3-(piperidine-1-sulfonyl)-phenyl]-1H-pyridazin-4-one

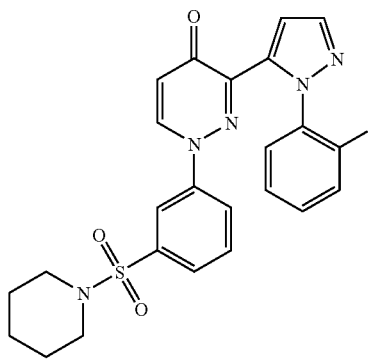

The product was obtained starting from 3-((E)-3-Dimethylamino-acryloyl)-1-[3-(piperidine-1-sulfonyl)-phenyl]-1H-pyridazin-4-one (A-26) and 2-fluoro-phenylhydrazine according to the method described for example 91. MS: M=480.1 (M+H)⁺

Example 232

3-[2-(2-Fluoro-phenyl)-2H-pyrazol-3-yl]-1-(4-trifluoromethanesulfonyl-phenyl)-1H-pyridazin-4-one

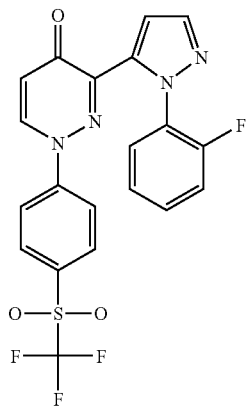

The product was obtained starting from 3-((E)-3-Dimethylamino-acryloyl)-1-(4-trifluoromethansulfonyl-phenyl)-1H-pyridazin-4-one (A-27) and 2-fluoro-phenylhydrazine according to the method described for example 91. MS: M=465.1 (M+H)⁺

Example 233

1-(4-dimethylaminomethyl-phenyl)-3-[2-(2-fluoro-phenyl)-2H-pyrazol-3-yl]-1H-pyridazin-4-one

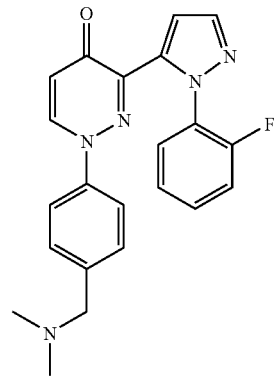

The product was obtained starting from 3-((E)-3-Dimethylamino-acryloyl)-1-(4-dimethylaminomethyl-phenyl)-1H-pyridazin-4-one (A-28) and 2-fluoro-phenylhydrazine according to the method described for example 91. MS: M=390.1 (M+H)⁺

Example 234

3-(2-Isoquinolin-5-yl-2H-pyrazol-3-yl)-1-(4-trifluoromethanesulfonyl-phenyl)-1H-pyridazin-4-one

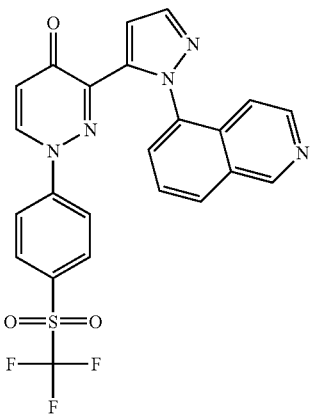

The product was obtained starting from 3-((E)-3-Dimethylamino-acryloyl)-1-(4-trifluoromethansulfonyl-phenyl)-1H-pyridazin-4-one (A-27) and isoquinolin-5-yl-hydrazine according to the method described for example 43. MS: M=498.0 (M+H)⁺

Example 235

3-(2-Quinolin-5-yl-2H-pyrazol-3-yl)-1-(4-trifluoromethanesulfonyl-phenyl)-1H-pyridazin-4-one

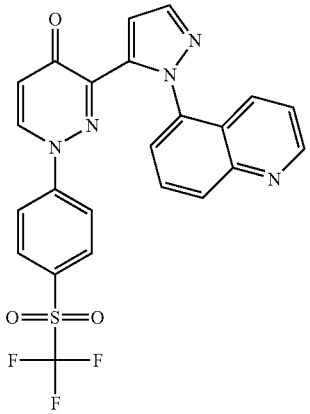

The product was obtained starting from 3-((E)-3-Dimethylamino-acryloyl)-1-(4-trifluoromethansulfonyl-phenyl)-1H-pyridazin-4-one (A-27) and quinolin-5-yl-hydrazine according to the method described for example 43. MS: M=498.1 (M+H)$^+$

Example 236

3-[2-(4-Chloro-naphthalen-1-yl)-2H-pyrazol-3-yl]-1-phenyl-1H-pyridazin-4-one

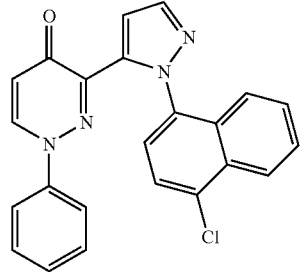

The product was obtained starting from 3-((E)-3-Dimethylamino-acryloyl)-1-phenyl-1H-pyridazin-4-one (A-1) and (4-chloro-naphthalen-1-yl)-hydrazine according to the method described for example 1. MS: M=399.1 (M+H)$^+$

Example 237

3-[2-(4-Chloro-naphthalen-1-yl)-2H-pyrazol-3-yl]-1-(4-trifluoromethyl-phenyl)-1H-pyridazin-4-one

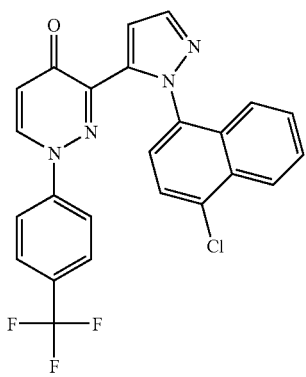

The product was obtained starting from 3-((E)-3-Dimethylamino-acryloyl)-1-(4-trifluoromethyl-phenyl)-1H-pyridazin-4-one (A-22) and (4-chloro-naphthalen-1-yl)-hydrazine according to the method described for example 1. MS: M=467.2 (M+H)$^+$

Example 238

3-[2-(2-Fluoro-phenyl)-2H-pyrazol-3-yl]-1-[3-(pyrrolidine-1-sulfonyl)-phenyl]-1H-pyridazin-4-one

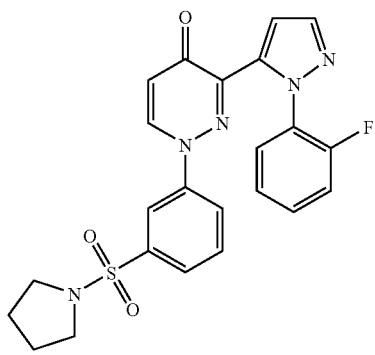

The product was obtained starting from 3-((E)-3-Dimethylamino-acryloyl)-1-[3-(pyrrolidine-1-sulfonyl)-phenyl]-1H-pyridazin-4-one (A-29) and 2-fluoro-phenylhydrazine according to the method described for example 91. MS: M=466.1 (M+H)$^+$

Example 239

4-{3-[2-(2-Fluoro-phenyl)-2H-pyrazol-3-yl]-4-oxo-4H-pyridazin-1-yl}-N-methyl-benzenesulfonamide

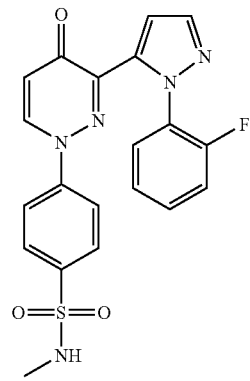

The product was obtained starting from 4-[3-((E)-3-Dimethylamino-acryloyl)-4-oxo-4H-pyridazin-1-yl]-N-methyl-benzenesulfonamide (A-30) and 2-fluoro-phenylhydrazine according to the method described for example 91. MS: M=426.1 (M+H)$^+$

Example 240

3-[2-(7-Chloro-quinolin-4-yl)-2H-pyrazol-3-yl]-1-(4-trifluoromethoxy-phenyl)-1H-pyridazin-4-one

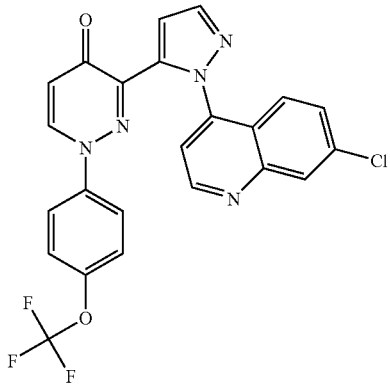

The product was obtained starting from 3-((E)-3-Dimethylamino-acryloyl)-1-(4-trifluoromethoxy-phenyl)-1H-pyridazin-4-one (A-8) and (7-chloro-quinolin-4-yl)-hydrazine according to the method described for example 91. MS: M=484.1 (M+H)+

Example 241

N,N-Diethyl-3-[4-oxo-3-(2-quinolin-5-yl-2H-pyrazol-3-yl)-4H-pyridazin-1-yl]-benzenesulfonamide

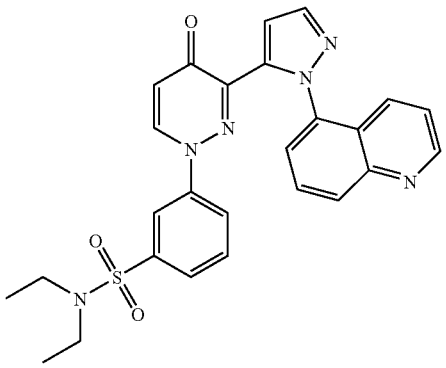

The product was obtained starting from 3-[3-((E)-3-Dimethylamino-acryloyl)-4-oxo-4H-pyridazin-1-yl]-N,N-diethyl-benzenesulfonamide (A-21) and quinolin-5-yl-hydrazine according to the method described for example 91. MS: M=501.2 (M+H)+

Example 242

3-(2-Quinolin-4-yl-2H-pyrazol-3-yl)-1-(4-trifluoromethanesulfonyl-phenyl)-1H-pyridazin-4-one

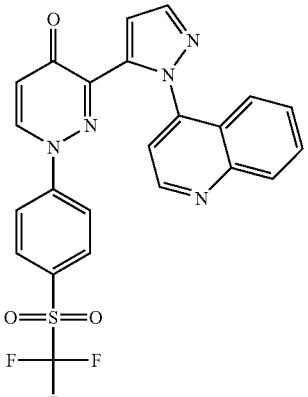

The product was obtained starting from 3-((E)-3-Dimethylamino-acryloyl)-1-(4-trifluoromethansulfonyl-phenyl)-1H-pyridazin-4-one (A-27) and quinolin-4-yl-hydrazine according to the method described for example 43. MS: M=498.1 (M+H)+

Example 243

3-[2-(4-Chloro-naphthalen-1-yl)-2H-pyrazol-3-yl]-1-(4-chloro-phenyl)-1H-pyridazin-4-one

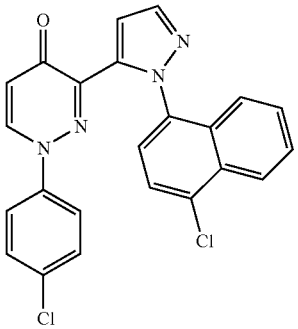

The product was obtained starting from 1-(4-Chloro-phenyl)-3-((E)-3-dimethylamino-acryloyl)-1H-pyridazin-4-one (A-24) and (4-chloro-naphthalen-1-yl)-hydrazine according to the method described for example 1. MS: M=433.1 (M+H)+

Example 244

3-[2-(4-Chloro-naphthalen-1-yl)-2H-pyrazol-3-yl]-1-(3-chloro-phenyl)-1H-pyridazin-4-one

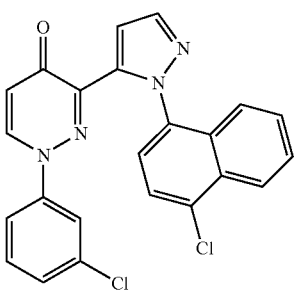

The product was obtained starting from 1-(3-Chloro-phenyl)-3-((E)-3-dimethylamino-acryloyl)-1H-pyridazin-4-one (A-23) and (4-chloro-naphthalen-1-yl)-hydrazine according to the method described for example 1. MS: M=433.1 (M+H)⁺

Example 245

N,N-Diethyl-3-[3-(2-isoquinolin-5-yl-2H-pyrazol-3-yl)-4-oxo-4H-pyridazin-1-yl]-benzenesulfonamide

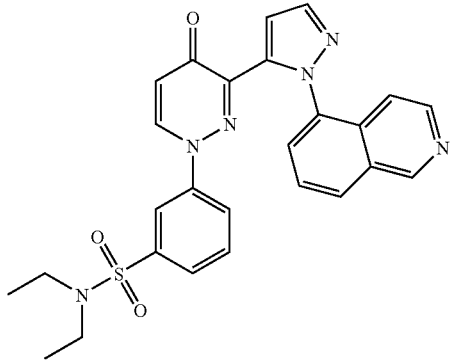

The product was obtained starting from 3-[3-((E)-3-Dimethylamino-acryloyl)-4-oxo-4H-pyridazin-1-yl]-N,N-diethyl-benzenesulfonamide (A-21) and isoquinolin-5-yl-hydrazine according to the method described for example 91. MS: M=501.2 (M+H)⁺

Example 246

3-(2-Isoquinolin-8-yl-2H-pyrazol-3-yl)-1-(4-trifluoromethoxy-phenyl)-1H-pyridazin-4-one

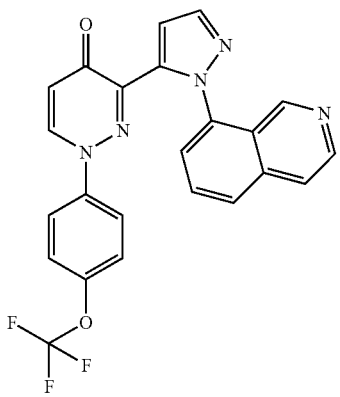

The product was obtained starting from 3-((E)-3-Dimethylamino-acryloyl)-1-(4-trifluoromethoxy-phenyl)-1H-pyridazin-4-one (A-8) and isoquinolin-8-yl-hydrazine according to the method described for example 91. MS: M=450.1 (M+H)⁺

Example 247

1-(4-Trifluoromethoxy-phenyl)-3-[2-(2-trifluoromethyl-pyridin-4-yl)-2H-pyrazol-3-yl]-1H-pyridazin-4-one

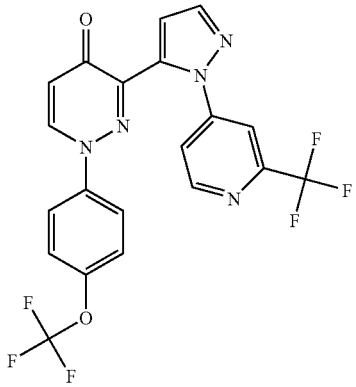

The product was obtained starting from 3-((E)-3-Dimethylamino-acryloyl)-1-(4-trifluoromethoxy-phenyl)-1H-pyridazin-4-one (A-8) and 4-hydrazino-2-trifluoromethylpyridine according to the method described for example 91. MS: M=468.1 (M+H)⁺

Example 248

3-[3-(2-Isoquinolin-5-yl-2H-pyrazol-3-yl)-4-oxo-4H-pyridazin-1-yl]-benzonitrile

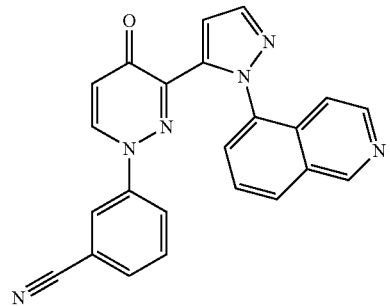

The product was obtained starting from 3-[3-((E)-3-Dimethylamino-acryloyl)-4-oxo-4H-pyridazin-1-yl]-benzonitrile (A-19) and isoquinolin-5-yl-hydrazine according to the method described for example 91. MS: M=391.2 (M+H)⁺

Example 249

3-{3-[2-(7-Chloro-quinolin-4-yl)-2H-pyrazol-3-yl]-4-oxo-4H-pyridazin-1-yl}-benzonitrile

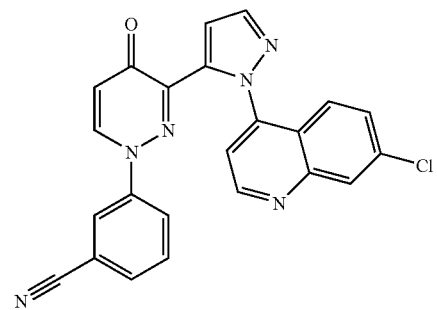

The product was obtained starting from 3-[3-((E)-3-Dimethylamino-acryloyl)-4-oxo-4H-pyridazin-1-yl]-benzonitrile (A-19) and (7-chloro-quinolin-4-yl)-hydrazine according to the method described for example 91. MS: M=425.1 (M+H)+

Example 250

1-[3-(Pyrrolidine-1-sulfonyl)-phenyl]-3-(2-quinolin-5-yl-2H-pyrazol-3-yl)-1H-pyridazin-4-one

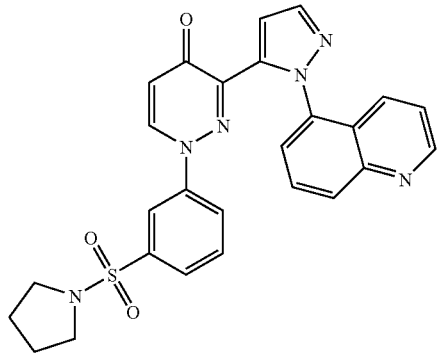

The product was obtained starting from 3-((E)-3-Dimethylamino-acryloyl)-1-[3-(pyrrolidine-1-sulfonyl)-phenyl]-1H-pyridazin-4-one (A-29) and quinolin-5-yl-hydrazine according to the method described for example 91. MS: M=499.2 (M+H)+

Example 251

3-[2-(7-Chloro-quinolin-4-yl)-2H-pyrazol-3-yl]-1-[3-(pyrrolidine-1-sulfonyl)-phenyl]-1H-pyridazin-4-one

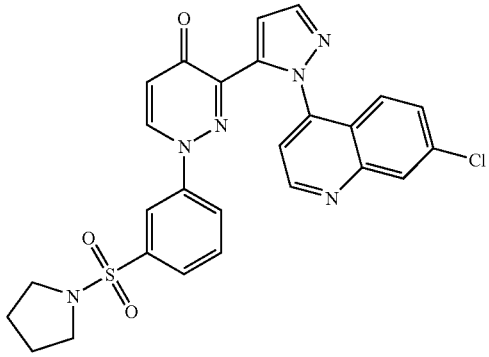

The product was obtained starting from 3-((E)-3-Dimethylamino-acryloyl)-1-[3-(pyrrolidine-1-sulfonyl)-phenyl]-1H-pyridazin-4-one (A-29) and (7-chloro-quinolin-4-yl)-hydrazine according to the method described for example 91. MS: M=533.1 (M+H)+

Example 252

3-{3-[2-(7-Chloro-quinolin-4-yl)-2H-pyrazol-3-yl]-4-oxo-4H-pyridazin-1-yl}-N,N-diethyl-benzenesulfonamide

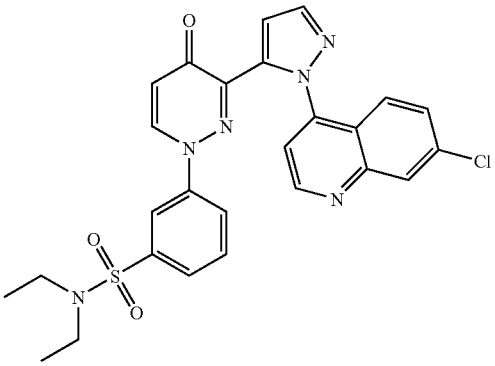

The product was obtained starting from 3-[3-((E)-3-Dimethylamino-acryloyl)-4-oxo-4H-pyridazin-1-yl]-N,N-diethyl-benzenesulfonamide (A-21) and (7-chloro-quinolin-4-yl)-hydrazine according to the method described for example 91. MS: M=533.1 (M+H)+

Example 253

3-{3-[2-(7-Chloro-quinolin-4-yl)-2H-pyrazol-3-yl]-4-oxo-4H-pyridazin-1-yl}-N-methyl-benzenesulfonamide

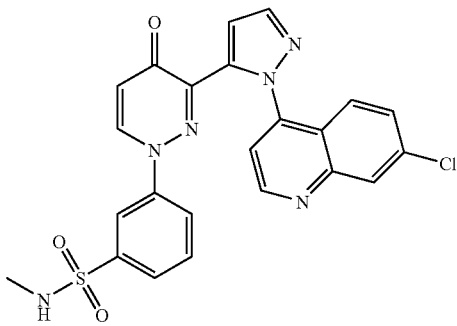

The product was obtained starting from 3-[3-((E)-3-Dimethylamino-acryloyl)-4-oxo-4H-pyridazin-1-yl]-N-methyl-benzenesulfonamide (A-31) and (7-chloro-quinolin-4-yl)-hydrazine according to the method described for example 91. MS: M=499.1 (M+H)+

Example 254

3-[3-(2-Isoquinolin-8-yl-2H-pyrazol-3-yl)-4-oxo-4H-pyridazin-1-yl]-N,N-dimethyl-benzenesulfonamide

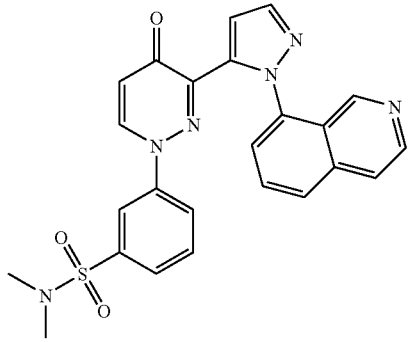

The product was obtained starting from 3-[3-((E)-3-Dimethylamino-acryloyl)-4-oxo-4H-pyridazin-1-yl]-N,N-dimethyl-benzenesulfonamide (A-12) and isoquinolin-8-yl-hydrazine according to the method described for example 91. MS: M=473.3 (M+H)+

Example 255

3-[2-(2-Fluoro-phenyl)-2H-pyrazol-3-yl]-1-[4-(2,2,2-trifluoro-ethoxy)-phenyl]-1H-pyridazin-4-one

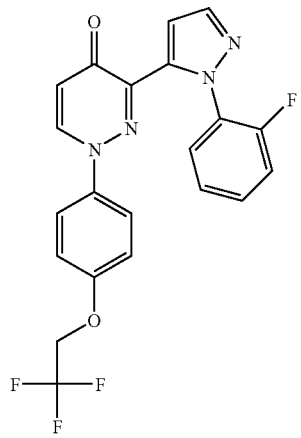

The product was obtained starting from 3-((E)-3-Dimethylamino-acryloyl)-1-[4-(2,2,2-trifluoro-ethoxy)-phenyl]-1H-pyridazin-4-one (A-32) and 2-fluoro-phenylhydrazine according to the method described for example 43. MS: M=431.1 (M+H)+

Example 256

3-(2-Phenyl-2H-pyrazol-3-yl)-1-[4-(2,2,2-trifluoro-ethoxy)-phenyl]-1H-pyridazin-4-one

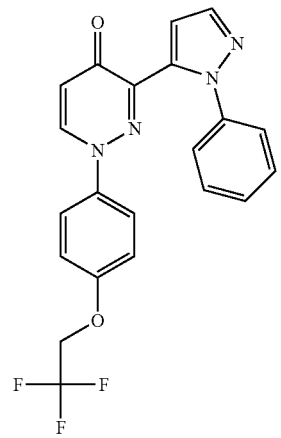

The product was obtained starting from 3-((E)-3-Dimethylamino-acryloyl)-1-[4-(2,2,2-trifluoro-ethoxy)-phenyl]-1H-pyridazin-4-one (A-32) and phenylhydrazine according to the method described for example 43. MS: M=413.1 (M+H)+

Example 257

3-[2-(3-Chloro-phenyl)-2H-pyrazol-3-yl]-1-[4-(2,2,2-trifluoro-ethoxy)-phenyl]-1H-pyridazin-4-one

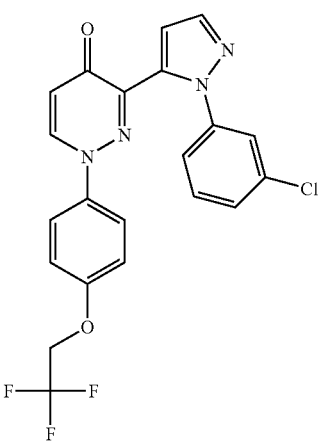

The product was obtained starting from 3-((E)-3-Dimethylamino-acryloyl)-1-[4-(2,2,2-trifluoro-ethoxy)-phenyl]-1H-pyridazin-4-one (A-32) and 3-chloro-phenylhydrazine according to the method described for example 43. MS: M=447.1 (M+H)+

Example 258

3-[2-(3-Fluoro-phenyl)-2H-pyrazol-3-yl]-1-[4-(2,2,2-trifluoro-ethoxy)-phenyl]-1H-pyridazin-4-one

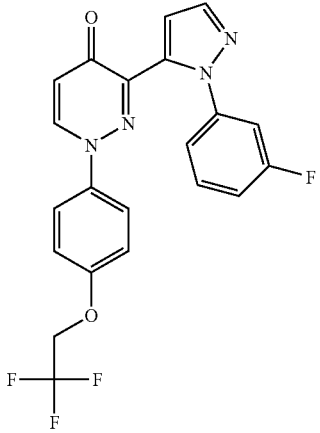

The product was obtained starting from 3-((E)-3-Dimethylamino-acryloyl)-1-[4-(2,2,2-trifluoro-ethoxy)-phenyl]-1H-pyridazin-4-one (A-32) and 3-fluoro-phenylhydrazine according to the method described for example 43. MS: M=431.1 (M+H)+

Example 259

3-(2-Quinolin-4-yl-2H-pyrazol-3-yl)-1-[4-(2,2,2-trifluoro-ethoxy)-phenyl]-1H-pyridazin-4-one

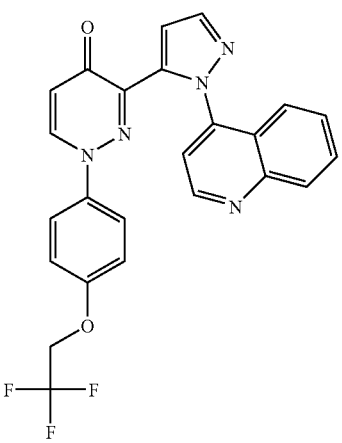

The product was obtained starting from 3-((E)-3-Dimethylamino-acryloyl)-1-[4-(2,2,2-trifluoro-ethoxy)-phenyl]-1H-pyridazin-4-one (A-32) and quinolin-4-yl-hydrazine according to the method described for example 43. MS: M=464.2 (M+H)+

Example 260

3-{3-[2-(2-Methyl-pyridin-4-yl)-2H-pyrazol-3-yl]-4-oxo-4H-pyridazin-1-yl}-benzonitrile

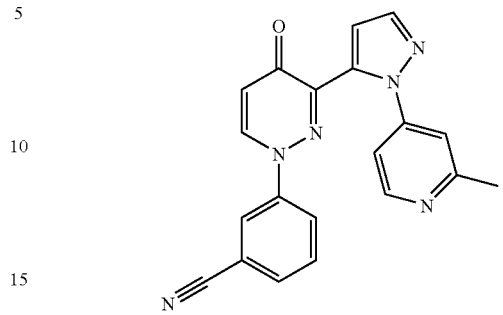

The product was obtained starting from 3-[3-((E)-3-Dimethylamino-acryloyl)-4-oxo-4H-pyridazin-1-yl]-benzonitrile (A-19) and 4-hydrazino-2-methylpyridine according to the method described for example 91. MS: M=355.2 (M+H)+

Example 261

3-(2-Isoquinolin-5-yl-2H-pyrazol-3-yl)-1-[3-(pyrrolidine-1-sulfonyl)-phenyl]-1H-pyridazin-4-one

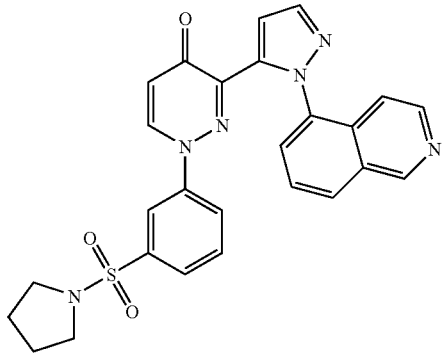

The product was obtained starting from 3-((E)-3-Dimethylamino-acryloyl)-1-[3-(pyrrolidine-1-sulfonyl)-phenyl]-1H-pyridazin-4-one (A-29) and isoquinolin-5-yl-hydrazine according to the method described for example 91. MS: M=499.3 (M+H)+

Example 262

N-Methyl-3-{3-[2-(2-methyl-pyridin-4-yl)-2H-pyrazol-3-yl]-4-oxo-4H-pyridazin-1-yl}-benzenesulfonamide

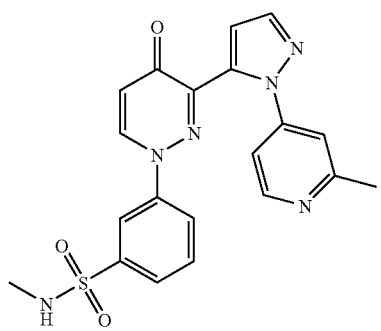

The product was obtained starting from 3-[3-((E)-3-Dimethylamino-acryloyl)-4-oxo-4H-pyridazin-1-yl]-N-methyl-benzenesulfonamide (A-31) and 4-hydrazino-2-methylpyridine according to the method described for example 91. MS: M=423.1 (M+H)+

Example 263

3-[3-(2-Isoquinolin-5-yl-2H-pyrazol-3-yl)-4-oxo-4H-pyridazin-1-yl]-N-methyl-benzenesulfonamide

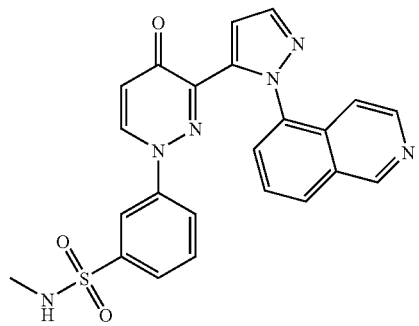

The product was obtained starting from 3-[3-((E)-3-Dimethylamino-acryloyl)-4-oxo-4H-pyridazin-1-yl]-N-methyl-benzenesulfonamide (A-31) and isoquinolin-5-yl-hydrazine according to the method described for example 91. MS: M=459.3 (M+H)+

Example 264

3-[2-(6-Chloro-quinolin-4-yl)-2H-pyrazol-3-yl]-1-[3-(pyrrolidine-1-sulfonyl)-phenyl]-1H-pyridazin-4-one

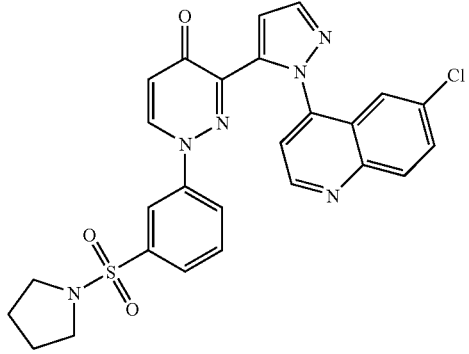

The product was obtained starting from 3-((E)-3-Dimethylamino-acryloyl)-1-[3-(pyrrolidine-1-sulfonyl)-phenyl]-1H-pyridazin-4-one (A-29) and (6-chloro-quinolin-4-yl)-hydrazine according to the method described for example 91. MS: M=533.1 (M+H)+

Example 265

1-[3-(Piperidine-1-sulfonyl)-phenyl]-3-(2-quinolin-5-yl-2H-pyrazol-3-yl)-1H-pyridazin-4-one

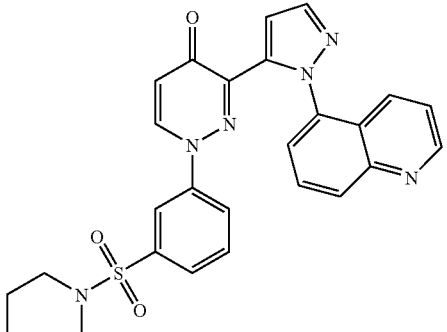

The product was obtained starting from 3-((E)-3-Dimethylamino-acryloyl)-1-[3-(piperidine-1-sulfonyl)-phenyl]-1H-pyridazin-4-one (A-26) and quinolin-5-yl-hydrazine according to the method described for example 91. MS: M=513.4 (M+H)+

Example 266

3-(2-Isoquinolin-5-yl-2H-pyrazol-3-yl)-1-[3-(piperidine-1-sulfonyl)-phenyl]-1H-pyridazin-4-one

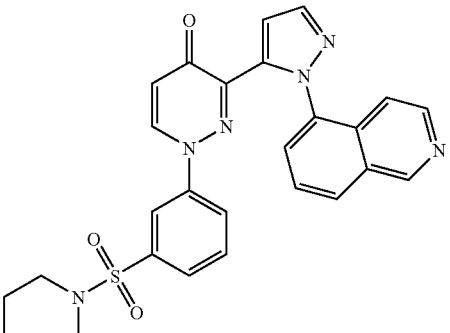

The product was obtained starting from 3-((E)-3-Dimethylamino-acryloyl)-1-[3-(piperidine-1-sulfonyl)-phenyl]-1H-pyridazin-4-one (A-26) and isoquinolin-5-yl-hydrazine according to the method described for example 91. MS: M=513.4 (M+H)+

Example 267

3-[2-(6-Chloro-quinolin-4-yl)-2H-pyrazol-3-yl]-1-[3-(piperidine-1-sulfonyl)-phenyl]-1H-pyridazin-4-one

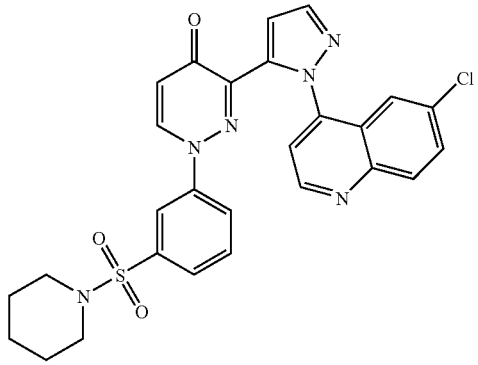

The product was obtained starting from 3-((E)-3-Dimethylamino-acryloyl)-1-[3-(piperidine-1-sulfonyl)-phenyl]-1H-pyridazin-4-one (A-26) and (6-chloro-quinolin-4-yl)-hydrazine according to the method described for example 91. MS: M=547.2 (M+H)+

Example 268

3-[2-(7-Chloro-quinolin-4-yl)-2H-pyrazol-3-yl]-1-[3-(piperidine-1-sulfonyl)-phenyl]-1H-pyridazin-4-one

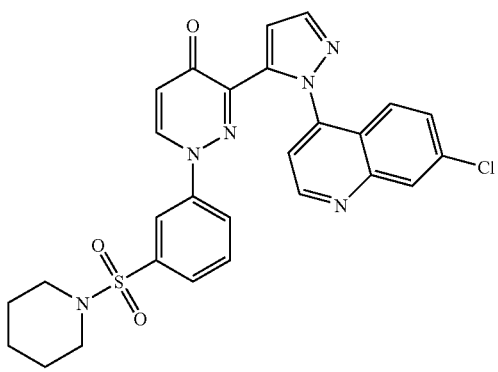

The product was obtained starting from 3-((E)-3-Dimethylamino-acryloyl)-1-[3-(piperidine-1-sulfonyl)-phenyl]-1H-pyridazin-4-one (A-26) and (7-chloro-quinolin-4-yl)-hydrazine according to the method described for example 91. MS: M=547.2 (M+H)+

Example 269

N,N-Diethyl-3-{3-[2-(2-fluoro-phenyl)-2H-pyrazol-3-yl]-4-oxo-4H-pyridazin-1-yl}-benzenesulfonamide

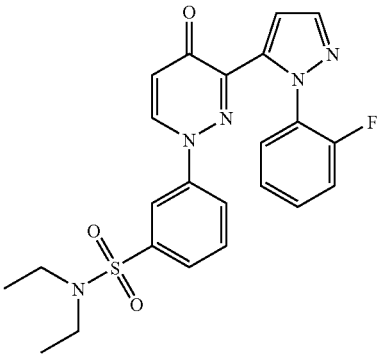

The product was obtained starting from 3-[3-((E)-3-Dimethylamino-acryloyl)-4-oxo-4H-pyridazin-1-yl]-N,N-diethyl-benzenesulfonamide (A-21) and 2-fluoro-phenylhydrazine according to the method described for example 91. MS: M=468.2 (M+H)+

Example 270

3-{3-[2-(3-Fluoro-phenyl)-2H-pyrazol-3-yl]-4-oxo-4H-pyridazin-1-yl}-benzonitrile

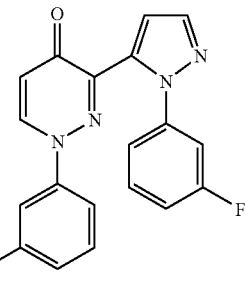

The product was obtained starting from 3-[3-((E)-3-Dimethylamino-acryloyl)-4-oxo-4H-pyridazin-1-yl]-benzonitrile (A-19) and 3-fluoro-phenylhydrazine according to the method described for example 91. MS: M=358.1 (M+H)+

Example 271

3-[2-(3-Fluoro-phenyl)-2H-pyrazol-3-yl]-1-[3-(pyrrolidine-1-sulfonyl)-phenyl]-1H-pyridazin-4-one

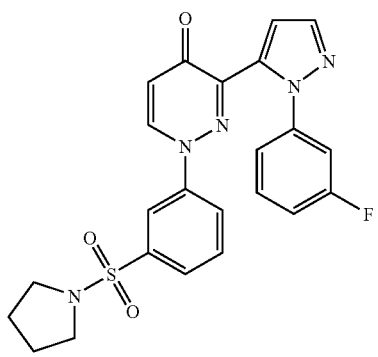

The product was obtained starting from 3-((E)-3-Dimethylamino-acryloyl)-1-[3-(pyrrolidine-1-sulfonyl)-phenyl]-1H-pyridazin-4-one (A-29) and 3-fluoro-phenylhydrazine according to the method described for example 91. MS: M=466.2 (M+H)⁺

Example 272

4-{3-[2-(3-Fluoro-phenyl)-2H-pyrazol-3-yl]-4-oxo-4H-pyridazin-1-yl}-N-methyl-benzenesulfonamide

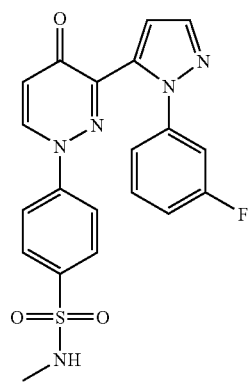

The product was obtained starting from 4-[3-((E)-3-Dimethylamino-acryloyl)-4-oxo-4H-pyridazin-1-yl]-N-methyl-benzenesulfonamide (A-30) and 3-fluoro-phenylhydrazine according to the method described for example 91. MS: M=426.1 (M+H)⁺

Example 273

3-[2-(3-Fluoro-phenyl)-2H-pyrazol-3-yl]-1-[3-(piperidine-1-sulfonyl)-phenyl]-1H-pyridazin-4-one

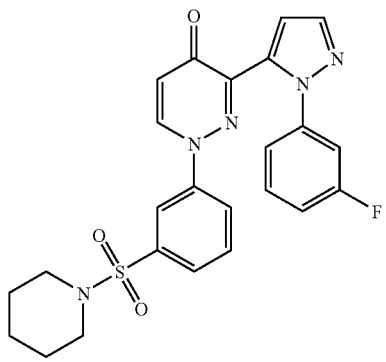

The product was obtained starting from 3-((E)-3-Dimethylamino-acryloyl)-1-[3-(piperidine-1-sulfonyl)-phenyl]-1H-pyridazin-4-one (A-26) and 3-fluoro-phenylhydrazine according to the method described for example 91. MS: M=480.1 (M+H)⁺

Example 274

3-{3-[2-(2,5-Difluoro-phenyl)-2H-pyrazol-3-yl]-4-oxo-4H-pyridazin-1-yl}-benzonitrile

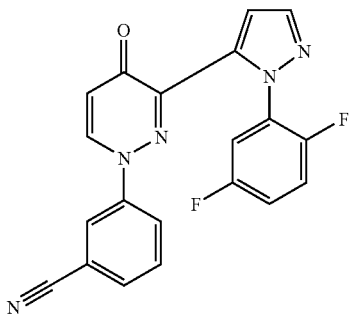

The product was obtained starting from 3-[3-((E)-3-Dimethylamino-acryloyl)-4-oxo-4H-pyridazin-1-yl]-benzonitrile (A-19) and 2,5-difluoro-phenylhydrazine according to the method described for example 91. MS: M=376.2 (M+H)⁺

Example 275

3-[2-(2,5-Difluoro-phenyl)-2H-pyrazol-3-yl]-1-[3-(pyrrolidine-1-sulfonyl)-phenyl]-1H-pyridazin-4-one

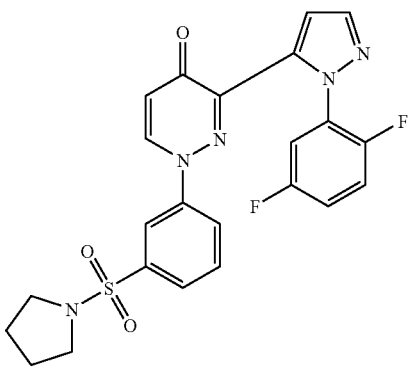

The product was obtained starting from 3-((E)-3-Dimethylamino-acryloyl)-1-[3-(pyrrolidine-1-sulfonyl)-phenyl]-1H-pyridazin-4-one (A-29) and 2,5-difluoro-phenylhydrazine according to the method described for example 91. MS: M=484.1 (M+H)⁺

Example 276

1-(3-Hydroxy-phenyl)-3-(2-naphthalen-1-yl-2H-pyrazol-3-yl)-1H-pyridazin-4-one

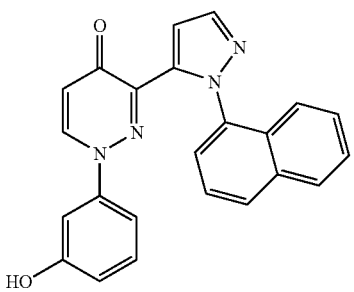

The product was obtained starting from 3-((E)-3-Dimethylamino-acryloyl)-1-(3-hydroxyphenyl)-1H-pyridazin-4-one (A-17) and naphthalen-1-yl-hydrazine according to the method described for example 91. MS: M=381.1 (M+H)+

Example 277

3-[2-(2,3-Dihydro-benzo[1,4]dioxin-6-yl)-2H-pyrazol-3-yl]-1-(3-hydroxy-phenyl)-1H-pyridazin-4-one

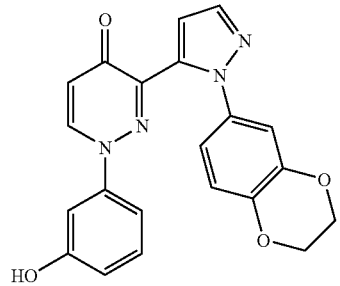

The product was obtained starting from 3-((E)-3-Dimethylamino-acryloyl)-1-(3-hydroxyphenyl)-1H-pyridazin-4-one (A-17) and (2,3-dihydro-benzo[1,4]dioxin-6-yl)-hydrazine according to the method described for example 91. MS: M=389.1 (M+H)+

Example 278

3-(2-Phenyl-2H-pyrazol-3-yl)-1-(4-trifluoromethane-sulfonyl-phenyl)-1H-pyridazin-4-one

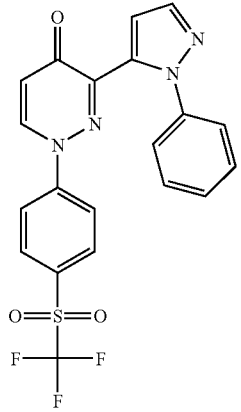

The product was obtained starting from 3-((E)-3-Dimethylamino-acryloyl)-1-(4-trifluoromethansulfonyl-phenyl)-1H-pyridazin-4-one (A-27) and phenylhydrazine according to the method described for example 1. MS: M=447.0 (M+H)+

Example 279

3-[2-(3-Chloro-phenyl)-2H-pyrazol-3-yl]-1-(4-trifluoromethanesulfonyl-phenyl)-1H-pyridazin-4-one

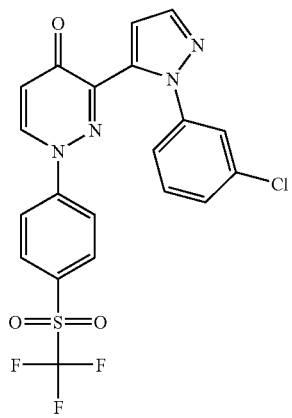

The product was obtained starting from 3-((E)-3-Dimethylamino-acryloyl)-1-(4-trifluoromethansulfonyl-phenyl)-1H-pyridazin-4-one (A-27) and 3-chloro-phenylhydrazine according to the method described for example 1. MS: M=481.1 (M+H)+

Example 280

3-[2-(2,3-Dichloro-phenyl)-2H-pyrazol-3-yl]-1-(4-trifluoromethanesulfonyl-phenyl)-1H-pyridazin-4-one

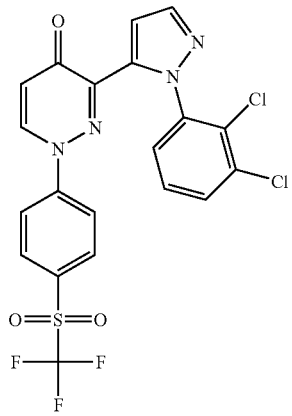

The product was obtained starting from 3-((E)-3-Dimethylamino-acryloyl)-1-(4-trifluoromethansulfonyl-phenyl)-1H-pyridazin-4-one (A-27) and 2,3-dichloro-phenylhydrazine according to the method described for example 1. MS: M=515.0 (M+H)+

Example 281

3-(2-Phenyl-2H-pyrazol-3-yl)-1-(3-trifluoromethane-sulfonyl-phenyl)-1H-pyridazin-4-one

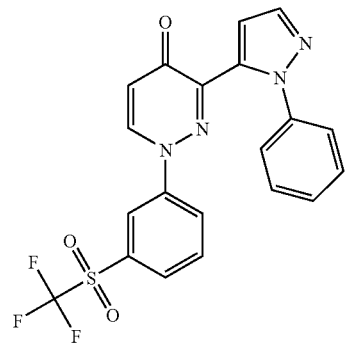

The product was obtained starting from 3-((E)-3-Dimethylamino-acryloyl)-1-(3-trifluoromethansulfonyl-phenyl)-1H-pyridazin-4-one (A-33) and phenylhydrazine according to the method described for example 1. MS: M=447.1 (M+H)+

Example 282

3-[2-(2-Fluoro-phenyl)-2H-pyrazol-3-yl]-1-(3-trifluoromethanesulfonyl-phenyl)-1H-pyridazin-4-one

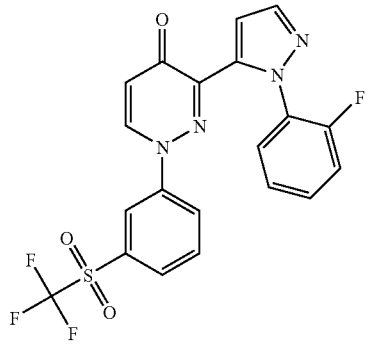

The product was obtained starting from 3-((E)-3-Dimethylamino-acryloyl)-1-(3-trifluoromethansulfonyl-phenyl)-1H-pyridazin-4-one (A-33) and 2-fluoro-phenylhydrazine according to the method described for example 1. MS: M=465.1 (M+H)+

Example 283

3-[2-(3-Chloro-phenyl)-2H-pyrazol-3-yl]-1-(3-trifluoromethanesulfonyl-phenyl)-1H-pyridazin-4-one

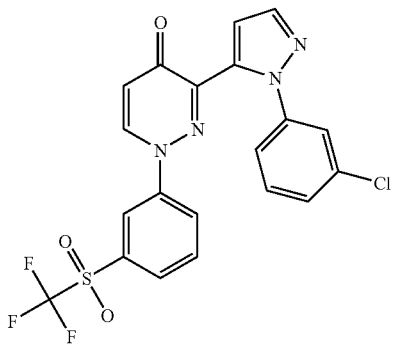

The product was obtained starting from 3-((E)-3-Dimethylamino-acryloyl)-1-(3-trifluoromethansulfonyl-phenyl)-1H-pyridazin-4-one (A-33) and 3-chloro-phenylhydrazine according to the method described for example 1. MS: M=481.0 (M+H)+

Example 284

3-{5-[4-Oxo-1-(3-trifluoromethanesulfonyl-phenyl)-1,4-dihydro-pyridazin-3-yl]-pyrazol-1-yl}-benzonitrile

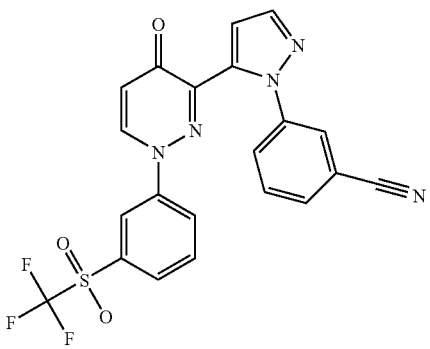

The product was obtained starting from 3-((E)-3-Dimethylamino-acryloyl)-1-(3-trifluoromethansulfonyl-phenyl)-1H-pyridazin-4-one (A-33) and 3-hydrazino-benzonitrile in ethanol as solvent according to the method described for example 1. MS: M=472.1 (M+H)+

Example 285

3-[2-(2,3-Dichloro-phenyl)-2H-pyrazol-3-yl]-1-(3-trifluoromethanesulfonyl-phenyl)-1H-pyridazin-4-one

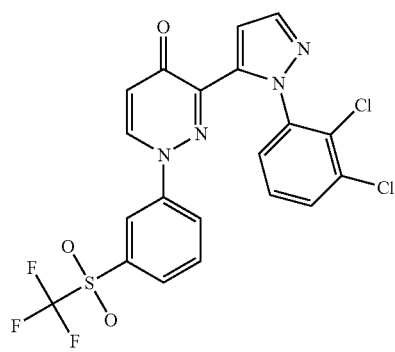

The product was obtained starting from 3-((E)-3-Dimethylamino-acryloyl)-1-(3-trifluoromethansulfonyl-phenyl)-1H-pyridazin-4-one (A-33) and 2,3-dichloro-phenylhydrazine according to the method described for example 1. MS: M=515.0 (M+H)+

Example 286

3-{3-[2-(2-Fluoro-phenyl)-2H-pyrazol-3-yl]-4-oxo-4H-pyridazin-1-yl}-benzonitrile

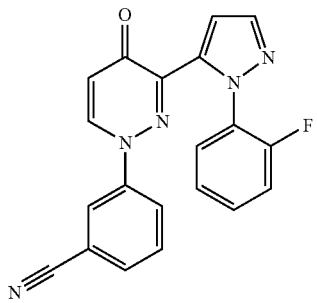

The product was obtained starting from 3-[3-((E)-3-Dimethylamino-acryloyl)-4-oxo-4H-pyridazin-1-yl]-benzonitrile (A-19) and 2-fluoro-phenylhydrazine according to the method described for example 1. MS: M=358.1 (M+H)$^+$

Example 287

3-{3-[2-(3-Chloro-phenyl)-2H-pyrazol-3-yl]-4-oxo-4H-pyridazin-1-yl}-benzonitrile

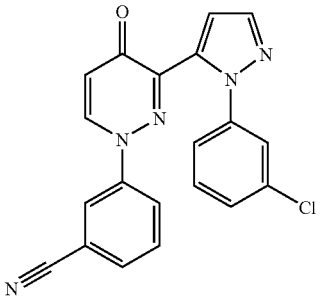

The product was obtained starting from 3-[3-((E)-3-Dimethylamino-acryloyl)-4-oxo-4H-pyridazin-1-yl]-benzonitrile (A-19) and 3-chloro-phenylhydrazine according to the method described for example 1. MS: M=374.1 (M+H)$^+$

Example 288

3-[2-(3-Chloro-2-fluoro-phenyl)-2H-pyrazol-3-yl]-1-(4-trifluoromethanesulfonyl-phenyl)-1H-pyridazin-4-one

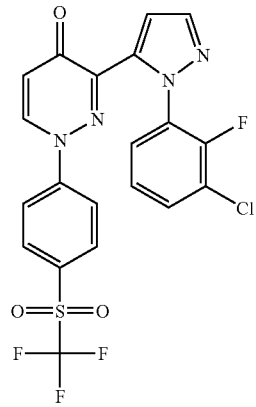

The product was obtained starting from 3-((E)-3-Dimethylamino-acryloyl)-1-(4-trifluoromethansulfonyl-phenyl)-1H-pyridazin-4-one (A-27) and 3-chloro-2-fluoro-phenylhydrazine according to the method described for example 1. MS: M=499.0 (M+H)$^+$

Example 289

3-[2-(3-Chloro-2-fluoro-phenyl)-2H-pyrazol-3-yl]-1-(3-trifluoromethanesulfonyl-phenyl)-1H-pyridazin-4-one

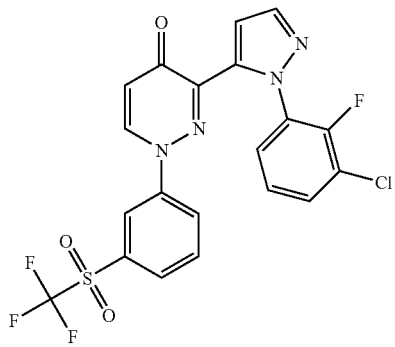

The product was obtained starting from 3-((E)-3-Dimethylamino-acryloyl)-1-(3-trifluoromethansulfonyl-phenyl)-1H-pyridazin-4-one (A-33) and 3-chloro-2-fluoro-phenylhydrazine according to the method described for example 1. MS: M=499.0 (M+H)$^+$

Example 290

3-[2-(2,3-Dihydro-benzo[1,4]dioxin-6-yl)-2H-pyrazol-3-yl]-1-(3-fluoromethoxy-phenyl)-1H-pyridazin-4-one

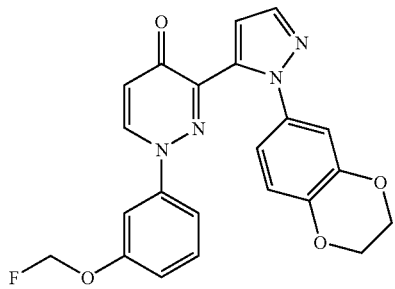

To a solution of 3-[2-(2,3-Dihydro-benzo[1,4]dioxin-6-yl)-2H-pyrazol-3-yl]-1-(3-hydroxy-phenyl)-1H-pyridazin-4-one (example 277) (50 mg, 0.13 mmol) in DMF (0.5 ml) were added CsCO$_3$ (80 mg, 0.25 mmol) and a solution of fluoromethyl tosylate (38 mg, 0.18 mmol; R. Iwata et al., J Label Compd Radiopharm 2003, 46, 555-566) in DMF (0.5 ml). The reaction mixture was heated under stirring in a sealed tube 2 h at 70° C. After cooling H$_2$O was added and the product was extracted with EtOAc. The organic layer was dried (Na$_2$SO$_4$) and the solvent was evaporated. Chromatography (5 g SiO$_2$, CH$_2$Cl$_2$/MeOH 95:5) afforded the product as a light brown foam (52 mg, 97%). MS: M=421.1 (M+H)$^+$

Example 291

1-(3-Fluoromethoxy-phenyl)-3-(2-naphthalen-1-yl-2H-pyrazol-3-yl)-1H-pyridazin-4-one

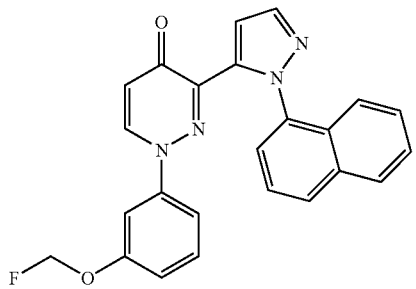

The product was obtained starting from 1-(3-Hydroxy-phenyl)-3-(2-naphthalen-1-yl-2H-pyrazol-3-yl)-1H-pyridazin-4-one (example 276) and fluoromethyl tosylate according to the method described in example 290. MS: M=413.1 (M+H)$^+$

Example 292

N-(3-{3-[2-(2-Fluoro-phenyl)-2H-pyrazol-3-yl]-4-oxo-4H-pyridazin-1-yl}-phenyl)-acetamide

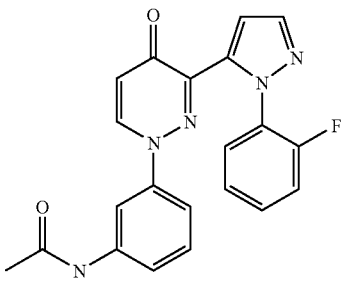

The product was obtained starting from N-{3-[3-((E)-3-Dimethylamino-acryloyl)-4-oxo-4H-pyridazin-1-yl]-phenyl}-acetamide (A-34) and 2-fluoro-phenylhydrazine according to the method described for example 1. MS: M=390.1 (M+H)$^+$

Example 293

3-{3-[2-(2-Fluoro-phenyl)-2H-pyrazol-3-yl]-4-oxo-4H-pyridazin-1-yl}-N-methyl-benzamide

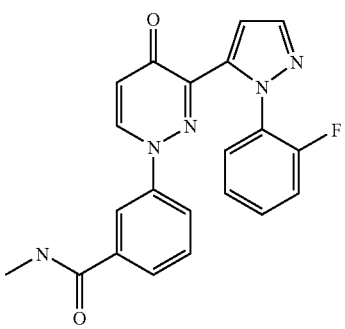

The product was obtained starting from 3-[3-((E)-3-Dimethylamino-acryloyl)-4-oxo-4H-pyridazin-1-yl]-N-methyl-benzamide (A-35) and 2-fluoro-phenylhydrazine according to the method described for example 1. MS: M=390.1 (M+H)$^+$

Example 294

N-(3-{3-[2-(2-Fluoro-phenyl)-2H-pyrazol-3-yl]-4-oxo-4H-pyridazin-1-yl}-phenyl)-N-methyl-acetamide

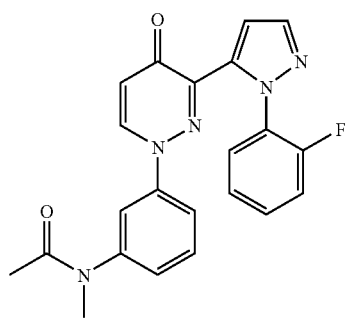

The product was obtained starting from N-(3-{3-[2-(2-Fluoro-phenyl)-2H-pyrazol-3-yl]-4-oxo-4H-pyridazin-1-yl}-phenyl)-acetamide (example 292) and methyl iodide in presence of sodium hydride in DMF at room temperature over night. MS: M=404.4 (M+H)$^+$

Example 295

3-[3-(2-Naphthalen-1-yl-2H-pyrazol-3-yl)-4-oxo-4H-pyridazin-1-yl]-benzoic acid 2-fluoro-ethyl ester

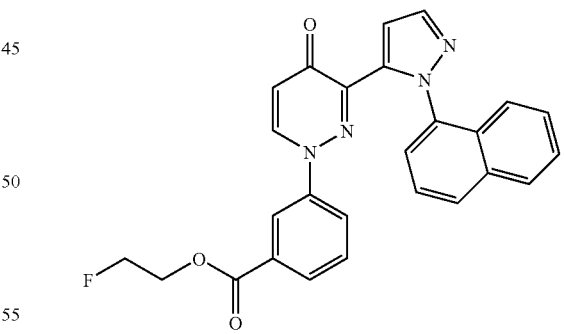

1-(3-Bromo-phenyl)-3-(2-naphthalen-1-yl-2H-pyrazol-3-yl)-1H-pyridazin-4-one (example 190) (100 mg, 0.23 mmol) was dissolved in EtOAc (3 ml) and the solution was placed in the reaction vessel. [PdCl$_2$(dppf)] (10 mg) was added followed by 2-fluoroethanol (97 mg, 1.5 mmol) and Et$_3$N (0.05 ml). The reactor was closed and the mixture was stirred 20 h under 70 bar carbon monoxide at 110° C. After evaporation of the solvents the residue was purified by chromatography (10 g SiO$_2$, Hept to Hept/EtOAc 1:1). The product was isolated as an off-white solid (69 mg, 67%). MS: M=455.1 (M+H)$^+$

Example 296

3-[3-(2-Naphthalen-1-yl-2H-pyrazol-3-yl)-4-oxo-4H-pyridazin-1-yl]-benzoic acid 3-fluoro-propyl ester

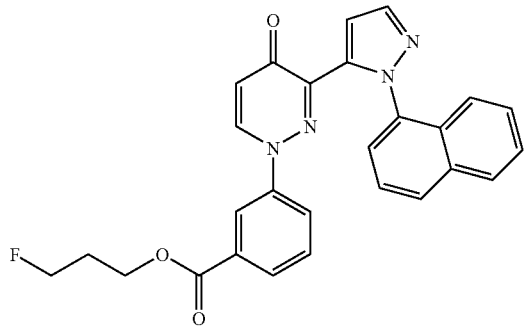

The product was obtained starting from 1-(3-Bromo-phenyl)-3-(2-naphthalen-1-yl-2H-pyrazol-3-yl)-1H-pyridazin-4-one (example 190) and 3-fluoropropan-1-ol according to the method described in example 295. MS: M=469.2 (M+H)$^+$

Example 297

3-[3-(2-Naphthalen-1-yl-2H-pyrazol-3-yl)-4-oxo-4H-pyridazin-1-yl]-benzoic acid methyl ester

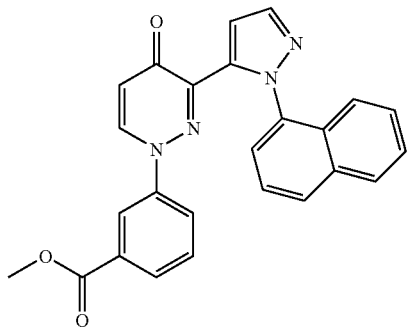

The product was obtained starting from 1-(3-Bromo-phenyl)-3-(2-naphthalen-1-yl-2H-pyrazol-3-yl)-1H-pyridazin-4-one (example 190) and methanol according to the method described in example 295. MS: M=423.1 (M+H)$^+$

Example 298

3-[2-(2-Fluoro-phenyl)-2H-pyrazol-3-yl]-1-[3-(1-hydroxy-ethyl)-phenyl]-1H-pyridazin-4-one

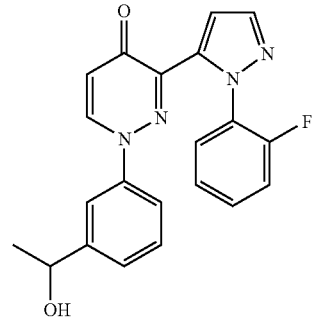

The product was obtained starting from 3-((E)-3-Dimethylamino-acryloyl)-1-[3-(1-hydroxy-ethyl)-phenyl]-1H-pyridazin-4-one (A-36) and 2-fluoro-phenylhydrazine according to the method described for example 1. MS: M=377.1 (M+H)$^+$

Example 299

1-(3-Acetyl-phenyl)-3-[2-(2-fluoro-phenyl)-2H-pyrazol-3-yl]-1H-pyridazin-4-one

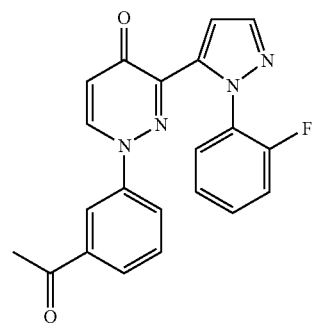

The product was obtained starting from 3-[2-(2-Fluoro-phenyl)-2H-pyrazol-3-yl]-1-[3-(1-hydroxy-ethyl)-phenyl]-1H-pyridazin-4-one (example 298) by treatment with manganese dioxide in dichloromethane at room temperature for 6 h. MS: M=375.1 (M+H)$^+$

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |

-continued

| Ingredients | Per tablet | |
|---|---|---|
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxyde (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 mL |

The active ingredient is dissolved in a mixture of Polyethylene Glycol 400 and water for injection (part). The pH is adjusted to 5.0 by Acetic Acid. The volume is adjusted to 1.0 mL by addition of the residual amount of water. The solution is filtered, filled into vials using an appropriate overage and sterilized.

Example D

Soft gelatin capsules containing the following ingredients can be manufactured in a conventional manner:

Capsule Contents

| | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |

Gelatin Capsule

| | |
|---|---|
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

The invention claimed is:

1. A compound of formula (I)

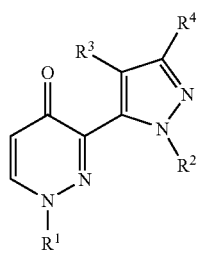

wherein
R¹ is aryl which is optionally substituted with 1 to 4 substituents independently selected from the group consisting of lower-alkyl, hydroxy-lower-alkyl, lower-alkoxy, fluoro-lower-alkyl, fluoro-lower-alkoxy, lower-alkyl-$SO_2$, fluoro-lower-alkyl-$SO_2$, halogen, lower-alkoxy-lower-alkyl, cyano, $NO_2$, lower-alkyl-SO, morpholinyl, $NH_2$-$SO_2$, N(H,lower-alkyl)-$SO_2$, N(lower-alkyl)$_2$-$SO_2$, piperidinyl-$SO_2$, pyrrolidinyl-$SO_2$, hydroxy, COOH, COO-lower-alkyl, COO-fluoro-lower-alkyl, lower-alkyl-C(O)O, CO-lower-alkyl, $CONH_2$, CON(H, lower-alkyl), CON(lower-alkyl)$_2$, lower-alkyl-CO—NH, lower-alkyl-CO—N(lower-alkyl), $NH_2$, N(H, lower-alkyl), N(lower-alkyl)$_2$, $NH_2$-lower-alkyl, N(H, lower-alkyl)-lower-alkyl, N(lower-alkyl)$_2$-lower-alkyl, cycloalkyl, phenyloxy and phenyl,
 or wherein two substituents at adjacent positions on the aryl group are bound together to form a ring and said two bound substituents together are lower-alkylene, dioxo-lower-alkylene, dioxo-fluoro-lower-alyklene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)—C(O)-lower-alkylene, lower-alkylene-NH—C(O)-lower-alkylene, lower-alkylene-N(lower alkyl)—C(O)-lower-alkylene, C(O)—NH-lower-alkylene or C(O)—N(lower-alkyl)-lower-alkylene;

R² is aryl or heteroaryl, which aryl or heteroaryl is optionally substituted with 1 to 4 substituents independently selected from the group consisting of halogen, cyano, lower-alkyl, lower-alkoxy, fluoro-lower-alkyl, fluoro-lower-alkoxy, lower-alkinyl, lower-alkyl-$SO_2$, fluoro-lower-alkyl-$SO_2$, tri(lower-alkyl)silyl-loweralkinyl, COOH, $CONH_2$, $NH_2$—$SO_2$, COO-lower-alkyl, 6-oxo-1,4,5,6-tetrahydropyridazinyl, lower-alkoxy-lower-alkyl, CON(H,lower-alkyl), CON(lower-alkyl)$_2$, N(H, lower-alkyl)—$SO_2$, N(lower-alkyl)$_2$-$SO_2$, lower-alkenyl, hydroxy, $NO_2$, morpholinyl, tetrahydropyridazinyl, piperidinyl, piperazinyl, (N-lower-alkyl)-piperazinyl, pyrrolidinyl, lower-alkyl-C(O)O, lower-alkyl-CO—NH, lower-alkyl-CO—N(lower-alkyl), imidazolyl, pyridinyl, CO-lower-alkyl, $NH_2$, N(H,lower-alkyl), N(lower-alkyl)$_2$, $NH_2$-lower-alkyl, N(H,lower-alkyl)-lower-alkyl, N(lower-alkyl)$_2$-lower-alkyl, cycloalkyl, phenyloxy and phenyl which is optionally substituted with 1 to 4 substituents independently selected from halogen, lower-alkoxy, lower-alkyl, fluoro-lower-alkyl, fluoro-lower-alkoxy, hydroxy and cyano, or wherein two substituents at adjacent positions on the aryl or heteroaryl group are bound together to form a ring and said two bound substituents together are lower-alkylene, dioxo-lower-alkylene, dioxo-fluoro-lower-alyklene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)—C(O)-lower-alkylene, lower-alkylene-NH—C(O)-lower-alkylene, lower-alkylene-N(lower alkyl)—C(O)-lower-alkylene, C(O)—NH-lower-alkylene or C(O)—N(lower-alkyl)-lower-alkylene;

R³ is hydrogen, lower-alkyl, fluoro-lower-alkyl, lower-alkoxy, fluoro-lower-alkoxy, halogen, hydroxy or phenyl; and R⁴ is hydrogen, lower-alkyl, fluoro-lower-alkyl, lower-alkoxy, fluoro-lower-alkoxy, halogen, hydroxy or phenyl;

or a pharmaceutically acceptable salt or ester thereof.

2. The compound of claim 1, wherein
R¹ is aryl which is optionally substituted with 1 to 4 substituents independently selected from the group consisting of lower-alkyl, lower-alkoxy, fluoro-lower-alkyl, fluoro-lower-alkoxy, lower-alkyl-$SO_2$, halogen, lower-alkoxy-lower-alkyl, cyano, $NO_2$, lower-alkyl-SO, morpholinyl, $NH_2$—$SO_2$, N(H,lower-alkyl)—$SO_2$, N(lower-alkyl)$_2$-$SO_2$, hydroxy, COOH, COO-lower-alkyl, lower-alkyl-C(O)O, CO-lower-alkyl, $CONH_2$, CON(H,lower-alkyl), CON(lower-alkyl)$_2$, lower-alkyl-CO—NH, lower-alkyl-CO—N(lower-alkyl), $NH_2$, N(H,lower-alkyl), N(lower-alkyl)$_2$, $NH_2$-lower-alkyl, N(H,lower-alkyl)-lower-alkyl, N(lower-alkyl)$_2$-lower-alkyl, cycloalkyl, phenyloxy and phenyl,
 or wherein two substituents at adjacent positions on the aryl group are bound together to form a ring and said two bound substituents together are lower-alkylene, dioxo-lower-alkylene, dioxo-fluoro-lower-alyklene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)—C(O)-lower-alkylene, lower-alkylene-NH—C(O)-lower-alkylene, lower-alkylene-N(lower alkyl)—C(O)-lower-alkylene, C(O)—NH-lower-alkylene or C(O)—N(lower-alkyl)-lower-alkylene;

and $R^2$ is aryl or heteroaryl, which aryl or heteroaryl is optionally substituted with 1 to 4 substituents independently selected from the group consisting of halogen, cyano, lower-alkyl, lower-alkoxy, fluoro-lower-alkyl, lower-alkinyl, lower-alkyl-$SO_2$, tri(lower-alkyl)silyl-lower-alkinyl, COOH, $CONH_2$, $NH_2$—$SO_2$, COO-lower-alkyl, 6-oxo-1,4,5,6-tetrahydropyridazinyl, lower-alkoxy-lower-alkyl, CON(H,lower-alkyl), CON(lower-alkyl)$_2$, N(H,lower-alkyl)—$SO_2$, N(lower-alkyl)$_2$-$SO_2$, lower-alkenyl, hydroxy, $NO_2$, morpholinyl, tetrahydropyridazinyl, piperidinyl, piperazinyl, (N-lower-alkyl)-piperazinyl, pyrrolidinyl, lower-alkyl-C(O)O, lower-alkyl-CO—NH, lower-alkyl-CO—N(lower-alkyl), imidazolyl, pyridinyl, CO-lower-alkyl, $NH_2$, N(H, lower-alkyl), N(lower-alkyl)$_2$, $NH_2$-lower-alkyl, N(H, lower-alkyl)-lower-alkyl, N(lower-alkyl)$_2$-lower-alkyl, cycloalkyl, phenyloxy and phenyl which is optionally substituted with 1 to 4 substituents independently selected from halogen, lower-alkoxy, lower-alkyl, fluoro-lower-alkyl, fluoro-lower-alkoxy, hydroxy and cyano, or wherein two substituents at adjacent positions on the aryl or heteroaryl group are bound together to form a ring and said two bound substituents together are lower-alkylene, dioxo-lower-alkylene, dioxo-fluoro-lower-alyklene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)—C(O)-lower-alkylene, lower-alkylene-NH—C(O)-lower-alkylene, lower-alkylene-N(lower alkyl)—C(O)-lower-alkylene, C(O)—NH-lower-alkylene or C(O)—N(lower-alkyl)-lower-alkylene.

3. The compound of claim 2, wherein $R^1$ is phenyl which is optionally substituted with 1 to 3 substituents independently selected from the group consisting of lower-alkyl, lower-alkoxy, fluoro-lower-alkyl, fluoro-lower-alkoxy and lower-alkyl-$SO_2$, or wherein two substituents at adjacent positions on the phenyl group are bound together to form a ring and said two bound substituents together are dioxo-fluoro-lower-alyklene.

4. The compound of claim 3, wherein $R^1$ is phenyl which is optionally substituted with fluoro-lower-alkyl, fluoro-lower-alkoxy or lower-alkyl-$SO_2$.

5. The compound of claim 4, wherein $R^1$ is phenyl, 3-trifluoromethyl-phenyl, 3-trifluoromethoxy-phenyl, 3-methylsulfonyl-phenyl, 4-trifluoromethoxy-phenyl or 4-difluoromethyl-phenyl.

6. The compound of claim 1, wherein $R^1$ is phenyl which is optionally substituted with 1 to 3 substituents independently selected from the group consisting of hydroxy-lower-alkyl, lower-alkoxy, fluoro-lower-alkyl, fluoro-lower-alkoxy, lower-alkyl-$SO_2$, fluoro-lower-alkyl-$SO_2$, halogen, cyano, N(H,lower-alkyl)—$SO_2$, N(lower-alkyl)$_2$-$SO_2$, piperidinyl-$SO_2$, pyrrolidinyl-$SO_2$, hydroxy, COO-lower-alkyl, COO-fluoro-lower-alkyl, CO-lower-alkyl, CON(H,lower-alkyl), CON(lower-alkyl)$_2$, lower-alkyl-CO—NH, lower-alkyl-CO—N(lower-alkyl) and N(lower-alkyl)$_2$-lower-alkyl, or wherein two substituents at adjacent positions on the aryl group are bound together to form a ring and said two bound substituents together are dioxo-lower-alkylene or dioxo-fluoro-lower-alyklene.

7. The compound of claim 6, wherein $R^1$ is phenyl which is optionally substituted with hydroxy-lower-alkyl, fluoro-lower-alkoxy, lower-alkyl-$SO_2$, fluoro-lower-alkyl-$SO_2$, cyano, hydroxy, COO-fluoro-lower-alkyl, CON(H,lower-alkyl), lower-alkyl-CO—NH or lower-alkyl-CO—N(lower-alkyl).

8. The compound of claim 7, wherein $R^1$ is 3-trifluoromethoxy-phenyl, 3-methylsulfonyl-phenyl, 3-difluoromethoxy-phenyl, 4-trifluoromethoxy-phenyl, 3-hydroxy-phenyl, 3-cyano-phenyl, 4-trifluoromethylsulfonyl-phenyl, 4-(2,2,2-trifluoroethoxy)-phenyl, 3-trifluoromethylsulfonyl-phenyl, 3-acetamide-phenyl, 3-(methylamide)-phenyl, 3-(N-methyl-acetamide)-phenyl, 3-(2-fluoro-ethoxycarbonyl)-phenyl or 3-(1-hydroxy-ethyl)-phenyl.

9. The compound of claim 2, wherein $R^2$ is aryl selected from the group consisting of phenyl and naphthyl or heteroaryl selected from the group consisting of pyridinyl and thiazolyl, which aryl or heteroaryl group is optionally substituted with 1 to 3 substituents independently selected from the group consisting of halogen, cyano, lower-alkyl, lower-alkoxy, fluoro-lower-alkyl, lower-alkinyl, lower-alkyl-$SO_2$, tri(lower-alkyl)silyl-loweralkinyl, COOH, $CONH_2$, $NH_2$—$SO_2$, COO-lower-alkyl, 6-oxo-1,4,5,6-tetrahydropyridazinyl, and phenyl which is optionally substituted with 1 to 3 substituents independently selected from halogen and lower-alkoxy, or wherein two substituents at adjacent positions on the aryl or heteroaryl group are bound together to form a ring and said two bound substituents together are lower-alkylene or dioxo-lower-alkylene.

10. The compound of claim 9, wherein $R^2$ is aryl selected from the group consisting of phenyl and naphthyl or pyridinyl, which aryl or pyridinyl is optionally substituted with 1 to 2 substituents independently selected from the group consisting of halogen, cyano, lower-alkyl, and lower-alkinyl, or wherein two substituents at adjacent positions on the aryl group are bound together to form a ring and said two bound substituents together are dioxo-lower-alkylene.

11. The compound of claim 10, wherein $R^2$ is phenyl, 2,5-difluoro-phenyl, 3-cyano-phenyl, 3-ethinyl-phenyl, 3-chloro-phenyl, 4-fluoro-phenyl, naphthyl, 3-fluoro-phenyl, pyridin-4-yl, 3-methyl-pyridin-4-yl or 2,3-dihydro-benzo[1,4]dioxin-6-yl.

12. The compound of claim 2, wherein $R^2$ is aryl selected from the group consisting of phenyl and naphthyl or heteroaryl selected from the group consisting of quinolinyl, thiazolyl, pyridinyl, isoquinolinyl and isothiazolyl, which aryl or heteroaryl group is optionally substituted with 1 to 3 substituents independently selected from the group consisting of halogen, cyano, lower-alkyl, lower-alkoxy, fluoro-lower-alkyl, fluoro-lower-alkoxy, lower-alkyl-$SO_2$, fluoro-lower-alkyl-$SO_2$, $NH_2$—$SO_2$, N(lower-alkyl)$_2$-$SO_2$, hydroxy and lower-alkyl-CO—NH, or wherein two substituents at adjacent positions on the aryl or heteroaryl group are bound together to form a ring and said two bound substituents together are dioxo-lower-alkylene or dioxo-fluoro-lower-alyklene.

13. The compound of claim 12, wherein $R^2$ is aryl selected from the group consisting of phenyl and naphthyl or heteroaryl selected from the group consisting of quinolinyl and pyridinyl, which aryl or heteroaryl group is optionally substituted with 1 to 2 substituents independently selected from the group consisting of halogen, cyano and lower-alkyl, or wherein two substituents at adjacent positions on the aryl or heteroaryl group are bound together to form a ring and said two bound substituents together are dioxo-lower-alkylene.

14. The compound of claim 13, wherein $R^2$ is 2,4-difluoro-phenyl, 3-cyano-phenyl, 2,5-difluoro-phenyl, phenyl, 2-fluoro-phenyl, 3-chloro-phenyl, naphthyl, 2,3-dihydro-benzo[1,4]dioxin-6-yl, 6-fluoro-quinolin-4-yl, 2-methyl-pyridin-4-yl or quinolin-4-yl.

15. The compound of claim 1, wherein $R^3$ is hydrogen or lower-alkyl.

16. The compound of claim 15, wherein $R^3$ is hydrogen.

17. The compound of claim 1, wherein $R^4$ is hydrogen.

18. The compound of claim 1, selected from the group consisting of
- 3-(2-Benzo[1,3]dioxol-5-yl-2H-pyrazol-3-yl)-1-phenyl-1H-pyridazin-4-one,
- 1-(4-Methoxy-phenyl)-3-(2-phenyl-2H-pyrazol-3-yl)-1H-pyridazin-4-one,
- 3-[2-(2-Methoxy-phenyl)-2H-pyrazol-3-yl]-1-phenyl-1H-pyridazin-4-one,
- 1-Phenyl-3-(2-o-tolyl-2H-pyrazol-3-yl)-1H-pyridazin-4-one,
- 1-Phenyl-3-[2-(3-trifluoromethyl-phenyl)-2H-pyrazol-3-yl]-1H-pyridazin-4-one,
- 3-[2-(2,5-Difluoro-phenyl)-2H-pyrazol-3-yl]-1-(3-trifluoromethyl-phenyl)-1H-pyridazin-4-one,
- 1-(3-Trifluoromethyl-phenyl)-3-[2-(2-trifluoromethyl-phenyl)-2H-pyrazol-3-yl]-1H-pyridazin-4-one,
- 3-[2-(2,5-Dimethyl-phenyl)-2H-pyrazol-3-yl]-1-(3-trifluoromethyl-phenyl)-1H-pyridazin-4-one,
- 3-[2-(2,5-Difluoro-phenyl)-2H-pyrazol-3-yl]-1-phenyl-1H-pyridazin-4-one, and
- 1-Phenyl-3-[2-(2-trifluoromethyl-phenyl)-2H-pyrazol-3-yl]-1H-pyridazin-4-one or a pharmaceutically acceptable salt or ester thereof.

19. The compound of claim 1, selected from the group consisting of
- 3-[2-(2,5-Dimethyl-phenyl)-2H-pyrazol-3-yl]-1-phenyl-1H-pyridazin-4-one,
- 3-[2-(2,5-Dichloro-phenyl)-2H-pyrazol-3-yl]-1-phenyl-1H-pyridazin-4-one,
- 1-Phenyl-3-(2-pyridin-2-yl-2H-pyrazol-3-yl)-1H-pyridazin-4-one,
- 3-{5-[4-Oxo-1-(3-trifluoromethyl-phenyl)-1,4-dihydro-pyridazin-3-yl]-pyrazol-1-yl}-benzonitrile,
- 1-Phenyl-3-(2-pyridin-4-yl-2H-pyrazol-3-yl)-1H-pyridazin-4-one,
- 3-[5-(4-Oxo-1-phenyl-1,4-dihydro-pyridazin-3-yl)-pyrazol-1-yl]-benzonitrile,
- 1-(3-Ethyl-phenyl)-3-(2-phenyl-2H-pyrazol-3-yl)-1H-pyridazin-4-one,
- 1-(3-Methoxy-phenyl)-3-(2-phenyl-2H-pyrazol-3-yl)-1H-pyridazin-4-one,
- 1-Phenyl-3-(2-phenyl-2H-pyrazol-3-yl)-1H-pyridazin-4-one, and
- 3-[2-(4-Methanesulfonyl-phenyl)-2H-pyrazol-3-yl]-1-phenyl-1H-pyridazin-4-one or a pharmaceutically acceptable salt or ester thereof.

20. The compound of claim 1, selected from the group consisting of
- 1-(3-Ethyl-phenyl)-3-[2-(4-methanesulfonyl-phenyl)-2H-pyrazol-3-yl]-1H-pyridazin-4-one,
- 1-(3-Ethyl-phenyl)-3-(2-pyridin-4-yl-2H-pyrazol-3-yl)-1H-pyridazin-4-one,
- 3-[2-(3-Bromo-phenyl)-2H-pyrazol-3-yl]-1-phenyl-1H-pyridazin-4-one,
- 3-[2-(2-Methyl-pyridin-4-yl)-2H-pyrazol-3-yl]-1-phenyl-1H-pyridazin-4-one,
- 3-[2-(2-Chloro-pyridin-4-yl)-2H-pyrazol-3-yl]-1-phenyl-1H-pyridazin-4-one,
- 3-(2-Phenyl-2H-pyrazol-3-yl)-1-(3-trifluoromethoxy-phenyl)-1H-pyridazin-4-one,
- 3-(2-Pyridin-4-yl-2H-pyrazol-3-yl)-1-(3-trifluoromethoxy-phenyl)-1H-pyridazin-4-one,
- 3-[2-(2-Fluoro-phenyl)-2H-pyrazol-3-yl]-1-(3-trifluoromethoxy-phenyl)-1H-pyridazin-4-one,
- 3-{5-[4-Oxo-1-(3-trifluoromethoxy-phenyl)-1,4-dihydro-pyridazin-3-yl]-pyrazol-1-yl}-benzonitrile, and
- 1-(3-Methanesulfonyl-phenyl)-3-(2-phenyl-2H-pyrazol-3-yl)-1H-pyridazin-4-one or a pharmaceutically acceptable salt or ester thereof.

21. The compound of claim 1, selected from the group consisting of
- 1-Phenyl-3-[2-(3-trimethylsilanylethynyl-phenyl)-2H-pyrazol-3-yl]-1H-pyridazin-4-one,
- 3-[2-(3-Ethynyl-phenyl)-2H-pyrazol-3-yl]-1-phenyl-1H-pyridazin-4-one,
- 3-(2-Phenyl-2H-pyrazol-3-yl)-1-(4-trifluoromethoxy-phenyl)-1H-pyridazin-4-one,
- 3-[2-(2-Fluoro-phenyl)-2H-pyrazol-3-yl]-1-(4-trifluoromethoxy-phenyl)-1H-pyridazin-4-one,
- 3-(2-Pyridin-4-yl-2H-pyrazol-3-yl)-1-(4-trifluoromethoxy-phenyl)-1H-pyridazin-4-one,
- 3-{5-[4-Oxo-1-(4-trifluoromethoxy-phenyl)-1,4-dihydro-pyridazin-3-yl]-pyrazol-1-yl}-benzonitrile,
- 3-[2-(2-Fluoro-phenyl)-2H-pyrazol-3-yl]-1-(3-trifluoromethyl-phenyl)-1H-pyridazin-4-one,
- 3-[2-(4-Chloro-phenyl)-2H-pyrazol-3-yl]-1-phenyl-1H-pyridazin-4-one,
- 1-Phenyl-3-(2-p-tolyl-2H-pyrazol-3-yl)-1H-pyridazin-4-one, and
- 3-(2-Phenyl-2H-pyrazol-3-yl)-1-(3-trifluoromethyl-phenyl)-1H-pyridazin-4-one or a pharmaceutically acceptable salt or ester thereof.

22. The compound of claim 1, selected from the group consisting of
- 3-[2-(4-Methoxy-phenyl)-2H-pyrazol-3-yl]-1-(3-trifluoromethyl-phenyl)-1H-pyridazin-4-one,
- 3-[2-(3-Chloro-phenyl)-2H-pyrazol-3-yl]-1-(3-trifluoromethyl-phenyl)-1H-pyridazin-4-one,
- 3-{5-[4-Oxo-1-(3-trifluoromethoxy-phenyl)-1,4-dihydro-pyridazin-3-yl]-pyrazol-1-yl}-benzamide,
- 3-(2-p-Tolyl-2H-pyrazol-3-yl)-1-(3-trifluoromethoxy-phenyl)-1H-pyridazin-4-one,
- 4-{5-[4-Oxo-1-(3-trifluoromethoxy-phenyl)-1,4-dihydro-pyridazin-3-yl]-pyrazol-1-yl}-benzoic acid,
- 4-{5-[4-Oxo-1-(3-trifluoromethoxy-phenyl)-1,4-dihydro-pyridazin-3-yl]-pyrazol-1-yl}-benzenesulfonamide,
- 3-[2-(4-Chloro-phenyl)-2H-pyrazol-3-yl]-1-(3-trifluoromethoxy-phenyl)-1H-pyridazin-4-one,
- 3-[2-(3-Chloro-phenyl)-2H-pyrazol-3-yl]-1-(3-trifluoromethoxy-phenyl)-1H-pyridazin-4-one,
- 3-[2-(4-Fluoro-phenyl)-2H-pyrazol-3-yl]-1-(3-trifluoromethoxy-phenyl)-1H-pyridazin-4-one, and
- 3-[2-(2,3-Dimethyl-phenyl)-2H-pyrazol-3-yl]-1-(3-trifluoromethoxy-phenyl)-1H-pyridazin-4-one or a pharmaceutically acceptable salt or ester thereof.

23. The compound of claim 1, selected from the group consisting of
- 3-[2-(3-Chloro-2-methyl-phenyl)-2H-pyrazol-3-yl]-1-(3-trifluoromethoxy-phenyl)-1H-pyridazin-4-one, 3-[2-(2-Bromo-4-fluoro-phenyl)-2H-pyrazol-3-yl]-1-(3-trifluoromethoxy-phenyl)-1H-pyridazin-4-one,
3-[2-(3-Fluoro-2-methyl-phenyl)-2H-pyrazol-3-yl]-1-(3-trifluoromethoxy-phenyl)-1H-pyridazin-4-one,
3-[2-(3-Fluoro-4-methyl-phenyl)-2H-pyrazol-3-yl]-1-(3-trifluoromethoxy-phenyl)-1H-pyridazin-4-one,
3-{5-[4-Oxo-1-(3-trifluoromethoxy-phenyl)-1,4-dihydro-pyridazin-3-yl]-pyrazol-1-yl}-benzoic acid methyl ester,
3-[2-(5,6,7,8-Tetrahydro-isoquinolin-1-yl)-2H-pyrazol-3-yl]-1-(3-trifluoromethoxy-phenyl)-1H-pyridazin-4-one,
2-{5-[4-Oxo-1-(3-trifluoromethoxy-phenyl)-1,4-dihydro-pyridazin-3-yl]-pyrazol-1-yl}-isonicotinic acid ethyl ester,
3-(2-Pyridin-2-yl-2H-pyrazol-3-yl)-1-(3-trifluoromethoxy-phenyl)-1H-pyridazin-4-one,
3-{5-[1-(3-Methanesulfonyl-phenyl)-4-oxo-1,4-dihydro-pyridazin-3-yl]-pyrazol-1-yl}-benzamide, and
1-(3-Methanesulfonyl-phenyl)-3-(2-p-tolyl-2H-pyrazol-3-yl)-1H-pyridazin-4-one
or a pharmaceutically acceptable salt or ester thereof.

24. The compound of claim 1, selected from the group consisting of
    4-{5-[1-(3-Methanesulfonyl-phenyl)-4-oxo-1,4-dihydro-pyridazin-3-yl]-pyrazol-1-yl}-benzoic acid,
    4-{5-[1-(3-Methanesulfonyl-phenyl)-4-oxo-1,4-dihydro-pyridazin-3-yl]-pyrazol-1-yl}-benzenesulfonamide,
    3-[2-(4-Chloro-phenyl)-2H-pyrazol-3-yl]-1-(3-methanesulfonyl-phenyl)-1H-pyridazin-4-one,
    3-[2-(3-Chloro-phenyl)-2H-pyrazol-3-yl]-1-(3-methanesulfonyl-phenyl)-1H-pyridazin-4-one,
    2-{5-[1-(3-Methanesulfonyl-phenyl)-4-oxo-1,4-dihydro-pyridazin-3-yl]-pyrazol-1-yl}-benzoic acid,
    3-[2-(4-Fluoro-phenyl)-2H-pyrazol-3-yl]-1-(3-methanesulfonyl-phenyl)-1H-pyridazin-4-one,
    3-[2-(2,3-Dimethyl-phenyl)-2H-pyrazol-3-yl]-1-(3-methanesulfonyl-phenyl)-1H-pyridazin-4-one,
    3-[2-(3-Chloro-2-methyl-phenyl)-2H-pyrazol-3-yl]-1-(3-methanesulfonyl-phenyl)-1H-pyridazin-4-one,
    3-[2-(3-Fluoro-2-methyl-phenyl)-2H-pyrazol-3-yl]-1-(3-methanesulfonyl-phenyl)-1H-pyridazin-4-one, and
    3-[2-(3-Fluoro-4-methyl-phenyl)-2H-pyrazol-3-yl]-1-(3-methanesulfonyl-phenyl)-1H-pyridazin-4-one
or a pharmaceutically acceptable salt or ester thereof.

25. The compound of claim 1, selected from the group consisting of
    3-{5-[1-(3-Methanesulfonyl-phenyl)-4-oxo-1,4-dihydro-pyridazin-3-yl]-pyrazol-1-yl}-benzoic acid methyl ester,
    1-(3-Methanesulfonyl-phenyl)-3-[2-(5,6,7,8-tetrahydro-isoquinolin-1-yl)-2H-pyrazol-3-yl]-1H-pyridazin-4-one,
    2-{5-[1-(3-Methanesulfonyl-phenyl)-4-oxo-1,4-dihydro-pyridazin-3-yl]-pyrazol-1-yl}-4,6-dimethyl-nicotinonitrile,
    2-{5-[1-(3-Methanesulfonyl-phenyl)-4-oxo-1,4-dihydro-pyridazin-3-yl]-pyrazol-1-yl}-isonicotinic acid ethyl ester,
    1-(3-Methanesulfonyl-phenyl)-3-(2-pyridin-2-yl-2H-pyrazol-3-yl)-1H-pyridazin-4-one,
    4-{5-[4-Oxo-1-(3-trifluoromethoxy-phenyl)-1,4-dihydro-pyridazin-3-yl]-pyrazol-1-yl}-benzonitrile,
    3-[2-(2,4-Difluoro-phenyl)-2H-pyrazol-3-yl]-1-(3-trifluoromethoxy-phenyl)-1H-pyridazin-4-one,
    3-{2-[4-(6-Oxo-1,4,5,6-tetrahydro-pyridazin-3-yl)-phenyl]-2H-pyrazol-3-yl}-1-(3-trifluoromethoxy-phenyl)-1H-pyridazin-4-one,
    3-[2-(2,3-Dihydro-benzo[1,4]dioxin-6-yl)-2H-pyrazol-3-yl]-1-(3-trifluoromethoxy-phenyl)-1H-pyridazin-4-one, and
    3-(2-Naphthalen-1-yl-2H-pyrazol-3-yl)-1-(3-trifluoromethoxy-phenyl)-1H-pyridazin-4-one
or a pharmaceutically acceptable salt or ester thereof.

26. The compound of claim 1, selected from the group consisting of
    3-[2-(3-Fluoro-phenyl)-2H-pyrazol-3-yl]-1-(3-trifluoromethoxy-phenyl)-1H-pyridazin-4-one,
    3-[2-(2,5-Difluoro-phenyl)-2H-pyrazol-3-yl]-1-(3-trifluoromethoxy-phenyl)-1H-pyridazin-4-one,
    3-[2-(4-Isopropyl-phenyl)-2H-pyrazol-3-yl]-1-(3-trifluoromethoxy-phenyl)-1H-pyridazin-4-one,
    3-[2-(2,3-Dihydro-benzo[1,4]dioxin-6-yl)-2H-pyrazol-3-yl]-1-(3-methanesulfonyl-phenyl)-1H-pyridazin-4-one,
    1-(3-Methanesulfonyl-phenyl)-3-(2-naphthalen-1-yl-2H-pyrazol-3-yl)-1H-pyridazin-4-one,
    3-[2-(3-Fluoro-phenyl)-2H-pyrazol-3-yl]-1-(3-methanesulfonyl-phenyl)-1H-pyridazin-4-one,
    3-[2-(2,5-Difluoro-phenyl)-2H-pyrazol-3-yl]-1-(3-methanesulfonyl-phenyl)-1H-pyridazin-4-one,
    3-[2-(4-Isopropyl-phenyl)-2H-pyrazol-3-yl]-1-(3-methanesulfonyl-phenyl)-1H-pyridazin-4-one,
    3-(4-Ethyl-2-phenyl-2H-pyrazol-3-yl)-1-(3-methanesulfonyl-phenyl)-1H-pyridazin-4-one, and
    1-(3-Methanesulfonyl-phenyl)-3-[2-(2-methyl-pyridin-4-yl)-2H-pyrazol-3-yl]-1H-pyridazin-4-one
or a pharmaceutically acceptable salt or ester thereof.

27. The compound of claim 1, selected from the group consisting of
    1-(3-Difluoromethoxy-phenyl)-3-(2-pyridin-2-yl-2H-pyrazol-3-yl)-1H-pyridazin-4-one,
    3-(2-Benzo[1,3]dioxol-5-yl-2H-pyrazol-3-yl)-1-(3-methanesulfonyl-phenyl)-1H-pyridazin-4-one,
    3-(2-Benzo[1,3]dioxol-5-yl-2H-pyrazol-3-yl)-1-(3-difluoromethoxy-phenyl)-1H-pyridazin-4-one,
    3-{5-[1-(3-Methanesulfonyl-phenyl)-4-oxo-1,4-dihydro-pyridazin-3-yl]-pyrazol-1-yl}-benzonitrile,
    3-{2-[4-(2-Fluoro-4-methoxy-phenyl)-thiazol-2-yl]-2H-pyrazol-3-yl}-1-(3-methanesulfonyl-phenyl)-1H-pyridazin-4-one,
    1-(3-Methanesulfonyl-phenyl)-3-{2-[4-(2-methoxy-phenyl)-thiazol-2-yl]-2H-pyrazol-3-yl}-1H-pyridazin-4-one,
    1-(3-Difluoromethoxy-phenyl)-3-[2-(2,3-dihydro-benzo[1,4]dioxin-6-yl)-2H-pyrazol-3-yl]-1H-pyridazin-4-one,
    1-(3-Difluoromethoxy-phenyl)-3-[2-(3-fluoro-phenyl)-2H-pyrazol-3-yl]-1H-pyridazin-4-one,
    1-(4-Difluoromethoxy-phenyl)-3-[2-(2,3-dihydro-benzo[1,4]dioxin-6-yl)-2H-pyrazol-3-yl]-1H-pyridazin-4-one,
    1-(4-Difluoromethoxy-phenyl)-3-[2-(3-fluoro-phenyl)-2H-pyrazol-3-yl]-1H-pyridazin-4-one, and
    1-(2,2-Difluoro-benzo[1,3]dioxol-5-yl)-3-[2-(2,3-dihydro-benzo[1,4]dioxin-6-yl)-2H-pyrazol-3-yl]-1H-pyridazin-4-one
or a pharmaceutically acceptable salt or ester thereof.

28. The compound of claim 1, selected from the group consisting of
    3-{5-[4-Oxo-1-(3-trifluoromethyl-phenyl)-1,4-dihydro-pyridazin-3-yl]-pyrazol-1-yl}-benzonitrile, 1-Phenyl-3-(2-pyridin-4-yl-2H-pyrazol-3-yl)-1H-pyridazin-4-one,
3-(2-Phenyl-2H-pyrazol-3-yl)-1-(3-trifluoromethoxy-phenyl)-1H-pyridazin-4-one,
3-(2-Pyridin-4-yl-2H-pyrazol-3-yl)-1-(3-trifluoromethoxy-phenyl)-1H-pyridazin-4-one,
1-(3-Methanesulfonyl-phenyl)-3-(2-phenyl-2H-pyrazol-3-yl)-1H-pyridazin-4-one,
3-[2-(3-Ethynyl-phenyl)-2H-pyrazol-3-yl]-1-phenyl-1H-pyridazin-4-one,
3-(2-Pyridin-4-yl-2H-pyrazol-3-yl)-1-(4-trifluoromethoxy-phenyl)-1H-pyridazin-4-one,
3-{5-[4-Oxo-1-(4-trifluoromethoxy-phenyl)-1,4-dihydro-pyridazin-3-yl]-pyrazol-1-yl}-benzonitrile,
3-[2-(4-Fluoro-phenyl)-2H-pyrazol-3-yl]-1-(3-trifluoromethoxy-phenyl)-1H-pyridazin-4-one,
3-[2-(3-Chloro-phenyl)-2H-pyrazol-3-yl]-1-(3-methanesulfonyl-phenyl)-1H-pyridazin-4-one,
3-[2-(2,3-Dihydro-benzo[1,4]dioxin-6-yl)-2H-pyrazol-3-yl]-1-(3-trifluoromethoxy-phenyl)-1H-pyridazin-4-one,
3-(2-Naphthalen-1-yl-2H-pyrazol-3-yl)-1-(3-trifluoromethoxy-phenyl)-1H-pyridazin-4-one,
1-(3-Methanesulfonyl-phenyl)-3-(2-naphthalen-1-yl-2H-pyrazol-3-yl)-1H-pyridazin-4-one,
3-[2-(3-Fluoro-phenyl)-2H-pyrazol-3-yl]-1-(3-methanesulfonyl-phenyl)-1H-pyridazin-4-one,
3-[2-(2,5-Difluoro-phenyl)-2H-pyrazol-3-yl]-1-(3-methanesulfonyl-phenyl)-1H-pyridazin-4-one,
1-(3-Methanesulfonyl-phenyl)-3-[2-(2-methyl-pyridin-4-yl)-2H-pyrazol-3-yl]-1H-pyridazin-4-one,
3-{5-[1-(3-Methanesulfonyl-phenyl)-4-oxo-1,4-dihydro-pyridazin-3-yl]-pyrazol-1-yl}-benzonitrile, and
1-(4-Difluoromethoxy-phenyl)-3-[2-(3-fluoro-phenyl)-2H-pyrazol-3-yl]-1H-pyridazin-4-one,
or a pharmaceutically acceptable salt or ester thereof.

29. The compound of claim 1, selected from the group consisting of
3-{3-[2-(3-Fluoro-phenyl)-2H-pyrazol-3-yl]-4-oxo-4H-pyridazin-1-yl}-N,N-dimethyl-benzenesulfonamide,
1-(2,2-Difluoro-benzo[1,3]dioxol-5-yl)-3-[2-(3-fluoro-phenyl)-2H-pyrazol-3-yl]-1H-pyridazin-4-one,
3-[2-(3,4-Difluoro-phenyl)-2H-pyrazol-3-yl]-1-(3-methanesulfonyl-phenyl)-1H-pyridazin-4-one,
3-[2-(2,4-Difluoro-phenyl)-2H-pyrazol-3-yl]-1-(3-methanesulfonyl-phenyl)-1H-pyridazin-4-one,
3-(2-Benzo[1,3]dioxol-4-yl-2H-pyrazol-3-yl)-1-(3-methanesulfonyl-phenyl)-1H-pyridazin-4-one,
3-[3-(2-Benzo[1,3]dioxol-5-yl-2H-pyrazol-3-yl)-4-oxo-4H-pyridazin-1-yl]-N,N-dimethyl-benzenesulfonamide,
3-{3-[2-(3-Cyano-phenyl)-2H-pyrazol-3-yl]-4-oxo-4H-pyridazin-1-yl}-N,N-dimethyl-benzenesulfonamide,
3-(2-Benzo[1,3]dioxol-5-yl-2H-pyrazol-3-yl)-1-(3-fluoro-phenyl)-1H-pyridazin-4-one,
1-(3-Fluoro-phenyl)-3-[2-(3-fluoro-phenyl)-2H-pyrazol-3-yl]-1H-pyridazin-4-one, and
3-{5-[1-(3-Fluoro-phenyl)-4-oxo-1,4-dihydro-pyridazin-3-yl]-pyrazol-1-yl}-benzonitrile
or a pharmaceutically acceptable salt or ester thereof.

30. The compound of claim 1, selected from the group consisting of
1-Benzo[1,3]dioxol-4-yl-3-(2-benzo[1,3]dioxol-5-yl-2H-pyrazol-3-yl)-1H-pyridazin-4-one,
1-Benzo[1,3]dioxol-4-yl-3-[2-(3-fluoro-phenyl)-2H-pyrazol-3-yl]-1H-pyridazin-4-one,
3-[5-(1-Benzo[1,3]dioxol-4-yl-4-oxo-1,4-dihydro-pyridazin-3-yl)-pyrazol-1-yl]-benzonitrile,
3-[2-(6-Fluoro-quinolin-4-yl)-2H-pyrazol-3-yl]-1-(3-methanesulfonyl-phenyl)-1H-pyridazin-4-one,
1-(3-Difluoromethoxy-phenyl)-3-[2-(2,5-difluoro-phenyl)-2H-pyrazol-3-yl]-1H-pyridazin-4-one,
1-(2,2-Difluoro-benzo[1,3]dioxol-5-yl)-3-[2-(2,5-difluoro-phenyl)-2H-pyrazol-3-yl]-1H-pyridazin-4-one,
3-{3-[2-(2,5-Difluoro-phenyl)-2H-pyrazol-3-yl]-4-oxo-4H-pyridazin-1-yl}-N,N-dimethyl-benzenesulfonamide,
3-{5-[1-(2,2-Difluoro-benzo[1,3]dioxol-5-yl)-4-oxo-1,4-dihydro-pyridazin-3-yl]-pyrazol-1-yl}-benzonitrile,
3-[2-(2,2-Difluoro-benzo[1,3]dioxol-4-yl)-2H-pyrazol-3-yl]-1-(3-methanesulfonyl-phenyl)-1H-pyridazin-4-one, and
1-(3-Methanesulfonyl-phenyl)-3-(2-thiazol-2-yl-2H-pyrazol-3-yl)-1H-pyridazin-4-one
or a pharmaceutically acceptable salt or ester thereof.

31. The compound of claim 1, selected from the group consisting of
1-(3-Methanesulfonyl-phenyl)-3-[2-(3-trifluoromethoxy-phenyl)-2H-pyrazol-3-yl]-1H-pyridazin-4-one,
3-[2-(2,3-Dihydro-benzo[1,4]dioxin-5-yl)-2H-pyrazol-3-yl]-1-(3-methanesulfonyl-phenyl)-1H-pyridazin-4-one,
3-[2-(2-Methyl-pyridin-4-yl)-2H-pyrazol-3-yl]-1-(3-trifluoromethoxy-phenyl)-1H-pyridazin-4-one,
3-(4-Ethyl-2-phenyl-2H-pyrazol-3-yl)-1-(3-trifluoromethoxy-phenyl)-1H-pyridazin-4-one,
3-[2-(3-Methanesulfonyl-phenyl)-2H-pyrazol-3-yl]-1-(3-trifluoromethoxy-phenyl)-1H-pyridazin-4-one,
1-(2,2-Difluoro-benzo[1,3]dioxol-4-yl)-3-[2-(3-fluoro-phenyl)-2H-pyrazol-3-yl]-1H-pyridazin-4-one,
1-(2,2-Difluoro-benzo[1,3]dioxol-4-yl)-3-[2-(2,5-difluoro-phenyl)-2H-pyrazol-3-yl]-1H-pyridazin-4-one,
3-{5-[1-(2,2-Difluoro-benzo[1,3]dioxol-4-yl)-4-oxo-1,4-dihydro-pyridazin-3-yl]-pyrazol-1-yl}-benzonitrile,
1-(2,2-Difluoro-benzo[1,3]dioxol-4-yl)-3-[2-(2-methyl-pyridin-4-yl)-2H-pyrazol-3-yl]-1H-pyridazin-4-one, and
3-[2-(2-Methyl-pyridin-4-yl)-2H-pyrazol-3-yl]-1-(4-trifluoromethoxy-phenyl)-1H-pyridazin-4-one
or a pharmaceutically acceptable salt or ester thereof.

32. The compound of claim 1, selected from the group consisting of
1-(2,2-Difluoro-benzo[1,3]dioxol-5-yl)-3-[2-(2-methyl-pyridin-4-yl)-2H-pyrazol-3-yl]-1H-pyridazin-4-one,
N,N-Dimethyl-3-{3-[2-(2-methyl-pyridin-4-yl)-2H-pyrazol-3-yl]-4-oxo-4H-pyridazin-1-yl}-benzenesulfonamide,
1-(3-Fluoro-phenyl)-3-[2-(2-methyl-pyridin-4-yl)-2H-pyrazol-3-yl]-1H-pyridazin-4-one,
3-[2-(3-Fluoro-phenyl)-2H-pyrazol-3-yl]-1-(4-trifluoromethoxy-phenyl)-1H-pyridazin-4-one,
3-[2-(2,5-Difluoro-phenyl)-2H-pyrazol-3-yl]-1-(4-trifluoromethoxy-phenyl)-1H-pyridazin-4-one,
3-[2-(6-Fluoro-quinolin-4-yl)-2H-pyrazol-3-yl]-1-(4-trifluoromethoxy-phenyl)-1H-pyridazin-4-one,
3-[2-(4-Fluoro-phenyl)-2H-pyrazol-3-yl]-1-(4-trifluoromethoxy-phenyl)-1H-pyridazin-4-one,
4-{5-[4-Oxo-1-(4-trifluoromethoxy-phenyl)-1,4-dihydro-pyridazin-3-yl]-pyrazol-1-yl}-benzonitrile,
3-(2-Pyridin-3-yl-2H-pyrazol-3-yl)-1-(4-trifluoromethoxy-phenyl)-1H-pyridazin-4-one, and
3-[2-(3-Methanesulfonyl-phenyl)-2H-pyrazol-3-yl]-1-(4-trifluoromethoxy-phenyl)-1H-pyridazin-4-one
or a pharmaceutically acceptable salt or ester thereof.

33. The compound of claim 1, selected from the group consisting of
- 1-(4-Trifluoromethoxy-phenyl)-3-[2-(3-trifluoromethoxy-phenyl)-2H-pyrazol-3-yl]-1H-pyridazin-4-one,
- N,N-Dimethyl-3-{5-[4-oxo-1-(4-trifluoromethoxy-phenyl)-1,4-dihydro-pyridazin-3-yl]-pyrazol-1-yl}-benzenesulfonamide,
- 3-[2-(3-Chloro-phenyl)-2H-pyrazol-3-yl]-1-(4-trifluoromethoxy-phenyl)-1H-pyridazin-4-one,
- 3-[2-(2,2-Difluoro-benzo[1,3]dioxol-4-yl)-2H-pyrazol-3-yl]-1-(4-trifluoromethoxy-phenyl)-1H-pyridazin-4-one,
- 3-[2-(2,2-Difluoro-benzo[1,3]dioxol-5-yl)-2H-pyrazol-3-yl]-1-(4-trifluoromethoxy-phenyl)-1H-pyridazin-4-one,
- 3-[2-(3-Trifluoromethanesulfonyl-phenyl)-2H-pyrazol-3-yl]-1-(4-trifluoromethoxy-phenyl)-1H-pyridazin-4-one,
- 3-[2-(6-Fluoro-quinolin-4-yl)-2H-pyrazol-3-yl]-1-(3-trifluoromethoxy-phenyl)-1H-pyridazin-4-one,
- 1-(4-Difluoromethoxy-phenyl)-3-[2-(6-fluoro-quinolin-4-yl)-2H-pyrazol-3-yl]-1H-pyridazin-4-one,
- 1-(3-Difluoromethoxy-phenyl)-3-[2-(6-fluoro-quinolin-4-yl)-2H-pyrazol-3-yl]-1H-pyridazin-4-one, and
- 1-(2,2-Difluoro-benzo[1,3]dioxol-5-yl)-3-[2-(6-fluoro-quinolin-4-yl)-2H-pyrazol-3-yl]-1H-pyridazin-4-one or a pharmaceutically acceptable salt or ester thereof.

34. The compound of claim 1, selected from the group consisting of
- 1-(4-Methanesulfonyl-phenyl)-3-(2-phenyl-2H-pyrazol-3-yl)-1H-pyridazin-4-one,
- 3-[2-(4-Fluoro-phenyl)-2H-pyrazol-3-yl]-1-(4-methanesulfonyl-phenyl)-1H-pyridazin-4-one,
- 3-[2-(3-Fluoro-phenyl)-2H-pyrazol-3-yl]-1-(4-methanesulfonyl-phenyl)-1H-pyridazin-4-one,
- 4-{5-[1-(4-Methanesulfonyl-phenyl)-4-oxo-1,4-dihydro-pyridazin-3-yl]-pyrazol-1-yl}-benzonitrile,
- 3-[2-(4-Chloro-phenyl)-2H-pyrazol-3-yl]-1-(4-methanesulfonyl-phenyl)-1H-pyridazin-4-one,
- 3-[2-(3-Chloro-phenyl)-2H-pyrazol-3-yl]-1-(4-methanesulfonyl-phenyl)-1H-pyridazin-4-one,
- 1-(4-Methanesulfonyl-phenyl)-3-[2-(4-trifluoromethoxy-phenyl)-2H-pyrazol-3-yl]-1H-pyridazin-4-one,
- 1-(3-Trifluoromethoxy-phenyl)-3-[2-(3-trifluoromethoxy-phenyl)-2H-pyrazol-3-yl]-1H-pyridazin-4-one,
- N,N-Dimethyl-3-{5-[4-oxo-1-(3-trifluoromethoxy-phenyl)-1,4-dihydro-pyridazin-3-yl]-pyrazol-1-yl}-benzenesulfonamide, and
- 3-[2-(2,2-Difluoro-benzo[1,3]dioxol-4-yl)-2H-pyrazol-3-yl]-1-(3-trifluoromethoxy-phenyl)-1H-pyridazin-4-one or a pharmaceutically acceptable salt or ester thereof.

35. The compound of claim 1, selected from the group consisting of
- 3-[2-(2,2-Difluoro-benzo[1,3]dioxol-5-yl)-2H-pyrazol-3-yl]-1-(3-trifluoromethoxy-phenyl)-1H-pyridazin-4-one,
- 3-[2-(3-Trifluoromethanesulfonyl-phenyl)-2H-pyrazol-3-yl]-1-(3-trifluoromethoxy-phenyl)-1H-pyridazin-4-one,
- 1-(4-Difluoromethoxy-phenyl)-3-[2-(3-methanesulfonyl-phenyl)-2H-pyrazol-3-yl]-1H-pyridazin-4-one,
- 1-(4-Difluoromethoxy-phenyl)-3-[2-(3-trifluoromethoxy-phenyl)-2H-pyrazol-3-yl]-1H-pyridazin-4-one,
- 3-[2-(2,2-Difluoro-benzo[1,3]dioxol-4-yl)-2H-pyrazol-3-yl]-1-(4-difluoromethoxy-phenyl)-1H-pyridazin-4-one,
- 1-(4-Difluoromethoxy-phenyl)-3-[2-(2-fluoro-phenyl)-2H-pyrazol-3-yl]-1H-pyridazin-4-one,
- 1-(3-Difluoromethoxy-phenyl)-3-[2-(3-methanesulfonyl-phenyl)-2H-pyrazol-3-yl]-1H-pyridazin-4-one,
- 1-(3-Difluoromethoxy-phenyl)-3-[2-(3-trifluoromethoxy-phenyl)-2H-pyrazol-3-yl]-1H-pyridazin-4-one,
- 3-[2-(2,2-Difluoro-benzo[1,3]dioxol-4-yl)-2H-pyrazol-3-yl]-1-(3-difluoromethoxy-phenyl)-1H-pyridazin-4-one, and
- 1-(3-Difluoromethoxy-phenyl)-3-[2-(2-fluoro-phenyl)-2H-pyrazol-3-yl]-1H-pyridazin-4-one or a pharmaceutically acceptable salt or ester thereof.

36. The compound of claim 1, selected from the group consisting of
- 1-(2,2-Difluoro-benzo[1,3]dioxol-5-yl)-3-[2-(3-methanesulfonyl-phenyl)-2H-pyrazol-3-yl]-1H-pyridazin-4-one,
- 1-(2,2-Difluoro-benzo[1,3]dioxol-5-yl)-3-[2-(2,2-difluoro-benzo[1,3]dioxol-4-yl)-2H-pyrazol-3-yl]-1H-pyridazin-4-one,
- 1-(2,2-Difluoro-benzo[1,3]dioxol-5-yl)-3-[2-(2-fluoro-phenyl)-2H-pyrazol-3-yl]-1H-pyridazin-4-one,
- 3-[2-(4-Fluoro-phenyl)-2H-pyrazol-3-yl]-1-(3-hydroxy-phenyl)-1H-pyridazin-4-one,
- N-(3-{5-[4-Oxo-1-(4-trifluoromethoxy-phenyl)-1,4-dihydro-pyridazin-3-yl]-pyrazol-1-yl}-phenyl)-acetamide,
- 3-[2-(6-Fluoro-2-methyl-quinolin-4-yl)-2H-pyrazol-3-yl]-1-(3-trifluoromethoxy-phenyl)-1H-pyridazin-4-one,
- 3-(2-Quinolin-4-yl-2H-pyrazol-3-yl)-1-(3-trifluoromethoxy-phenyl)-1H-pyridazin-4-one,
- N-(3-{5-[4-Oxo-1-(3-trifluoromethoxy-phenyl)-1,4-dihydro-pyridazin-3-yl]-pyrazol-1-yl}-phenyl)-acetamide,
- N-(3-{5-[1-(3-Dimethylsulfamoyl-phenyl)-4-oxo-1,4-dihydro-pyridazin-3-yl]-pyrazol-1-yl}-phenyl)-acetamide, and
- 3-[2-(4-Hydroxy-phenyl)-2H-pyrazol-3-yl]-1-(3-methanesulfonyl-phenyl)-1H-pyridazin-4-one or a pharmaceutically acceptable salt or ester thereof.

37. The compound of claim 1, selected from the group consisting of
- 3-[2-(3-Chloro-phenyl)-2H-pyrazol-3-yl]-1-phenyl-1H-pyridazin-4-one,
- 3-[2-(2-Fluoro-phenyl)-2H-pyrazol-3-yl]-1-phenyl-1H-pyridazin-4-one,
- 3-(2-Naphthalen-1-yl-2H-pyrazol-3-yl)-1-phenyl-1H-pyridazin-4-one,
- 4-{5-[4-Oxo-1-(4-trifluoromethoxy-phenyl)-1,4-dihydro-pyridazin-3-yl]-pyrazol-1-yl}-benzenesulfonamide,
- 3-(2-Quinolin-4-yl-2H-pyrazol-3-yl)-1-(4-trifluoromethoxy-phenyl)-1H-pyridazin-4-one,
- 3-[2-(6-Fluoro-quinolin-4-yl)-2H-pyrazol-3-yl]-1-phenyl-1H-pyridazin-4-one,
- 3-(2-Naphthalen-1-yl-2H-pyrazol-3-yl)-1-(3-trifluoromethyl-phenyl)-1H-pyridazin-4-one,
- 3-[2-(6-Fluoro-quinolin-4-yl)-2H-pyrazol-3-yl]-1-(3-trifluoromethyl-phenyl)-1H-pyridazin-4-one,
- 1-(3-Bromo-phenyl)-3-(2-naphthalen-1-yl-2H-pyrazol-3-yl)-1H-pyridazin-4-one, and
- 1-(4-Methanesulfonyl-phenyl)-3-(2-quinolin-4-yl-2H-pyrazol-3-yl)-1H-pyridazin-4-one or a pharmaceutically acceptable salt or ester thereof.

38. The compound of claim 1, selected from the group consisting of
- 3-(2-Isoquinolin-5-yl-2H-pyrazol-3-yl)-1-(4-methanesulfonyl-phenyl)-1H-pyridazin-4-one,
- 3-[2-(2-Chloro-pyridin-4-yl)-2H-pyrazol-3-yl]-1-(4-trifluoromethoxy-phenyl)-1H-pyridazin-4-one,
- 3-[2-(6-Fluoro-2-methyl-quinolin-4-yl)-2H-pyrazol-3-yl]-1-(4-trifluoromethoxy-phenyl)-1H-pyridazin-4-one,
- 3-{3-[2-(6-Fluoro-2-methyl-quinolin-4-yl)-2H-pyrazol-3-yl]-4-oxo-4H-pyridazin-1-yl}-N,N-dimethyl-benzenesulfonamide,
- N,N-Dimethyl-3-[4-oxo-3-(2-quinolin-4-yl-2H-pyrazol-3-yl)-4H-pyridazin-1-yl]-benzenesulfonamide,
- 1-(3-Methoxy-phenyl)-3-(2-quinolin-4-yl-2H-pyrazol-3-yl)-1H-pyridazin-4-one,
- 3-[2-(6-Fluoro-quinolin-4-yl)-2H-pyrazol-3-yl]-1-(3-methoxy-phenyl)-1H-pyridazin-4-one,
- 3-[2-(6-Fluoro-2-methyl-quinolin-4-yl)-2H-pyrazol-3-yl]-1-(3-methoxy-phenyl)-1H-pyridazin-4-one,
- 3-[2-(2-Ethoxy-pyridin-4-yl)-2H-pyrazol-3-yl]-1-(4-trifluoromethoxy-phenyl)-1H-pyridazin-4-one, and
- 1-(3-Methoxy-phenyl)-3-(2-naphthalen-1-yl-2H-pyrazol-3-yl)-1H-pyridazin-4-one or a pharmaceutically acceptable salt or ester thereof.

39. The compound of claim 1, selected from the group consisting of
- 3-[2-(2,3-Dihydro-benzo[1,4]dioxin-6-yl)-2H-pyrazol-3-yl]-1-(3-methoxy-phenyl)-1H-pyridazin-4-one,
- 3-(2-Quinolin-5-yl-2H-pyrazol-3-yl)-1-(3-trifluoromethoxy-phenyl)-1H-pyridazin-4-one,
- 1-(3-Difluoromethoxy-phenyl)-3-(2-quinolin-5-yl-2H-pyrazol-3-yl)-1H-pyridazin-4-one,
- 3-[2-(2-Chloro-pyridin-4-yl)-2H-pyrazol-3-yl]-1-(3-difluoromethoxy-phenyl)-1H-pyridazin-4-one,
- 3-[2-(3-Chloro-phenyl)-2H-pyrazol-3-yl]-1-(3-difluoromethoxy-phenyl)-1H-pyridazin-4-one,
- 3-[4-Oxo-3-(2-quinolin-4-yl-2H-pyrazol-3-yl)-4H-pyridazin-1-yl]-benzonitrile,
- 3-{3-[2-(2-Fluoro-phenyl)-2H-pyrazol-3-yl]-4-oxo-4H-pyridazin-1-yl}-N,N-dimethyl-benzamide,
- 3-{3-[2-(3-Chloro-phenyl)-2H-pyrazol-3-yl]-4-oxo-4H-pyridazin-1-yl}-N,N-dimethyl-benzamide,
- N,N-Diethyl-3-{3-[2-(3-fluoro-phenyl)-2H-pyrazol-3-yl]-4-oxo-4H-pyridazin-1-yl}-benzenesulfonamide, and
- 3-(2-Phenyl-2H-pyrazol-3-yl)-1-(4-trifluoromethyl-phenyl)-1H-pyridazin-4-one or a pharmaceutically acceptable salt or ester thereof.

40. The compound of claim 1, selected from the group consisting of
- 3-[2-(2-Fluoro-phenyl)-2H-pyrazol-3-yl]-1-(4-trifluoromethyl-phenyl)-1H-pyridazin-4-one,
- 3-[2-(3-Chloro-phenyl)-2H-pyrazol-3-yl]-1-(4-trifluoromethyl-phenyl)-1H-pyridazin-4-one,
- 3-(2-Quinolin-4-yl-2H-pyrazol-3-yl)-1-(3-trifluoromethyl-phenyl)-1H-pyridazin-4-one,
- 3-(2-Quinolin-8-yl-2H-pyrazol-3-yl)-1-(4-trifluoromethoxy-phenyl)-1H-pyridazin-4-one,
- 3-(2-o-Tolyl-2H-pyrazol-3-yl)-1-(4-trifluoromethyl-phenyl)-1H-pyridazin-4-one,
- 3-{5-[4-Oxo-1-(4-trifluoromethyl-phenyl)-1,4-dihydropyridazin-3-yl]-pyrazol-1-yl}-benzonitrile,
- 1-(3-Chloro-phenyl)-3-[2-(2-fluoro-phenyl)-2H-pyrazol-3-yl]-1H-pyridazin-4-one,
- 1-(3-Chloro-phenyl)-3-[2-(3-chloro-phenyl)-2H-pyrazol-3-yl]-1H-pyridazin-4-one,
- 3-[2-(3-Methyl-isothiazol-5-yl)-2H-pyrazol-3-yl]-1-(4-trifluoromethoxy-phenyl)-1H-pyridazin-4-one, and
- 1-(3-Chloro-phenyl)-3-(2-naphthalen-1-yl-2H-pyrazol-3-yl)-1H-pyridazin-4-one or a pharmaceutically acceptable salt or ester thereof.

41. The compound of claim 1, selected from the group consisting of
- 3-(2-Naphthalen-1-yl-2H-pyrazol-3-yl)-1-(4-trifluoromethyl-phenyl)-1H-pyridazin-4-one,
- 1-(4-Chloro-phenyl)-3-(2-naphthalen-1-yl-2H-pyrazol-3-yl)-1H-pyridazin-4-one,
- 3-[2-(6-Chloro-quinolin-4-yl)-2H-pyrazol-3-yl]-1-(4-trifluoromethoxy-phenyl)-1H-pyridazin-4-one,
- 3-(2-Isoquinolin-5-yl-2H-pyrazol-3-yl)-1-(4-trifluoromethoxy-phenyl)-1H-pyridazin-4-one,
- 3-(2-Isoquinolin-4-yl-2H-pyrazol-3-yl)-1-(4-trifluoromethoxy-phenyl)-1H-pyridazin-4-one,
- 3-(2-Quinolin-5-yl-2H-pyrazol-3-yl)-1-(4-trifluoromethoxy-phenyl)-1H-pyridazin-4-one,
- 1-(4-Chloro-phenyl)-3-[2-(2-fluoro-phenyl)-2H-pyrazol-3-yl]-1H-pyridazin-4-one,
- 1-(4-Chloro-phenyl)-3-[2-(3-chloro-phenyl)-2H-pyrazol-3-yl]-1H-pyridazin-4-one,
- 1-(3-Dimethylaminomethyl-phenyl)-3-[2-(2-fluoro-phenyl)-2H-pyrazol-3-yl]-1H-pyridazin-4-one, and
- 3-[2-(2-Fluoro-phenyl)-2H-pyrazol-3-yl]-1-[3-(piperidine-1-sulfonyl)-phenyl]-1H-pyridazin-4-one or a pharmaceutically acceptable salt or ester thereof.

42. The compound of claim 1, selected from the group consisting of
- 3-[2-(2-Fluoro-phenyl)-2H-pyrazol-3-yl]-1-(4-trifluoromethane sulfonyl-phenyl)-1H-pyridazin-4-one,
- 1-(4-Dimethylaminomethyl-phenyl)-3-[2-(2-fluoro-phenyl)-2H-pyrazol-3-yl]-1H-pyridazin-4-one,
- 3-(2-Isoquinolin-5-yl-2H-pyrazol-3-yl)-1-(4-trifluoromethanesulfonyl-phenyl)-1H-pyridazin-4-one,
- 3-(2-Quinolin-5-yl-2H-pyrazol-3-yl)-1-(4-trifluoromethanesulfonyl-phenyl)-1H-pyridazin-4-one,
- 3-[2-(4-Chloro-naphthalen-1-yl)-2H-pyrazol-3-yl]-1-phenyl-1H-pyridazin-4-one,
- 3-[2-(4-Chloro-naphthalen-1-yl)-2H-pyrazol-3-yl]-1-(4-trifluoromethyl-phenyl)-1H-pyridazin-4-one,
- 3-[2-(2-Fluoro-phenyl)-2H-pyrazol-3-yl]-1-[3-(pyrrolidine-1-sulfonyl)-phenyl]-1H-pyridazin-4-one,
- 4-{3-[2-(2-Fluoro-phenyl)-2H-pyrazol-3-yl]-4-oxo-4H-pyridazin-1-yl}-N-methyl-benzenesulfonamide,
- 3-[2-(7-Chloro-quinolin-4-yl)-2H-pyrazol-3-yl]-1-(4-trifluoromethoxy-phenyl)-1H-pyridazin-4-one, and
- N,N-Diethyl-3-[4-oxo-3-(2-quinolin-5-yl-2H-pyrazol-3-yl)-4H-pyridazin-1-yl]-benzenesulfonamide or a pharmaceutically acceptable salt or ester thereof.

43. The compound of claim 1, selected from the group consisting of
- 3-(2-Quinolin-4-yl-2H-pyrazol-3-yl)-1-(4-trifluoromethanesulfonyl-phenyl)-1H-pyridazin-4-one,
- 3-[2-(4-Chloro-naphthalen-1-yl)-2H-pyrazol-3-yl]-1-(4-chloro-phenyl)-1H-pyridazin-4-one,
- 3-[2-(4-Chloro-naphthalen-1-yl)-2H-pyrazol-3-yl]-1-(3-chloro-phenyl)-1H-pyridazin-4-one,
- N,N-Diethyl-3-[3-(2-isoquinolin-5-yl-2H-pyrazol-3-yl)-4-oxo-4H-pyridazin-1-yl]-benzenesulfonamide,
- 3-(2-Isoquinolin-8-yl-2H-pyrazol-3-yl)-1-(4-trifluoromethoxy-phenyl)-1H-pyridazin-4-one,
- 1-(4-Trifluoromethoxy-phenyl)-3-[2-(2-trifluoromethylpyridin-4-yl)-2H-pyrazol-3-yl]-1H-pyridazin-4-one,
- 3-[3-(2-Isoquinolin-5-yl-2H-pyrazol-3-yl)-4-oxo-4H-pyridazin-1-yl]-benzonitrile, 3-{3-[2-(7-Chloro-quinolin-4-yl)-2H-pyrazol-3-yl]-4-oxo-4H-pyridazin-1-yl}-benzonitrile,
1-[3-(Pyrrolidine-1-sulfonyl)-phenyl]-3-(2-quinolin-5-yl-2H-pyrazol-3-yl)-1H-pyridazin-4-one, and
3-[2-(7-Chloro-quinolin-4-yl)-2H-pyrazol-3-yl]-1-[3-(pyrrolidine-1-sulfonyl)-phenyl]-1H-pyridazin-4-one
or a pharmaceutically acceptable salt or ester thereof.

44. The compound of claim 1, selected from the group consisting of
3-{3-[2-(7-Chloro-quinolin-4-yl)-2H-pyrazol-3-yl]-4-oxo-4H-pyridazin-1-yl}-N,N-diethyl-benzenesulfonamide,
3-{3-[2-(7-Chloro-quinolin-4-yl)-2H-pyrazol-3-yl]-4-oxo-4H-pyridazin-1-yl}-N-methyl-benzenesulfonamide,
3-[3-(2-Isoquinolin-8-yl-2H-pyrazol-3-yl)-4-oxo-4H-pyridazin-1-yl]-N,N-dimethyl-benzenesulfonamide,
3-[2-(2-Fluoro-phenyl)-2H-pyrazol-3-yl]-1-[4-(2,2,2-trifluoro-ethoxy)-phenyl]-1H-pyridazin-4-one,
3-(2-Phenyl-2H-pyrazol-3-yl)-1-[4-(2,2,2-trifluoro-ethoxy)-phenyl]-1H-pyridazin-4-one,
3-[2-(3-Chloro-phenyl)-2H-pyrazol-3-yl]-1-[4-(2,2,2-trifluoro-ethoxy)-phenyl]-1H-pyridazin-4-one,
3-[2-(3-Fluoro-phenyl)-2H-pyrazol-3-yl]-1-[4-(2,2,2-trifluoro-ethoxy)-phenyl]-1H-pyridazin-4-one,
3-(2-Quinolin-4-yl-2H-pyrazol-3-yl)-1-[4-(2,2,2-trifluoro-ethoxy)-phenyl]-1H-pyridazin-4-one,
3-{3-[2-(2-Methyl-pyridin-4-yl)-2H-pyrazol-3-yl]-4-oxo-4H-pyridazin-1-yl}-benzonitrile, and
3-(2-Isoquinolin-5-yl-2H-pyrazol-3-yl)-1-[3-(pyrrolidine-1-sulfonyl)-phenyl]-1H-pyridazin-4-one
or a pharmaceutically acceptable salt or ester thereof.

45. The compound of claim 1, selected from the group consisting of
N-Methyl-3-{3-[2-(2-methyl-pyridin-4-yl)-2H-pyrazol-3-yl]-4-oxo-4H-pyridazin-1-yl}-benzenesulfonamide,
3-[3-(2-Isoquinolin-5-yl-2H-pyrazol-3-yl)-4-oxo-4H-pyridazin-1-yl]-N-methyl-benzenesulfonamide,
3-[2-(6-Chloro-quinolin-4-yl)-2H-pyrazol-3-yl]-1-[3-(pyrrolidine-1-sulfonyl)-phenyl]-1H-pyridazin-4-one,
1-[3-(Piperidine-1-sulfonyl)-phenyl]-3-(2-quinolin-5-yl-2H-pyrazol-3-yl)-1H-pyridazin-4-one,
3-(2-Isoquinolin-5-yl-2H-pyrazol-3-yl)-1-[3-(piperidine-1-sulfonyl)-phenyl]-1H-pyridazin-4-one,
3-[2-(6-Chloro-quinolin-4-yl)-2H-pyrazol-3-yl]-1-[3-(piperidine-1-sulfonyl)-phenyl]-1H-pyridazin-4-one,
3-[2-(7-Chloro-quinolin-4-yl)-2H-pyrazol-3-yl]-1-[3-(piperidine-1-sulfonyl)-phenyl]-1H-pyridazin-4-one,
N,N-Diethyl-3-{3-[2-(2-fluoro-phenyl)-2H-pyrazol-3-yl]-4-oxo-4H-pyridazin-1-yl}-benzenesulfonamide,
3-{3-[2-(3-Fluoro-phenyl)-2H-pyrazol-3-yl]-4-oxo-4H-pyridazin-1-yl}-benzonitrile, and
3-[2-(3-Fluoro-phenyl)-2H-pyrazol-3-yl]-1-[3-(pyrrolidine-1-sulfonyl)-phenyl]-1H-pyridazin-4-one
or a pharmaceutically acceptable salt or ester thereof.

46. The compound of claim 1, selected from the group consisting of
4-{3-[2-(3-Fluoro-phenyl)-2H-pyrazol-3-yl]-4-oxo-4H-pyridazin-1-yl}-N-methyl-benzenesulfonamide,
3-[2-(3-Fluoro-phenyl)-2H-pyrazol-3-yl]-1-[3-(piperidine-1-sulfonyl)-phenyl]-1H-pyridazin-4-one,
3-{3-[2-(2,5-Difluoro-phenyl)-2H-pyrazol-3-yl]-4-oxo-4H-pyridazin-1-yl}-benzonitrile,
3-[2-(2,5-Difluoro-phenyl)-2H-pyrazol-3-yl]-1-[3-(pyrrolidine-1-sulfonyl)-phenyl]-1H-pyridazin-4-one,
1-(3-Hydroxy-phenyl)-3-(2-naphthalen-1-yl-2H-pyrazol-3-yl)-1H-pyridazin-4-one,
3-[2-(2,3-Dihydro-benzo[1,4]dioxin-6-yl)-2H-pyrazol-3-yl]-1-(3-hydroxy-phenyl)-1H-pyridazin-4-one,
3-(2-Phenyl-2H-pyrazol-3-yl)-1-(4-trifluoromethanesulfonyl-phenyl)-1H-pyridazin-4-one,
3-[2-(3-Chloro-phenyl)-2H-pyrazol-3-yl]-1-(4-trifluoromethanesulfonyl-phenyl)-1H-pyridazin-4-one,
3-[2-(2,3-Dichloro-phenyl)-2H-pyrazol-3-yl]-1-(4-trifluoromethanesulfonyl-phenyl)-1H-pyridazin-4-one, and
3-(2-Phenyl-2H-pyrazol-3-yl)-1-(3-trifluoromethanesulfonyl-phenyl)-1H-pyridazin-4-one
or a pharmaceutically acceptable salt or ester thereof.

47. The compound of claim 1, selected from the group consisting of
3-[2-(2-Fluoro-phenyl)-2H-pyrazol-3-yl]-1-(3-trifluoromethanesulfonyl-phenyl)-1H-pyridazin-4-one,
3-[2-(3-Chloro-phenyl)-2H-pyrazol-3-yl]-1-(3-trifluoromethanesulfonyl-phenyl)-1H-pyridazin-4-one,
3-{5-[4-Oxo-1-(3-trifluoromethanesulfonyl-phenyl)-1,4-dihydro-pyridazin-3-yl]-pyrazol-1-yl}-benzonitrile,
3-[2-(2,3-Dichloro-phenyl)-2H-pyrazol-3-yl]-1-(3-trifluoromethane sulfonyl-phenyl)-1H-pyridazin-4-one,
3-{3-[2-(2-Fluoro-phenyl)-2H-pyrazol-3-yl]-4-oxo-4H-pyridazin-1-yl}-benzonitrile,
3-{3-[2-(3-Chloro-phenyl)-2H-pyrazol-3-yl]-4-oxo-4H-pyridazin-1-yl}-benzonitrile,
3-[2-(3-Chloro-2-fluoro-phenyl)-2H-pyrazol-3-yl]-1-(4-trifluoromethanesulfonyl-phenyl)-1H-pyridazin-4-one,
3-[2-(3-Chloro-2-fluoro-phenyl)-2H-pyrazol-3-yl]-1-(3-trifluoromethanesulfonyl-phenyl)-1H-pyridazin-4-one,
3-[2-(2,3-Dihydro-benzo[1,4]dioxin-6-yl)-2H-pyrazol-3-yl]-1-(3-fluoromethoxy-phenyl)-1H-pyridazin-4-one, and
1-(3-Fluoromethoxy-phenyl)-3-(2-naphthalen-1-yl-2H-pyrazol-3-yl)-1H-pyridazin-4-one.
or a pharmaceutically acceptable salt and or ester thereof.

48. The compound of claim 1, selected from the group consisting of
N-(3-{3-[2-(2-Fluoro-phenyl)-2H-pyrazol-3-yl]-4-oxo-4H-pyridazin-1-yl}-phenyl)-acetamide,
3-{3-[2-(2-Fluoro-phenyl)-2H-pyrazol-3-yl]-4-oxo-4H-pyridazin-1-yl}-N-methyl-benzamide,
N-(3-{3-[2-(2-Fluoro-phenyl)-2H-pyrazol-3-yl]-4-oxo-4H-pyridazin-1-yl}-phenyl)-N-methyl-acetamide,
3-[3-(2-Naphthalen-1-yl-2H-pyrazol-3-yl)-4-oxo-4H-pyridazin-1-yl]-benzoic acid 2-fluoro-ethyl ester,
3-[3-(2-Naphthalen-1-yl-2H-pyrazol-3-yl)-4-oxo-4H-pyridazin-1-yl]-benzoic acid 3-fluoro-propyl ester,
3-[3-(2-Naphthalen-1-yl-2H-pyrazol-3-yl)-4-oxo-4H-pyridazin-1-yl]-benzoic acid methyl ester,
3-[2-(2-Fluoro-phenyl)-2H-pyrazol-3-yl]-1-[3-(1-hydroxy-ethyl)-phenyl]-1H-pyridazin-4-one, and
1-(3-Acetyl-phenyl)-3-[2-(2-fluoro-phenyl)-2H-pyrazol-3-yl]-1H-pyridazin-4-one,
or a pharmaceutically acceptable salt or ester thereof.

49. The compound of claim 1, selected from the group consisting of
3-[2-(2,4-Difluoro-phenyl)-2H-pyrazol-3-yl]-1-(3-methanesulfonyl-phenyl)-1H-pyridazin-4-one,
1-(3-Difluoromethoxy-phenyl)-3-[2-(2,5-difluoro-phenyl)-2H-pyrazol-3-yl]-1H-pyridazin-4-one,
3-[2-(2-Methyl-pyridin-4-yl)-2H-pyrazol-3-yl]-1-(3-trifluoromethoxy-phenyl)-1H-pyridazin-4-one,
1-(3-Difluoromethoxy-phenyl)-3-[2-(6-fluoro-quinolin-4-yl)-2H-pyrazol-3-yl]-1H-pyridazin-4-one,
3-(2-Quinolin-4-yl-2H-pyrazol-3-yl)-1-(4-trifluoromethoxy-phenyl)-1H-pyridazin-4-one, 3-[2-(3-Chloro-phenyl)-2H-pyrazol-3-yl]-1-(3-difluoromethoxy-phenyl)-1H-pyridazin-4-one,
3-[4-Oxo-3-(2-quinolin-4-yl-2H-pyrazol-3-yl)-4H-pyridazin-1-yl]-benzonitrile,
3-[2-(2-Fluoro-phenyl)-2H-pyrazol-3-yl]-1-(4-trifluoromethanesulfonyl-phenyl)-1H-pyridazin-4-one,
3-[2-(2-Fluoro-phenyl)-2H-pyrazol-3-yl]-1-[4-(2,2,2-trifluoro-ethoxy)-phenyl]-1H-pyridazin-4-one,
3-[2-(3-Chloro-phenyl)-2H-pyrazol-3-yl]-1-[4-(2,2,2-trifluoro-ethoxy)-phenyl]-1H-pyridazin-4-one,
3-(2-Quinolin-4-yl-2H-pyrazol-3-yl)-1-[4-(2,2,2-trifluoro-ethoxy)-phenyl]-1H-pyridazin-4-one,
3-[2-(2,3-Dihydro-benzo[1,4]dioxin-6-yl)-2H-pyrazol-3-yl]-1-(3-hydroxy-phenyl)-1H-pyridazin-4-one,
3-(2-Phenyl-2H-pyrazol-3-yl)-1-(3-trifluoromethanesulfonyl-phenyl)-1H-pyridazin-4-one, 3-{5-[4-Oxo-1-(3-trifluoromethanesulfonyl-phenyl)-1,4-dihydro-pyridazin-3-yl]-pyrazol-1-yl}-benzonitrile,
3-{3-[2-(3-Chloro-phenyl)-2H-pyrazol-3-yl]-4-oxo-4H-pyridazin-1-yl}-benzonitrile,
N-(3-{3-[2-(2-Fluoro-phenyl)-2H-pyrazol-3-yl]-4-oxo-4H-pyridazin-1-yl}-phenyl)-acetamide,
3-{3-[2-(2-Fluoro-phenyl)-2H-pyrazol-3-yl]-4-oxo-4H-pyridazin-1-yl}-N-methyl-benzamide,
N-(3-{3-[2-(2-Fluoro-phenyl)-2H-pyrazol-3-yl]-4-oxo-4H-pyridazin-1-yl}-phenyl)-N-methyl-acetamide,
3-[3-(2-Naphthalen-1-yl-2H-pyrazol-3-yl)-4-oxo-4H-pyridazin-1-yl]-benzoic acid 2-fluoro-ethyl ester, and
3-[2-(2-Fluoro-phenyl)-2H-pyrazol-3-yl]-1-[3-(1-hydroxy-ethyl)-phenyl]-1H-pyridazin-4-one,
or a pharmaceutically acceptable salt or ester thereof.

50. A pharmaceutical composition comprising a therapeutically effective amount of a compound of formula I

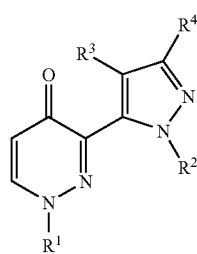

(I)

wherein
$R^1$ is aryl which is optionally substituted with 1 to 4 substituents independently selected from the group consisting of lower-alkyl, hydroxy-lower-alkyl, lower-alkoxy, fluoro-lower-alkyl, fluoro-lower-alkoxy, lower-alkyl-$SO_2$, fluoro-lower-alkyl-$SO_2$, halogen, lower-alkoxy-lower-alkyl, cyano, $NO_2$, lower-alkyl-SO, morpholinyl, $NH_2$—$SO_2$, N(H,lower-alkyl)—$SO_2$, N(lower-alkyl)$_2$-$SO_2$, piperidinyl-$SO_2$, pyrrolidinyl-$SO_2$, hydroxy, COOH, COO-lower-alkyl, COO-fluoro-lower-alkyl, lower-alkyl-C(O)O, CO-lower-alkyl, $CONH_2$, CON(H, lower-alkyl), CON(lower-alkyl)$_2$, lower-alkyl-CO—NH, lower-alkyl-CO—N(lower-alkyl), $NH_2$, N(H, lower-alkyl), N(lower-alkyl)$_2$, $NH_2$-lower-alkyl, N(H, lower-alkyl)-lower-alkyl, N(lower-alkyl)$_2$-lower-alkyl, cycloalkyl, phenyloxy and phenyl, or wherein two substituents at adjacent positions on the aryl group are bound together to form a ring and said two bound substituents together are lower-alkylene, dioxo-lower-alkylene, dioxo-fluoro-lower-alyklene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)-C(O)-lower-alkylene, lower-alkylene-NH—C(O)-lower-alkylene, lower-alkylene-N(lower alkyl)-C(O)-lower-alkylene, C(O)—NH-lower-alkylene or C(O)—N(lower-alkyl)-lower-alkylene;

$R^2$ is aryl or heteroaryl, which aryl or heteroaryl is optionally substituted with 1 to 4 substituents independently selected from the group consisting of halogen, cyano, lower-alkyl, lower-alkoxy, fluoro-lower-alkyl, fluoro-lower-alkoxy, lower-alkinyl, lower-alkyl-$SO_2$, fluoro-lower-alkyl-$SO_2$, tri(lower-alkyl)silyl-loweralkinyl, COOH, $CONH_2$, $NH_2$—$SO_2$, COO-lower-alkyl, 6-oxo-1,4,5,6-tetrahydropyridazinyl, lower-alkoxy-lower-alkyl, CON(H,lower-alkyl), CON(lower-alkyl)$_2$, N(H, lower-alkyl)-$SO_2$, N(lower-alkyl)$_2$-$SO_2$, lower-alkenyl, hydroxy, $NO_2$, morpholinyl, tetrahydropyridazinyl, piperidinyl, piperazinyl, (N-lower-alkyl)-piperazinyl, pyrrolidinyl, lower-alkyl-C(O)O, lower-alkyl-CO—NH, lower-alkyl-CO—N(lower-alkyl), imidazolyl, pyridinyl, CO-lower-alkyl, $NH_2$, N(H,lower-alkyl), N(lower-alkyl)$_2$, $NH_2$-lower-alkyl, N(H,lower-alkyl)-lower-alkyl, N(lower-alkyl)$_2$-lower-alkyl, cycloalkyl, phenyloxy and phenyl which is optionally substituted with 1 to 4 substituents independently selected from halogen, lower-alkoxy, lower-alkyl, fluoro-lower-alkyl, fluoro-lower-alkoxy, hydroxy and cyano, or wherein two substituents at adjacent positions on the aryl or heteroaryl group are bound together to form a ring and said two bound substituents together are lower-alkylene, dioxo-lower-alkylene, dioxo-fluoro-lower-alyklene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)-C(O)-lower-alkylene, lower-alkylene-NH—C(O)-lower-alkylene, lower-alkylene-N(lower alkyl)-C(O)-lower-alkylene, C(O)—NH-lower-alkylene or C(O)—N(lower-alkyl)-lower-alkylene;

$R^3$ is hydrogen, lower-alkyl, fluoro-lower-alkyl, lower-alkoxy, fluoro-lower-alkoxy, halogen, hydroxy or phenyl; and $R^4$ is hydrogen, lower-alkyl, fluoro-lower-alkyl, lower-alkoxy, fluoro-lower-alkoxy, halogen, hydroxy or phenyl;

or a pharmaceutically acceptable salt or ester thereof and a pharmaceutically acceptable carrier.

* * * * *